(12) United States Patent
Han et al.

(10) Patent No.: US 12,233,062 B2
(45) Date of Patent: Feb. 25, 2025

(54) HETEROCYCLIC DERIVATIVES USEFUL AS SHP2 INHIBITORS

(71) Applicant: Jacobio Pharmaceuticals Co., Ltd., Beijing (CN)

(72) Inventors: Huifeng Han, Beijing (CN); Panliang Gao, Beijing (CN); Cunbo Ma, Beijing (CN); Di Kang, Beijing (CN)

(73) Assignee: Jacobio Pharmaceuticals Co., Ltd., Beijing (CN)

( * ) Notice: Subject to any disclaimer, the term of this patent is extended or adjusted under 35 U.S.C. 154(b) by 0 days.

(21) Appl. No.: 18/591,753

(22) Filed: Feb. 29, 2024

(65) Prior Publication Data
US 2024/0285617 A1     Aug. 29, 2024

Related U.S. Application Data

(63) Continuation of application No. 18/215,381, filed on Jun. 28, 2023, now abandoned, which is a
(Continued)

(30) Foreign Application Priority Data

Sep. 26, 2018 (WO) ................ PCT/CN2018/107492

(51) Int. Cl.
| | | |
|---|---|---|
| *A61K 31/497* | (2006.01) |
| *A61K 31/438* | (2006.01) |
| *A61K 31/444* | (2006.01) |
| *A61K 31/4545* | (2006.01) |
| *A61K 31/4985* | (2006.01) |
| *A61K 31/501* | (2006.01) |
| *A61K 31/506* | (2006.01) |
| *A61K 31/513* | (2006.01) |
| *A61K 31/519* | (2006.01) |
| *A61K 31/53* | (2006.01) |
| *A61K 31/5377* | (2006.01) |
| *C07D 401/04* | (2006.01) |
| *C07D 401/14* | (2006.01) |
| *C07D 405/14* | (2006.01) |
| *C07D 417/04* | (2006.01) |
| *C07D 471/10* | (2006.01) |
| *C07D 487/04* | (2006.01) |

(Continued)

(52) U.S. Cl.
CPC .......... *A61K 31/497* (2013.01); *A61K 31/438* (2013.01); *A61K 31/444* (2013.01); *A61K 31/4545* (2013.01); *A61K 31/4985* (2013.01); *A61K 31/501* (2013.01); *A61K 31/506* (2013.01); *A61K 31/513* (2013.01); *A61K 31/519* (2013.01); *A61K 31/53* (2013.01); *A61K 31/5377* (2013.01); *C07D 401/04* (2013.01); *C07D 401/14* (2013.01); *C07D 405/14* (2013.01); *C07D 417/04* (2013.01); *C07D 471/10* (2013.01); *C07D 487/04* (2013.01); *C07D 491/107* (2013.01); *C07D 495/10* (2013.01); *C07D 513/04* (2013.01); *C07D 513/10* (2013.01); *C07D 519/00* (2013.01); *C07B 2200/05* (2013.01)

(58) Field of Classification Search
CPC .. A61K 31/497; A61K 31/438; A61K 31/444; A61K 31/4545; A61K 31/4985; A61K 31/501; A61K 31/506; A61K 31/513; A61K 31/519; A61K 31/53; A61K 31/5377; C07D 401/04; C07D 401/14; C07D 405/14; C07D 417/04; C07D 471/10; C07D 487/04; C07D 491/107; C07D 495/10; C07D 513/04; C07D 513/10; C07D 519/00; C07B 2200/05
See application file for complete search history.

(56) References Cited

U.S. PATENT DOCUMENTS

| | | |
|---|---|---|
| 5,876,628 A | 3/1999 | Illian et al. |
| 6,025,382 A | 2/2000 | Bastian et al. |
| (Continued) | | |

FOREIGN PATENT DOCUMENTS

| | | |
|---|---|---|
| CN | 1934100 A | 3/2007 |
| CN | 103201267 A | 7/2013 |
| (Continued) | | |

OTHER PUBLICATIONS

Camille G. Wermuth, Molecular Variations Based on Isosteric Replacements, The Practice of Medicinal Chemistry, (1996), 203-237 (Year: 1996).*

(Continued)

*Primary Examiner* — Alicia L Otton
*Assistant Examiner* — David M Shim
(74) *Attorney, Agent, or Firm* — Foley Hoag LLP; Hathaway P. Russell; Benjamin A. Vaughan

(57) ABSTRACT

This invention provides a compound of formula I, their synthesis and their use for treating a SHP2 mediated disorder. More particularly, this invention provides a pharmaceutical composition comprising the said compound.

Formula I

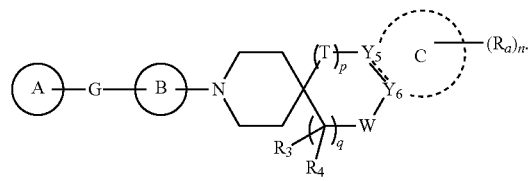

11 Claims, No Drawings

Related U.S. Application Data continuation of application No. 17/985,399, filed on Nov. 11, 2022, now abandoned, which is a continuation of application No. 17/714,547, filed on Apr. 6, 2022, now abandoned, which is a continuation of application No. 17/280,573, filed as application No. PCT/CN2019/108181 on Sep. 26, 2019, now abandoned.

(51) Int. Cl.

| | | |
|---|---|---|
| *C07D 491/107* | (2006.01) | |
| *C07D 495/10* | (2006.01) | |
| *C07D 513/04* | (2006.01) | |
| *C07D 513/10* | (2006.01) | |
| *C07D 519/00* | (2006.01) | |

(56) References Cited

U.S. PATENT DOCUMENTS

| | | |
|---|---|---|
| 7,056,911 B1 | 6/2006 | Rosowsky |
| 7,435,830 B2 | 10/2008 | Pennell et al. |
| 7,435,831 B2 | 10/2008 | Chen et al. |
| 7,439,374 B2 | 10/2008 | Thurkauf et al. |
| 7,605,159 B2 | 10/2009 | McInally et al. |
| 7,691,863 B2 | 4/2010 | Dietz et al. |
| 7,723,369 B2 | 5/2010 | Mjalli et al. |
| 7,790,929 B2 | 9/2010 | Reiffenrath et al. |
| 7,838,523 B2 | 11/2010 | Blomgren et al. |
| 8,012,983 B2 | 9/2011 | Andrews et al. |
| 8,138,206 B2 | 3/2012 | Ishikawa et al. |
| 8,153,635 B2 | 4/2012 | Alper et al. |
| 8,252,803 B2 | 8/2012 | Rivkin |
| 8,258,156 B2 | 9/2012 | Alper et al. |
| 8,313,729 B2 | 11/2012 | Neumann et al. |
| 8,338,437 B2 | 12/2012 | Wahhab et al. |
| 8,389,533 B2 | 3/2013 | Connors et al. |
| 8,404,731 B2 | 3/2013 | Mjalli et al. |
| 8,431,575 B2 | 4/2013 | Gohimukkula et al. |
| 8,450,327 B2 | 5/2013 | Gottschling et al. |
| 8,461,329 B2 | 6/2013 | Takayama et al. |
| 8,575,168 B2 | 11/2013 | Azimioara et al. |
| 8,623,906 B2 | 1/2014 | Wu et al. |
| 8,637,500 B2 | 1/2014 | Allen et al. |
| 8,759,377 B2 | 6/2014 | Conn et al. |
| 8,791,136 B2 | 7/2014 | Goff et al. |
| 8,809,370 B2 | 8/2014 | Goff et al. |
| 8,822,497 B2 | 9/2014 | Burger et al. |
| 8,889,730 B2 | 11/2014 | Bhattacharya et al. |
| 8,912,219 B2 | 12/2014 | Fauber et al. |
| 8,952,014 B2 | 2/2015 | Gottschling et al. |
| 8,980,921 B2 | 3/2015 | Goff et al. |
| 8,987,303 B2 | 3/2015 | Goff et al. |
| 9,062,015 B2 | 6/2015 | Stieber et al. |
| 9,221,766 B2 | 12/2015 | Cheung et al. |
| 9,266,856 B2 | 2/2016 | Goff et al. |
| 9,624,199 B2 | 4/2017 | Becker-Pelster et al. |
| 9,663,496 B2 | 5/2017 | Irving et al. |
| 9,815,813 B2 | 11/2017 | Chen et al. |
| 9,969,719 B2 | 5/2018 | Ding et al. |
| 10,077,276 B2 | 9/2018 | Chen et al. |
| 10,253,046 B2 | 4/2019 | Dahlgren et al. |
| 10,287,266 B2 | 5/2019 | Chen et al. |
| 10,301,278 B2 | 5/2019 | Chen et al. |
| 10,329,270 B2 | 6/2019 | Qiu et al. |
| 10,377,742 B2 | 8/2019 | Goff et al. |
| 10,463,662 B2 | 11/2019 | Lu |
| 10,629,773 B2 | 4/2020 | Even et al. |
| 10,858,359 B2 | 12/2020 | Ma et al. |
| 10,934,302 B1 | 3/2021 | Taylor et al. |
| 10,988,466 B2 | 4/2021 | Ma et al. |
| 2007/0037794 A1 | 2/2007 | Ungashe et al. |
| 2007/0043057 A1 | 2/2007 | Matteucci et al. |
| 2008/0269217 A1 | 10/2008 | Vos et al. |
| 2008/0269251 A1 | 10/2008 | Andre-Gil et al. |
| 2009/0023701 A1 | 1/2009 | Aungst et al. |
| 2009/0111801 A1 | 4/2009 | Andres-Gil et al. |
| 2009/0281099 A1 | 11/2009 | Andres-Gil et al. |
| 2009/0286831 A1 | 11/2009 | Koegel et al. |
| 2010/0016319 A1 | 1/2010 | Ohno et al. |
| 2010/0216816 A1 | 8/2010 | Barrow et al. |
| 2011/0098269 A1 | 4/2011 | Becknell et al. |
| 2011/0152246 A1 | 6/2011 | Buckman et al. |
| 2012/0157471 A1 | 6/2012 | Nair et al. |
| 2012/0184572 A1 | 7/2012 | Song et al. |
| 2014/0005103 A1 | 1/2014 | Coburn et al. |
| 2014/0142094 A1 | 5/2014 | Reddy et al. |
| 2015/0087673 A1 | 3/2015 | Hitoshi et al. |
| 2016/0057478 A1 | 2/2016 | Mitchell et al. |
| 2016/0159773 A1 | 6/2016 | Saitoh et al. |
| 2018/0207054 A1 | 7/2018 | Sitsihovskiy et al. |
| 2019/0127378 A1 | 5/2019 | Ma et al. |
| 2019/0300533 A1 | 10/2019 | Wang et al. |
| 2020/0392128 A1 | 12/2020 | Ma et al. |
| 2021/0393623 A1 | 12/2021 | Han et al. |

FOREIGN PATENT DOCUMENTS

| | | |
|---|---|---|
| CN | 104341386 A | 2/2015 |
| CN | 103201267 B | 8/2016 |
| CN | 105899491 A | 8/2016 |
| CN | 105899493 A | 8/2016 |
| CN | 105916845 A | 8/2016 |
| CN | 106232581 A | 12/2016 |
| CN | 107286150 A | 10/2017 |
| CN | 107922388 A | 4/2018 |
| CN | 110143949 A | 8/2019 |
| CN | 112839935 A | 5/2021 |
| EP | 3290412 A1 | 3/2018 |
| EP | 2985334 B1 | 6/2018 |
| EP | 2883934 B1 | 11/2019 |
| EP | 3608321 A1 | 2/2020 |
| JP | 2007/13804 A | 1/2007 |
| JP | 2017/502993 A | 1/2017 |
| JP | 2019/521181 A | 7/2019 |
| KR | 2019/0104530 A | 9/2019 |
| WO | WO-2002/032872 A1 | 4/2002 |
| WO | WO-2003/059354 A2 | 7/2003 |
| WO | WO-2003/072548 A1 | 9/2003 |
| WO | WO-2004/033406 A1 | 4/2004 |
| WO | WO-2004/046092 A2 | 6/2004 |
| WO | WO-2004/071426 A2 | 8/2004 |
| WO | WO-2004/074266 A1 | 9/2004 |
| WO | WO-2004/099158 A1 | 11/2004 |
| WO | WO-2004/085409 A3 | 12/2004 |
| WO | WO-2005/004810 A2 | 1/2005 |
| WO | WO-2005/005435 A1 | 1/2005 |
| WO | WO-2005/033105 A2 | 4/2005 |
| WO | WO-2005/044797 A1 | 5/2005 |
| WO | WO-2005/066156 A1 | 7/2005 |
| WO | WO-2005/090332 A1 | 8/2005 |
| WO | WO-2006/012226 A2 | 2/2006 |
| WO | WO-2006/045828 A1 | 5/2006 |
| WO | WO-2006/067466 A2 | 6/2006 |
| WO | WO-2006/071759 A2 | 7/2006 |
| WO | WO-2006/084186 A2 | 8/2006 |
| WO | WO-2006/087305 A1 | 8/2006 |
| WO | WO-2007/016496 A2 | 2/2007 |
| WO | WO-2007/045462 A2 | 4/2007 |
| WO | WO-2007/046867 A2 | 4/2007 |
| WO | WO-2007/057742 A2 | 5/2007 |
| WO | WO-2007/057775 A1 | 5/2007 |
| WO | WO-2007/063868 A1 | 6/2007 |
| WO | WO-2007/084728 A2 | 7/2007 |
| WO | WO-2008/008431 A2 | 1/2008 |
| WO | WO-2007/103308 A2 | 2/2008 |
| WO | WO-2008/033857 A2 | 3/2008 |
| WO | WO-2008/100412 A1 | 8/2008 |
| WO | WO-2008/112674 A1 | 9/2008 |
| WO | WO-2009/033084 A1 | 3/2009 |
| WO | WO-2009/036066 A1 | 3/2009 |
| WO | WO-2009/108766 A1 | 9/2009 |
| WO | WO-2010/008739 A2 | 1/2010 |
| WO | WO-2010/020675 A1 | 2/2010 |

(56) References Cited

FOREIGN PATENT DOCUMENTS

| | | |
|---|---|---|
| WO | WO-2010/036380 A1 | 4/2010 |
| WO | WO-2010/070022 A1 | 6/2010 |
| WO | WO-2010/074244 A1 | 7/2010 |
| WO | WO-2010/085700 A2 | 7/2010 |
| WO | WO-2010/086613 A1 | 8/2010 |
| WO | WO-2010/103547 A2 | 9/2010 |
| WO | WO-2010/112502 A1 | 10/2010 |
| WO | WO-2011/004162 A2 | 1/2011 |
| WO | WO-2011/022440 A2 | 2/2011 |
| WO | WO-2011/072791 A1 | 6/2011 |
| WO | WO-2011/103091 A1 | 8/2011 |
| WO | WO-2011/130232 A1 | 10/2011 |
| WO | WO-2011/135276 A1 | 11/2011 |
| WO | WO-2011/146401 A1 | 11/2011 |
| WO | WO-2011/150156 A2 | 12/2011 |
| WO | WO-2012/016217 A1 | 2/2012 |
| WO | WO-2012/026495 A1 | 3/2012 |
| WO | WO-2012/041158 A1 | 4/2012 |
| WO | WO-2012/068106 A2 | 5/2012 |
| WO | WO-2012/069852 A1 | 5/2012 |
| WO | WO-2012/088438 A1 | 6/2012 |
| WO | WO-2012/080729 A4 | 11/2012 |
| WO | WO-2012/158784 A2 | 11/2012 |
| WO | WO-2012/170931 A2 | 12/2012 |
| WO | WO-2013/017461 A1 | 2/2013 |
| WO | WO-2013/039851 A1 | 3/2013 |
| WO | WO-2013/090454 A2 | 6/2013 |
| WO | WO-2013/124040 A1 | 8/2013 |
| WO | WO-2013/139882 A1 | 9/2013 |
| WO | WO-2013/161308 A1 | 10/2013 |
| WO | WO-2013/167633 A1 | 11/2013 |
| WO | WO-2014/000178 A1 | 1/2014 |
| WO | WO-2014/001377 A1 | 1/2014 |
| WO | WO-2014/004416 A1 | 1/2014 |
| WO | WO-2014/028829 A1 | 2/2014 |
| WO | WO-2014/043068 A1 | 3/2014 |
| WO | WO-2014/140704 A1 | 9/2014 |
| WO | WO-2014/144326 A1 | 9/2014 |
| WO | WO-2014/184014 A1 | 11/2014 |
| WO | WO-2014/184074 A1 | 11/2014 |
| WO | WO-2014/191737 A1 | 12/2014 |
| WO | WO-2014/201172 A1 | 12/2014 |
| WO | WO-2015/003094 A2 | 1/2015 |
| WO | WO-2015/016206 A1 | 2/2015 |
| WO | WO-2015/017305 A1 | 2/2015 |
| WO | WO-2015/048547 A3 | 6/2015 |
| WO | WO-2015/091420 A1 | 6/2015 |
| WO | WO-2015/107493 A1 | 7/2015 |
| WO | WO-2015/107494 A1 | 7/2015 |
| WO | WO-2015/107495 A1 | 7/2015 |
| WO | WO-2015/123437 A1 | 8/2015 |
| WO | WO-2015/123533 A1 | 8/2015 |
| WO | WO-2015/148714 A1 | 10/2015 |
| WO | WO-2015/155042 A1 | 10/2015 |
| WO | WO-2015/177325 A1 | 11/2015 |
| WO | WO-2016/015604 A1 | 2/2016 |
| WO | WO-2016/022644 A1 | 2/2016 |
| WO | WO-2016/022645 A1 | 2/2016 |
| WO | WO-2016/037005 A1 | 3/2016 |
| WO | WO-2016/040449 A1 | 3/2016 |
| WO | WO-2016/138352 A1 | 9/2016 |
| WO | WO-2016/141881 A1 | 9/2016 |
| WO | WO-2016/151501 A1 | 9/2016 |
| WO | WO-2016/195776 A1 | 12/2016 |
| WO | WO-2016/197027 A1 | 12/2016 |
| WO | WO-2016/203404 A1 | 12/2016 |
| WO | WO-2016/203405 A1 | 12/2016 |
| WO | WO-2016/203406 A1 | 12/2016 |
| WO | WO-2017/021784 A2 | 2/2017 |
| WO | WO-2017/049321 A1 | 3/2017 |
| WO | WO-2017/114351 A1 | 7/2017 |
| WO | WO-2017/156397 A1 | 9/2017 |
| WO | WO-2017/210134 A1 | 12/2017 |
| WO | WO-2017/211303 A1 | 12/2017 |
| WO | WO-2017/216706 A1 | 12/2017 |
| WO | WO-2018/013597 A1 | 1/2018 |
| WO | WO-2018/057884 A1 | 3/2018 |
| WO | WO-2018/013597 A4 | 4/2018 |
| WO | WO-2018/089433 A1 | 5/2018 |
| WO | WO-2018/127801 A1 | 7/2018 |
| WO | WO-2018/130926 A1 | 7/2018 |
| WO | WO-2018/140286 A1 | 8/2018 |
| WO | WO 2018/172984 A1 * | 9/2018 ........... C07D 241/18 |
| WO | WO-2018/177403 A1 | 10/2018 |
| WO | WO-2019/014427 A1 | 1/2019 |
| WO | WO-2019/075265 A1 | 4/2019 |
| WO | WO-2019/079783 A1 | 4/2019 |
| WO | WO-2019/126696 A1 | 6/2019 |
| WO | WO-2019/148132 A1 | 8/2019 |
| WO | WO-2019/148136 A1 | 8/2019 |
| WO | WO-2019/152454 A1 | 8/2019 |
| WO | WO-2019/154950 A1 | 8/2019 |
| WO | WO-2019/167000 A1 | 9/2019 |
| WO | WO-2019/182924 A1 | 9/2019 |
| WO | WO 2019/183367 A1 * | 9/2019 ........... C07D 401/14 |
| WO | WO-2020/063760 A1 | 4/2020 |

OTHER PUBLICATIONS

Ahronian, Leanne G., "Strategies for Monitoring and Combating Resistance to Combination Kinase Inhibitors for Cancer Therapy," Genome Medicine (2017) 9:37; DOI: 10.1186/s13073-017-0431-3 (12 pages).

Bentires-Alj, Mohamed et al., "Activating Mutations of the Noonan Syndrome-Associated SHP2/PTPN11 Gene in Human Solid Tumors and Adult Acute Myelogenous Leukemia," Cancer Research 64, 8816-8820, Dec. 15, 2004.

Bunda, Severa et al., "Inhibition of SHP2-Mediated Dephosphorylation of Ras Suppresses Oncogenesis," Nature Communications, 6:8859 (2015), DOI: 10.1038/ncomms9859/www.nature.com/naturecommunications (12 pages).

Butterworth, Sam et al., "Targeting Protein Tyrosine Phosphatase SHP2 for Therapeutic Intervention," Future Med. Chem. 6(12), 1423-1437 (2014).

Chen, Chuan et al., "Discovery of a Novel Inhibitor of the Protein Tyrosine Phosphatase Shp2," Scientific Reports 5: 17626, DOI: 10:1038/srep 17626 (2015) (13 pages).

Chen, Liwei et al., "Discovery of a Novel Shp2 Protein Tyrosine Phosphatase Inhibitor," Molecular Pharmacology, vol. 70, No. 2 562-570 (2006).

Chen, Wendy S. et al., "Treating Leukemia at the Risk of Inducing Severe Anemia," Exp Henatol. 2016, 44(5): 329-331: doi:10.1016/j.exphem.2016.01.004.

Chen, Ying-Nan P., et al., "Allosteric Inhibition of SHP2 Phosphatase Inhibits Cancers Driven by Receptor Tyrosine Kinases," Nature 535, (17 pages) (2016).

Chichger, Havovi et al., "SH2-Domain-Containing Protein Tyrosine Phosphatase 2 and Focal Adhesion Kinase Protein Interactions Regulate Pulmonary Endothelium Barrier Function," Am. J. Respir. Cell Biol. vol. 52, Issue 6, 695-707, Jun. 2015.

Chio, Cynthia M. et al., "Targeting a Cryptic Allosteric Site for Selective Inhibition of the Oncogenic Protein Tyrosine Phosphatase Shp2," Biochemistry 54, 497-504 (2015).

Dardaei, Leila et al., "SHP2 Inhibition Restores Sensitivity in ALK-rearranged non-small-cell Lung Cancer Resistant to ALK Inhibitors," Nature Medicine, 24, (8 pages) (2018).

Dong, Lei et al., "Leukaemogenic Effects of Ptpn11 Activating Mutations in the Stem Cell Microenvironment," Nature, 539, (17 pages) (2016).

Extended European Search Report for EP Application No. 17809742.4 dated Mar. 25, 2019.

Extended European Search Report for EP Application No. 18770877.1 dated Apr. 17, 2020.

Extended European Search Report for EP Application No. 21212393.9 dated Nov. 24, 2022.

Fodor, Michelle et al., "Dual Allosteric Inhibition of SHP2 Phosphatase," ACS Chem. Biol. 2018, 13, 3, (34 pages).

(56) References Cited

OTHER PUBLICATIONS

Fortanet, Jorge Garcia et al., "Allosteric Inhibition of SHP2: Identification of a Potent, Selective, and Orally Efficacious Phosphatase Inhibitor," Journal of Medical Chemistry, 2016, 59, 17, (37 pages).
Frankson, Rochelle et al., "Therapeutic Targeting of Oncogenic Tyrosine Phosphatases," Cancer Res, Nov. 1, 2017, (77) (21) 5701-5705.
Grosskopf, Stefanie et al., "Selective Inhibitors of the Protein Tyrosine Phosphatase SHP2 Block Cellular Motility and Growth of Cancer Cells In Vitro and In Vivo," ChemMedChem 2015, 10, 815-826.
Guo, Wenjie et al., "Tyrosine Phosphatase SHP2 Negatively Regulates NLRP3 Inflammasome Activation via ANTI-dependent Mitochondrial Homeostasis," Nature Communications, 8:2168 (2017); (14 pages).
He, Rongjun et al., "Exploring the Existing Drug Space for Novel pTyr Mimetic and SHP2 Inhibitors," ACS Med. Chem. Lett. 2015, 6, 7, 782-786.
Hellmuth, Klaus et al., "Specific Inhibitors of the Protein Tyrosine Phosphatase Shp2 Identified by High-Throughput Docking," PNAS, May 20, 2008, vol. 105, No. 20, 7275-7280.
Huang, Wen-Qing et al., "Structure, Function, and Pathogensis of SHP2 in Developmental Disorders and Tumorigenesis," Current Cancer Drug Targets, 2014, 14, 567-588.
International Search Report and Written Opinion for International Application No. PCT/CN2017/087471 dated Aug. 18, 2017.
International Search Report and Written Opinion for International Application No. PCT/CN2019/108181 dated Jan. 6, 2020.
International Search Report and Written Opinion for International Application No. PCT/IB2018/051973 dated Jul. 11, 2018.
International Search Report for International Application No. PCT/CN2017/087471, Aug. 18, 2017. (5 pages).
Lappalainen, Ilkka et al., "Genome Wide Analysis of Pathogenic SH2 Domain Mutations," Proteins 2008; 72:779-792.
LaRochelle, J.R. et al., "Identification of an Allosteric Benzothiazoloprymidone Inhibitor of the Oncogenic Protein Tyrosine Phosphatase SHP2," Bioorganic & Medicinal Chemistry Letters, vol. 25, Issue 24, Dec. 15, 2017, (9 pages).
LaRochelle, Jonathan R., "Structural and Functional Consequences of Three Cancer-Associated Mutations of the Oncogenic Phosphatase SHP2," Biochemistry 55, 2269-2277 (2016).
Lawrence, Harshani R. et al., "Inhibitors of Src Homology-2 Domain Containing Protein Tyrosine Phosphatase-2 (Shp2) Based on Oxindole Scaffolds," J. Med. Chem 2008: 51 (16): (22 pages).
Leibowitz, Michael S. et al., "SHP2 is Overexpressed and Inhibits pSTAT1-Mediated APM Component Expression, T Cell Attracting Chemokine Secretion, and CTL Recognition in Head and Neck Cancer Cells," Clin Cancer Res. 19(4): (20 pages) (2013).
Li, Jing et al., "PD-1/SHP-2 Inhibits Tc1/Th1 Phenotypic Responses and the Activation of T Cells in the Tumor Microenvironment," Cancer Research, Feb. 1, 2015 (75) (3) 508-518.
Liu, Kun-Wei et al., "SHP-2/PTPN11 Mediates Gliomagenesis Driven by PDGFRA and /NK4A/ARF Aberrations in Mice and Humans," The Journal of Clinical Investigation, vol. 121, No. 3, Mar. 2011; pp. 905-917.
Liu, Wei et al., "Identification of Cryptotanshinone as an Inhibitor of Oncogenic Protein Tyrosine Phosphatase SHP2 (PTPN11)," J. Med. Chem. 2013; 56(18): (26 pages).
Liu, Wen et al., "T Lymphocyte SHP2-deficiency Triggers Anti-Tumor Immunity to Inhibit Colitis-Associated Cancer in Mice," Oncotarget, 2017, vol. 8, (No. 5), pp. 7586-7597.
Liu, Wen et al., "T Lymphocyte SHP2-deficiency Triggers Anti-Tumor Immunity to Inhibit Colitis-Associated Cancer in Mice," Oncotarget, Advance Publications 2016; (12 pages).
Manguso, Robert T. et al., "In vivo CRISPR Screening Identifies Ptpn2 as a Cancer Immunotherapy Target," Nature 2017, (17 pages).
Martin, Katie R. et al., "Integrating Virtual and Biochemical Screening for Protein Tyrosine Phosphatase Inhibitor Discovery," Methods, 65 (2014) 219-228.

Matozaki, Takashi et al., "Protein Tyrosine Phosphatase SHP-2: A Protooncogene Product that Promotes Ras Activation," Cancer Science, Oct. 2009, vol. 100, No. 10, 1786-1793.
Mazharian, Alexandra et al., "Megakaryocyte-specific Deletion of the Protein-Tyrosine Phosphatases Shp1 and Shp2 Causes Abnormal Megakaryocyte Development, Platelet Production, and Function," Blood. May 16, 2013; 121(20):4205-4220.
Meanwell., "Synopsis of Some Recent Tactical Application of Bioisosteres in Drug Design," Journal of Medicinal Chemistry, 54: 2529-2591 (2011).
Mohi, M. Golam et al., "The Role of Shp2 (PTPN11) in cancer," Current Opinion in Genetics & Development 2007, 17:23-30.
Nichols, Robert J. et al., "Efficacy of SHP2 Phosphatase Inhibition in Cancers With Nucleotide-Cycling Oncogenic RAS, RAS-GTP Dependent Oncogenic BRAF and NF1 Loss," BioRxiv Sep. 14, 2017 (16 pages).
Pandey, Ruchi et al., "Role of SHP2 in Hematopoiesis and Leukemogenesis," Curr Opin Hematol. Jul. 4, 2017(4):307-313.
Peled, Michael et al., "Affinity Purification Mass Spectrometry Analysis of PD-1 Uncovers SAP as a New Checkpoint Inhibitor," Proc Natl Acad Sci USA. Jan. 16, 2018;115(3): pp. E468-E477.
Prahallad, Anirudh et al., "PTPN11 Is a Central Node in Intrinsic and Acquired Resistance to Targeted Cancer Drugs," Cell Reports, 12, 1978-1985, Sep. 29, 2015.
Protein Tyrosine Phosphatase, PTPN11 (SHP-2) (Human), Dec. 2005 (1 page).
Qi, Chen et al., "Shp2 Inhibits Proliferation of Esophageal Squamous Cell Cancer via Dephosphorylation of Stat3," International Journal of Molecular Sciences, 18, 134 (2017) (12 pages).
Ran, Hao et al., "Sticking It to Cancer with Molecular Glue for SHP2," Cancer Cell 30, Aug. 8, 2016; 8;30(2):194-196.
Scott, Latanya M. et al., "Shp2 Protein Tyrosine Phosphatase Inhibitor Activity of Estramustine Phosphate and its Triterpenoid Analogs," Bioorg Med Chem Lett., 21 (2), (9 pages) Jan. 15, 2011.
Simoncic, Paul D., "T-Cell Protein Tyrosine Phosphatase (Tcptp) Is a Negative Regulator of Colony-Stimulating Factor 1 Signaling and Macrophage Differentiation," Molecular and Cellular Biology, vol. 26, No. 11, Jun. 2006, p. 4149-4160.
Stephan, Matthias T. et al., "Synapse-directed Delivery of Immunomodulators Using T-Cell-Conjugated Nanoparticles," Biomaterials 33, 5776-5787 (2012).
Sun, X. et al., "Selective Inhibition of Leukemia-Associated SHP2E59K Mutant by the Allosteric SHP2 Inhibitor SHP099," Leukemia, 32, (12 pages) (2018).
Supplementary European Search Report for corresponding EP Application No. EP 17809742 dated Mar. 15, 2019 (2 pages).
Wang, Wen-Long et al., "Benzo[c][1,2,5]thiadiazole Derivatives: A New Class of Potent Src Homology-2-domain Containing Protein Tyrosine Phosphatase-2 (SHP2) Inhibitors," Bioorganic & Medicinal Chemistry Letters Dec. 1, 2017 ;27(23): pp. 5154-5157.
Written Opinion of the International Search Authority for International Application No. PCT/CN2017/087471. (8 pages).
Xie, Jingjing et al., "Allosteric Inhibitors of SHP2 with Therapeutic Potential for Cancer Treatment," Journal of Medicinal Chemistry, Nov. 20, 2017; 60, 24, (55 pages).
Xu, Jie et al., "Targeting SHP2 for EGFR Inhibitor Resistant Non-Small Cell Lung Carcinoma," Biochem Biophys Res Commun., 439(4), Oct. 4, 2013;439(4): (13 pages).
Yokosuka, Tadashi et al., "Programmed Cell Death 1 Forms Negative Costimulatory Microclusters that Directly Inhibit T Cell Receptor Signaling by Recruiting Phosphatase SHP2," J. Exp. Med., vol. 209, No. 6, 1201-1217 (2012).
Yu, Bing et al., "Targeting Protein Tyrosine Phosphatase SHP2 for the Treatment of PTPN11-Associated Malignancies," Mol Cancer Ther; 12(9) Sep. 2013 pp. 1738-1748.
Zeng, Li-Fan et al., "Therapeutic Potential of Targeting the Oncogenic SHP2 Phosphatase," J. Med Chem. 2014, 57, 6594-6609.
Zhang, Jie et al., "Functions of Shp2 in Cancer," J. Cell. Mol. Med. vol. 19, No. 9, pp. 2075-2083 (2015).
Zheng, Jian et al., "Pancreatic Cancer Risk Variant in LINC00673 Creates a miR-1231 Binding Site and Interferes with PTPN11 Degradation," Nature Genetics, vol. 48, No. 7, Jul. 2016; (14 pages).

(56) References Cited

OTHER PUBLICATIONS

Zhu, Helen He et al., "Shp2 and Pten Have Antagonistic roles in Myeloproliferation but Cooperate to Promote Erythropoiesis in Mammals," PNAS, vol. 12, No. 43, 13342-13347, 2015.

* cited by examiner

HETEROCYCLIC DERIVATIVES USEFUL AS SHP2 INHIBITORS

RELATED APPLICATIONS

This application is a continuation of U.S. application Ser. No. 18/215,381, filed Jun. 28, 2023; which is a continuation of U.S. application Ser. No. 17/985,399, filed Nov. 11, 2022; which is a continuation of U.S. application Ser. No. 17/714,547, filed Apr. 6, 2022; which is a continuation of U.S. application Ser. No. 17/280,573, filed Mar. 26, 2021; which is a national phase entry pursuant to 35 U.S.C. § 371 of International Application No. PCT/CN2019/108181, filed Sep. 26, 2019; which claims priority to International Patent Application No. PCT/CN2018/107492, filed Sep. 26, 2018. The entire contents of International Application No. PCT/CN2019/108181, U.S. Ser. No. 17/280,573, U.S. Ser. No. 17/714,547, U.S. Ser. No. 17/985,399, and U.S. Ser. No. 18/215,381 are incorporated herein by reference.

TECHNICAL FIELD

This invention relates to certain novel heterocyclic derivatives (Formula I) as SHP2 inhibitors which is shown as formula I, their synthesis and their use for treating a SHP2 mediated disorder. More particularly, this invention is directed to fused heterocyclic derivatives useful as inhibitors of SHP2, methods for producing such compounds and methods for treating a SHP2-mediated disorder.

BACKGROUND ART

SHP2 (The Src Homolgy-2 phosphateese) is a non-receptor protein tyrosine phosphatase encoded by the PTPN11 gene that harbors a classical tyrosine phosphatase domain and two N-terminal Src homology 2 (SH2) domains and a C-terminal tail. The two SH2 domains control the subcellular localization and functional regulation of SHP2. In its inactive state, the N-terminal SH2 domain blocks the PTP domain and this autoinhibition is relieved by binding of the SH2 domains to specific phosphotyrosine sites on receptors or receptor-associated adaptor proteins. The stimulation, for example, by cytokines or growth factors leads to exposure of the catalytic site resulting in enzymatic activation of SHP2.

SHP2 is widely expressed and participated in multiple cell signaling processes, such as the Ras-Erk, PI3K-Akt, Jak-Stat, Met, FGFR, EGFR, and insulin receptors and NF-kB pathways, in which plays an important role in proliferation, differentiation, cell cycle maintenance and migration.

The hyperactivation of SHP2 catalytic activity caused by either germline or somatic mutations in PTPN11 have been identified in patients with Noonan syndrome, Leopard syndrome, juvenile myelomonocytic leukemias, myelodysplastic syndrome, B cell acute lymphoblastic leukemia/lymphoma, and acute myeloid leukemia. In addition, activating mutation s of PTPN11 have been found in solid tumors as well, such as lung cancer, colon cancer, melanoma, neuroblastoma, and hepatocellular carcinoma. Therefore, the presence of activated or up-regulated SHP2 protein in human cancers and other disease make SHP2 an excellent target for development of novel therapies. The compounds of the present invention fulfill the need of small molecules in order to inhibit the activity of SHP2.

SUMMARY OF INVENTION

The present invention relates to certain novel heterocyclic compounds useful as SHP2 inhibitors and their use for treating a SHP2 mediated disorder. The compounds of the invention have the general structure as Formula I or a pharmaceutically acceptable salt:

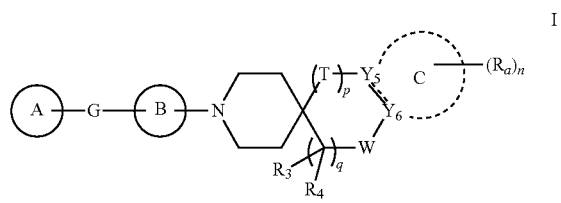

I ring A is a 5-12 membered aromatic ring, a 5-12 membered heteroaromatic ring or a 5-12 membered heterocyclic ring, and each of the ring systems is independently optionally substituted or unsubstituted;

G is selected from absent, S, —SO—, —SO$_2$—, O, —CO—, —NR$_G$—, —NR$_G$—SO$_2$—,

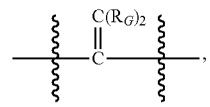

—C(R$_G$)$_2$— or —SO$_2$—NR$_G$—;

each of R$_G$ is independently selected from hydrogen, deuterium, halogen, —NH$_2$, —CN, —OH, —C$_{1-6}$alkyl or —C$_{1-6}$alkoxy, and each of which is independently optionally substituted or unsubstituted;

ring B is a 5-12 membered aromatic ring, a 5-12 membered heteroaromatic ring or a 5-12 membered heterocyclic ring, and each of the ring systems is independently optionally substituted or unsubstituted;

T is absent, O, NR$_1$ or CR$_1$R$_2$;

each of R$_1$ and R$_2$ is independently selected from hydrogen, deuterium, halogen, —NH$_2$, —CN, —OH, —NO$_2$, carboxyl, —NH—C$_{1-6}$alkyl, —N(C$_{1-6}$alkyl)$_2$, substituted or unsubstituted —C$_{1-6}$alkoxy, or substituted or unsubstituted —C$_{1-6}$alkyl; or R$_1$ and R$_2$ together with the carbon atom to which they are both attached form CO or C=NR$_5$;

p is 0, 1, 2, 3 or 4;

each of R$_3$ and R$_4$ is independently selected from hydrogen, deuterium, halogen, —NH$_2$, —CN, —OH, —NO$_2$, carboxyl, —NH—C$_{1-6}$alkyl, —N(C$_{1-6}$alkyl)$_2$, substituted or unsubstituted —C$_{1-6}$alkoxy, or substituted or unsubstituted —C$_{1-6}$alkyl; or R$_3$ and R$_4$ together with the carbon atom to which they are both attached form a 3-12 membered heterocyclic ring or a 5-12 membered heteroaromatic ring or C=NR$_5$, and each of the ring systems is independently optionally substituted or unsubstituted;

each of R$_5$ is independently selected from hydrogen, deuterium, halogen, —NH$_2$, —CN, —OH, —C$_{1-6}$alkyl or —C$_{1-6}$alkoxy;

q is 0, 1, 2, 3 or 4;

W is absent, O, S or —C(R$_W$)$_2$—; and each of R$_W$ is independently selected from hydrogen, deuterium, halogen, —NH$_2$, —CN, —OH, —NO$_2$, carboxyl, —CO—C$_{1-6}$alkyl, —CO—OC$_{1-6}$alkyl, —C$_{1-6}$alkylene-O—C$_{1-6}$alkoxy, substituted or unsubstituted —C$_{1-6}$alkoxy, or substituted or unsubstituted —C$_{1-6}$alkyl;

ring C is absent, a 5-12 membered aromatic ring, a 5-12 membered heteroaromatic ring or a 5-12 membered heterocyclic ring, and each of the ring systems is independently optionally substituted or unsubstituted;
when ring C is absent, Y5 is $CR_{5a}R_{5b}$, $NR_{5a}$ or O, and $Y_6$ is $CR_{6a}R_{6b}$, $NR_{6a}$ or O;
when ring C is a 5-12 membered aromatic ring, a 5-12 membered heteroaromatic ring or a 5-12 membered heterocyclic ring;
i) $Y_5$ is $CR_{5a}$ or N, and $Y_6$ is $CR_{6a}$ or N, when the "------" in the term "$Y_5$------$Y_6$" represents a single bond; or
ii) $Y_5$ is C, and $Y_6$ is C, when the "------" in the term "$Y_5$------$Y_6$" represents a double bond;
each of $R_{5a}$ and $R_{5b}$ is independently selected from hydrogen, deuterium, halogen, —$NH_2$, —CN, —OH, —$NO_2$, carboxyl, substituted or unsubstituted —$C_{1-6}$alkoxy, or substituted or unsubstituted —$C_{1-6}$alkyl;
each of $R_{6a}$ and $R_{6b}$ is independently selected from hydrogen, deuterium, halogen, —$NH_2$, —CN, —OH, —$NO_2$, carboxyl, substituted or unsubstituted —$C_{1-6}$alkoxy, or substituted or unsubstituted —$C_{1-6}$alkyl;
each of Ra is independently selected from hydrogen, deuterium, halogen, —$NR_{a1}R_{a2}$, —CN, —OH, —$NO_2$, oxo, =O, carboxyl, —$C_{1-6}$alkoxy, —$C_{1-6}$alkyl, —$C_{3-8}$cycloalkyl, —$C_{1-6}$alkylene-$NR_{a1}R_{a2}$, —$C_{1-6}$alkylene-O—$C_{1-6}$alkyl, —$C_{1-6}$alkylene-CO—$OR_{a1}$, —$C_{1-6}$alkylene-(3-10 membered heterocyclic), —$C_{1-6}$alkylene-(5-10 membered heteroaryl), —$C_{1-6}$alkylene-CO—$NR_{a1}R_{a2}$, —$C_{1-6}$alkylene-$NR_{a1}$—CO—$NR_{a1}R_{a2}$, —$C_{1-6}$alkylene-$NR_{a1}$—CO—$C_{1-6}$alkyl, —CO—$NR_{a1}R_{a2}$, —CO—CO—$NR_{a1}R_{a2}$, —$C_{3-10}$carbocyclic, -5-10 membered heteroaryl, -3-10 membered heterocyclic, —CO—$C_{1-6}$alkyl, —COO—$C_{1-6}$alkyl, —CO—$C_{1-6}$alkylene-$NR_{a1}R_{a2}$, —CO—$NR_{a1}$-(3-10 membered heterocyclic), —CO—$NR_{a1}$-(3-10 membered heterocyclic), —CO-(3-10 membered heterocyclic), —O—$C_{1-6}$alkylene-CO—$OR_{a1}$, —O—$C_{1-6}$alkylene-CO—$NR_{a1}R_{a2}$, —O—$C_{1-6}$alkylene-$NR_{a1}R_{a2}$, —O—$C_{3-10}$carbocyclic, —O-(3-10 membered heterocyclic), —$NR_1$—CO—$C_{1-6}$alkyl, —$NR_1$—CO—$NR_{a1}R_{a2}$, —$NR_{a1}$—CO-(5-10 membered heteroaryl), —$NR_{a1}$—CO—$C_{3-8}$cycloalkyl, —$NR_{a1}$—$C_{1-6}$alkylene-$NR_{a1}R_{a2}$, —$NR_{a1}$—$C_{1-6}$alkylene-(3-10 membered heterocyclic), —$NR_{a1}$—$C_{1-6}$alkylene-(5-10 membered heteroaryl), —$NR_{a1}$—$SO_2C_{1-6}$alkyl, —S—$C_{1-6}$alkyl, —$SONR_{a1}R_{a2}$, —$SO_2NR_{a1}R_{a2}$, —SO—$C_{1-6}$alkyl, —$SO_2$—$C_{1-6}$alkyl, —PO($C_{1-6}$alkyl)$_2$, —PO($C_{1-6}$alkoxy)$_2$, -3-10 membered heterocyclic or -5-10 membered heteroaryl; each of which is independently optionally substituted; and n is 0, 1, 2, 3, 4, 5 or 6; or
two adjacent Ra can be joined together to form a 6-membered aromatic ring, a 5-membered heteroaromatic ring, a 6-membered heteroaromatic ring, a 3-6 membered heterocyclic ring or a 3-6 membered carbocyclic ring, wherein each of the ring systems is independently optionally substituted; or
Ra and $R_W$ with the atom to which they are both attached form a 3-10 membered aromatic ring, 3-10 membered heteroaromatic ring or 3-10 membered heterocyclic ring; and each of the ring systems is independently optionally substituted;
each of $R_{a1}$ and $R_{a2}$ is independently selected from hydrogen, deuterium, halogen, —$NH_2$, —CN, —OH, —$NO_2$, carboxyl, substituted or unsubstituted —$C_{1-6}$alkoxy, or substituted or unsubstituted —$C_{1-6}$alkyl.

In some embodiments of Formula I, ring A is a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, ring A is a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, ring A is a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring or a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, ring A is

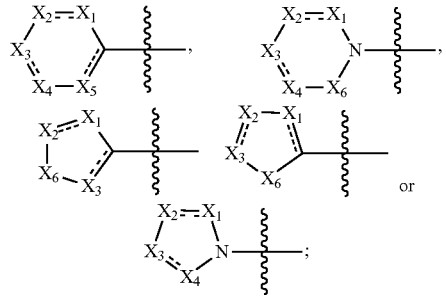

------ represents a single bond or a double bond;
$X_1$ is N, S, $NR_{X1}$, $C(R_{X1})_2$, or $CR_{X1}$;
each of $R_{X1}$ is independently selected from hydrogen, deuterium, halogen, —$NH_2$, —$CONH_2$, —CN, —$C_{1-6}$alkyl or —$C_{1-6}$alkoxy, and each of which is independently optionally substituted with 1, 2, 3, 4, 5, or 6 substituents, and the said each substituents is independently selected from deuterium, halogen, —$NH_2$, —CN, —OH, —$NO_2$, carboxyl, —$C_{1-6}$alkyl or —$C_{1-6}$alkoxy;
X2 is N, S, $NR_{X2}$, $C(R_{X2})_2$, $CR_{X2}$ or CO;
each of $R_{X2}$ is independently selected from hydrogen, deuterium, halogen, —$NH_2$, —CN, —$C_{1-6}$alkyl, —$C_{1-6}$alkoxy, —CO—$C_{1-6}$alkyl, —NH—$C_{1-6}$alkyl, —N—($C_{1-6}$alkyl)$_2$, —$SF_5$, —NHCO—$C_{3-8}$cycloalkyl, —NH—$C_{3-8}$cycloalkyl, —$C_{1-6}$alkylene-(3-8 membered heterocyclyl), —NHCO-(5-12 membered heterocyclyl), —NH—$C_{1-6}$alkylene-$C_{3-8}$cycloalkyl or 3-8 membered heterocyclic, and each of which is independently optionally substituted with 1, 2, 3, 4, 5, or 6 substituents, and the said each substituents is independently selected from deuterium, halogen, —NH$_2$, —CN, —OH, -oxo, =O, —NO$_2$, carboxyl, —C$_{1-6}$alkyl or —C$_{1-6}$alkoxy; or R$_{X1}$ and R$_{X2}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;

X$_3$ is N, S, O, NR$_{X3}$, C(R$_{X3}$)$_2$ or CR$_{X3}$;

each of R$_{X3}$ is independently selected from hydrogen, deuterium, halogen, carboxyl, —NO$_2$, —NH$_2$, —CN, —CONH$_2$, —C$_{1-6}$alkyl, —C$_{1-6}$alkoxy, C$_{3-8}$cycloalkyl, C$_{5-8}$aryl, —S—C$_{1-6}$alkyl, 3-12 membered heterocyclyl, —O—C$_{3-8}$cycloalkyl, —O—C$_{1-6}$alkylene-C$_{1-6}$alkoxy, —O—C$_{5-8}$aryl or —O—C$_{1-6}$alkylene-C$_{5-8}$aryl, and each of which is independently optionally substituted with 1, 2, 3, 4, 5, or 6 substituents, and the said each substituents is independently selected from deuterium, halogen, —NH$_2$, —CN, —OH, —NO$_2$, carboxyl, —C$_{1-6}$alkyl or —C$_{1-6}$alkoxy; or R$_{X2}$ and R$_{X3}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;

X$_4$ is N, S, NR$_{X4}$, C(R$_{X4}$)$_2$ or CR$_{X4}$;

each of R$_{X4}$ is independently selected from hydrogen, deuterium, halogen, —NH$_2$, —CN, —OH, —C$_{1-6}$alkyl, —C$_{1-6}$alkoxy, —NHCO-(5-12 membered heterocyclyl) or a 5-12 membered heteroaryl, and each of which is independently optionally substituted with 1, 2, 3, 4, 5, or 6 substituents, and the said each substituents is independently selected from deuterium, halogen, —NH$_2$, —CN, —OH, oxo, =O, —NO$_2$, carboxyl, —C$_{1-6}$alkyl or —C$_{1-6}$alkoxy; or R$_{X3}$ and R$_{X4}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;

X$_5$ is N, S, NR$_{X5}$, C(R$_{X5}$)$_2$ or CR$_{X5}$;

each of R$_{X5}$ is independently selected from hydrogen, deuterium, halogen, —NH$_2$, —CN, —C$_{1-6}$alkyl or —C$_{1-6}$alkoxy, and each of which is independently optionally substituted with 1, 2, 3, 4, 5, or 6 substituents, and the said each substituents is independently selected from deuterium, halogen, —NH$_2$, —CN, —OH, —NO$_2$, carboxyl, —C$_{1-6}$alkyl or —C$_{1-6}$alkoxy; or R$_{X4}$ and R$_{X5}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;

X$_6$ is O, S, CO or NR$_{X6}$, or C(R$_{X6}$)$_2$;

each of R$_{X6}$ is independently selected from hydrogen, deuterium, halogen, —NH$_2$, —CN, —C$_{1-6}$alkyl or —C$_{1-6}$alkoxy, and each of which is independently optionally substituted with 1, 2, 3, 4, 5, or 6 substituents, and the said each substituents is independently selected from deuterium, halogen, —NH$_2$, —CN, —OH, —NO$_2$, carboxyl, —C$_{1-6}$alkyl or —C$_{1-6}$alkoxy.

In some embodiments of Formula I, X$_1$ is N, S, NR$_{X1}$, C(R$_{X1}$)$_2$, or CR$_{X1}$; each of R$_{X1}$ is independently selected from hydrogen, deuterium, F, Cl, Br, —NH$_2$, —CONH$_2$, —CN, —C$_{1-6}$alkyl or —C$_{1-6}$alkoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-6}$alkyl or —C$_{1-6}$alkoxy.

In some embodiments of Formula I, X$_1$ is N, S, NR$_{X1}$, C(R$_{X1}$)$_2$, or CR$_{X1}$; each of R$_{X1}$ is independently selected from hydrogen, deuterium, F, Cl, Br, —NH$_2$, —CONH$_2$, —CN, —C$_{1-6}$alkyl or —C$_{1-6}$alkoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-3}$alkyl or —C$_{1-3}$alkoxy.

In some embodiments of Formula I, X$_1$ is N, S, NR$_{X1}$, C(R$_{X1}$)$_2$, or CR$_{X1}$; each of R$_{X1}$ is independently selected from hydrogen, deuterium, F, Cl, Br, —NH$_2$, —CONH$_2$, —CN, —C$_{1-3}$alkyl or —C$_{1-3}$alkoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-3}$alkyl or —C$_{1-3}$alkoxy.

In some embodiments of Formula I, X$_1$ is N, S, NR$_{X1}$, C(R$_{X1}$)$_2$, or CR$_{X1}$; each of R$_{X1}$ is independently selected from hydrogen, deuterium, F, Cl, Br, —NH$_2$, —CONH$_2$, —CN, methyl, ethyl, propyl, isopropyl, methoxy, ethoxy, propoxy or isopropoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, methyl, ethyl, propyl, isopropyl, methoxy, ethoxy, propoxy or isopropoxy.

In some embodiments of Formula I, X$_1$ is N, S, NR$_{X1}$, C(R$_{X1}$)$_2$, or CR$_{X1}$; each of R$_{X1}$ is independently selected from hydrogen, deuterium, F, Cl, Br, —NH$_2$, —CONH$_2$, —CN, methyl, ethyl, propyl, isopropyl, methoxy, ethoxy, propoxy or isopropoxy, and each of which is independently optionally substituted with 1, 2 or 3 substituents, and the said each substituents is independently selected from deuterium, F, Cl, Br, I, —NH$_2$, —CN, —OH, —NO$_2$, carboxyl, methyl, ethyl, propyl, isopropyl, methoxy, ethoxy, propoxy or isopropoxy.

In some embodiments of Formula I, X2 is N, S, NR$_{X2}$, C(R$_{X2}$)$_2$, CR$_{X2}$ or CO; each of R$_{X2}$ is independently selected from hydrogen, deuterium, F, Cl, Br, —NH$_2$, —CN, —C$_{1-6}$alkyl, —C$_{1-6}$alkoxy, —CO—C$_{1-6}$alkyl, —NH—C$_{1-6}$alkyl, —N—(C$_{1-6}$alkyl)$_2$, —SF$_5$, —NHCO—C$_{3-8}$cycloalkyl, —NH—C$_{3-8}$cycloalkyl, —C$_{1-6}$alkylene-(3-8 membered heterocyclyl), —NHCO-(5-12 membered heterocyclyl), —NH—C$_{1-6}$alkylene-C$_{3-8}$cycloalkyl or 3-8 membered heterocyclic, and each of which is independently optionally substituted with 1, 2, 3, 4, 5, or 6 substituents, and the said each substituents is independently selected from deuterium, F, Cl, Br, I, —NH$_2$, —CN, —OH, -oxo, =O, —NO$_2$, carboxyl, —C$_{1-6}$alkyl or —C$_{1-6}$alkoxy.

In some embodiments of Formula I, X2 is N, S, NR$_{X2}$, C(R$_{X2}$)$_2$, CR$_{X2}$ or CO; each of R$_{X2}$ is independently selected from hydrogen, deuterium, F, Cl, Br, —NH$_2$, —CN, —C$_{1-6}$alkyl, —C$_{1-6}$alkoxy, —CO—C$_{1-6}$alkyl, —NH—C$_{1-6}$alkyl, —N—(C$_{1-6}$alkyl)$_2$, —SF$_5$, —NHCO—C$_{3-8}$cycloalkyl, —NH—C$_{3-8}$cycloalkyl, —C$_{1-6}$alkylene-(3-8 membered heterocyclyl), —NHCO-(5-12 membered heterocyclyl), —NH—C$_{1-6}$alkylene-C$_{3-8}$cycloalkyl or 3-8 membered heterocyclic, and each of which is independently optionally substituted with 1, 2, 3, 4, 5, or 6 substituents, and the said each substituents is independently selected from deuterium, F, Cl, Br, I, —NH$_2$, —CN, —OH, -oxo, =O, —NO$_2$, carboxyl, —C$_{1-3}$alkyl or —C$_{1-3}$alkoxy.

In some embodiments of Formula I, X2 is N, S, $NR_{X2}$, $C(R_X)_2$, $CR_{X2}$ or CO; each of $R_{X2}$ is independently selected from hydrogen, deuterium, F, Cl, Br, $-NH_2$, $-CN$, $-C_{1-4}$alkyl, $-C_{1-3}$alkoxy, $-CO-C_{1-3}$alkyl, $-NH-C_{1-3}$alkyl, $-N-(C_{1-3}$alkyl$)_2$, $-SF_5$, $-NHCO-C_{3-6}$cycloalkyl, $-NH-C_{3-6}$cycloalkyl, $-C_{1-3}$alkylene-(3-6 membered heterocyclyl), $-NHCO$-(5-10 membered heterocyclyl), $-NH-C_{1-3}$alkylene-$C_{3-6}$cycloalkyl or 3-6 membered heterocyclic, and each of which is independently optionally substituted with 1, 2, 3, 4, 5, or 6 substituents, and the said each substituents is independently selected from deuterium, F, Cl, Br, I, $-NH_2$, $-CN$, $-OH$, -oxo, $=O$, $-NO_2$, carboxyl, $-C_{1-3}$alkyl or $-C_{1-3}$alkoxy.

In some embodiments of Formula I, X2 is N, S, $NR_{X2}$, $C(R_{X2})_2$, $CR_{X2}$ or CO; each of $R_{X2}$ is independently selected from hydrogen, deuterium, F, Cl, Br, $-NH_2$, $-CN$, methyl, ethyl, propyl, isopropyl, butyl, isobutyl, methoxy, ethoxy, propoxy, isopropoxy, $-CO-C_{1-3}$alkyl, $-NH-C_{1-3}$alkyl, $-N-(C_{1-3}$alkyl$)_2$, $-SF_5$, $-NHCO-C_{3-6}$cycloalkyl, $-NH-C_{3-6}$cycloalkyl, $-C_{1-3}$alkylene-(3-6 membered heterocyclyl), $-NHCO$-(5-10 membered heterocyclyl), $-NH-C_{1-3}$alkylene-$C_{3-6}$cycloalkyl, 3 membered heterocyclic, 4 membered heterocyclic, 5 membered heterocyclic or 6 membered heterocyclic, and each of which is independently optionally substituted with 1, 2, 3, 4, 5, or 6 substituents, and the said each substituents is independently selected from deuterium, F, Cl, Br, I, $-NH_2$, $-CN$, $-OH$, -oxo, $=O$, $-NO_2$, carboxyl, methyl, ethyl, propyl, isopropyl, methoxy, ethoxy, propoxy or isopropoxy.

In some embodiments of Formula I, X2 is N, S, $NR_{X2}$, $C(R_{X2})_2$, $CR_{X2}$ or CO; each of $R_{X2}$ is independently selected from hydrogen, deuterium, F, Cl, Br, $-NH_2$, $-CN$, methyl, ethyl, propyl, isopropyl, butyl, isobutyl, methoxy, ethoxy, propoxy, isopropoxy, $-CO-C_{1-3}$alkyl, $-NH-C_{1-3}$alkyl, $-N-(C_{1-3}$alkyl$)_2$, $-SF_5$, $-NHCO-C_{3-6}$cycloalkyl, $-NH-C_{3-6}$cycloalkyl, $-C_{1-3}$alkylene-(3-6 membered heterocyclyl), $-NHCO$-(5-10 membered heterocyclyl), $-NH-C_{1-3}$alkylene-$C_{3-6}$cycloalkyl, 3 membered heterocyclic, 4 membered heterocyclic, 5 membered heterocyclic or 6 membered heterocyclic, and each of which is independently optionally substituted with 1, 2 or 3 substituents, and the said each substituents is independently selected from deuterium, F, Cl, Br, I, $-NH_2$, $-CN$, $-OH$, -oxo, $=O$, $-NO_2$, carboxyl, methyl, ethyl, propyl, isopropyl, methoxy, ethoxy, propoxy or isopropoxy.

In some embodiments of Formula I, $R_{X1}$ and $R_{X2}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, $R_{X1}$ and $R_{X2}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, $R_{X1}$ and $R_{X2}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring or a 10 membered heterocyclic ring, and each of the heteroaromatic ring contains 1, 2 or 3 heteroatoms selected from N, O or S, and each of the heterocyclic ring contains 1, 2 or 3 heteroatoms selected from N or O, and each of the ring systems is independently optionally substituted or unsubstituted.

In some embodiments of Formula I, X3 is N, S, O, $NR_{X3}$, $C(R_{X3})_2$ or $CR_{X3}$; each of $R_{X3}$ is independently selected from hydrogen, deuterium, F, Cl, Br, carboxyl, $-NO_2$, $-NH_2$, $-CN$, $-CONH_2$, $-C_{1-6}$alkyl, $-C_{1-6}$alkoxy, $C_{3-8}$cycloalkyl, $C_{5-8}$aryl, $-S-C_{1-6}$alkyl, 3-12 membered heterocyclyl, $-O-C_{3-8}$cycloalkyl, $-O-C_{1-6}$alkylene-$C_{1-6}$alkoxy, $-O-C_{5-8}$aryl or $-O-C_{1-6}$alkylene-$C_{5-8}$aryl, and each of which is independently optionally substituted with 1, 2, 3, 4, 5, or 6 substituents, and the said each substituents is independently selected from deuterium, F, Cl, Br, I, $-NH_2$, $-CN$, $-OH$, $-NO_2$, carboxyl, $-C_{1-6}$alkyl or $-C_{1-6}$alkoxy.

In some embodiments of Formula I, X3 is N, S, O, $NR_{X3}$, $C(R_{X3})_2$ or $CR_{X3}$; each of $R_{X3}$ is independently selected from hydrogen, deuterium, F, Cl, Br, carboxyl, $-NO_2$, $-NH_2$, $-CN$, $-CONH_2$, $-C_{1-6}$alkyl, $-C_{1-6}$alkoxy, $C_{3-8}$cycloalkyl, $C_{5-8}$aryl, $-S-C_{1-6}$alkyl, 3-12 membered heterocyclyl, $-O-C_{3-8}$cycloalkyl, $-O-C_{1-6}$alkylene-$C_{1-6}$alkyl, $-O-C_{5-8}$aryl or $-O-C_{1-6}$alkylene-$C_{5-8}$aryl, and each of which is independently optionally substituted with 1, 2, 3, 4, 5, or 6 substituents, and the said each substituents is independently selected from deuterium, F, Cl, Br, I, $-NH_2$, $-CN$, $-OH$, $-NO_2$, carboxyl, $-C_{1-3}$alkyl or $-C_{1-3}$alkoxy.

In some embodiments of Formula I, X3 is N, S, O, $NR_{X3}$, $C(R_{X3})_2$ or $CR_{X3}$; each of $R_{X3}$ is independently selected from hydrogen, deuterium, F, Cl, Br, carboxyl, $-NO_2$, $-NH_2$, $-CN$, $-CONH_2$, $-C_{1-3}$alkyl, $-C_{1-3}$alkoxy, $C_{3-6}$cycloalkyl, $C_{5-8}$aryl, $-S-C_{1-3}$alkyl, 3-10 membered heterocyclyl, $-O-C_{3-6}$cycloalkyl, $-O-C_{1-3}$alkylene-$C_{1-3}$alkyl, $-O-C_{5-6}$aryl or $-O-C_{1-3}$alkylene-$C_{5-6}$aryl, and each of which is independently optionally substituted with 1, 2, 3, 4, 5, or 6 substituents, and the said each substituents is independently selected from deuterium, F, Cl, Br, I, $-NH_2$, $-CN$, $-OH$, $-NO_2$, carboxyl, $-C_{1-3}$alkyl or $-C_{1-3}$alkoxy.

In some embodiments of Formula I, X3 is N, S, O, $NR_{X3}$, $C(R_{X3})_2$ or $CR_{X3}$; each of $R_{X3}$ is independently selected from hydrogen, deuterium, F, Cl, Br, carboxyl, $-NO_2$, $-NH_2$, $-CN$, $-CONH_2$, methyl, ethyl, propyl, isopropyl, methoxy, ethoxy, propoxy, isopropoxy, $C_{3-6}$cycloalkyl, $C_{5-8}$aryl, $-S-C_{1-3}$alkyl, 3-10 membered heterocyclyl, $-O-C_{3-6}$cycloalkyl, $-O-C_{1-3}$alkylene-$C_{1-3}$alkyl, $-O-C_{5-6}$aryl or $-O-C_{1-3}$alkylene-$C_{5-6}$aryl, and each of which is independently optionally substituted with 1, 2, 3, 4, 5, or 6 substituents, and the said each substituents is independently selected from deuterium, F, Cl, Br, I, $-NH_2$, $-CN$, $-OH$, $-NO_2$, carboxyl, methyl, ethyl, propyl, isopropyl, methoxy, ethoxy, propoxy or isopropoxy.

In some embodiments of Formula I, X3 is N, S, O, $NR_{X3}$, $C(R_{X3})_2$ or $CR_{X3}$; each of $R_{X3}$ is independently selected from hydrogen, deuterium, F, Cl, Br, carboxyl, $-NO_2$, $-NH_2$, $-CN$, $-CONH_2$, methyl, ethyl, propyl, isopropyl, methoxy, ethoxy, propoxy, isopropoxy, $C_{3-6}$cycloalkyl, $C_{5-8}$aryl, —S—$C_{1-3}$alkyl, 3-10 membered heterocyclyl, —O—$C_{3-6}$cycloalkyl, —O—$C_{1-3}$alkylene-$C_{1-3}$alkyl, —O—$C_{5-6}$aryl or —O—$C_{1-3}$alkylene-$C_{5-6}$aryl, and each of which is independently optionally substituted with 1, 2 or 3 substituents, and the said each substituents is independently selected from deuterium, F, Cl, Br, I, —NH$_2$, —CN, —OH, —NO$_2$, carboxyl, methyl, ethyl, propyl, isopropyl, methoxy, ethoxy, propoxy or isopropoxy.

In some embodiments of Formula I, $R_{X2}$ and $R_{X3}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, $R_{X2}$ and $R_{X3}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, $R_{X2}$ and $R_{X3}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, an 10 membered heteroaromatic ring, a 5 membered heterocyclic ring, a 6 membered heterocyclic ring, a 7 membered heterocyclic ring, an 8 membered heterocyclic ring, a 9 membered heterocyclic ring, or a 10 membered heterocyclic ring, and each of the heteroaromatic ring contains 1, 2 or 3 heteroatoms selected from N, O or S, and each of the heterocyclic ring contains 1, 2 or 3 heteroatoms selected from N or O, and each of the ring systems is independently optionally substituted or unsubstituted.

In some embodiments of Formula I, X4 is N, S, NR$_{X4}$, C(R$_{X4}$)$_2$ or CR$_{X4}$; each of R$_{X4}$ is independently selected from hydrogen, deuterium, F, Cl, Br, —NH$_2$, —CN, —OH, —$C_{1-6}$alkyl, —$C_{1-6}$alkoxy, —NHCO-(5-12 membered heterocyclyl) or 5-12 membered heteroaryl, and each of which is independently optionally substituted with 1, 2, 3, 4, 5, or 6 substituents, and the said each substituents is independently selected from deuterium, F, Cl, Br, I, —NH$_2$, —CN, —OH, oxo, =O, —NO$_2$, carboxyl, —$C_{1-6}$alkyl or —$C_{1-6}$alkoxy.

In some embodiments of Formula I, X4 is N, S, NR$_{X4}$, C(R$_{X4}$)$_2$ or CR$_{X4}$; each of R$_{X4}$ is independently selected from hydrogen, deuterium, F, Cl, Br, —NH$_2$, —CN, —OH, —$C_{1-6}$alkyl, —$C_{1-6}$alkoxy, —NHCO-(5-12 membered heterocyclyl) or 5-12 membered heteroaryl, and each of which is independently optionally substituted with 1, 2, 3, 4, 5, or 6 substituents, and the said each substituents is independently selected from deuterium, F, Cl, Br, I, —NH$_2$, —CN, —OH, oxo, =O, —NO$_2$, carboxyl, —$C_{1-3}$alkyl or —$C_{1-3}$alkoxy.

In some embodiments of Formula I, X4 is N, S, NR$_{X4}$, C(R$_{X4}$)$_2$ or CR$_{X4}$; each of R$_{X4}$ is independently selected from hydrogen, deuterium, F, Cl, Br, —NH$_2$, —CN, —OH, —$C_{1-3}$alkyl, —$C_{1-3}$alkoxy, —NHCO-(5-10 membered heterocyclyl) or 5-10 membered heteroaryl, and each of which is independently optionally substituted with 1, 2, 3, 4, 5, or 6 substituents, and the said each substituents is independently selected from deuterium, F, Cl, Br, I, —NH$_2$, —CN, —OH, oxo, =O, —NO$_2$, carboxyl, —$C_{1-3}$alkyl or —$C_{1-3}$alkoxy.

In some embodiments of Formula I, X4 is N, S, NR$_{X4}$, C(R$_{X4}$)$_2$ or CR$_{X4}$; each of R$_{X4}$ is independently selected from hydrogen, deuterium, F, Cl, Br, —NH$_2$, —CN, —OH, methyl, ethyl, propyl, isopropyl, methoxy, ethoxy, propoxy, isopropoxy, —NHCO-(5-10 membered heterocyclyl), 5 membered heteroaryl, 6 membered heteroaryl, 7 membered heteroaryl, 8 membered heteroaryl, 9 membered heteroaryl or 10 membered heteroaryl, and each of which is independently optionally substituted with 1, 2, 3, 4, 5, or 6 substituents, and the said each substituents is independently selected from deuterium, F, Cl, Br, I, —NH$_2$, —CN, —OH, oxo, =O, —NO$_2$, carboxyl, methyl, ethyl, propyl, isopropyl, methoxy, ethoxy, propoxy or isopropoxy.

In some embodiments of Formula I, X4 is N, S, NR$_{X4}$, C(R$_{X4}$)$_2$ or CR$_{X4}$; each of R$_{X4}$ is independently selected from hydrogen, deuterium, F, Cl, Br, —NH$_2$, —CN, —OH, methyl, ethyl, propyl, isopropyl, methoxy, ethoxy, propoxy, isopropoxy, —NHCO-(5-10 membered heterocyclyl), 5 membered heteroaryl, 6 membered heteroaryl, 7 membered heteroaryl, 8 membered heteroaryl, 9 membered heteroaryl or 10 membered heteroaryl, and each of which is independently optionally substituted with 1, 2 or 3 substituents, and the said each substituents is independently selected from deuterium, F, Cl, Br, I, —NH$_2$, —CN, —OH, oxo, =O, —NO$_2$, carboxyl, methyl, ethyl, propyl, isopropyl, methoxy, ethoxy, propoxy or isopropoxy.

In some embodiments of Formula I, $R_{X3}$ and $R_{X4}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, $R_{X3}$ and $R_{X4}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, $R_{X3}$ and $R_{X4}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring or a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, X5 is N, S, NR$_{X5}$, C(R$_{X5}$)$_2$ or CR$_{X5}$; each of R$_{X5}$ is independently selected from hydrogen, deuterium, F, Cl, Br, —NH$_2$, —CN, —C$_{1-6}$alkyl or —C$_{1-6}$alkoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-6}$alkyl or —C$_{1-6}$alkoxy.

In some embodiments of Formula I, X5 is N, S, NR$_{X5}$, C(R$_{X5}$)$_2$ or CR$_{X5}$; each of R$_{X5}$ is independently selected from hydrogen, deuterium, F, Cl, Br, —NH$_2$, —CN, —C$_{1-6}$alkyl or —C$_{1-6}$alkoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-3}$alkyl or —C$_{1-3}$alkoxy.

In some embodiments of Formula I, X5 is N, S, NR$_{X5}$, C(R$_{X5}$)$_2$ or CR$_{X5}$; each of R$_{X5}$ is selected from hydrogen, deuterium, F, Cl, Br, —NH$_2$, —CN, —C$_{1-3}$alkyl or —C$_{1-3}$alkoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-3}$alkyl or —C$_{1-3}$alkoxy.

In some embodiments of Formula I, X5 is N, S, NR$_{X5}$, C(R$_{X5}$)$_2$ or CR$_{X5}$; each of R$_{X5}$ is independently selected from hydrogen, deuterium, F, Cl, Br, —NH$_2$, —CN, methyl, ethyl, propyl, isopropyl, methoxy, ethoxy, propoxy or isopropoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, methyl, ethyl, propyl, isopropyl, methoxy, ethoxy, propoxy or isopropoxy.

In some embodiments of Formula I, X5 is N, S, NR$_{X5}$, C(R$_{X5}$)$_2$ or CR$_{X5}$; each of R$_{X5}$ is independently selected from hydrogen, deuterium, F, Cl, Br, —NH$_2$, —CN, methyl, ethyl, propyl, isopropyl, methoxy, ethoxy, propoxy or isopropoxy, and each of which is independently optionally substituted with 1, 2 or 3 substituents, and the said each substituents is independently selected from deuterium, F, Cl, Br, I, —NH$_2$, —CN, —OH, —NO$_2$, carboxyl, methyl, ethyl, propyl, isopropyl, methoxy, ethoxy, propoxy or isopropoxy.

In some embodiments of Formula I, R$_{X4}$ and R$_{X5}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, R$_{X4}$ and R$_{X5}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, R$_{X4}$ and R$_{X5}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring or a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, X$_6$ is O, S, CO or NR$_{X6}$, or C(R$_{X6}$)$_2$; each of R$_{X6}$ is independently selected from hydrogen, deuterium, F, Cl, Br, —NH$_2$, —CN, —C$_{1-6}$alkyl or —C$_{1-6}$alkoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-6}$alkyl or —C$_{1-6}$alkoxy.

In some embodiments of Formula I, X$_6$ is O, S, CO or NR$_{X6}$, or C(R$_{X6}$)$_2$; each of R$_{X6}$ is independently selected from hydrogen, deuterium, F, Cl, Br, —NH$_2$, —CN, —C$_{1-6}$alkyl or —C$_{1-6}$alkoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-3}$alkyl or —C$_{1-3}$alkoxy.

In some embodiments of Formula I, X$_6$ is O, S, CO or NR$_{X6}$, or C(R$_{X6}$)$_2$; each of R$_{X6}$ is independently selected from hydrogen, deuterium, F, Cl, Br, —NH$_2$, —CN, —C$_{1-3}$alkyl or —C$_{1-3}$alkoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-3}$alkyl or —C$_{1-3}$alkoxy.

In some embodiments of Formula I, X$_6$ is O, S, CO or NR$_{X6}$, or C(R$_{X6}$)$_2$; each of R$_{X6}$ is independently selected from hydrogen, deuterium, F, Cl, Br, —NH$_2$, —CN, methyl, ethyl, propyl, isopropyl, methoxy, ethoxy, propoxy or isopropoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, methyl, ethyl, propyl, isopropyl, methoxy, ethoxy, propoxy or isopropoxy.

In some embodiments of Formula I, X$_6$ is O, S, CO or NR$_{X6}$, or C(R$_{X6}$)$_2$; each of R$_{X6}$ is independently selected from hydrogen, deuterium, F, Cl, Br, —NH$_2$, —CN, methyl, ethyl, propyl, isopropyl, methoxy, ethoxy, propoxy or isopropoxy, and each of which is independently optionally substituted with 1, 2 or 3 substituents, and the said each substituents is independently selected from deuterium, F, Cl, Br, I, —NH$_2$, —CN, —OH, —NO$_2$, carboxyl, methyl, ethyl, propyl, isopropyl, methoxy, ethoxy, propoxy or isopropoxy.

In some embodiments of Formula I, ring A is selected from

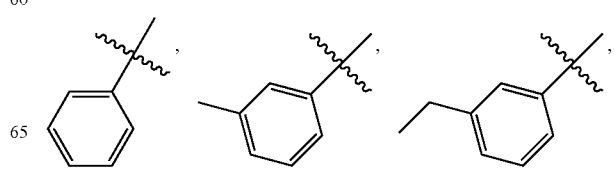

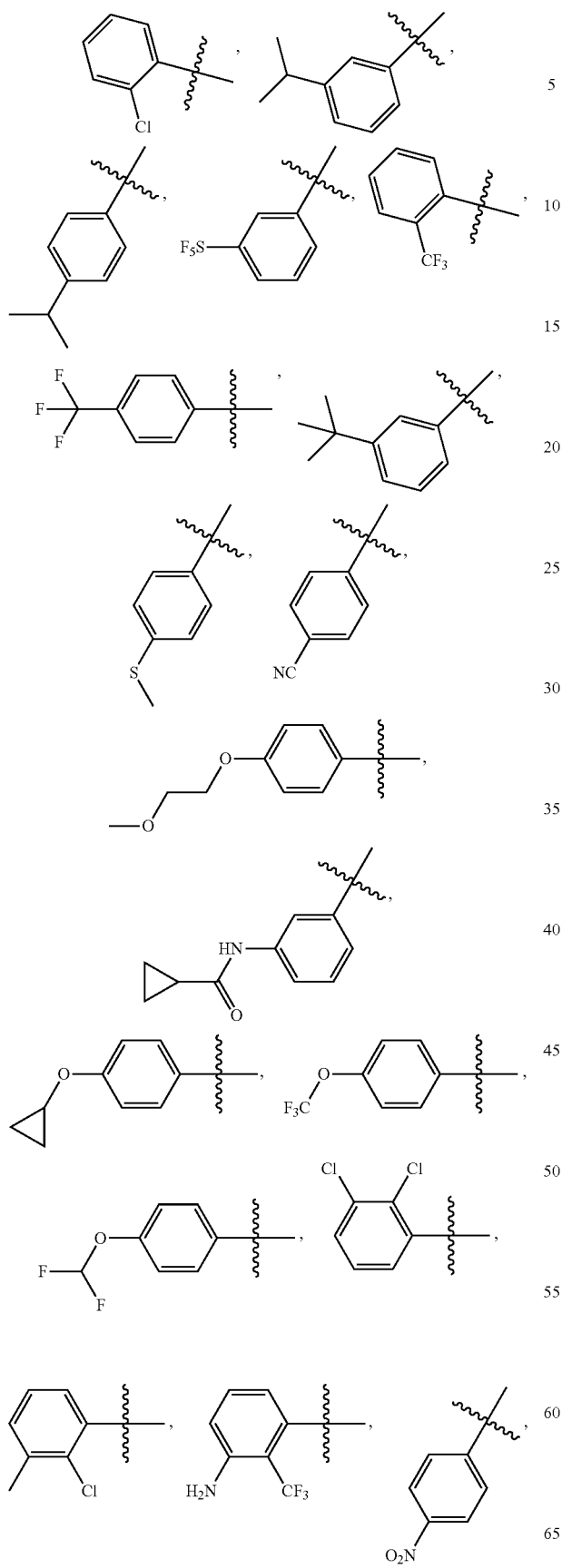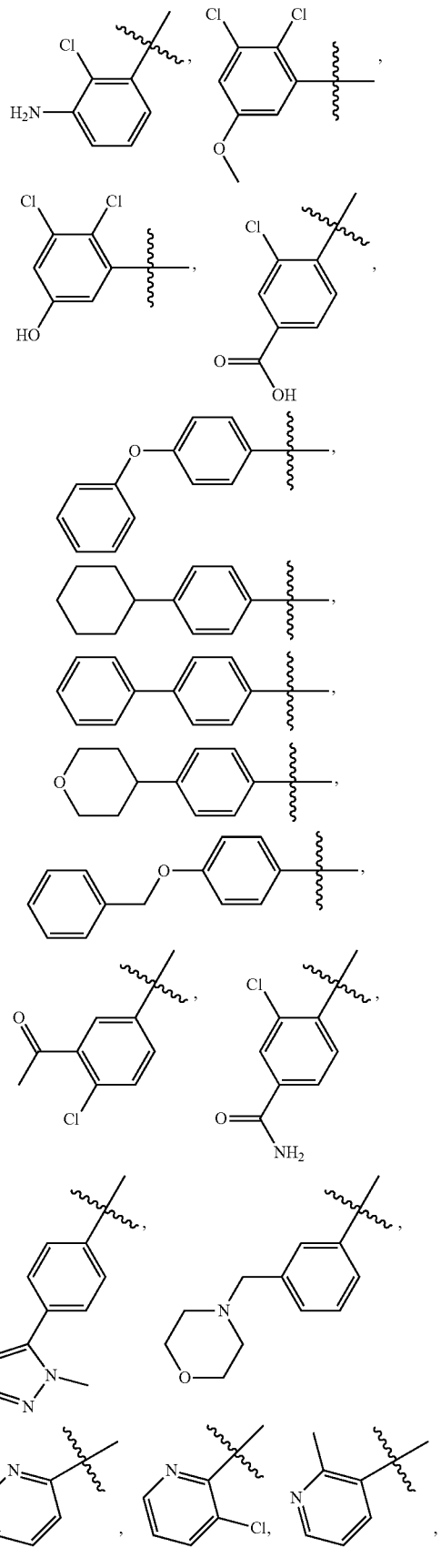

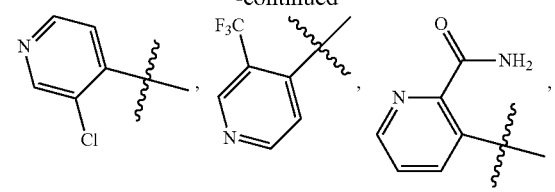
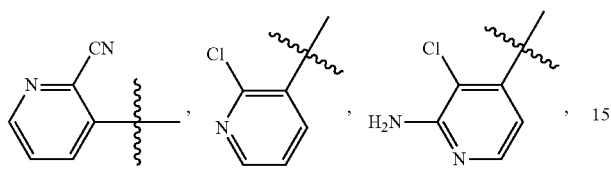
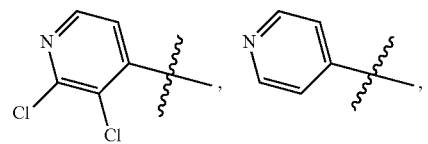
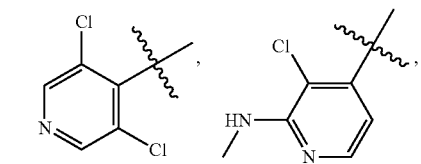
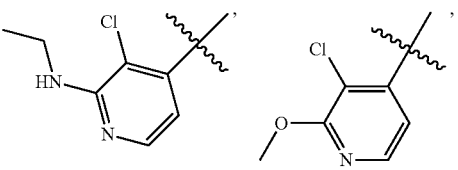
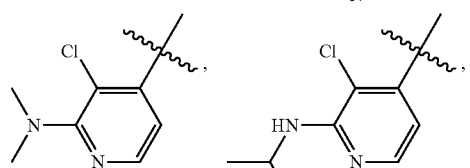
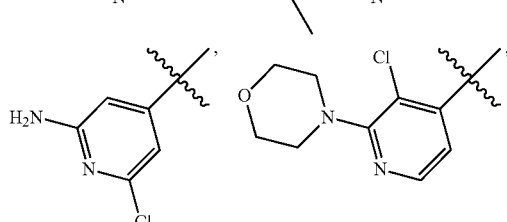
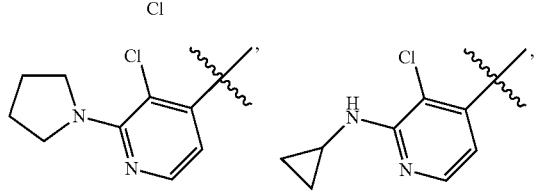
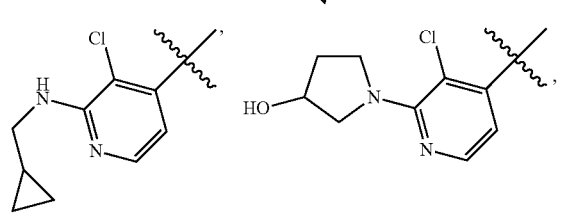
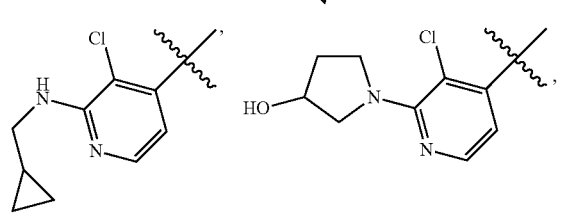
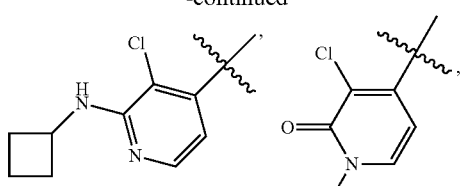
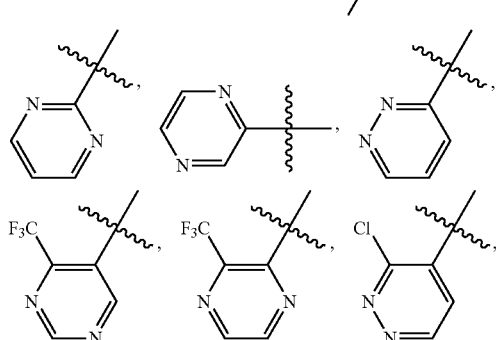
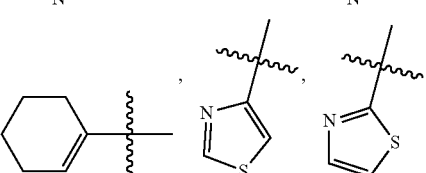
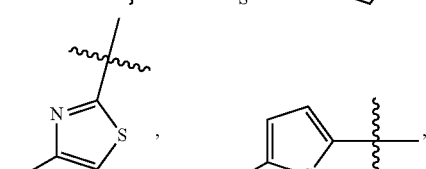
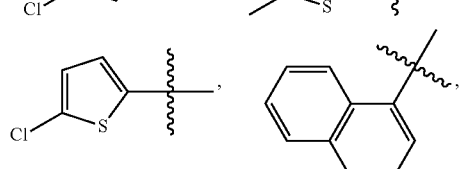
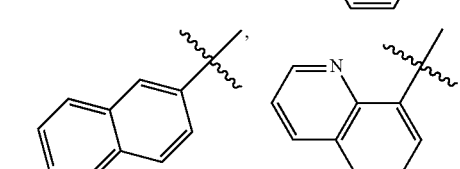
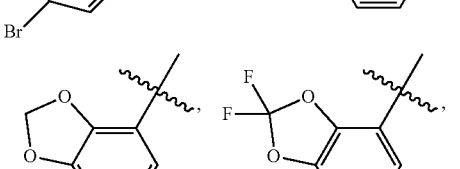
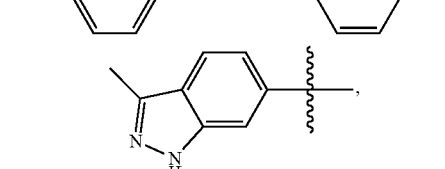
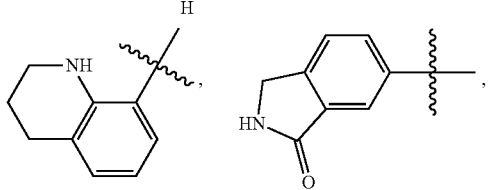
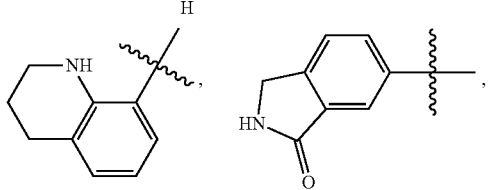
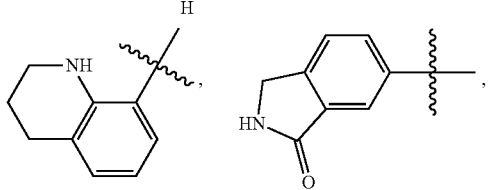
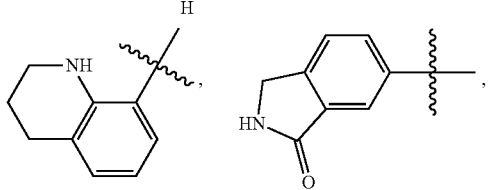

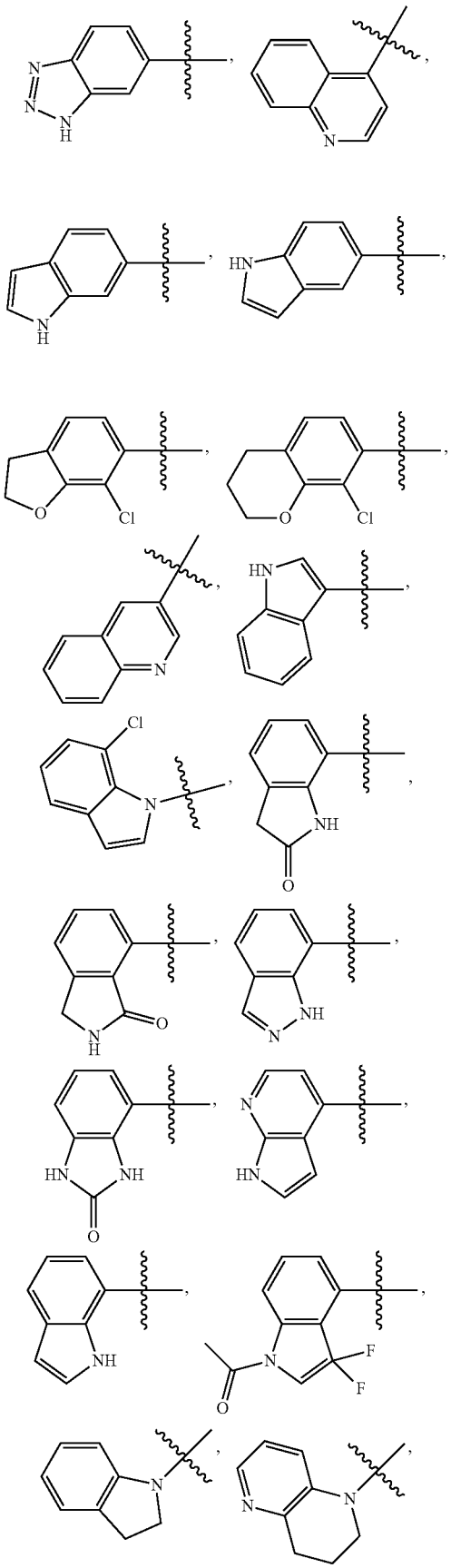

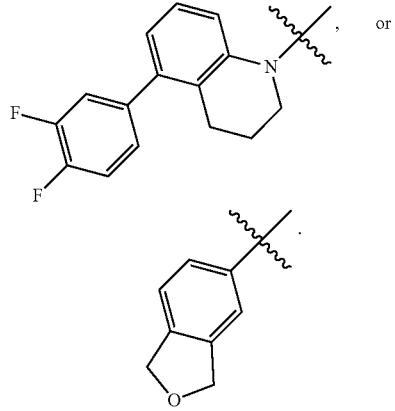

In some embodiments of Formula I, G is selected from absent, S, —SO—, —SO$_2$—, O, —CO—, —NR$_G$—, —NR$_G$—SO$_2$—,

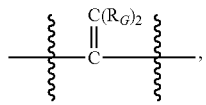

—C(R$_G$)$_2$— or —SO$_2$—NR$_G$—; each of R$_G$ is independently selected from hydrogen, deuterium, F, Cl, Br, —NH$_2$, —CN, —OH, —C$_{1-6}$alkyl or —C$_{1-6}$alkoxy, and each of which is independently optionally substituted or unsubstituted.

In some embodiments of Formula I, G is selected from absent, S, —SO—, —SO$_2$—, O, —CO—, —NR$_G$—, —NR$_G$—SO$_2$—,

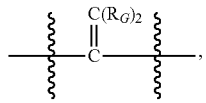

—C(R$_G$)$_2$— or —SO$_2$—NR$_G$—; each of R$_G$ is independently selected from hydrogen, deuterium, F, Cl, Br, —NH$_2$, —CN, —OH, —C$_{1-3}$alkyl or —C$_{1-3}$alkoxy, and each of which is independently optionally substituted or unsubstituted.

In some embodiments of Formula I, G is selected from absent, S, —SO—, —SO$_2$—, O, —CO—, —NR$_G$—, —NR$_G$—SO$_2$—,

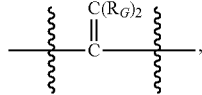

—C(R$_G$)$_2$— or —SO$_2$—NR$_G$—; each of R$_G$ is independently selected from hydrogen, deuterium, F, Cl, Br, —NH$_2$, —CN, —OH, methyl, ethyl, propyl, isopropyl, methoxy, ethoxy, propoxy or isopropoxy, and each of which is independently optionally substituted or unsubstituted.

In some embodiments of Formula I, ring B is a 5-12 membered aromatic ring, a 5-12 membered heteroaromatic ring or a 5-12 membered heterocyclic ring, and each of the heteroaromatic ring contains 1, 2, 3, 4, 5 or 6 heteroatoms selected from N, O or S, and each of the heterocyclic ring contains 1, 2, 3, 4, 5 or 6 heteroatoms selected from N, O or S, and each of the ring systems is independently optionally substituted or unsubstituted.

In some embodiments of Formula I, wherein ring B is a 5-10 membered aromatic ring, a 5-10 membered heteroaromatic ring or a 5-10 membered heterocyclic ring, and each of the heteroaromatic ring contains 1, 2, 3, 4, 5 or 6 heteroatoms selected from N, O or S, and each of the heterocyclic ring contains 1, 2, 3, 4, 5 or 6 heteroatoms selected from N, O or S, and each of the ring systems is independently optionally substituted or unsubstituted.

In some embodiments of Formula I, ring B is a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, a 8 membered heterocyclic ring, a 9 membered heterocyclic ring or a 10 membered heterocyclic ring, and each of the heteroaromatic ring contains 1, 2, 3 or 4 heteroatoms selected from N, O or S, and each of the heterocyclic ring contains 1, 2, 3 or 4 heteroatoms selected from N, O or S, and each of the ring systems is independently optionally substituted or unsubstituted.

In some embodiments of Formula I, ring B is

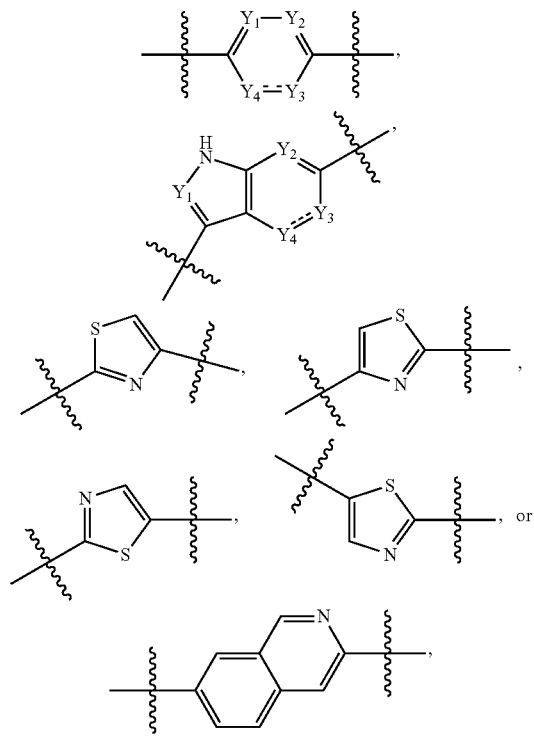

$Y_1$ is N or $CR_{Y1}$;

$R_{Y1}$ is selected from hydrogen, deuterium, halogen, —$NH_2$, —OH, —CN, —$C_{1-6}$alkyl, —$C_{1-6}$alkoxy, —NH—$C_{1-6}$alkyl, —N—$(C_{1-6}$alkyl$)_2$, —$C_{1-6}$alkenyl, —$C_{3-8}$cycloalkyl or —$C_{5-10}$aryl, and each of which is independently optionally substituted with 1, 2, 3, 4, 5, or 6 substituents, and the said each substituents is independently selected from deuterium, halogen, —$NH_2$, —CN, —OH, —$NO_2$, carboxyl, —$C_{1-6}$alkyl or —$C_{1-6}$alkoxy;

$Y_2$ is N or $CR_{Y2}$;

$R_{Y2}$ is selected from hydrogen, deuterium, halogen, —$NH_2$, —CN, —$C_{1-6}$alkyl, —$C_{1-6}$alkoxy, —NH—$C_{1-6}$alkyl, —N—$(C_{1-6}$alkyl$)_2$, —$C_{1-6}$ alkenyl, —$C_{3-8}$cycloalkyl or —$C_{5-10}$aryl, and each of which is independently optionally substituted with 1, 2, 3, 4, 5, or 6 substituents, and the said each substituents is independently selected from deuterium, halogen, —$NH_2$, —CN, —OH, —$NO_2$, carboxyl, —$C_{1-6}$alkyl or —$C_{1-6}$alkoxy; or $R_{Y1}$ and $R_{Y2}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;

when the "------" in the term "$Y_3$------$Y_4$" represents a single bond, $Y_3$ is $NR_{Y3}$ or $C(R_{Y3})_2$, and $Y_4$ is CO, $C(R_{Y4})_2$ or $NR_{Y4}$;

when the "------" in the term "$Y_3$------$Y_4$" represents a double bond, $Y_3$ is N or $CR_{Y3}$, and $Y_4$ is N or $CR_{Y4}$;

$R_{Y3}$ and $R_{Y4}$ are independently selected from hydrogen, deuterium, halogen, —$NH_2$, —OH, —CN, —$C_{1-6}$alkyl, carboxyl, —COO—$C_{1-6}$alkyl, —NH—$C_{1-6}$alkylene-OH, —$C_{1-6}$alkylene-OH, —$CONH_2$ or -5-8 membered heteroaryl, and each of which is independently optionally substituted with 1, 2, 3, 4, 5, or 6 substituents, and the said each substituents is independently selected from deuterium, halogen, —$NH_2$, —CN, —OH, —$NO_2$, carboxyl, —$C_{1-6}$alkyl or —$C_{1-6}$alkoxy; or $R_{Y3}$ and $R_{Y4}$ together with the ring to which they are attached form a 5-12 membered aromatic ring, a 5-12 membered heteroaromatic ring or a 5-12 membered heterocyclic ring, and each of the ring systems is independently optionally substituted or unsubstituted.

In some embodiments of Formula I, $Y_1$ is N or $CR_{Y1}$; $R_{Y1}$ is selected from hydrogen, deuterium, F, Cl, Br, I, —$NH_2$, —OH, —CN, —$C_{1-6}$alkyl, —$C_{1-6}$alkoxy, —NH—$C_{1-6}$alkyl, —N—$(C_{1-6}$alkyl$)_2$, —$C_{1-6}$alkenyl, —$C_{3-6}$cycloalkyl or —$C_{5-10}$aryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-6}$alkyl or —$C_{1-6}$alkoxy.

In some embodiments of Formula I, $Y_1$ is N or $CR_{Y1}$; $R_{Y1}$ is selected from hydrogen, deuterium, F, Cl, Br, I, —$NH_2$, —OH, —CN, —$C_{1-6}$alkyl, —$C_{1-6}$alkoxy, —NH—$C_{1-6}$alkyl, —N—$(C_{1-6}$alkyl$)_2$, —$C_{1-6}$alkenyl, —$C_{3-8}$cycloalkyl or —$C_{5-8}$aryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula I, $Y_1$ is N or $CR_{Y1}$; $R_{Y1}$ is selected from hydrogen, deuterium, F, Cl, Br, I, —$NH_2$, —OH, —CN, —$C_{1-3}$alkyl, —$C_{1-3}$alkoxy, —NH—$C_{1-3}$alkyl, —N—$(C_{1-3}$alkyl$)_2$, —$C_{1-3}$alkenyl, —$C_{3-6}$cycloalkyl or —$C_{5-8}$aryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula I, $Y_1$ is N or $CR_{Y1}$; $R_{Y1}$ is selected from hydrogen, deuterium, F, Cl, Br, I, —$NH_2$, —OH, —CN, methyl, ethyl, propyl, isopropyl, methoxy, ethoxy, propoxy, isopropoxy, —NH—$C_{1-3}$alkyl, —N—($C_{1-3}$alkyl)$_2$, —$C_{1-3}$alkenyl, —$C_{3-6}$cycloalkyl or —$C_{5-8}$aryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, methyl, ethyl, propyl, isopropyl, methoxy, ethoxy, propoxy or isopropoxy.

In some embodiments of Formula I, $Y_2$ is N or $CR_{Y2}$; $R_{Y2}$ is selected from hydrogen, deuterium, F, Cl, Br, —$NH_2$, —CN, —$C_{1-6}$alkyl, —$C_{1-6}$alkoxy, —NH—$C_{1-6}$alkyl, —N—($C_{1-6}$alkyl)$_2$, —$C_{1-6}$ alkenyl, —$C_{3-8}$cycloalkyl or —$C_{5-10}$aryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-6}$alkyl or —$C_{1-6}$alkoxy.

In some embodiments of Formula I, $Y_2$ is N or $CR_{Y2}$; $R_{Y2}$ is selected from hydrogen, deuterium, F, Cl, Br, —$NH_2$, —CN, —$C_{1-6}$alkyl, —$C_{1-6}$alkoxy, —NH—$C_{1-6}$alkyl, —N—($C_{1-6}$alkyl)$_2$, —$C_{1-6}$ alkenyl, —$C_{3-8}$cycloalkyl or —$C_{5-10}$aryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula I, $Y_2$ is N or $CR_{Y2}$; $R_{Y2}$ is selected from hydrogen, deuterium, F, Cl, Br, —$NH_2$, —CN, —$C_{1-3}$alkyl, —$C_{1-3}$alkoxy, —NH—$C_{1-3}$alkyl, —N—($C_{1-3}$alkyl)$_2$, —$C_{1-3}$alkenyl, —$C_{3-6}$cycloalkyl or —$C_{5-8}$aryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula I, $Y_2$ is N or $CR_{Y2}$; $R_{Y2}$ is selected from hydrogen, deuterium, F, Cl, Br, —$NH_2$, —CN, methyl, ethyl, propyl, isopropyl, methoxy, ethoxy, propoxy, isopropoxy, —NH—$C_{1-3}$alkyl, —N—($C_{1-3}$alkyl)$_2$, —$C_{1-3}$alkenyl, —$C_{3-6}$cycloalkyl or —$C_{5-8}$aryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, methyl, ethyl, propyl, isopropyl, methoxy, ethoxy, propoxy or isopropoxy.

In some embodiments of Formula I, $R_{Y1}$ and $R_{Y2}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, wherein $R_{Y1}$ and $R_{Y2}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, $R_{Y1}$ and $R_{Y2}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring, a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, $R_{Y3}$ and $R_{Y4}$ are independently selected from hydrogen, deuterium, F, Cl, Br, —$NH_2$, —OH, —CN, —$C_{1-6}$alkyl, carboxyl, —COO—$C_{1-6}$alkyl, —NH—$C_{1-6}$alkylene-OH, —$C_{1-6}$alkylene-OH, —$CONH_2$ or -5-8 membered heteroaryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-6}$alkyl or —$C_{1-6}$alkoxy.

In some embodiments of Formula I, $R_{Y3}$ and $R_{Y4}$ are independently selected from hydrogen, deuterium, F, Cl, Br, —$NH_2$, —OH, —CN, —$C_{1-6}$alkyl, carboxyl, —COO—$C_{1-6}$alkyl, —NH—$C_{1-6}$alkylene-OH, —$C_{1-6}$alkylene-OH, —$CONH_2$ or -5-8 membered heteroaryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy. In some embodiments of Formula I, $R_{Y3}$ and $R_{Y4}$ are independently selected from hydrogen, deuterium, F, Cl, Br, —$NH_2$, —OH, —CN, —$C_{1-3}$alkyl, carboxyl, —COO—$C_{1-3}$alkyl, —NH—$C_{1-3}$alkylene-OH, —$C_{1-3}$alkylene-OH, —$CONH_2$ or -5-8 membered heteroaryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula I, $R_{Y3}$ and $R_{Y4}$ are independently selected from hydrogen, deuterium, F, Cl, Br, —$NH_2$, —OH, —CN, methyl, ethyl, propyl, isopropyl, carboxyl, —COO—$C_{1-3}$alkyl, —NH—$C_{1-3}$alkylene-OH, —$C_{1-3}$alkylene-OH, —$CONH_2$ or -5-8 membered heteroaryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, methyl, ethyl, propyl, isopropyl, methoxy, ethoxy, propoxy or isopropoxy.

In some embodiments of Formula I, $R_{Y3}$ and $R_{Y4}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, $R_{Y3}$ and $R_{Y4}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, $R_{Y3}$ and $R_{Y4}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring, a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, ring B is selected from

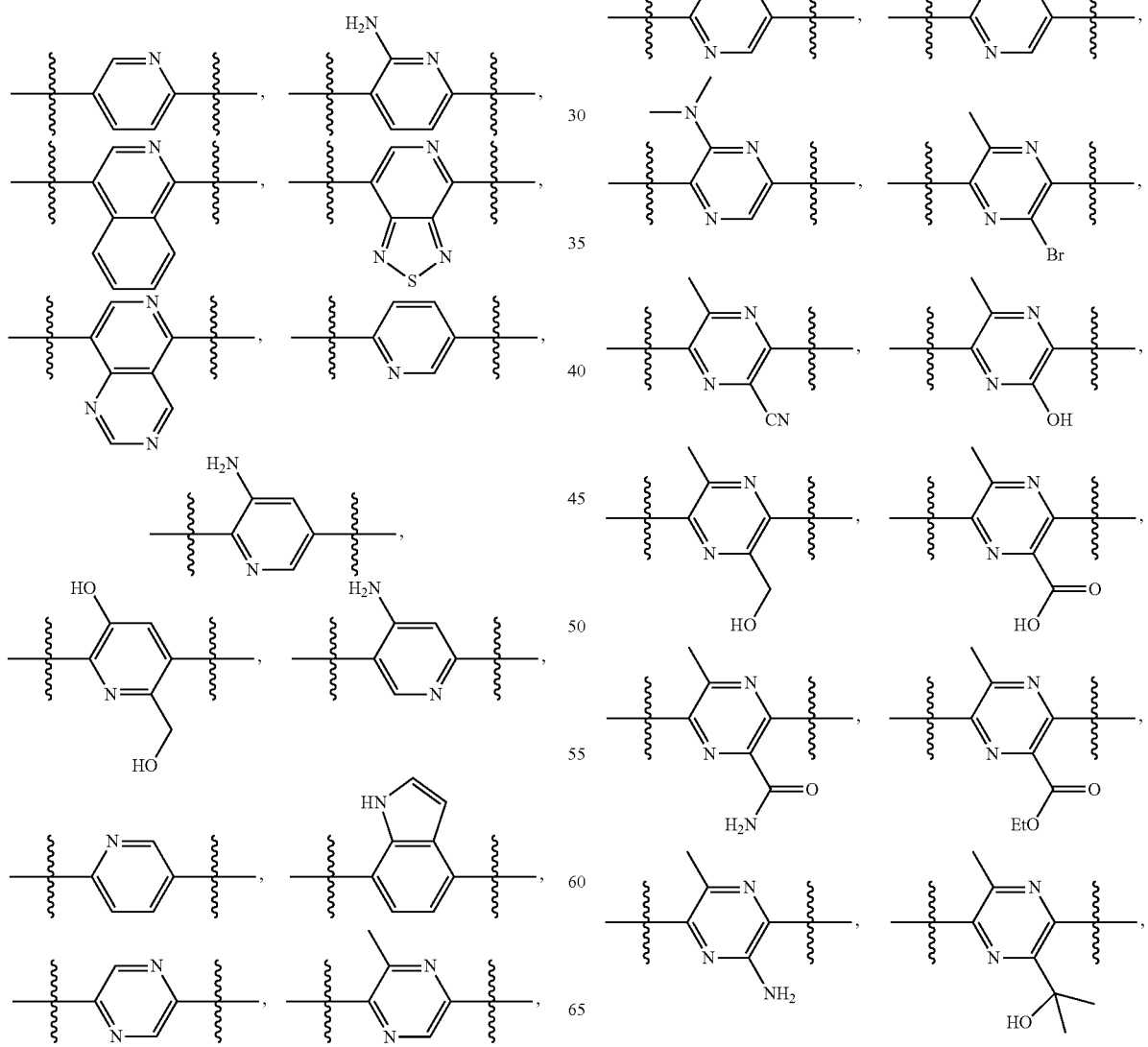

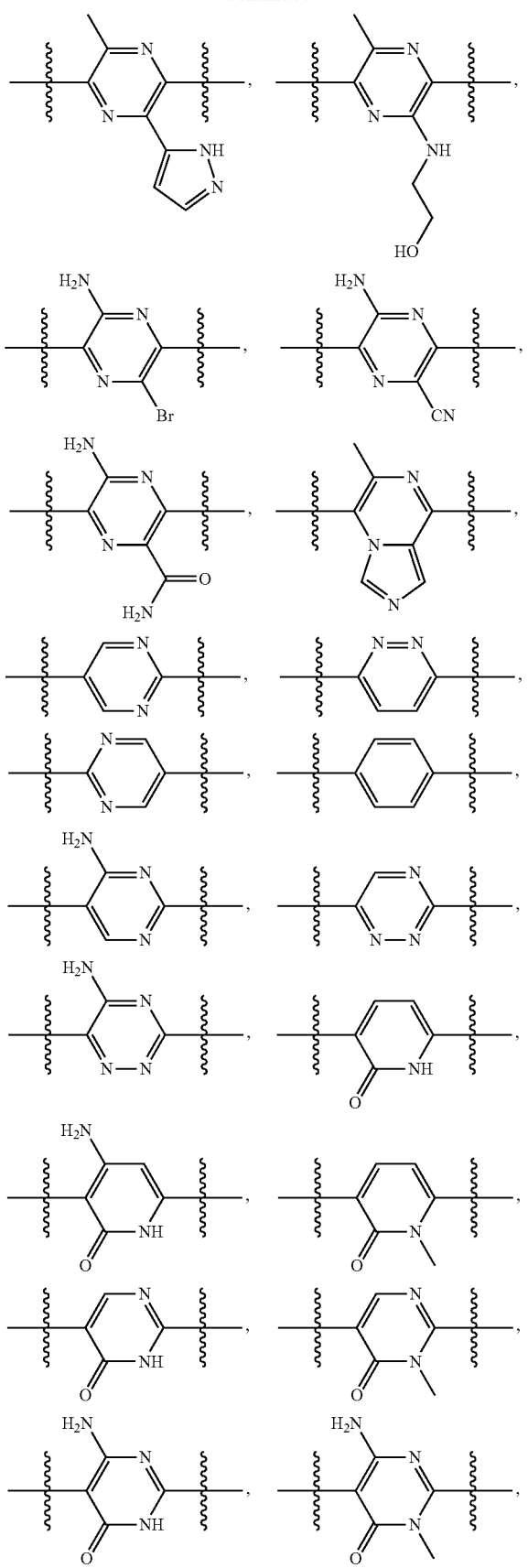
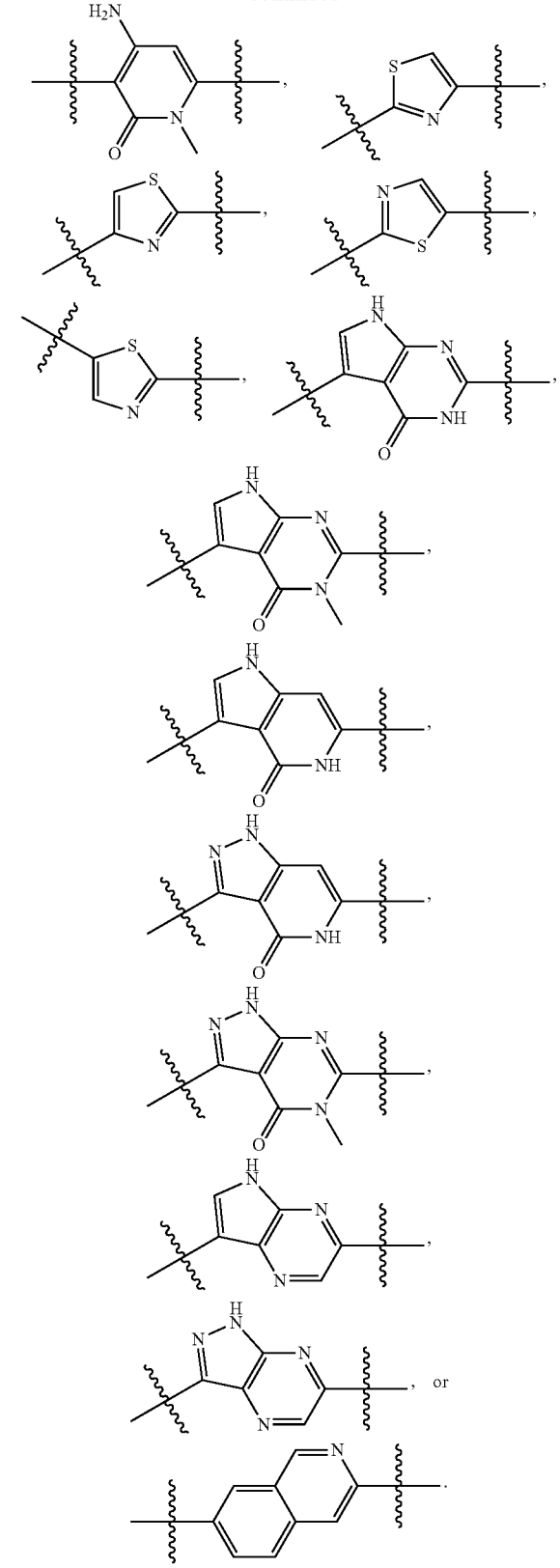
In some embodiments of Formula I, each of $R_1$ and $R_2$ is independently selected from hydrogen, deuterium, F, Cl, Br, —$NH_2$, —CN, —OH, —$NO_2$, carboxyl, —NH—$C_{1-6}$alkyl, —N(C$_{1-6}$alkyl)$_2$, substituted or unsubstituted —C$_{1-6}$alkoxy, or substituted or unsubstituted —C$_{1-6}$alkyl.

In some embodiments of Formula I, each of R$_1$ and R$_2$ is independently selected from hydrogen, deuterium, F, Cl, Br, —NH$_2$, —CN, —OH, —NO$_2$, carboxyl, —NH—C$_{1-3}$alkyl, —N(C$_{1-3}$alkyl)$_2$, substituted or unsubstituted —C$_{1-3}$alkoxy, or substituted or unsubstituted —C$_{1-3}$alkyl.

In some embodiments of Formula I, each of R$_1$ and R$_2$ is independently selected from hydrogen; deuterium; F; Cl; Br; —NH$_2$; —CN; —OH; —NO$_2$; carboxyl; —NH—C$_{1-3}$alkyl; —N(C$_{1-3}$alkyl)$_2$; methoxy; ethoxy; propoxy; isopropoxy; —C$_{1-3}$alkoxy substituted with halogen, NH$_2$, CN, OH, NO$_2$, carboxyl, C$_{1-3}$alkyl or C$_{1-3}$alkoxy; methyl; ethyl; propyl; isopropyl; —C$_{1-3}$alkyl substituted with halogen, NH$_2$, CN, OH, NO$_2$, carboxyl, C$_{1-3}$alkyl or C$_{1-3}$alkoxy.

In some embodiments of Formula I, each of R$_1$ and R$_2$ is independently selected from hydrogen; deuterium; F; Cl; Br; —NH$_2$; —CN; —OH; —NO$_2$; carboxyl; —NH—C$_{1-3}$alkyl; —N(C$_{1-3}$alkyl)$_2$; methoxy; ethoxy; propoxy; isopropoxy; —C$_{1-3}$alkoxy substituted with F, Cl, Br, NH$_2$, CN, OH, NO$_2$, carboxyl, methyl, ethyl, propyl, isopropyl, methoxy, ethoxy, propoxy or isopropoxy; methyl; ethyl; propyl; isopropyl; —C$_{1-3}$alkyl substituted with F, Cl, Br, NH$_2$, CN, OH, NO$_2$, carboxyl, methyl, ethyl, propyl, isopropyl, methoxy, ethoxy, propoxy or isopropoxy.

In some embodiments of Formula I, R$_1$ and R$_2$ together with the carbon atom to which they are both attached form CO or C=NR$_5$.

In some embodiments of Formula I, R$_1$ and R$_2$ together with the carbon atom to which they are both attached form CO.

In some embodiments of Formula I, R$_1$ and R$_2$ together with the carbon atom to which they are both attached form C=NR$_5$.

In some embodiments of Formula I, each of R$_3$ and R$_4$ is independently selected from hydrogen, deuterium, F, Cl, Br, —NH$_2$, —CN, —OH, —NO$_2$, carboxyl, —NH—C$_{1-6}$alkyl, —N(C$_{1-6}$alkyl)$_2$, substituted or unsubstituted —C$_{1-6}$alkoxy, or substituted or unsubstituted —C$_{1-6}$alkyl.

In some embodiments of Formula I, each of R$_3$ and R$_4$ is independently selected from hydrogen, deuterium, F, Cl, Br, —NH$_2$, —CN, —OH, —NO$_2$, carboxyl, —NH—C$_{1-3}$alkyl, —N(C$_{1-3}$alkyl)$_2$, substituted or unsubstituted —C$_{1-3}$alkoxy, or substituted or unsubstituted —C$_{1-3}$alkyl.

In some embodiments of Formula I, each of R$_3$ and R$_4$ is independently selected from hydrogen; deuterium; F; Cl; Br; —NH$_2$; —CN; —OH; —NO$_2$; carboxyl; —NH—C$_{1-3}$alkyl; —N(C$_{1-3}$alkyl)$_2$; methoxy; ethoxy; propoxy; isopropoxy; —C$_{1-3}$alkoxy substituted with halogen, NH$_2$, CN, OH, NO$_2$, carboxyl, C$_{1-3}$alkyl or C$_{1-3}$alkoxy; methyl; ethyl; propyl; isopropyl; —C$_{1-3}$alkyl substituted with halogen, NH$_2$, CN, OH, NO$_2$, carboxyl, C$_{1-3}$alkyl or C$_{1-3}$alkoxy.

In some embodiments of Formula I, each of R$_3$ and R$_4$ is independently selected from hydrogen; deuterium; F; Cl; Br; —NH$_2$; —CN; —OH; —NO$_2$; carboxyl; —NH—C$_{1-3}$alkyl; —N(C$_{1-3}$alkyl)$_2$; methoxy; ethoxy; propoxy; isopropoxy; —C$_{1-3}$alkoxy substituted with F, Cl, Br, NH$_2$, CN, OH, NO$_2$, carboxyl, methyl, ethyl, propyl, isopropyl, methoxy, ethoxy, propoxy or isopropoxy; methyl; ethyl; propyl; isopropyl; —C$_{1-3}$alkyl substituted with F, Cl, Br, NH$_2$, CN, OH, NO$_2$, carboxyl, methyl, ethyl, propyl, isopropyl, methoxy, ethoxy, propoxy or isopropoxy.

In some embodiments of Formula I, R$_3$ and R$_4$ together with the carbon atom to which they are both attached form 3-12 membered heterocyclic ring or 5-12 membered heteroaromatic ring or C=NR$_5$, and each of the heterocyclic ring contains 1, 2 or 3 heteroatoms selected from N, O or S, and each of the heteroaromatic ring contains 1, 2 or 3 heteroatoms selected from N, O or S, and each of the ring systems is independently optionally substituted or unsubstituted.

In some embodiments of Formula I, R$_3$ and R$_4$ together with the carbon atom to which they are both attached form 3-10 membered heterocyclic ring or 5-10 membered heteroaromatic ring or C=NR$_5$, and each of the heterocyclic ring contains 1, 2 or 3 heteroatoms selected from N, O or S, and each of the heteroaromatic ring contains 1, 2 or 3 heteroatoms selected from N, O or S, and each of the ring systems is independently optionally substituted or unsubstituted.

In some embodiments of Formula I, R$_3$ and R$_4$ together with the carbon atom to which they are both attached form 3 membered heterocyclic ring, 4 membered heterocyclic ring, 5 membered heterocyclic ring, 6 membered heterocyclic ring, 7 membered heterocyclic ring, 8 membered heterocyclic ring, 9 membered heterocyclic ring, 10 membered heterocyclic ring, 5 membered heteroaromatic ring, 6 membered heteroaromatic ring, 7 membered heteroaromatic ring, 8 membered heteroaromatic ring, 9 membered heteroaromatic ring, 10 membered heteroaromatic ring or C=NR$_5$, and each of the heterocyclic ring contains 1, 2 or 3 heteroatoms selected from N, O or S, and each of the heteroaromatic ring contains 1, 2 or 3 heteroatoms selected from N, O or S, and each of the ring systems is independently optionally substituted or unsubstituted.

In some embodiments of Formula I, each of R$_5$ is selected from hydrogen, deuterium, F, Cl, Br, —NH$_2$, —CN, —OH, —C$_{1-6}$alkyl or —C$_{1-6}$alkoxy.

In some embodiments of Formula I, each of R$_5$ is selected from hydrogen, deuterium, F, Cl, Br, —NH$_2$, —CN, —OH, —C$_{1-3}$alkyl or —C$_{1-3}$alkoxy.

In some embodiments of Formula I, each of R$_5$ is selected from hydrogen, deuterium, F, Cl, Br, —NH$_2$, —CN, —OH, methyl, ethyl, propyl, isopropyl, methoxy, ethoxy, propoxy or isopropoxy.

In some embodiments of Formula I, W is absent, —O, —S or —C(R$_W$)$_2$—; and each of R$_W$ is independently selected from hydrogen, deuterium, F, Cl, Br, —NH$_2$, —CN, —OH, —NO$_2$, carboxyl, —CO—C$_{1-6}$alkyl, —CO—OC$_{1-6}$alkyl, —C$_{1-6}$alkylene-O—C$_{1-6}$alkoxy, substituted or unsubstituted —C$_{1-6}$alkoxy, or substituted or unsubstituted —C$_{1-6}$alkyl.

In some embodiments of Formula I, W is absent, —O, —S or —C(R$_W$)$_2$—; and each of R$_W$ is independently selected from hydrogen, deuterium, F, Cl, Br, —NH$_2$, —CN, —OH, —NO$_2$, carboxyl, —CO—C$_{1-3}$alkyl, —CO—OC$_{1-3}$alkyl, —C$_{1-3}$alkylene-O—C$_{1-3}$alkoxy, substituted or unsubstituted —C$_{1-3}$alkoxy, or substituted or unsubstituted —C$_{1-3}$alkyl.

In some embodiments of Formula I, W is absent, —O, —S or —C(R$_W$)$_2$—; and each of R$_W$ is independently selected from hydrogen; deuterium; F; Cl; Br; —NH$_2$; —CN; —OH; —NO$_2$; carboxyl; —CO—C$_{1-3}$alkyl; —CO—OC$_{1-3}$alkyl; —C$_{1-3}$alkylene-O—C$_{1-3}$alkoxy; methoxy; ethoxy; propoxy; isopropoxy; —C$_{1-3}$alkoxy substituted with halogen, NH$_2$, CN, OH, NO$_2$, carboxyl, C$_{1-3}$alkyl or C$_{1-3}$alkoxy; methyl; ethyl; propyl; isopropyl; —C$_{1-3}$alkyl substituted with halogen, NH$_2$, CN, OH, NO$_2$, carboxyl, C$_{1-3}$alkyl or C$_{1-3}$alkoxy.

In some embodiments of Formula I, W is absent, —O, —S or —C(R$_W$)$_2$—; and each of R$_W$ is independently selected from hydrogen; deuterium; F; Cl; Br; —NH$_2$; —CN; —OH; —NO$_2$; carboxyl; —CO—C$_{1-3}$alkyl; —CO—OC$_{1-3}$alkyl; —C$_{1-3}$alkylene-O—C$_{1-3}$alkoxy;

methoxy; ethoxy; propoxy; isopropoxy; —C$_{1-3}$alkoxy substituted with halogen, NH$_2$, CN, OH, NO$_2$, carboxyl, C$_{1-3}$alkyl or C$_{1-3}$alkoxy; methyl; ethyl; propyl; isopropyl; —C$_{1-3}$alkyl substituted with halogen, NH$_2$, CN, OH, NO$_2$, carboxyl, C$_{1-3}$alkyl or C$_{1-3}$alkoxy.

In some embodiments of Formula I, W is absent, —O, —S or —C(R$_W$)$_2$—; and each of R$_W$ is independently selected from hydrogen; deuterium; F; Cl; Br; —NH$_2$; —CN; —OH; —NO$_2$; carboxyl; —CO—C$_{1-3}$alkyl; —CO—OC$_{1-3}$alkyl; —C$_{1-3}$alkylene-O—C$_{1-3}$alkoxy; methoxy; ethoxy; propoxy; isopropoxy; —C$_{1-3}$alkoxy substituted with F, Cl, Br, NH$_2$, CN, OH, NO$_2$, carboxyl, methyl, ethyl, propyl, isopropyl, methoxy, ethoxy, propoxy or isopropoxy; methyl; ethyl; propyl; isopropyl; —C$_{1-3}$alkyl substituted with F, Cl, Br, NH$_2$, CN, OH, NO$_2$, carboxyl, methyl, ethyl, propyl, isopropyl, methoxy, ethoxy, propoxy or isopropoxy.

In some embodiments of Formula I, ring C is absent, a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, ring C is absent, a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, ring C is absent, a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring, a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula I, ring C is selected from

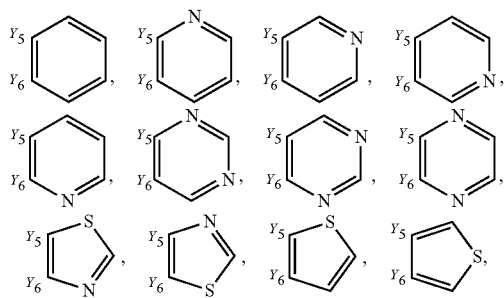

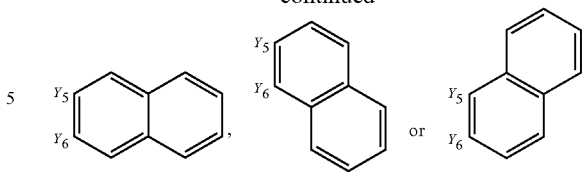

In some embodiments of Formula I, each of R$_{5a}$ and R$_{5b}$ is independently selected from hydrogen, deuterium, F, Cl, Br, —NH$_2$, —CN, —OH, —NO$_2$, carboxyl, substituted or unsubstituted —C$_{1-6}$alkoxy, or substituted or unsubstituted —C$_{1-6}$alkyl.

In some embodiments of Formula I, each of R$_{5a}$ and R$_{5b}$ is independently selected from hydrogen, deuterium, F, Cl, Br, —NH$_2$, —CN, —OH, —NO$_2$, carboxyl, substituted or unsubstituted —C$_{1-3}$alkoxy, or substituted or unsubstituted —C$_{1-3}$alkyl.

In some embodiments of Formula I, each of R$_{5a}$ and R$_{5b}$ is independently selected from hydrogen; deuterium; F; Cl; Br; —NH$_2$; —CN; —OH; —NO$_2$; carboxyl; methoxy; ethoxy; propoxy; isopropoxy; —C$_{1-3}$alkoxy substituted with halogen, NH$_2$, CN, OH, NO$_2$, carboxyl, C$_{1-3}$alkyl or C$_{1-3}$alkoxy; methyl; ethyl; propyl; isopropyl; —C$_{1-3}$alkyl substituted with halogen, NH$_2$, CN, OH, NO$_2$, carboxyl, C$_{1-3}$alkyl or C$_{1-3}$alkoxy.

In some embodiments of Formula I, each of R$_{5a}$ and R$_{5b}$ is independently selected from hydrogen; deuterium; F; Cl; Br; —NH$_2$; —CN; —OH; —NO$_2$; carboxyl; methoxy; ethoxy; propoxy; isopropoxy; —C$_{1-3}$alkoxy substituted with F, Cl, Br, NH$_2$, CN, OH, NO$_2$, carboxyl, methyl, ethyl, propyl, isopropyl, methoxy, ethoxy, propoxy or isopropoxy; —C$_{1-3}$alkyl substituted with F, Cl, Br, NH$_2$, CN, OH, NO$_2$, carboxyl, methyl, ethyl, propyl, isopropyl, methoxy, ethoxy, propoxy or isopropoxy.

In some embodiments of Formula I, each of R$_{6a}$ and R$_{6b}$ is independently selected from hydrogen, deuterium, F, Cl, Br, —NH$_2$, —CN, —OH, —NO$_2$, carboxyl, substituted or unsubstituted —C$_{1-6}$alkoxy, or substituted or unsubstituted —C$_{1-6}$alkyl.

In some embodiments of Formula I, each of R$_{6a}$ and R$_{6b}$ is independently selected from hydrogen, deuterium, F, Cl, Br, —NH$_2$, —CN, —OH, —NO$_2$, carboxyl, substituted or unsubstituted —C$_{1-3}$alkoxy, or substituted or unsubstituted —C$_{1-3}$alkyl.

In some embodiments of Formula I, each of R$_{6a}$ and R$_{6b}$ is independently selected from hydrogen; deuterium; F; Cl; Br; —NH$_2$; —CN; —OH; —NO$_2$; carboxyl; methoxy; ethoxy; propoxy; isopropoxy; —C$_{1-3}$alkoxy substituted with halogen, NH$_2$, CN, OH, NO$_2$, carboxyl, C$_{1-3}$alkyl or C$_{1-3}$alkoxy; methyl; ethyl; propyl; isopropyl; —C$_{1-3}$alkyl substituted with halogen, NH$_2$, CN, OH, NO$_2$, carboxyl, C$_{1-3}$alkyl or C$_{1-3}$alkoxy.

In some embodiments of Formula I, each of R$_{6a}$ and R$_{6b}$ is independently selected from hydrogen; deuterium; F; Cl; Br; —NH$_2$; —CN; —OH; —NO$_2$; carboxyl; methoxy; ethoxy; propoxy; isopropoxy; —C$_{1-3}$alkoxy substituted with F, Cl, Br, NH$_2$, CN, OH, NO$_2$, carboxyl, methyl, ethyl, propyl, isopropyl, methoxy, ethoxy, propoxy or isopropoxy; methyl; ethyl; propyl; isopropyl; —C$_{1-3}$alkyl substituted with F, Cl, Br, NH$_2$, CN, OH, NO$_2$, carboxyl, methyl, ethyl, propyl, isopropyl, methoxy, ethoxy, propoxy or isopropoxy.

In some embodiments of Formula I, each of Ra is independently hydrogen, deuterium, F, Cl, Br, —NR$_{a1}$R$_{a2}$, —CN, —OH, —NO$_2$, oxo, =O, carboxyl, —C$_{1-3}$alkoxy, —C$_{1-4}$alkyl, —C$_{3-8}$cycloalkyl, —C$_{1-3}$alkylene-NR$_{a1}$R$_{a2}$, —$C_{1-3}$alkylene-O—$C_{1-6}$alkyl, —$C_{1-3}$alkylene-CO—$OR_{a1}$, —$C_{1-3}$alkylene-(3-8 membered heterocyclic), —$C_{1-3}$alkylene-(5-8 membered heteroaryl), —$C_{1-3}$alkylene-CO—$NR_{a1}R_{a2}$, —$C_{1-3}$alkylene-$NR_{a1}$—CO—$NR_{a1}R_{a2}$, —$C_{1-3}$alkylene-$NR_{a1}$—CO—$C_{1-3}$alkyl, —CO—$NR_{a1}R_{a2}$, —CO—CO—$NR_{a1}R_{a2}$, —$C_{3-8}$carbocyclic, —5-8 membered heteroaryl, -3-8 membered heterocyclic, —CO—$C_{1-3}$alkyl, —COO—$C_{1-3}$alkyl, —CO—$C_{1-3}$alkylene-$NR_{a1}R_{a2}$, —CO—$NR_{a1}$-(3-8 membered heterocyclic), —CO—$NR_1$-(3-8 membered heterocyclic), —CO-(3-8 membered heterocyclic), —O—$C_{1-3}$alkylene-CO—$OR_{a1}$, —O—$C_{1-3}$alkylene-CO—$NR_{a1}R_{a2}$, —O—$C_{1-3}$alkylene-$NR_{a1}R_{a2}$, —O—$C_{3-8}$carbocyclic, —O-(3-8 membered heterocyclic), —$NR_{a1}$—CO—$C_{1-3}$alkyl, —$NR_{a1}$—CO—$NR_{a1}R_{a2}$, —$NR_{a1}$—CO-(5-8 membered heteroaryl), —$NR_{a1}$—CO—$C_{3-6}$cycloalkyl, —$NR_{a1}$—$C_{1-3}$alkylene-$NR_{a1}R_{a2}$, —$NR_{a1}$—$C_{1-3}$alkylene-(3-8 membered heterocyclic), —$NR_{a1}$—$C_{1-3}$alkylene-(5-8 membered heteroaryl), —$NR_{a1}$—$SO_2C_{1-3}$alkyl, —S—$C_{1-3}$alkyl, —$SONR_{a1}R_{a2}$, —$SO_2NR_{a1}R_{a2}$, —SO—$C_{1-3}$alkyl, —$SO_2$—$C_{1-3}$alkyl, —PO($C_{1-3}$alkyl)$_2$, —PO($C_{1-3}$alkoxy)$_2$, -3-8 membered heterocyclic or -5-8 membered heteroaryl; each of which is independently optionally substituted; and n is 0, 1, 2, 3, 4, 5 or 6.

In some embodiments of Formula I, each of Ra is independently hydrogen, deuterium, F, Cl, Br, —$NR_{a1}R_{a2}$, —CN, —OH, —$NO_2$, oxo, =O, carboxyl, methoxy, ethoxy, propoxy, isopropoxy methyl, ethyl, propyl, isopropyl, butyl, isobutyl, —$C_{3-6}$cycloalkyl, —$C_{1-3}$alkylene-$NR_{a1}R_{a2}$, —$C_{1-3}$alkylene-O—$C_{1-6}$alkyl, —$C_{1-3}$alkylene-CO—$OR_{a1}$, —$C_{1-3}$alkylene-(3-8 membered heterocyclic), —$C_{1-3}$alkylene-(5-8 membered heteroaryl), —$C_{1-3}$alkylene-CO—$NR_{a1}R_{a2}$, —$C_{1-3}$alkylene-$NR_{a1}$—CO—$NR_{a1}R_{a2}$, —$C_{1-3}$alkylene-$NR_{a1}$—CO—$C_{1-3}$alkyl, —CO—$NR_{a1}R_{a2}$, —CO—CO—$NR_{a1}R_{a2}$, —$C_{3-8}$carbocyclic, -5-8 membered heteroaryl, -3-8 membered heterocyclic, —CO—$C_{1-3}$alkyl, —COO—$C_{1-3}$alkyl, —CO—$C_{1-3}$alkylene-$NR_{a1}R_{a2}$, —CO—$NR_{a1}$-(3-8 membered heterocyclic), —CO—$NR_{a1}$-(3-8 membered heterocyclic), —CO-(3-8 membered heterocyclic), —O—$C_{1-3}$alkylene-CO—$OR_{a1}$, —O—$C_{1-3}$alkylene-CO—$NR_{a1}R_{a2}$, —O—$C_{1-3}$alkylene-$NR_{a1}R_{a2}$, —O—$C_{3-8}$carbocyclic, —O-(3-8 membered heterocyclic), —$NR_{a1}$—CO—$C_{1-3}$alkyl, —$NR_{a1}$—CO—$NR_{a1}R_{a2}$, —$NR_{a1}$—CO-(5-8 membered heteroaryl), —$NR_{a1}$—CO—$C_{3-6}$cycloalkyl, —$NR_{a1}$—$C_{1-3}$alkylene-$NR_{a1}R_{a2}$, —$NR_{a1}$—$C_{1-3}$alkylene-(3-8 membered heterocyclic), —$NR_{a1}$—$C_{1-3}$alkylene-(5-8 membered heteroaryl), —$NR_{a1}$—$SO_2C_{1-3}$alkyl, —S—$C_{1-3}$alkyl, —$SONR_{a1}R_{a2}$, —$SO_2NR_{a1}R_{a2}$, —SO—$C_{1-3}$alkyl, —$SO_2$—$C_{1-3}$alkyl, —PO($C_{1-3}$alkyl)$_2$, —PO($C_{1-3}$alkoxy)$_2$, -3-8 membered heterocyclic or -5-8 membered heteroaryl; each of which is independently optionally substituted; and n is 0, 1, 2, 3, 4, 5 or 6.

In some embodiments of Formula I, two adjacent Ra can be joined together to form a 6-membered aromatic ring, a 5-membered heteroaromatic ring, a 6-membered heteroaromatic ring, a 3-6 membered heterocyclic ring or a 3-6 membered carbocyclic ring, wherein each of the ring systems is independently optionally substituted with deuterium, halogen, —$NH_2$, —CN, —OH, —$NO_2$, carboxyl, —$C_{1-6}$alkyl or —$C_{1-6}$alkoxy.

In some embodiments of Formula I, two adjacent Ra can be joined together to form a 6-membered aromatic ring, a 5-membered heteroaromatic ring, a 6-membered heteroaromatic ring, a 3-6 membered heterocyclic ring or a 3-6 membered carbocyclic ring, wherein each of the ring systems is independently optionally substituted with deuterium, F, Cl, Br, —$NH_2$, —CN, —OH, —$NO_2$, carboxyl, —$C_{1-3}$alkyl or —$C_{1-3}$alkoxy.

In some embodiments of Formula I, two adjacent Ra can be joined together to form a 6-membered aromatic ring, a 5-membered heteroaromatic ring, a 6-membered heteroaromatic ring, a 3 membered heterocyclic ring, a 4 membered heterocyclic ring, a 5 membered heterocyclic ring, a 6 membered heterocyclic ring, a 3 membered carbocyclic ring, a 4 membered carbocyclic ring, a 5 membered carbocyclic ring, a 6 membered carbocyclic ring, wherein each of the heteroaryl contains 1, 2 or 3 heteroatoms selected from N, O or S, and each of the heterocyclic ring contains 1, 2 or 3 heteroatoms selected from N, O or S, each of the ring systems is independently optionally substituted with deuterium, F, Cl, Br, —$NH_2$, —CN, —OH, —$NO_2$, carboxyl, —$C_{1-3}$alkyl or —$C_{1-3}$alkoxy.

In some embodiments of Formula I, Ra and $R_W$ with the atom to which they are both attached form a 3-10 membered aromatic ring, 3-10 membered heteroaromatic ring or 3-10 membered heterocyclic ring; and each of the ring systems is independently optionally substituted with deuterium, halogen, —$NH_2$, —CN, —OH, —$NO_2$, carboxyl, —$C_{1-6}$alkyl or —$C_{1-6}$alkoxy.

In some embodiments of Formula I, Ra and $R_W$ with the atom to which they are both attached form a 3-10 membered aromatic ring, 3-10 membered heteroaromatic ring or 3-10 membered heterocyclic ring; and each of the ring systems is independently optionally substituted with deuterium, F, Cl, Br, —$NH_2$, —CN, —OH, —$NO_2$, carboxyl, —$C_{1-3}$alkyl or —$C_{1-3}$alkoxy.

In some embodiments of Formula I, Ra and $R_W$ with the atom to which they are both attached form a 3-10 membered aromatic ring, 3-10 membered heteroaromatic ring or 3-10 membered heterocyclic ring; each of the heteroaromatic ring contains 1, 2 or 3 heteroatoms selected from N, O or S; each of the heterocyclic ring contains 1, 2 or 3 heteroatoms selected from N, O or S; and each of the ring systems is independently optionally substituted with deuterium, F, Cl, Br, —$NH_2$, —CN, —OH, —$NO_2$, carboxyl, —$C_{1-3}$alkyl or —$C_{1-3}$alkoxy.

In some embodiments of Formula I, Ra and $R_W$ with the atom to which they are both attached form a 5 membered aromatic ring, a 6 membered aromatic ring, a 5 membered heteroaryl ring, a 6 membered heteroaryl ring, a 5 membered heterocyclic ring or a 6 membered heterocyclic ring; each of the heteroaromatic ring contains 1, 2 or 3 heteroatoms selected from N, O or S; each of the heterocyclic ring contains 1, 2 or 3 heteroatoms selected from N, O or S; and each of the ring systems is independently optionally substituted with deuterium, F, Cl, Br, —$NH_2$, —CN, —OH, —$NO_2$, carboxyl, —$C_{1-3}$alkyl or —$C_{1-3}$alkoxy.

In some embodiments of Formula I, each of $R_{a1}$ and $R_{a2}$ is independently selected from hydrogen, deuterium, F, Cl, Br, —$NH_2$, —CN, —OH, —$NO_2$, carboxyl, substituted or unsubstituted —$C_{1-6}$alkoxy, or substituted or unsubstituted —$C_{1-6}$alkyl.

In some embodiments of Formula I, each of $R_{a1}$ and $R_{a2}$ is independently selected from hydrogen, deuterium, F, Cl, Br, —$NH_2$, —CN, —OH, —$NO_2$, carboxyl, substituted or unsubstituted —$C_{1-3}$alkoxy, or substituted or unsubstituted —$C_{1-3}$alkyl.

In some embodiments of Formula I, each of $R_{a1}$ and $R_{a2}$ is independently selected from hydrogen; deuterium; F; Cl; Br; —$NH_2$; —CN; —OH; —$NO_2$; carboxyl; methoxy; ethoxy; propoxy; isopropoxy; —$C_{1-3}$alkoxy substituted with halogen, $NH_2$, CN, OH, $NO_2$, carboxyl, $C_{1-3}$alkyl or $C_{1-3}$alkoxy; methyl; ethyl; propyl; isopropyl; —$C_{1-3}$alkyl substituted with halogen, $NH_2$, CN, OH, $NO_2$, carboxyl, $C_{1-3}$alkyl or $C_{1-3}$alkoxy.

In some embodiments of Formula I, each of $R_{a1}$ and $R_{a2}$ is independently selected from hydrogen; deuterium; F; Cl; Br; —$NH_2$; —CN; —OH; —$NO_2$; carboxyl; methoxy; ethoxy; propoxy; isopropoxy; —$C_{1-3}$alkoxy substituted with F, Cl, Br, $NH_2$, CN, OH, $NO_2$, carboxyl, methyl, ethyl, propyl, isopropyl, methoxy, ethoxy, propoxy or isopropoxy; methyl; ethyl; propyl; isopropyl; —$C_{1-3}$alkyl substituted with F, Cl, Br, $NH_2$, CN, OH, $NO_2$, carboxyl, methyl, ethyl, propyl, isopropyl, methoxy, ethoxy, propoxy or isopropoxy.

The present invention further provides the compound of Formula II or a pharmaceutically acceptable salt thereof:

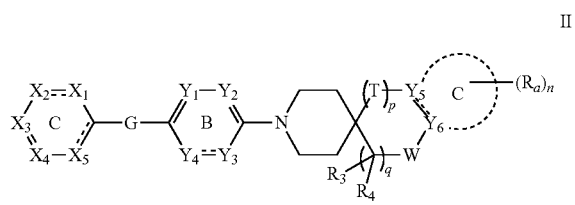

II

- $X_1$ is N, S, $NR_{X1}$, $C(R_{X1})_2$, or $CR_{X1}$;
- each of $R_{X1}$ is independently selected from hydrogen, deuterium, halogen, —$NH_2$, —$CONH_2$, —CN, —$C_{1-6}$alkyl or —$C_{1-6}$alkoxy, and each of which is independently optionally substituted with 1, 2, 3, 4, 5, or 6 substituents, and the said each substituents is independently selected from deuterium, halogen, —$NH_2$, —CN, —OH, —$NO_2$, carboxyl, —$C_{1-6}$alkyl or —$C_{1-6}$alkoxy;
- $X_2$ is N, S, $NR_{X2}$, $C(R_{X2})_2$, $CR_{X2}$ or CO;
- each of $R_{X2}$ is independently selected from hydrogen, deuterium, halogen, —$NH_2$, —CN, —$C_{1-6}$alkyl, —$C_{1-6}$alkoxy, —CO—$C_{1-6}$alkyl, —NH—$C_{1-6}$alkyl, —N—($C_{1-6}$alkyl)$_2$, —$SF_5$, —NHCO—$C_{3-8}$cycloalkyl, —NH—$C_{3-8}$cycloalkyl, —$C_{1-6}$alkylene-(3-8 membered heterocyclyl), —NHCO-(5-12 membered heterocyclyl), —NH—$C_{1-6}$alkylene-$C_{3-8}$cycloalkyl or 3-8 membered heterocyclic, and each of which is independently optionally substituted with 1, 2, 3, 4, 5, or 6 substituents, and the said each substituents is independently selected from deuterium, halogen, —$NH_2$, —CN, —OH, -oxo, =O, —$NO_2$, carboxyl, —$C_{1-6}$alkyl or —$C_{1-6}$alkoxy; or
- $R_{X1}$ and $R_{X2}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;
- $X_3$ is N, S, $NR_{X3}$, $C(R_{X3})_2$ or $CR_{X3}$;
- each of $R_{X3}$ is independently selected from hydrogen, deuterium, halogen, carboxyl, —$NO_2$, —$NH_2$, —CN, —$CONH_2$, —$C_{1-6}$alkyl, —$C_{1-6}$alkoxy, $C_{3-8}$cycloalkyl, $C_{5-8}$aryl, —S—$C_{1-6}$alkyl, 3-12 membered heterocyclyl, —O—$C_{3-8}$cycloalkyl, —O—$C_{1-6}$alkylene-$C_{1-6}$alkoxy, —O—$C_{5-8}$aryl or —O—$C_{1-6}$alkylene-$C_{5-8}$aryl, and each of which is independently optionally substituted with 1, 2, 3, 4, 5, or 6 substituents, and the said each substituents is independently selected from deuterium, halogen, —$NH_2$, —CN, —OH, —$NO_2$, carboxyl, —$C_{1-6}$alkyl or —$C_{1-6}$alkoxy; or
- $R_{X2}$ and $R_{X3}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;
- $X_4$ is N, S, $NR_{X4}$, $C(R_{X4})_2$ or $CR_{X4}$;
- each of $R_{X4}$ is independently selected from hydrogen, deuterium, halogen, —$NH_2$, —CN, —OH, —$C_{1-6}$alkyl, —$C_{1-6}$alkoxy, —NHCO-(5-12 membered heterocyclyl) or 5-12 membered heteroaryl, and each of which is independently optionally substituted with 1, 2, 3, 4, 5, or 6 substituents, and the said each substituents is independently selected from deuterium, halogen, —$NH_2$, —CN, —OH, oxo, =O, —$NO_2$, carboxyl, —$C_{1-6}$alkyl or —$C_{1-6}$alkoxy; or
- $R_{X3}$ and $R_{X4}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;
- $X_5$ is N, S, $NR_{X5}$, $C(R_{X5})_2$ or $CR_{X5}$;
- each of $R_{X5}$ is independently selected from hydrogen, deuterium, halogen, —$NH_2$, —CN, —$C_{1-6}$alkyl or —$C_{1-6}$alkoxy, and each of which is independently optionally substituted with 1, 2, 3, 4, 5, or 6 substituents, and the said each substituents is independently selected from deuterium, halogen, —$NH_2$, —CN, —OH, —$NO_2$, carboxyl, —$C_{1-6}$alkyl or —$C_{1-6}$alkoxy; or
- $R_{X4}$ and $R_{X5}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;
- ------ represents a single bond or a double bond;
- G is selected from absent, S, —SO—, —$SO_2$—, O, —CO—, —$NR_G$—, —$NR_G$—$SO_2$—,

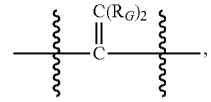

—$C(R_G)_2$— or —$SO_2$—$NR_G$—;
- each of $R_G$ is independently selected from hydrogen, deuterium, halogen, —$NH_2$, —CN, —OH, —$C_{1-6}$alkyl or —$C_{1-6}$alkoxy, and each of which is independently optionally substituted or unsubstituted;
- $Y_1$ is N or $CR_{Y1}$;
- $R_{Y1}$ is selected from hydrogen, deuterium, halogen, —$NH_2$, —OH, —CN, —$C_{1-6}$alkyl, —$C_{1-6}$alkoxy, —NH—$C_{1-6}$alkyl, —N—($C_{1-6}$alkyl)$_2$, —$C_{1-6}$alkenyl, —$C_{3-8}$cycloalkyl or —$C_{5-10}$aryl, and each of which is independently optionally substituted with 1, 2, 3, 4, 5, or 6 substituents, and the said each substituents is independently selected from deuterium, halogen, —$NH_2$, —CN, —OH, —$NO_2$, carboxyl, —$C_{1-6}$alkyl or —$C_{1-6}$alkoxy;
- $Y_2$ is N or $CR_{Y2}$;
- $R_{Y2}$ is selected from hydrogen, deuterium, halogen, —$NH_2$, —CN, —$C_{1-6}$alkyl, —$C_{1-6}$alkoxy, —NH—$C_{1-6}$alkyl, —N—($C_{1-6}$alkyl)$_2$, —$C_{1-6}$alkenyl, —$C_{3-8}$cycloalkyl or —$C_{5-10}$aryl, and each of which is independently optionally substituted with 1, 2, 3, 4, 5, or 6 substituents, and the said each substituents is independently selected from deuterium, halogen, —NH$_2$, —CN, —OH, —NO$_2$, carboxyl, —C$_{1-6}$alkyl or —C$_{1-6}$alkoxy; or R$_{Y1}$ and R$_{Y2}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;

when the "=====" in the term "Y$_3$===== Y$_4$" represents a single bond, Y$_3$ is NR$_{Y3}$ or C(R$_{Y3}$)$_2$, and Y$_4$ is CO, C(R$_{Y4}$)$_2$ or NR$_{Y4}$;

when the "=====" in the term "Y$_3$===== Y$_4$" represents a double bond, Y$_3$ is N or ===== CR$_{Y3}$, and Y$_4$ is N or CR$_{Y4}$;

R$_{Y3}$ and R$_{Y4}$ are independently selected from hydrogen, deuterium, halogen, —NH$_2$, —OH, —CN, —C$_{1-6}$alkyl, carboxyl, —COO—C$_{1-6}$alkyl, —NH—C$_{1-6}$alkylene-OH, —C$_{1-6}$alkylene-OH, —CONH$_2$ or -5-8 membered heteroaryl, and each of which is independently optionally substituted with 1, 2, 3, 4, 5, or 6 substituents, and the said each substituents is independently selected from deuterium, halogen, —NH$_2$, —CN, —OH, —NO$_2$, carboxyl, —C$_{1-6}$alkyl or —C$_{1-6}$alkoxy; or R$_{Y3}$ and R$_{Y4}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;

T is absent, O, NR$_1$ or CR$_1$R$_2$;

each of R$_1$ and R$_2$ is independently selected from hydrogen, deuterium, halogen, —NH$_2$, —CN, —OH, —NO$_2$, carboxyl, —NH—C$_{1-6}$alkyl, —N(C$_{1-6}$alkyl)$_2$, substituted or unsubstituted —C$_{1-6}$alkoxy, or substituted or unsubstituted —C$_{1-6}$alkyl; or R$_1$ and R$_2$ together with the carbon atom to which they are both attached form CO or C=NR$_5$;

p is 0, 1, 2 or 3;

each of R$_3$ and R$_4$ is independently selected from hydrogen, deuterium, halogen, —NH$_2$, —CN, —OH, —NO$_2$, carboxyl, —NH—C$_{1-6}$alkyl, —N(C$_{1-6}$alkyl)$_2$, substituted or unsubstituted —C$_{1-6}$alkoxy, or substituted or unsubstituted —C$_{1-6}$alkyl; or R$_3$ and R$_4$ together with the carbon atom to which they are both attached form a 3-12 membered heterocyclic ring or a 5-12 membered heteroaromatic ring or C=NR$_5$, and each of the ring systems is independently optionally substituted or unsubstituted;

each of R$_5$ is independently selected from hydrogen, deuterium, halogen, —NH$_2$, —CN, —OH, —C$_{1-6}$alkyl or —C$_{1-6}$alkoxy;

q is 0, 1, 2, 3 or 4;

W is absent, —O, —S or —C(R$_W$)$_2$—; and each of R$_W$ is independently selected from hydrogen, deuterium, halogen, —NH$_2$, —CN, —OH, —NO$_2$, carboxyl, —CO—C$_{1-6}$alkyl, —CO—OC$_{1-6}$alkyl, —C$_{1-6}$alkyl-O— C$_{1-6}$alkoxy, substituted or unsubstituted —C$_{1-6}$alkoxy, or substituted or unsubstituted —C$_{1-6}$alkyl;

ring C is absent, a 5-12 membered aromatic ring, a 5-12 membered heteroaromatic ring or a 5-12 membered heterocyclic ring, and each of the ring systems is independently optionally substituted or unsubstituted;

when ring C is absent, Y$_5$ is CR$_{5a}$R$_{5b}$, NR$_{5a}$ or O, and Y$_6$ is CR$_{6a}$R$_{6b}$, NR$_{6a}$ or O;

when ring C is a 5-12 membered aromatic ring, a 5-12 membered heteroaromatic ring or a 5-12 membered heterocyclic ring;

i) Y$_5$ is CR$_{5a}$ or N, and Y$_6$ is CR$_{6a}$ or N, when the "=====" in the term "Y$_5$===== Y$_6$" represents a single bond; or ii) Y$_5$ is C, and Y$_6$ is C, when the "=====" in the term "Y$_5$===== Y$_6$" represents a double bond;

each of R$_{5a}$ and R$_{5b}$ is independently selected from hydrogen, deuterium, halogen, —NH$_2$, —CN, —OH, —NO$_2$, carboxyl, substituted or unsubstituted —C$_{1-6}$alkoxy, or substituted or unsubstituted —C$_{1-6}$alkyl;

each of R$_{6a}$ and R$_{6b}$ is independently selected from hydrogen, deuterium, halogen, —NH$_2$, —CN, —OH, —NO$_2$, carboxyl, substituted or unsubstituted —C$_{1-6}$alkoxy, or substituted or unsubstituted —C$_{1-6}$alkyl;

each of Ra is independently hydrogen, deuterium, halogen, —NR$_{a1}$R$_{a2}$, —CN, —OH, —NO$_2$, oxo, =O, carboxyl, —C$_{1-6}$alkoxy, —C$_{1-6}$alkyl, —C$_{3-8}$cycloalkyl, —C$_{1-6}$alkylene-NR$_{a1}$R$_{a2}$, —C$_{1-6}$alkylene-O—C$_{1-6}$alkyl, —C$_{1-6}$alkylene-CO—OR$_{a1}$, —C$_{1-6}$alkylene-(3-10 membered heterocyclic), —C$_{1-6}$alkylene-(5-10 membered heteroaryl), —C$_{1-6}$alkylene-CO—NR$_{a1}$R$_{a2}$, —C$_{1-6}$alkylene-NR$_{a1}$—CO—NR$_{a1}$R$_{a2}$, —C$_{1-6}$alkylene-NR$_{a1}$—CO—C$_{1-6}$alkyl, —CO—NR$_{a1}$R$_{a2}$, —CO—CO—NR$_{a1}$R$_{a2}$, —C$_{3-10}$carbocyclic, -5-10 membered heteroaryl, -3-10 membered heterocyclic, —CO—C$_{1-6}$alkyl, —COO—C$_{1-6}$alkyl, —CO—C$_{1-6}$alkylene-NR$_{a1}$R$_{a2}$, —CO—NR$_{a1}$-(3-10 membered heterocyclic), —CO—NR$_{a1}$-(3-10 membered heterocyclic), —CO-(3-10 membered heterocyclic), —O—C$_{1-6}$alkylene-CO—OR$_{a1}$, —O—C$_{1-6}$alkylene-CO—NR$_{a1}$R$_{a2}$, —O—C$_{1-6}$alkylene-NR$_{a1}$R$_{a2}$, —O—C$_{3-10}$carbocyclic, —O-(3-10 membered heterocyclic), —NR$_1$—CO—C$_{1-6}$alkyl, —NR$_{a1}$—CO—NR$_{a1}$R$_{a2}$, —NR$_{a1}$—CO-(5-10 membered heteroaryl), —NR$_{a1}$—CO—C$_{3-8}$cycloalkyl, —NR$_1$—C$_{1-6}$alkylene-NR$_{a1}$R$_{a2}$, —NR$_{a1}$—C$_{1-6}$alkylene-(3-10 membered heterocyclic), —NR$_{a1}$—C$_{1-6}$alkylene-(5-10 membered heteroaryl), —NR$_{a1}$—SO$_2$C$_{1-6}$alkyl, —S—C$_{1-6}$alkyl, —SONR$_{a1}$R$_{a2}$, —SO$_2$NR$_{a1}$R$_{a2}$, —SO—C$_{1-6}$alkyl, —SO$_2$—C$_{1-6}$alkyl, —PO(C$_{1-6}$alkyl)$_2$, —PO(C$_{1-6}$alkoxy)$_2$, -3-10 membered heterocyclic or -5-10 membered heteroaryl; each of which is independently optionally substituted; and n is 0, 1, 2, 3, 4, 5 or 6; or two adjacent Ra can be joined together to form a 6-membered aromatic ring, a 5-membered heteroaomatic ring, a 6-membered heteroaromatic ring, a 3-6 membered heterocyclic ring or a 3-6 membered carbocyclic ring, wherein each of the ring systems is independently optionally substituted;

each of R$_1$ and R$_2$ is independently selected from hydrogen, deuterium, halogen, —NH$_2$, —CN, —OH, —NO$_2$, carboxyl, substituted or unsubstituted —C$_{1-6}$alkoxy, or substituted or unsubstituted —C$_{1-6}$alkyl.

In some embodiments of Formula II, X$_1$ is N, S, NR$_{X1}$, C(R$_{X1}$)$_2$, or CR$_{X1}$; each of R$_{X1}$ is independently selected from hydrogen, deuterium, F, Cl, Br, —NH$_2$, —CONH$_2$, —CN, —C$_{1-6}$alkyl or —C$_{1-6}$alkoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-6}$alkyl or —C$_{1-6}$alkoxy.

In some embodiments of Formula II, X$_1$ is N, S, NR$_{X1}$, C(R$_{X1}$)$_2$, or CR$_{X1}$; each of R$_{X1}$ is independently selected from hydrogen, deuterium, F, Cl, Br, —NH$_2$, —CONH$_2$, —CN, —C$_{1-6}$alkyl or —C$_{1-6}$alkoxy, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula II, $X_1$ is N, S, $NR_{X1}$, $C(R_{X1})_2$, or $CR_{X1}$; each of $R_{X1}$ is independently selected from hydrogen, deuterium, F, Cl, Br, —$NH_2$, —$CONH_2$, —CN, —$C_{1-3}$alkyl or —$C_{1-3}$alkoxy, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula II, $X_1$ is N, S, $NR_{X1}$, $C(R_{X1})_2$, or $CR_{X1}$; each of $R_{X1}$ is independently selected from hydrogen, deuterium, F, Cl, Br, —$NH_2$, —$CONH_2$, —CN, methyl, ethyl, propyl, isopropyl, methoxy, ethoxy, propoxy or isopropoxy, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, methyl, ethyl, propyl, isopropyl, methoxy, ethoxy, propoxy or isopropoxy.

In some embodiments of Formula II, $X_1$ is N, S, $NR_{X1}$, $C(R_{X1})_2$, or $CR_{X1}$; each of $R_{X1}$ is independently selected from hydrogen, deuterium, F, Cl, Br, —$NH_2$, —$CONH_2$, —CN, methyl, ethyl, propyl, isopropyl, methoxy, ethoxy, propoxy or isopropoxy, and each of which is independently optionally substituted with 1, 2 or 3 substituents, and the said each substituents is independently selected from deuterium, F, Cl, Br, I, —$NH_2$, —CN, —OH, —$NO_2$, carboxyl, methyl, ethyl, propyl, isopropyl, methoxy, ethoxy, propoxy or isopropoxy.

In some embodiments of Formula II, $X_2$ is N, S, $NR_{X2}$, $C(R_{X2})_2$, $CR_{X2}$ or CO; each of $R_{X2}$ is independently selected from hydrogen, deuterium, F, Cl, Br, —$NH_2$, —CN, —$C_{1-6}$alkyl, —$C_{1-6}$alkoxy, —CO—$C_{1-6}$alkyl, —NH—$C_{1-6}$alkyl, —N—($C_{1-6}$alkyl)$_2$, —$SF_5$, —NHCO—$C_{3-8}$cycloalkyl, —NH—$C_{3-8}$cycloalkyl, —$C_{1-6}$alkylene-(3-8 membered heterocyclyl), —NHCO-(5-12 membered heterocyclyl), —NH—$C_{1-6}$alkylene-$C_{3-8}$cycloalkyl or 3-8 membered heterocyclic, and each of which is independently optionally substituted with 1, 2, 3, 4, 5, or 6 substituents, and the said each substituents is independently selected from deuterium, F, Cl, Br, I, —$NH_2$, —CN, —OH, -oxo, =O, —$NO_2$, carboxyl, —$C_{1-6}$alkyl or —$C_{1-6}$alkoxy.

In some embodiments of Formula II, $X_2$ is N, S, $NR_{X2}$, $C(R_{X2})_2$, $CR_{X2}$ or CO; each of $R_{X2}$ is independently selected from hydrogen, deuterium, F, Cl, Br, —$NH_2$, —CN, —$C_{1-6}$alkyl, —$C_{1-6}$alkoxy, —CO—$C_{1-6}$alkyl, —NH—$C_{1-6}$alkyl, —N—($C_{1-6}$alkyl)$_2$, —$SF_5$, —NHCO—$C_{3-8}$cycloalkyl, —NH—$C_{3-8}$cycloalkyl, —$C_{1-6}$alkylene-(3-8 membered heterocyclyl), —NHCO-(5-12 membered heterocyclyl), —NH—$C_{1-6}$alkylene-$C_{3-8}$cycloalkyl or 3-8 membered heterocyclic, and each of which is independently optionally substituted with 1, 2, 3, 4, 5, or 6 substituents, and the said each substituents is independently selected from deuterium, F, Cl, Br, I, —$NH_2$, —CN, —OH, -oxo, =O, —$NO_2$, carboxyl, —$C_{1-3}$alkyl or —$C_{1-3}$alkoxy.

In some embodiments of Formula II, $X_2$ is N, S, $NR_{X2}$, $C(R_{X2})_2$, $CR_{X2}$ or CO; each of $R_{X2}$ is independently selected from hydrogen, deuterium, F, Cl, Br, —$NH_2$, —CN, —$C_{1-3}$alkyl, —$C_{1-3}$alkoxy, —CO—$C_{1-3}$alkyl, —NH—$C_{1-3}$alkyl, —N—($C_{1-3}$alkyl)$_2$, —$SF_5$, —NHCO—$C_{3-6}$cycloalkyl, —NH—$C_{3-6}$cycloalkyl, —$C_{1-3}$alkylene-(3-6 membered heterocyclyl), —NHCO-(5-10 membered heterocyclyl), —NH—$C_{1-3}$alkylene-$C_{3-6}$cycloalkyl or 3-6 membered heterocyclic, and each of which is independently optionally substituted with 1, 2, 3, 4, 5, or 6 substituents, and the said each substituents is independently selected from deuterium, F, Cl, Br, I, —$NH_2$, —CN, —OH, -oxo, =O, —$NO_2$, carboxyl, —$C_{1-3}$alkyl or —$C_{1-3}$alkoxy.

In some embodiments of Formula II, $X_2$ is N, S, $NR_{X2}$, $C(R_{X2})_2$, $CR_{X2}$ or CO; each of $R_{X2}$ is independently selected from hydrogen, deuterium, F, Cl, Br, —$NH_2$, —CN, methyl, ethyl, propyl, isopropyl, methoxy, ethoxy, propoxy, isopropoxy, —CO—$C_{1-3}$alkyl, —NH—$C_{1-3}$alkyl, —N—($C_{1-3}$alkyl)$_2$, —$SF_5$, —NHCO—$C_{3-6}$cycloalkyl, —NH—$C_{3-6}$cycloalkyl, —$C_{1-3}$alkylene-(3-6 membered heterocyclyl), —NHCO-(5-10 membered heterocyclyl), —NH—$C_{1-3}$alkylene-$C_{3-6}$cycloalkyl, 3 membered heterocyclic, 4 membered heterocyclic, 5 membered heterocyclic or 6 membered heterocyclic, and each of which is independently optionally substituted with 1, 2, 3, 4, 5, or 6 substituents, and the said each substituents is independently selected from deuterium, F, Cl, Br, I, —$NH_2$, —CN, —OH, -oxo, =O, —$NO_2$, carboxyl, methyl, ethyl, propyl, isopropyl, methoxy, ethoxy, propoxy or isopropoxy.

In some embodiments of Formula II, $X_2$ is N, S, $NR_{X2}$, $C(R_{X2})_2$, $CR_{X2}$ or CO; each of $R_{X2}$ is independently selected from hydrogen, deuterium, F, Cl, Br, —$NH_2$, —CN, methyl, ethyl, propyl, isopropyl, methoxy, ethoxy, propoxy, isopropoxy, —CO—$C_{1-3}$alkyl, —NH—$C_{1-3}$alkyl, —N—($C_{1-3}$alkyl)$_2$, —$SF_5$, —NHCO—$C_{3-6}$cycloalkyl, —NH—$C_{3-6}$cycloalkyl, —$C_{1-3}$alkylene-(3-6 membered heterocyclyl), —NHCO-(5-10 membered heterocyclyl), —NH—$C_{1-3}$alkylene-$C_{3-6}$cycloalkyl, 3 membered heterocyclic, 4 membered heterocyclic, 5 membered heterocyclic or 6 membered heterocyclic, and each of which is independently optionally substituted with 1, 2 or 3 substituents, and the said each substituents is independently selected from deuterium, F, Cl, Br, I, —$NH_2$, —CN, —OH, -oxo, =O, —$NO_2$, carboxyl, methyl, ethyl, propyl, isopropyl, methoxy, ethoxy, propoxy or isopropoxy.

In some embodiments of Formula II, $R_{X1}$ and $R_{X2}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, $R_{X1}$ and $R_{X2}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, $R_{X1}$ and $R_{X2}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring or a 10 membered heterocyclic ring, and each of the heteroaromatic ring contains 1, 2 or 3 heteroatoms selected from N, O or S, and each of the heterocyclic ring contains 1, 2 or 3 heteroatoms selected from N or O, and each of the ring systems is independently optionally substituted or unsubstituted.

In some embodiments of Formula II, $X_3$ is N, S, $NR_{X3}$, $C(R_{X3})_2$ or $CR_{X3}$; each of $R_{X3}$ is independently selected from hydrogen, deuterium, F, Cl, Br, carboxyl, —$NO_2$, —$NH_2$, —CN, —$CONH_2$, —$C_{1-6}$alkyl, —$C_{1-6}$alkoxy, $C_{3-8}$cycloalkyl, $C_{5-8}$aryl, —S—$C_{1-6}$alkyl, 3-12 membered heterocyclyl, —O—$C_{3-8}$cycloalkyl, —O—$C_{1-6}$alkylene-$C_{1-6}$alkoxy, —O—$C_{5-8}$aryl or —O—$C_{1-4}$alkylene-$C_{5-8}$aryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-6}$alkyl or —$C_{1-6}$alkoxy.

In some embodiments of Formula II, $X_3$ is N, S, $NR_{X3}$, $C(R_{X3})_2$ or $CR_{X3}$; each of $R_{X3}$ is independently selected from hydrogen, deuterium, F, Cl, Br, carboxyl, —$NO_2$, —$NH_2$, —CN, —$CONH_2$, —$C_{1-6}$alkyl, —$C_{1-6}$alkoxy, $C_{3-8}$cycloalkyl, $C_{5-8}$aryl, —S—$C_{1-6}$alkyl, 3-12 membered heterocyclyl, —O—$C_{3-8}$cycloalkyl, —O—$C_{1-6}$alkylene-$C_{1-6}$alkoxy, —O—$C_{5-8}$aryl or —O—$C_{1-6}$alkylene-$C_{5-8}$aryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula II, $X_3$ is N, S, $NR_{X3}$, $C(R_{X3})_2$ or $CR_{X3}$; each of $R_{X3}$ is independently selected from hydrogen, deuterium, F, Cl, Br, carboxyl, —$NO_2$, —$NH_2$, —CN, —$CONH_2$, —$C_{1-3}$alkyl, —$C_{1-3}$alkoxy, $C_{3-6}$cycloalkyl, $C_{5-8}$aryl, —S—$C_{1-3}$alkyl, 3-10 membered heterocyclyl, —O—$C_{3-8}$cycloalkyl, —O—$C_{1-3}$alkylene-$C_{1-3}$alkoxy, —O—$C_{5-8}$aryl or —O—$C_{1-6}$alkylene-$C_{5-8}$aryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula II, $X_3$ is N, S, $NR_{X3}$, $C(R_{X3})_2$ or $CR_{X3}$; each of $R_{X3}$ is independently selected from hydrogen, deuterium, F, Cl, Br, carboxyl, —$NO_2$, —$NH_2$, —CN, —$CONH_2$, methyl, ethyl, propyl, isopropyl, methoxy, ethoxy, propoxy, isopropoxy, $C_{3-6}$cycloalkyl, $C_{5-8}$aryl, —S—$C_{1-3}$alkyl, 3-10 membered heterocyclyl, —O—$C_{3-6}$cycloalkyl or —O—$C_{1-3}$alkylene-$C_{1-3}$alkoxy, —O—$C_{5-8}$aryl or —O—$C_{1-3}$alkylene-$C_{5-8}$aryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, methyl, ethyl, propyl, isopropyl, methoxy, ethoxy, propoxy or isopropoxy.

In some embodiments of Formula II, $X_3$ is N, S, $NR_{X3}$, $C(R_{X3})_2$ or $CR_{X3}$; each of $R_{X3}$ is independently selected from hydrogen, deuterium, F, Cl, Br, carboxyl, —$NO_2$, —$NH_2$, —CN, —$CONH_2$, methyl, ethyl, propyl, isopropyl, methoxy, ethoxy, propoxy, isopropoxy, $C_{3-6}$cycloalkyl, $C_{5-8}$aryl, —S—$C_{1-3}$alkyl, 3-10 membered heterocyclyl, —O—$C_{3-6}$cycloalkyl or —O—$C_{1-3}$alkylene-$C_{1-3}$alkoxy, —O—$C_{5-8}$aryl or —O—$C_{1-3}$alkylene-$C_{5-8}$aryl, and each of which is independently optionally substituted with 1, 2 or 3 substituents, and the said each substituents is independently selected from deuterium, F, Cl, Br, I, —$NH_2$, —CN, —OH, —$NO_2$, carboxyl, methyl, ethyl, propyl, isopropyl, methoxy, ethoxy, propoxy or isopropoxy.

In some embodiments of Formula II, $R_{X2}$ and $R_{X3}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, $R_{X2}$ and $R_{X3}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, $R_{X2}$ and $R_{X3}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring, or a 10 membered heterocyclic ring, and each of the heteroaromatic ring contains 1, 2 or 3 heteroatoms selected from N, O or S, and each of the heterocyclic ring contains 1, 2 or 3 heteroatoms selected from N or O, and each of the ring systems is independently optionally substituted or unsubstituted.

In some embodiments of Formula II, $X_4$ is N, S, $NR_{X4}$, $C(R_{X4})_2$ or $CR_{X4}$; each of $R_{X4}$ is independently selected from hydrogen, deuterium, F, Cl, Br, —$NH_2$, —CN, —OH, —$C_{1-6}$alkyl, —$C_{1-6}$alkoxy, —NHCO-(5-12 membered heterocyclyl) or 5-12 membered heteroaryl, and each of which is independently optionally substituted with 1, 2, 3, 4, 5, or 6 substituents, and the said each substituents is independently selected from deuterium, F, Cl, Br, I, —$NH_2$, —CN, —OH, oxo, =O, —$NO_2$, carboxyl, —$C_{1-6}$alkyl or —$C_{1-6}$alkoxy.

In some embodiments of Formula II, $X_4$ is N, S, $NR_{X4}$, $C(R_{X4})_2$ or $CR_{X4}$; each of $R_{X4}$ is independently selected from hydrogen, deuterium, F, Cl, Br, —$NH_2$, —CN, —OH, —$C_{1-6}$alkyl, —$C_{1-6}$alkoxy, —NHCO-(5-12 membered heterocyclyl) or 5-12 membered heteroaryl, and each of which is independently optionally substituted with 1, 2, 3, 4, 5, or 6 substituents, and the said each substituents is independently selected from deuterium, F, Cl, Br, I, —$NH_2$, —CN, —OH, oxo, =O, —$NO_2$, carboxyl, —$C_{1-3}$alkyl or —$C_{1-3}$alkoxy.

In some embodiments of Formula II, $X_4$ is N, S, $NR_{X4}$, $C(R_{X4})_2$ or $CR_{X4}$; each of $R_{X4}$ is independently selected from hydrogen, deuterium, F, Cl, Br, —$NH_2$, —CN, —OH, —$C_{1-3}$alkyl, —$C_{1-3}$alkoxy, —NHCO-(5-10 membered heterocyclyl) or 5-10 membered heteroaryl, and each of which is independently optionally substituted with 1, 2, 3, 4, 5, or 6 substituents, and the said each substituents is independently selected from deuterium, F, Cl, Br, I, —$NH_2$, —CN, —OH, oxo, =O, —$NO_2$, carboxyl, —$C_{1-3}$alkyl or —$C_{1-3}$alkoxy.

In some embodiments of Formula II, $X_4$ is N, S, $NR_{X4}$, $C(R_{X4})_2$ or $CR_{X4}$; each of $R_{X4}$ is independently selected from hydrogen, deuterium, F, Cl, Br, —$NH_2$, —CN, —OH, methyl, ethyl, propyl, isopropyl, methoxy, ethoxy, propoxy, isopropoxy, —NHCO-(5-10 membered heterocyclyl), 5 membered heteroaryl, 6 membered heteroaryl, 7 membered heteroaryl, 8 membered heteroaryl, 9 membered heteroaryl or 10 membered heteroaryl, and each of which is independently optionally substituted with 1, 2, 3, 4, 5, or 6 substituents, and the said each substituents is independently selected from deuterium, F, Cl, Br, I, —NH$_2$, —CN, —OH, oxo, =O, —NO$_2$, carboxyl, methyl, ethyl, propyl, isopropyl, methoxy, ethoxy, propoxy or isopropoxy.

In some embodiments of Formula II, $X_4$ is N, S, NR$_{X4}$, C(R$_{X4}$)$_2$ or CR$_{X4}$; each of R$_{X4}$ is independently selected from hydrogen, deuterium, F, Cl, Br, —NH$_2$, —CN, —OH, methyl, ethyl, propyl, isopropyl, methoxy, ethoxy, propoxy, isopropoxy, —NHCO-(5-10 membered heterocyclyl), 5 membered heteroaryl, 6 membered heteroaryl, 7 membered heteroaryl, 8 membered heteroaryl, 9 membered heteroaryl or 10 membered heteroaryl, and each of which is independently optionally substituted with 1, 2 or 3 substituents, and the said each substituents is independently selected from deuterium, F, Cl, Br, I, —NH$_2$, —CN, —OH, oxo, =O, —NO$_2$, carboxyl, methyl, ethyl, propyl, isopropyl, methoxy, ethoxy, propoxy or isopropoxy.

In some embodiments of Formula II, R$_{X3}$ and R$_{X4}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, R$_{X3}$ and R$_{X4}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, R$_{X3}$ and R$_{X4}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring or a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, $X_5$ is N, S, NR$_{X5}$, C(R$_{X5}$)$_2$ or CR$_{X5}$; each of R$_{X5}$ is independently selected from hydrogen, deuterium, F, Cl, Br, —NH$_2$, —CN, —C$_{1-6}$alkyl or —C$_{1-6}$alkoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-6}$alkyl or —C$_{1-6}$alkoxy.

In some embodiments of Formula II, $X_5$ is N, S, NR$_{X5}$, C(R$_{X5}$)$_2$ or CR$_{X5}$; each of R$_{X5}$ is independently selected from hydrogen, deuterium, F, Cl, Br, —NH$_2$, —CN, —C$_{1-6}$alkyl or —C$_{1-6}$alkoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-3}$alkyl or —C$_{1-3}$alkoxy.

In some embodiments of Formula II, $X_5$ is N, S, NR$_{X5}$, C(R$_{X5}$)$_2$ or CR$_{X5}$; each of R$_{X5}$ is independently selected from hydrogen, deuterium, F, Cl, Br, —NH$_2$, —CN, —C$_{1-3}$alkyl or —C$_{1-3}$alkoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-3}$alkyl or —C$_{1-3}$alkoxy.

In some embodiments of Formula II, $X_5$ is N, S, NR$_{X5}$, C(R$_{X5}$)$_2$ or CR$_{X5}$; each of R$_{X5}$ is independently selected from hydrogen, deuterium, F, Cl, Br, —NH$_2$, —CN, methyl, ethyl, propyl, isopropyl, methoxy, ethoxy, propoxy or isopropoxy, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, methyl, ethyl, propyl, isopropyl, methoxy, ethoxy, propoxy or isopropoxy.

In some embodiments of Formula II, $X_5$ is N, S, NR$_{X5}$, C(R$_{X5}$)$_2$ or CR$_{X5}$; each of R$_{X5}$ is independently selected from hydrogen, deuterium, F, Cl, Br, —NH$_2$, —CN, methyl, ethyl, propyl, isopropyl, methoxy, ethoxy, propoxy or isopropoxy, and each of which is independently optionally substituted with 1, 2 or 3 substituents, and the said each substituents is independently selected from deuterium, F, Cl, Br, I, —NH$_2$, —CN, —OH, —NO$_2$, carboxyl, methyl, ethyl, propyl, isopropyl, methoxy, ethoxy, propoxy or isopropoxy.

In some embodiments of Formula II, R$_{X4}$ and R$_{X5}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, R$_{X4}$ and R$_{X5}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, R$_{X4}$ and R$_{X5}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring or a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.
In some embodiments of Formula II, ring A is selected from
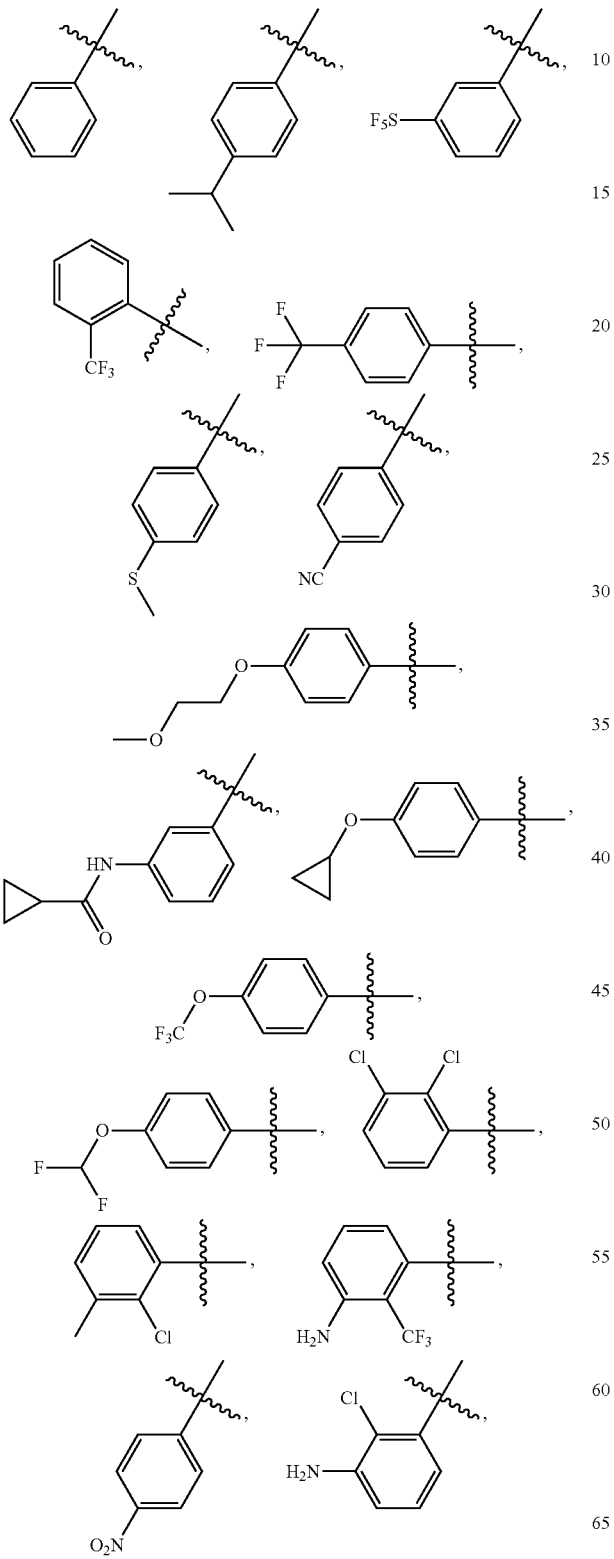
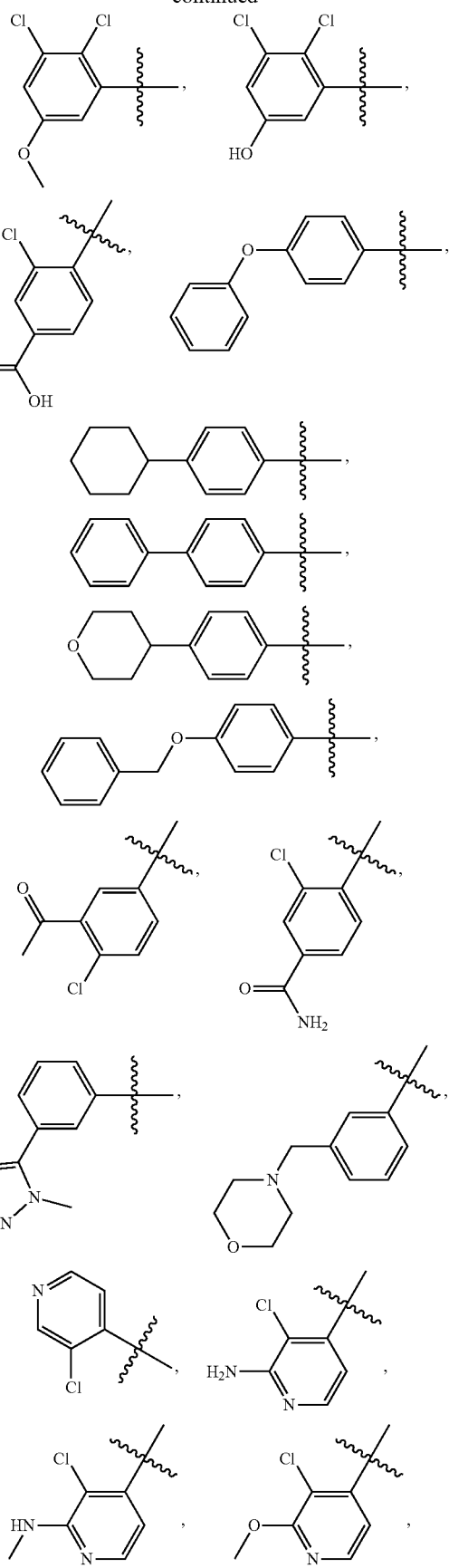

-continued

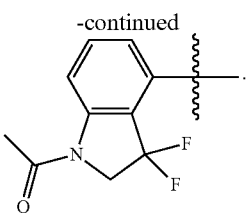

In some embodiments of Formula II, G is selected from absent, S, —SO—, —SO$_2$—, O, —CO—, —NR$_G$—, —NR$_G$—SO$_2$—,

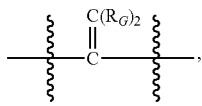

—C(R$_G$)$_2$— or —SO$_2$—NR$_G$—; each of R$_G$ is independently selected from hydrogen, deuterium, F, Br, —NH$_2$, —CN, —OH, —C$_{1-6}$alkyl or —C$_{1-6}$alkoxy, and each of which is independently optionally substituted or unsubstituted.

In some embodiments of Formula II, G is selected from absent, S, —SO—, —SO$_2$—, O, —CO—, —NR$_G$—, —NR$_G$—SO$_2$—,

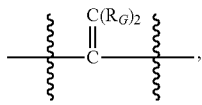

—C(R$_G$)$_2$— or —SO$_2$—NR$_G$—; each of R$_G$ is independently selected from hydrogen, deuterium, F, Cl, Br, —NH$_2$, —CN, —OH, —C$_{1-3}$alkyl or —C$_{1-3}$alkoxy, and each of which is independently optionally substituted or unsubstituted.

In some embodiments of Formula II, G is selected from absent, S, —SO—, —SO$_2$—, O, —CO—, —NR$_G$—, —NR$_G$—SO$_2$—,

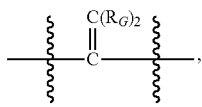

—C(R$_G$)$_2$— or —SO$_2$—NR$_G$—; each of R$_G$ is independently selected from hydrogen, deuterium, F, Cl, Br, —NH$_2$, —CN, —OH, methyl, ethyl, propyl, isopropyl, methoxy, ethoxy, propoxy or isopropoxy, and each of which is independently optionally substituted or unsubstituted.

In some embodiments of Formula II, Y$_1$ is N or CR$_{Y1}$; R$_{Y1}$ is selected from hydrogen, deuterium, F, Cl, Br, —NH$_2$, —OH, —CN, —C$_{1-6}$alkyl, —C$_{1-6}$alkoxy, —NH—C$_{1-6}$alkyl, —N—(C$_{1-6}$alkyl)$_2$, —C$_{1-6}$alkenyl, —C$_{3-4}$cycloalkyl or —C$_{5-10}$aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-6}$alkyl or —C$_{1-6}$alkoxy.

In some embodiments of Formula II, Y$_1$ is N or CR$_{Y1}$; R$_{Y1}$ is selected from hydrogen, deuterium, F, Cl, Br, —NH$_2$, —OH, —CN, —C$_{1-6}$alkyl, —C$_{1-6}$alkoxy, —NH—C$_{1-6}$alkyl, —N—(C$_{1-6}$alkyl)$_2$, —C$_{1-6}$alkenyl, —C$_{3-8}$cycloalkyl or —Cm-aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-3}$alkyl or —C$_{1-3}$alkoxy.

In some embodiments of Formula II, Y$_1$ is N or CR$_{Y1}$; R$_{Y1}$ is selected from hydrogen, deuterium, F, Cl, Br, —NH$_2$, —OH, —CN, —C$_{1-3}$alkyl, —C$_{1-3}$alkoxy, —NH—C$_{1-3}$alkyl, —N—(C$_{1-3}$alkyl)$_2$, —C$_{1-3}$alkenyl, —C$_3$cycloalkyl or —Cm-aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-3}$alkyl or —C$_{1-3}$alkoxy.

In some embodiments of Formula II, Y$_1$ is N or CR$_{Y1}$; R$_{Y1}$ is selected from hydrogen, deuterium, F, Cl, Br, —NH$_2$, —OH, —CN, methyl, ethyl, propyl, isopropyl, methoxy, ethoxy, propoxy, isopropoxy, —NH—C$_{1-3}$alkyl, —N—(C$_{1-3}$alkyl)$_2$, —C$_{1-3}$alkenyl, —C$_{3-6}$cycloalkyl or —Cm-aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, methyl, ethyl, propyl, isopropyl, methoxy, ethoxy, propoxy or isopropoxy.

In some embodiments of Formula II, Y$_2$ is N or CR$_{Y2}$; R$_{Y2}$ is selected from hydrogen, deuterium, F, Cl, Br, —NH$_2$, —CN, —C$_{1-6}$alkyl, —C$_{1-6}$alkoxy, —NH—C$_{1-6}$alkyl, —N—(C$_{1-6}$alkyl)$_2$, —C$_{1-6}$ alkenyl, —C$_{3-8}$cycloalkyl or —C$_{5-10}$aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-6}$alkyl or —C$_{1-6}$alkoxy.

In some embodiments of Formula II, Y$_2$ is N or CR$_{Y2}$; R$_{Y2}$ is selected from hydrogen, deuterium, F, Cl, Br, —NH$_2$, —CN, —C$_{1-6}$alkyl, —C$_{1-6}$alkoxy, —NH—C$_{1-6}$alkyl, —N—(C$_{1-6}$alkyl)$_2$, —C$_{1-6}$ alkenyl, —C$_{3-8}$cycloalkyl or —C$_{5-10}$aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-3}$alkyl or —C$_{1-3}$alkoxy.

In some embodiments of Formula II, Y$_2$ is N or CR$_{Y2}$; R$_{Y2}$ is selected from hydrogen, deuterium, F, Cl, Br, —NH$_2$, —CN, —C$_{1-3}$alkyl, —C$_{1-3}$alkoxy, —NH—C$_{1-3}$alkyl, —N—(C$_{1-3}$alkyl)$_2$, —C$_{1-3}$alkenyl, —C$_{3-6}$cycloalkyl or —C$_{5-8}$aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —C$_{1-3}$alkyl or —C$_{1-3}$alkoxy.

In some embodiments of Formula II, Y$_2$ is N or CR$_{Y2}$; R$_{Y2}$ is selected from hydrogen, deuterium, F, Cl, Br, —NH$_2$, —CN, methyl, ethyl, propyl, isopropyl, methoxy, ethoxy, propoxy, isopropoxy, —NH—C$_{1-3}$alkyl, —N—(C$_{1-3}$alkyl)$_2$, —C$_{1-3}$alkenyl, —C$_{3-6}$cycloalkyl or —C$_{5-8}$aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, methyl, ethyl, propyl, isopropyl, methoxy, ethoxy, propoxy or isopropoxy.

In some embodiments of Formula II, R$_{Y1}$ and R$_{Y2}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, $R_{Y1}$ and $R_{Y2}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, $R_{Y1}$ and $R_{Y2}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring, a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, $R_{Y3}$ and $R_{Y4}$ are independently selected from hydrogen, deuterium, F, Cl, Br, —$NH_2$, —OH, —CN, —$C_{1-6}$alkyl, carboxyl, —COO—$C_{1-6}$alkyl, —NH—$C_{1-6}$alkylene-OH, —$C_{1-6}$alkylene-OH, —$CONH_2$ or -5-8 membered heteroaryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-6}$alkyl or —$C_{1-6}$alkoxy.

In some embodiments of Formula II, $R_{Y3}$ and $R_{Y4}$ are independently selected from hydrogen, deuterium, F, Cl, Br, —$NH_2$, —OH, —CN, —$C_{1-6}$alkyl, carboxyl, —COO—$C_{1-6}$alkyl, —NH—$C_{1-6}$alkylene-OH, —$C_{1-6}$alkylene-OH, —$CONH_2$ or -5-8 membered heteroaryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula II, $R_{Y3}$ and $R_{Y4}$ are independently selected from hydrogen, deuterium, F, Cl, Br, —$NH_2$, —OH, —CN, —$C_{1-3}$alkyl, carboxyl, —COO—$C_{1-3}$alkyl, —NH—$C_{1-3}$alkylene-OH, —$C_{1-3}$alkylene-OH, —$CONH_2$ or -5-8 membered heteroaryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula II, $R_{Y3}$ and $R_{Y4}$ are independently selected from hydrogen, deuterium, F, Cl, Br, —$NH_2$, —OH, —CN, methyl, ethyl, propyl, isopropyl, carboxyl, —COO—$C_{1-3}$alkyl, —NH—$C_{1-3}$alkylene-OH, —$C_{1-3}$alkylene-OH, —$CONH_2$ or -5-8 membered heteroaryl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, methyl, ethyl, propyl, isopropyl, methoxy, ethoxy, propoxy or isopropoxy.

In some embodiments of Formula II, $R_{Y3}$ and $R_{Y4}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, $R_{Y3}$ and $R_{Y4}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, $R_{Y3}$ and $R_{Y4}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring, a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, ring B is selected from

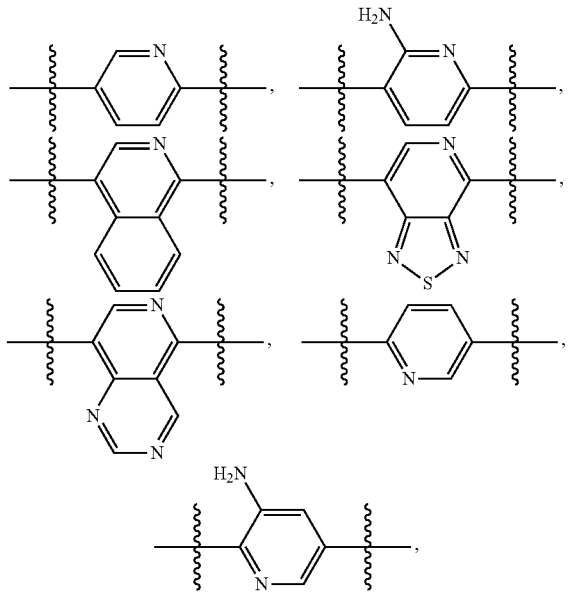

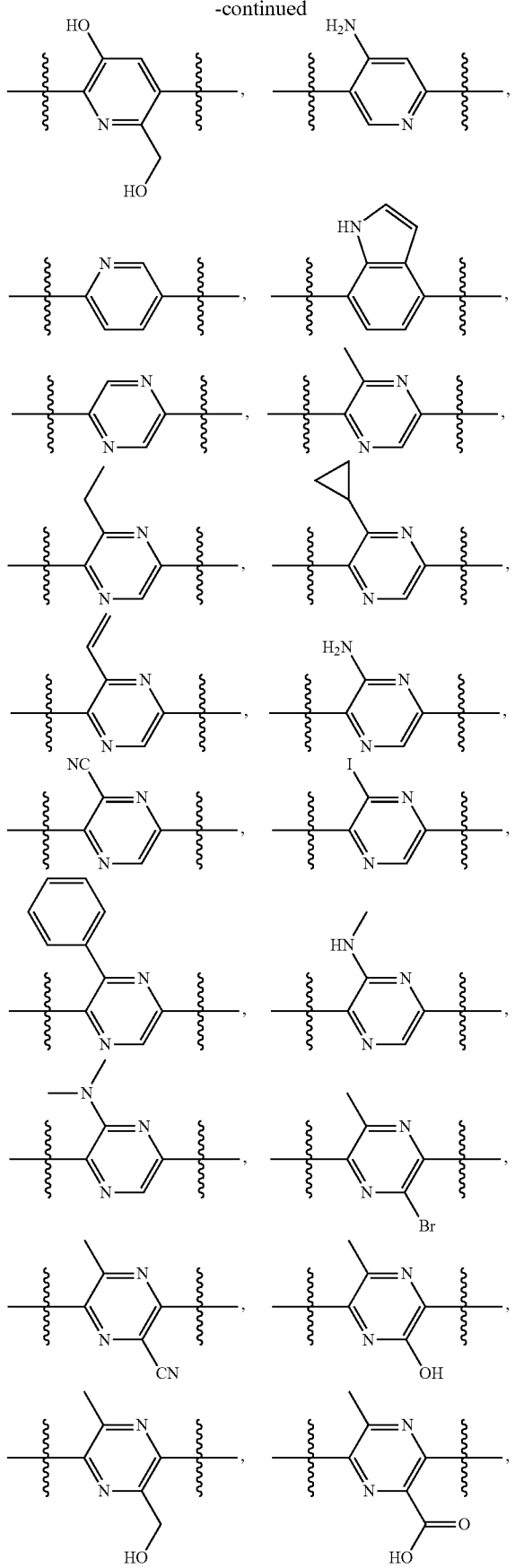
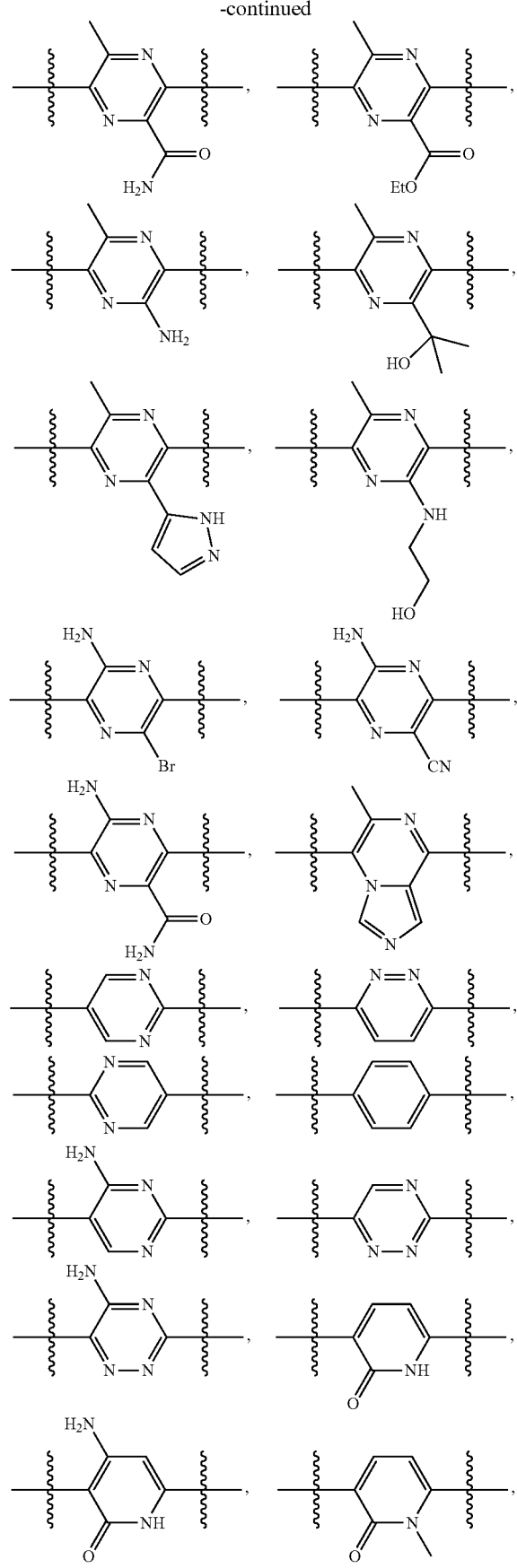

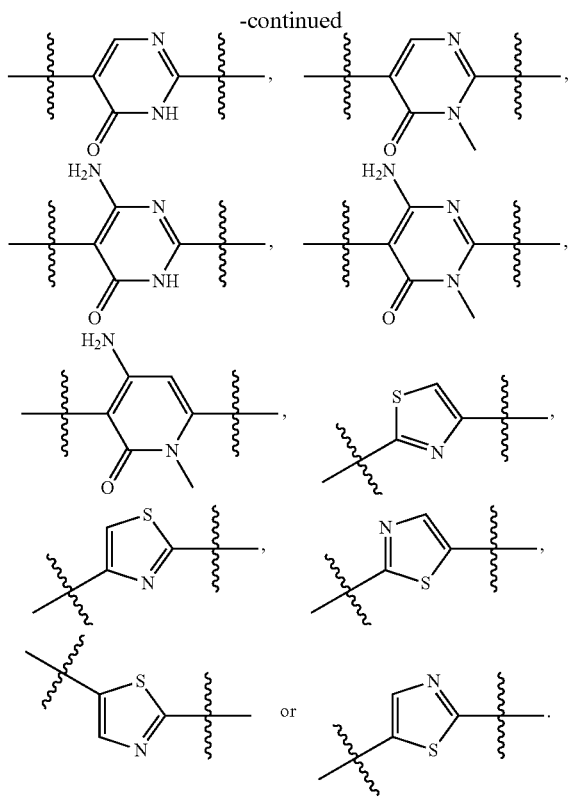

In some embodiments of Formula II, each of $R_1$ and $R_2$ is independently selected from hydrogen, deuterium, F, Cl, Br, —$NH_2$, —CN, —OH, —$NO_2$, carboxyl, —NH—$C_{1-6}$alkyl, —N($C_{1-6}$alkyl)$_2$, substituted or unsubstituted —$C_{1-6}$alkoxy, or substituted or unsubstituted —$C_{1-6}$alkyl.

In some embodiments of Formula II, each of $R_1$ and $R_2$ is independently selected from hydrogen, deuterium, F, Cl, Br, —$NH_2$, —CN, —OH, —$NO_2$, carboxyl, —NH—$C_{1-3}$alkyl, —N($C_{1-3}$alkyl)$_2$, substituted or unsubstituted —$C_{1-3}$alkoxy, or substituted or unsubstituted —$C_{1-3}$alkyl.

In some embodiments of Formula II, each of $R_1$ and $R_2$ is independently selected from hydrogen; deuterium; F; Cl; Br; —$NH_2$; —CN; —OH; —$NO_2$; carboxyl; —NH—$C_{1-3}$alkyl; —N($C_{1-3}$alkyl)$_2$; methoxy; ethoxy; propoxy; isopropoxy; —$C_{1-3}$alkoxy substituted with halogen, $NH_2$, CN, OH, $NO_2$, carboxyl, $C_{1-3}$alkyl or $C_{1-3}$alkoxy; methyl; ethyl; propyl; isopropyl; —$C_{1-3}$alkyl substituted with halogen, $NH_2$, CN, OH, $NO_2$, carboxyl, $C_{1-3}$alkyl or $C_{1-3}$alkoxy.

In some embodiments of Formula II, each of $R_1$ and $R_2$ is independently selected from hydrogen; deuterium; F; Cl; Br; —$NH_2$; —CN; —OH; —$NO_2$; carboxyl; —NH—$C_{1-3}$alkyl; —N($C_{1-3}$alkyl)$_2$; methoxy; ethoxy; propoxy; isopropoxy; —$C_{1-3}$alkoxy substituted with F, Cl, Br, $NH_2$, CN, OH, $NO_2$, carboxyl, methyl, ethyl, propyl, isopropyl, methoxy, ethoxy, propoxy or isopropoxy; methyl; ethyl; propyl; isopropyl; —$C_{1-3}$alkyl substituted with F, Cl, Br, $NH_2$, CN, OH, $NO_2$, carboxyl, methyl, ethyl, propyl, isopropyl, methoxy, ethoxy, propoxy or isopropoxy.

In some embodiments of Formula II, $R_1$ and $R_2$ together with the carbon atom to which they are both attached form CO or C=$NR_5$.

In some embodiments of Formula II, $R_1$ and $R_2$ together with the carbon atom to which they are both attached form CO.

In some embodiments of Formula II, $R_1$ and $R_2$ together with the carbon atom to which they are both attached form C=$NR_5$.

In some embodiments of Formula II, each of $R_3$ and $R_4$ is independently selected from hydrogen, deuterium, F, Cl, Br, —$NH_2$, —CN, —OH, —$NO_2$, carboxyl, —NH—$C_{1-6}$alkyl, —N($C_{1-6}$alkyl)$_2$, substituted or unsubstituted —$C_{1-6}$alkoxy, or substituted or unsubstituted —$C_{1-6}$alkyl.

In some embodiments of Formula II, each of $R_3$ and $R_4$ is independently selected from hydrogen, deuterium, F, Cl, Br, —$NH_2$, —CN, —OH, —$NO_2$, carboxyl, —NH—$C_{1-3}$alkyl, —N($C_{1-3}$alkyl)$_2$, substituted or unsubstituted —$C_{1-3}$alkoxy, or substituted or unsubstituted —$C_{1-3}$alkyl.

In some embodiments of Formula II, each of $R_3$ and $R_4$ is independently selected from hydrogen; deuterium; F; Cl; Br; —$NH_2$; —CN; —OH; —$NO_2$; carboxyl; —NH—$C_{1-3}$alkyl; —N($C_{1-3}$alkyl)$_2$; methoxy; ethoxy; propoxy; isopropoxy; —$C_{1-3}$alkoxy substituted with halogen, $NH_2$, CN, OH, $NO_2$, carboxyl, $C_{1-3}$alkyl or $C_{1-3}$alkoxy; methyl; ethyl; propyl; isopropyl; —$C_{1-3}$alkyl substituted with halogen, $NH_2$, CN, OH, $NO_2$, carboxyl, $C_{1-3}$alkyl or $C_{1-3}$alkoxy.

In some embodiments of Formula II, each of $R_3$ and $R_4$ is independently selected from hydrogen; deuterium; F; Cl; Br; —$NH_2$; —CN; —OH; —$NO_2$; carboxyl; —NH—$C_{1-3}$alkyl; —N($C_{1-3}$alkyl)$_2$; methoxy; ethoxy; propoxy; isopropoxy; —$C_{1-3}$alkoxy substituted with F, Cl, Br, $NH_2$, CN, OH, $NO_2$, carboxyl, methyl, ethyl, propyl, isopropyl, methoxy, ethoxy, propoxy or isopropoxy; methyl; ethyl; propyl; isopropyl; —$C_{1-3}$alkyl substituted with F, Cl, Br, $NH_2$, CN, OH, $NO_2$, carboxyl, methyl, ethyl, propyl, isopropyl, methoxy, ethoxy, propoxy or isopropoxy.

In some embodiments of Formula II, $R_3$ and $R_4$ together with the carbon atom to which they are both attached form a 3-12 membered heterocyclic ring or a 5-12 membered heteroaromatic ring or C=$NR_5$, and each of the heterocyclic ring contains 1, 2 or 3 heteroatoms selected from N, O or S, and each of the heteroaromatic ring contains 1, 2 or 3 heteroatoms selected from N, O or S, and each of the ring systems is independently optionally substituted or unsubstituted.

In some embodiments of Formula II, $R_3$ and $R_4$ together with the carbon atom to which they are both attached form a 3-10 membered heterocyclic ring or a 5-10 membered heteroaromatic ring or C=$NR_5$, and each of the heterocyclic ring contains 1, 2 or 3 heteroatoms selected from N, O or S, and each of the heteroaromatic ring contains 1, 2 or 3 heteroatoms selected from N, O or S, and each of the ring systems is independently optionally substituted or unsubstituted.

In some embodiments of Formula II, $R_3$ and $R_4$ together with the carbon atom to which they are both attached form a 3 membered heterocyclic ring, a 4 membered heterocyclic ring, a 5 membered heterocyclic ring, a 6 membered heterocyclic ring, a 7 membered heterocyclic ring, an 8 membered heterocyclic ring, a 9 membered heterocyclic ring, a 10 membered heterocyclic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring or C=$NR_5$, and each of the heterocyclic ring contains 1, 2 or 3 heteroatoms selected from N, O or S, and each of the heteroaromatic ring contains 1, 2 or 3 heteroatoms selected from N, O or S, and each of the ring systems is independently optionally substituted or unsubstituted.

In some embodiments of Formula II, each of $R_5$ is independently selected from hydrogen, deuterium, F, Cl, Br, —$NH_2$, —CN, —OH, —$C_{1-6}$alkyl or —$C_{1-6}$alkoxy.

In some embodiments of Formula II, each of $R_5$ is independently selected from hydrogen, deuterium, F, Cl, Br, —$NH_2$, —CN, —OH, —$C_{1-3}$alkyl or —$C_{1-3}$alkoxy.

In some embodiments of Formula II, each of $R_5$ is independently selected from hydrogen, deuterium, F, Cl, Br, —$NH_2$, —CN, —OH, methyl, ethyl, propyl, isopropyl, methoxy, ethoxy, propoxy or isopropoxy.

In some embodiments of Formula II, W is absent, —O, —S or —$C(R_W)_2$—; and each of $R_W$ is independently selected from hydrogen, deuterium, F, Cl, Br, —$NH_2$, —CN, —OH, —$NO_2$, carboxyl, —CO—$C_{1-6}$alkyl, —CO—$OC_{1-6}$alkyl, —$C_{1-6}$alkyl-O—$C_{1-6}$alkoxy, substituted or unsubstituted —$C_{1-6}$alkoxy, or substituted or unsubstituted —$C_{1-6}$alkyl.

In some embodiments of Formula II, W is absent, —O, —S or —$C(R_W)_2$—; and each of $R_W$ is independently selected from hydrogen, deuterium, F, Cl, Br, —$NH_2$, —CN, —OH, —$NO_2$, carboxyl, —CO—$C_{1-3}$alkyl, —CO—$OC_{1-3}$alkyl, —$C_{1-3}$alkyl-O—$C_{1-3}$alkoxy, substituted or unsubstituted —$C_{1-3}$alkoxy, or substituted or unsubstituted —$C_{1-3}$alkyl.

In some embodiments of Formula II, W is absent, —O, —S or —$C(R_W)_2$—; and each of $R_W$ is independently selected from hydrogen; deuterium; F; Cl; Br; —$NH_2$; —CN; —OH; —$NO_2$; carboxyl; —CO—$C_{1-3}$alkyl; —CO—$OC_{1-3}$alkyl; —$C_{1-3}$alkyl-O—$C_{1-3}$alkoxy; methoxy; ethoxy; propoxy; isopropoxy; —$C_{1-3}$alkoxy substituted with halogen, $NH_2$, CN, OH, $NO_2$, carboxyl, $C_{1-3}$alkyl or $C_{1-3}$alkoxy; methyl; ethyl; propyl; isopropyl; —$C_{1-3}$alkyl substituted with halogen, $NH_2$, CN, OH, $NO_2$, carboxyl, $C_{1-3}$alkyl or $C_{1-3}$alkoxy.

In some embodiments of Formula II, W is absent, —O, —S or —$C(R_W)_2$—; and each of $R_W$ is independently selected from hydrogen; deuterium; F; Cl; Br; —$NH_2$; —CN; —OH; —$NO_2$; carboxyl; —CO—$C_{1-3}$alkyl; —CO—$OC_{1-3}$alkyl; —$C_{1-3}$alkyl-O—$C_{1-3}$alkoxy; methoxy; ethoxy; propoxy; isopropoxy; —$C_{1-3}$alkoxy substituted with halogen, $NH_2$, CN, OH, $NO_2$, carboxyl, $C_{1-3}$alkyl or $C_{1-3}$alkoxy; methyl; ethyl; propyl; isopropyl; —$C_{1-3}$alkyl substituted with halogen, $NH_2$, CN, OH, $NO_2$, carboxyl, $C_{1-3}$alkyl or $C_{1-3}$alkoxy.

In some embodiments of Formula II, W is absent, —O, —S or —$C(R_W)_2$—; and each of $R_W$ is independently selected from hydrogen; deuterium; F; Cl; Br; —$NH_2$; —CN; —OH; —$NO_2$; carboxyl; —CO—$C_{1-3}$alkyl; —CO—$OC_{1-3}$alkyl; —$C_{1-3}$alkyl-O—$C_{1-3}$alkoxy; methoxy; ethoxy; propoxy; isopropoxy; —$C_{1-3}$alkoxy substituted with F, Cl, Br, $NH_2$, CN, OH, $NO_2$, carboxyl, methyl, ethyl, propyl, isopropyl, methoxy, ethoxy, propoxy or isopropoxy; methyl; ethyl; propyl; isopropyl; —$C_{1-3}$alkyl substituted with F, Cl, Br, $NH_2$, CN, OH, $NO_2$, carboxyl, methyl, ethyl, propyl, isopropyl, methoxy, ethoxy, propoxy or isopropoxy.

In some embodiments of Formula II, ring C is absent, a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, ring C is absent, a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, ring C is absent, a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, a 8 membered heterocyclic ring, a 9 membered heterocyclic ring, a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula II, ring C is selected from

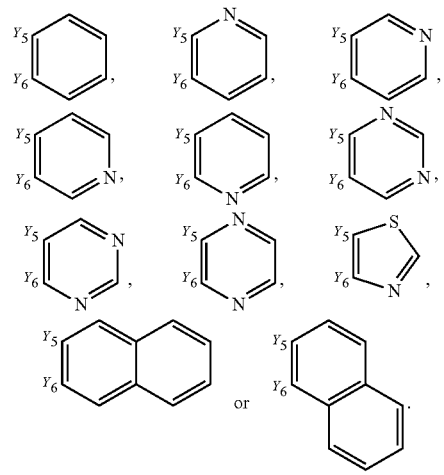

In some embodiments of Formula II, each of $R_{5a}$ and $R_{5b}$ is independently selected from hydrogen, deuterium, F, Cl, Br, —$NH_2$, —CN, —OH, —$NO_2$, carboxyl, substituted or unsubstituted —$C_{1-6}$alkoxy, or substituted or unsubstituted —$C_{1-6}$alkyl.

In some embodiments of Formula II, each of Ra and $R_{5b}$ is independently selected from hydrogen, deuterium, F, Cl, Br, —$NH_2$, —CN, —OH, —$NO_2$, carboxyl, substituted or unsubstituted —$C_{1-3}$alkoxy, or substituted or unsubstituted —$C_{1-3}$alkyl.

In some embodiments of Formula II, each of Ra and Rb is independently selected from hydrogen; deuterium; F; Cl; Br; —$NH_2$; —CN; —OH; —$NO_2$; carboxyl; methoxy; ethoxy; propoxy; isopropoxy; —$C_{1-3}$alkoxy substituted with halogen, $NH_2$, CN, OH, $NO_2$, carboxyl, $C_{1-3}$alkyl or $C_{1-3}$alkoxy; methyl; ethyl; propyl; isopropyl; —$C_{1-3}$alkyl substituted with halogen, $NH_2$, CN, OH, $NO_2$, carboxyl, $C_{1-3}$alkyl or $C_{1-3}$alkoxy.

In some embodiments of Formula II, each of Ra and Rb is independently selected from hydrogen; deuterium; F; Cl; Br; —$NH_2$; —CN; —OH; —$NO_2$; carboxyl; methoxy; ethoxy; propoxy; isopropoxy; —$C_{1-3}$alkoxy substituted with F, Cl, Br, $NH_2$, CN, OH, $NO_2$, carboxyl, methyl, ethyl, propyl, isopropyl, methoxy, ethoxy, propoxy or isopropoxy; —$C_{1-3}$alkyl substituted with F, Cl, Br, $NH_2$, CN, OH, $NO_2$, carboxyl, methyl, ethyl, propyl, isopropyl, methoxy, ethoxy, propoxy or isopropoxy.

In some embodiments of Formula II, each of $R_{6a}$ and $R_{6b}$ is independently selected from hydrogen, deuterium, F, Cl, Br, —$NH_2$, —CN, —OH, —$NO_2$, carboxyl, substituted or unsubstituted —$C_{1-6}$alkoxy, or substituted or unsubstituted —$C_{1-6}$alkyl.

In some embodiments of Formula II, each of $R_{6a}$ and $R_{6b}$ is independently selected from hydrogen, deuterium, F, Cl, Br, —$NH_2$, —CN, —OH, —$NO_2$, carboxyl, substituted or unsubstituted —$C_{1-3}$alkoxy, or substituted or unsubstituted —$C_{1-3}$alkyl.

In some embodiments of Formula II, each of $R_{6a}$ and $R_{6b}$ is independently selected from hydrogen; deuterium; F; Cl; Br; —$NH_2$; —CN; —OH; —$NO_2$; carboxyl; methoxy; ethoxy; propoxy; isopropoxy; —$C_{1-3}$alkoxy substituted with halogen, $NH_2$, CN, OH, $NO_2$, carboxyl, $C_{1-3}$alkyl or $C_{1-3}$alkoxy; methyl; ethyl; propyl; isopropyl; —$C_{1-3}$alkyl substituted with halogen, $NH_2$, CN, OH, $NO_2$, carboxyl, $C_{1-3}$alkyl or $C_{1-3}$alkoxy.

In some embodiments of Formula II, each of $R_{6a}$ and $R_{6b}$ is independently selected from hydrogen; deuterium; F; Cl; Br; —$NH_2$; —CN; —OH; —$NO_2$; carboxyl; methoxy; ethoxy; propoxy; isopropoxy; —$C_{1-3}$alkoxy substituted with F, Cl, Br, $NH_2$, CN, OH, $NO_2$, carboxyl, methyl, ethyl, propyl, isopropyl, methoxy, ethoxy, propoxy or isopropoxy; methyl; ethyl; propyl; isopropyl; —$C_{1-3}$alkyl substituted with F, Cl, Br, $NH_2$, CN, OH, $NO_2$, carboxyl, methyl, ethyl, propyl, isopropyl, methoxy, ethoxy, propoxy or isopropoxy.

In some embodiments of Formula II, each of Ra is independently selected from hydrogen, deuterium, F, Cl, Br, —$NR_{a1}R_{a2}$, —CN, —OH, —$NO_2$, oxo, =O, carboxyl, —$C_{1-3}$alkoxy, —$C_{1-3}$alkyl, —$C_{3-6}$cycloalkyl, —$C_{1-3}$alkylene-$NR_{a1}R_{a2}$, —$C_{1-3}$alkylene-O—$C_{1-6}$alkyl, —$C_{1-3}$alkylene-CO—$OR_{a1}$, —$C_{1-3}$alkylene-(3-8 membered heterocyclic), —$C_{1-3}$alkylene-(5-8 membered heteroaryl), —$C_{1-3}$alkylene-CO—$NR_{a1}R_{a2}$, —$C_{1-3}$alkylene-$NR_{a1}$—CO—$NR_{a1}R_{a2}$, —$C_{1-3}$alkylene-$NR_{a1}$—CO—$C_{1-3}$alkyl, —CO—$NR_{a1}R_{a2}$, —CO—CO—$NR_{a1}R_{a2}$, —$C_{3-8}$carbocyclic, -5-10 membered heteroaryl, -3-8 membered heterocyclic, —CO—$C_{1-3}$alkyl, —COO—$C_{1-3}$alkyl, —CO—$C_{1-3}$alkylene-$NR_{a1}R_{a2}$, —CO—$NR_{a1}$-(3-8 membered heterocyclic), —CO—$NR_{a1}$-(3-8 membered heterocyclic), —CO-(3-8 membered heterocyclic), —O—$C_{1-3}$alkylene-CO—$OR_{a1}$, —O—$C_{1-3}$alkylene-CO—$NR_{a1}R_{a2}$, —O—$C_{1-3}$alkylene-$NR_{a1}R_{a2}$, —O—$C_{3-8}$carbocyclic, —O-(3-8 membered heterocyclic), —$NR_{a1}$—CO—$C_{1-3}$alkyl, —$NR_{a1}$—CO—$NR_{a1}R_{a2}$, —$NR_{a1}$—CO-(5-8 membered heteroaryl), —$NR_{a1}$—CO—$C_{3-6}$cycloalkyl, —$NR_{a1}$—$C_{1-3}$alkylene-$NR_{a1}R_{a2}$, —$NR_{a1}$—$C_{1-3}$alkylene-(3-8 membered heterocyclic), —$NR_{a1}$—$C_{1-3}$alkylene-(5-8 membered heteroaryl), —$NR_{a1}$—$SO_2C_{1-3}$alkyl, —S—$C_{1-3}$alkyl, —$SONR_{a1}R_{a2}$, —$SO_2NR_{a1}R_{a2}$, —SO—$C_{1-3}$alkyl, —$SO_2C_{1-3}$alkyl, —PO($C_{1-3}$alkyl)$_2$, —PO($C_{1-3}$alkoxy)$_2$, -3-8 membered heterocyclic or -5-8 membered heteroaryl; each of which is independently optionally substituted; and n is 0, 1, 2, 3, 4, 5 or 6.

In some embodiments of Formula II, each of Ra is independently selected from hydrogen, deuterium, F, Cl, Br, —$NR_{a1}R_{a2}$, —CN, —OH, —$NO_2$, oxo, =O, carboxyl, methoxy, ethoxy, propoxy, isopropoxy methyl, ethyl, propyl, isopropyl, —$C_{3-6}$cycloalkyl, —$C_{1-3}$alkylene-$NR_{a1}R_{a2}$, —$C_{1-3}$alkylene-O—$C_{1-6}$alkyl, —$C_{1-3}$alkylene-CO—$OR_{a1}$, —$C_{1-3}$alkylene-(3-8 membered heterocyclic), —$C_{1-3}$alkylene-(5-8 membered heteroaryl), —$C_{1-3}$alkylene-CO—$NR_{a1}R_{a2}$, —$C_{1-3}$alkylene-$NR_{a1}$—CO—$NR_{a1}R_{a2}$, —$C_{1-3}$alkylene-$NR_{a1}$—CO—$C_{1-3}$alkyl, —CO—$NR_{a1}R_{a2}$, —CO—CO—$NR_{a1}R_{a2}$, —$C_{3-8}$carbocyclic, -3-8 membered heterocyclic, —CO—$C_{1-3}$alkyl, —COO—$C_{1-3}$alkyl, —CO—$C_{1-3}$alkylene-$NR_{a1}R_{a2}$, —CO—$NR_{a1}$-(3-8 membered heterocyclic), —CO—$NR_{a1}$-(3-8 membered heterocyclic), —CO-(3-8 membered heterocyclic), —O—$C_{1-3}$alkylene-CO—$OR_{a1}$, —O—$C_{1-3}$alkylene-CO—$NR_{a1}R_{a2}$, —O—$C_{1-3}$alkylene-$NR_{a1}R_{a2}$, —O—$C_{3-8}$carbocyclic, —O-(3-8 membered heterocyclic), —$NR_{a1}$—CO—$C_{1-3}$alkyl, —$NR_{a1}$—CO—$NR_{a1}R_{a2}$, —$NR_{a1}$—CO-(5-8 membered heteroaryl), —$NR_{a1}$—CO—$C_{3-6}$cycloalkyl, —$NR_{a1}$—$C_{1-3}$alkylene-$NR_{a1}R_{a2}$, —$NR_{a1}$—$C_{1-3}$alkylene-(3-8 membered heterocyclic), —$NR_{a1}$—$C_{1-3}$alkylene-(5-8 membered heteroaryl), —$NR_{a1}$—$SO_2C_{1-3}$alkyl, —S—$C_{1-3}$alkyl, —$SONR_{a1}R_{a2}$, —$SO_2NR_{a1}R_{a2}$, —SO—$C_{1-3}$alkyl, —$SO_2C_{1-3}$alkyl, —PO($C_{1-3}$alkyl)$_2$, —PO($C_{1-3}$alkoxy)$_2$, -3-8 membered heterocyclic or -5-8 membered heteroaryl; each of which is independently optionally substituted; and n is 0, 1, 2, 3, 4, 5 or 6.

In some embodiments of Formula II, two adjacent Ra can be joined together to form a 6-membered aromatic ring, a 5-membered heteroaromatic ring, a 6-membered heteroaromatic ring, a 3-6 membered heterocyclic ring or a 3-6 membered carbocyclic ring, wherein each of the ring systems is independently optionally substituted with deuterium, halogen, —$NH_2$, —CN, —OH, —$NO_2$, carboxyl, —$C_{1-6}$alkyl or —$C_{1-6}$alkoxy.

In some embodiments of Formula II, two adjacent Ra can be joined together to form a 6-membered aromatic ring, a 5-membered heteroaromatic ring, a 6-membered heteroaromatic ring, a 3-6 membered heterocyclic ring or a 3-6 membered carbocyclic ring, wherein each of the ring systems is independently optionally substituted with deuterium, F, Cl, Br, —$NH_2$, —CN, —OH, —$NO_2$, carboxyl, —$C_{1-3}$alkyl or —$C_{1-3}$alkoxy.

In some embodiments of Formula II, two adjacent Ra can be joined together to form a 6-membered aromatic ring, a 5-membered heteroaromatic ring, a 6-membered heteroaromatic ring, a 3 membered heterocyclic ring, a 4 membered heterocyclic ring, a 5 membered heterocyclic ring, a 6 membered heterocyclic ring, a 3 membered carbocyclic ring, a 4 membered carbocyclic ring, a 5 membered carbocyclic ring, a 6 membered carbocyclic ring, wherein each of the heteroaryl contains 1, 2 or 3 heteroatoms selected from N, O or S, and each of the heterocyclic ring contains 1, 2 or 3 heteroatoms selected from N, O or S, each of the ring systems is independently optionally substituted with deuterium, F, Cl, Br, —$NH_2$, —CN, —OH, —$NO_2$, carboxyl, —$C_{1-3}$alkyl or —$C_{1-3}$alkoxy.

In some embodiments of Formula II, each of $R_{a1}$ and $R_{a2}$ is independently selected from hydrogen, deuterium, F, Cl, Br, —$NH_2$, —CN, —OH, —$NO_2$, carboxyl, substituted or unsubstituted —$C_{1-6}$alkoxy, or substituted or unsubstituted —$C_{1-6}$alkyl.

In some embodiments of Formula II, each of $R_{a1}$ and $R_{a2}$ is independently selected from hydrogen, deuterium, F, Cl, Br, —$NH_2$, —CN, —OH, —$NO_2$, carboxyl, substituted or unsubstituted —$C_{1-3}$alkoxy, or substituted or unsubstituted —$C_{1-3}$alkyl.

In some embodiments of Formula II, each of $R_{a1}$ and $R_{a2}$ is independently selected from hydrogen; deuterium; F; Cl; Br; —$NH_2$; —CN; —OH; —$NO_2$; carboxyl; methoxy; ethoxy; propoxy; isopropoxy; —$C_{1-3}$alkoxy substituted with halogen, $NH_2$, CN, OH, $NO_2$, carboxyl, $C_{1-3}$alkyl or $C_{1-3}$alkoxy; methyl; ethyl; propyl; isopropyl; —$C_{1-3}$alkyl substituted with halogen, $NH_2$, CN, OH, $NO_2$, carboxyl, $C_{1-3}$alkyl or $C_{1-3}$alkoxy.

In some embodiments of Formula II, each of $R_{a1}$ and $R_{a2}$ is independently selected from hydrogen; deuterium; F; Cl; Br; —$NH_2$; —CN; —OH; —$NO_2$; carboxyl; methoxy; ethoxy; propoxy; isopropoxy; —$C_{1-3}$alkoxy substituted with F, Cl, Br, $NH_2$, CN, OH, $NO_2$, carboxyl, methyl, ethyl, propyl, isopropyl, methoxy, ethoxy, propoxy or isopropoxy; methyl; ethyl; propyl; isopropyl; —$C_{1-3}$alkyl substituted with F, Cl, Br, $NH_2$, CN, OH, $NO_2$, carboxyl, methyl, ethyl, propyl, isopropyl, methoxy, ethoxy, propoxy or isopropoxy.

In some embodiments of Formula II, the compound is of Formula II-a:

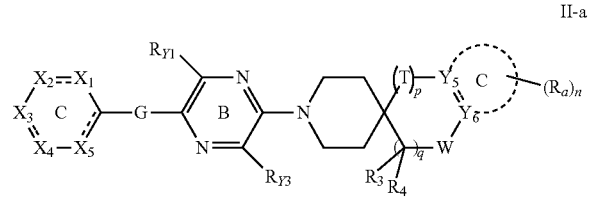

II-a $X_1, X_2, X_3, X_4, X_5, G, R_{Y1}, R_{Y3}, T, R_3, R_4, W, Y_5, Y_6, R_a$, p, q and n are as defined herein.

In some embodiments of Formula II, the compound is of Formula II-b

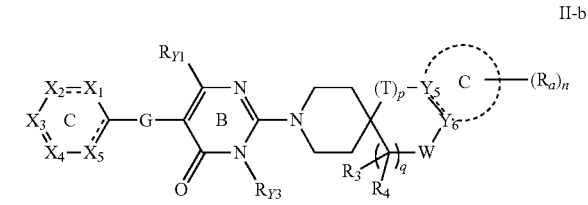

II-b $X_1, X_2, X_3, X_4, X_5, G, R_{Y1}, R_{Y3}, T, R_3, R_4, W, Y_5, Y_6, R_a$, p, q and n are as defined herein.

In some embodiments of Formula II, the compound is of Formula II-c

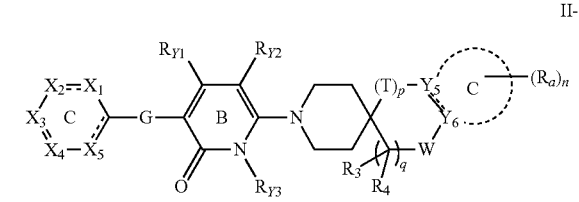

II-c

Wherein $X_1, X_2, X_3, X_4, X_5, G, R_{Y1}, R_{Y2}, R_{Y3}, T, R_3, R_4, W, Y_5, Y_6, R_a$, p, q and n are as defined herein.

The present invention further provides the compound of Formula III or a pharmaceutically acceptable salt thereof:

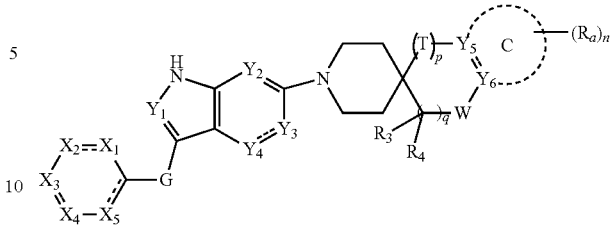

III $X_1$ is N, S, $NR_{X1}$, $C(R_{X1})_2$, or $CR_{X1}$;

each of $R_{X1}$ is selected from hydrogen, deuterium, halogen, —$NH_2$, —$CONH_2$, —CN, —$C_{1-6}$alkyl or —$C_{1-6}$alkoxy, and each of which is independently optionally substituted with 1, 2, 3, 4, 5, or 6 substituents, and the said each substituents is independently selected from deuterium, halogen, —$NH_2$, —CN, —OH, —$NO_2$, carboxyl, —$C_{1-6}$alkyl or —$C_{1-6}$alkoxy;

$X_2$ is N, S, $NR_{X2}$, $C(R_{X2})_2$, $CR_{X2}$ or CO;

each of $R_{X2}$ is selected from hydrogen, deuterium, halogen, —$NH_2$, —CN, —$C_{1-6}$alkyl, —$C_{1-6}$alkoxy, —CO—$C_{1-6}$alkyl, —NH—$C_{1-6}$alkyl, —$SF_5$, —NHCO—$C_{3-8}$cycloalkyl, —NH—$C_{3-8}$cycloalkyl, —$C_{1-6}$alkylene-(3-8 membered heterocyclyl), —NHCO-(5-12 membered heterocyclyl), —NH—$C_{1-6}$alkylene-$C_{3-8}$cycloalkyl or 3-8 membered heterocyclic, and each of which is independently optionally substituted with 1, 2, 3, 4, 5, or 6 substituents, and the said each substituents is independently selected from deuterium, halogen, —$NH_2$, —CN, —OH, -oxo, =O, —$NO_2$, carboxyl, —$C_{1-6}$alkyl or —$C_{1-6}$alkoxy; or $R_{X1}$ and $R_{X2}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;

$X_3$ is N, S, O, $NR_{X3}$, $C(R_{X3})_2$ or $CR_{X3}$;

each of $R_{X3}$ is independently selected from hydrogen, deuterium, halogen, carboxyl, —$NO_2$, —$NH_2$, —CN, —$CONH_2$, —$C_{1-6}$alkyl, —$C_{1-6}$alkoxy, $C_{3-8}$cycloalkyl, $C_{5-8}$aryl, —S—$C_{1-6}$alkyl, 3-12 membered heterocyclyl, —O—$C_{3-8}$cycloalkyl or —O—$C_{1-6}$alkylene-$C_{1-6}$alkyl, and each of which is independently optionally substituted with 1, 2, 3, 4, 5, or 6 substituents, and the said each substituents is independently selected from deuterium, halogen, —$NH_2$, —CN, —OH, —$NO_2$, carboxyl, —$C_{1-6}$alkyl or —$C_{1-6}$alkoxy; or $R_{X2}$ and $R_{X3}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;

$X_4$ is N, S, $NR_{X4}$, $C(R_{X4})_2$ or $CR_{X4}$;

each of $R_{X4}$ is independently selected from hydrogen, deuterium, halogen, —$NH_2$, —CN, —OH, —$C_{1-6}$alkyl, —$C_{1-6}$alkoxy, —NHCO-(5-12 membered heterocyclyl) or 5-12 membered heteroaryl, and each of which is independently optionally substituted with 1, 2, 3, 4, 5, or 6 substituents, and the said each substituents is independently selected from deuterium, halogen, —$NH_2$, —CN, —OH, oxo, =O, —$NO_2$, carboxyl, —$C_{1-6}$alkyl or —$C_{1-6}$alkoxy; or $R_{X3}$ and $R_{X4}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;

$X_5$ is N, $NR_{X5}$ $C(R_{X5})_2$ or $CR_{X5}$;

each of $R_{X5}$ is independently selected from hydrogen, deuterium, halogen, $-NH_2$, $-CN$, $-C_{1-6}$alkyl or $-C_{1-6}$alkoxy, and each of which is independently optionally substituted with 1, 2, 3, 4, 5, or 6 substituents, and the said each substituents is independently selected from deuterium, halogen, $-NH_2$, $-CN$, $-OH$, $-NO_2$, carboxyl, $-C_{1-6}$alkyl or $-C_{1-6}$alkoxy; or $R_{X4}$ and $R_{X5}$ together with the ring to which they are attached form a 5-12 membered aromatic ring, a 5-12 membered heteroaromatic ring or a 5-12 membered heterocyclic ring, and each of the ring systems is independently optionally substituted or unsubstituted;

------ represents a single bond or a double bond;

G is selected from absent, S, $-SO-$, $-SO_2-$, O, $-CO-$, $-NR_G-$, $-NR_G-SO_2-$,

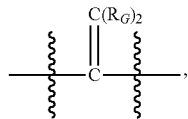

$-C(R_G)_2-$ or $-SO_2-NR_G-$;

each of $R_G$ is independently selected from hydrogen, deuterium, halogen, $-NH_2$, $-CN$, $-OH$, $-C_{1-6}$alkyl or $-C_{1-6}$alkoxy, and each of which is independently optionally substituted or unsubstituted;

$Y_1$ is N or $CR_{Y1}$;

$R_{Y1}$ is selected from hydrogen, deuterium, halogen, $-NH_2$, $-CN$, $-C_{1-6}$alkyl, $-C_{1-6}$alkoxy, $-NH-C_{1-6}$alkyl, $-N-(C_{1-6}$alkyl$)_2$, $-C_{1-6}$alkenyl, $-C_{3-8}$cycloalkyl or $-C_{5-10}$aryl, and each of which is independently optionally substituted with 1, 2, 3, 4, 5, or 6 substituents, and the said each substituents is independently selected from deuterium, halogen, $-NH_2$, $-CN$, $-OH$, $-NO_2$, carboxyl, $-C_{1-6}$alkyl or $-C_{1-6}$alkoxy;

$Y_2$ is N or $CR_{Y2}$;

$R_{Y2}$ is selected from hydrogen, deuterium, halogen, $-NH_2$, $-CN$, $-C_{1-6}$alkyl, $-C_{1-6}$alkoxy, $-NH-C_{1-6}$alkyl, $-N-(C_{1-6}$alkyl$)_2$, $-C_{1-6}$ alkenyl, $-C_{3-8}$cycloalkyl or $-C_{5-10}$aryl, and each of which is independently optionally substituted with 1, 2, 3, 4, 5, or 6 substituents, and the said each substituents is independently selected from deuterium, halogen, $-NH_2$, $-CN$, $-OH$, $-NO_2$, carboxyl, $-C_{1-6}$alkyl or $-C_{1-6}$alkoxy;

when the "------" in the term "$Y_3$------ $Y_4$" represents a single bond, $Y_3$ is $NR_{Y3}$, and $Y_4$ is CO;

when the "------" in the term "$Y_3$------ $Y_4$" represents a double bond, $Y_3$ is N or $CR_{Y3}$, and $Y_4$ is N or $CR_{Y4}$;

$R_{Y3}$ and $R_{Y4}$ are independently selected from hydrogen, deuterium, halogen, $-NH_2$, $-OH$, $-CN$, $-C_{1-6}$alkyl, carboxyl, $-COO-C_{1-6}$alkyl, $-NH-C_{1-6}$alkylene-OH, $-C_{1-6}$alkylene-OH, $-CONH_2$ or -5-8 membered heteroaryl, and each of which is independently optionally substituted with 1, 2, 3, 4, 5, or 6 substituents, and the said each substituents is independently selected from deuterium, halogen, $-NH_2$, $-CN$, $-OH$, $-NO_2$, carboxyl, $-C_{1-6}$alkyl or $-C_{1-6}$alkoxy;

T is absent, O, $NR_1$ or $CR_1R_2$;

each of $R_1$ and $R_2$ is independently selected from hydrogen, deuterium, halogen, $-NH_2$, $-CN$, $-OH$, $-NO_2$, carboxyl, $-NH-C_{1-6}$alkyl, $-N(C_{1-6}$alkyl$)_2$, substituted or unsubstituted $-C_{1-6}$alkoxy, or substituted or unsubstituted $-C_{1-6}$alkyl; or $R_1$ and $R_2$ together with the carbon atom to which they are both attached form CO or C=$NR_5$;

p is 0, 1, 2 or 3;

each of $R_3$ and $R_4$ is independently selected from hydrogen, deuterium, halogen, $-NH_2$, $-CN$, $-OH$, $-NO_2$, carboxyl, $-NH-C_{1-6}$alkyl, $-N(C_{1-6}$alkyl$)_2$, substituted or unsubstituted $-C_{1-6}$alkoxy, or substituted or unsubstituted $-C_{1-6}$alkyl; or $R_3$ and $R_4$ together with the carbon atom to which they are both attached form a 3-12 membered heterocyclic ring or 5-12 membered heteroaromatic ring or C=$NR_5$, and each of the ring systems is independently optionally substituted or unsubstituted;

each of $R_5$ is selected from hydrogen, deuterium, halogen, $-NH_2$, $-CN$, $-OH$, $-C_{1-6}$alkyl or $-C_{1-6}$alkoxy;

q is 0, 1, 2, 3 or 4;

W is absent, $-O$, $-S$ or $-C(R_W)_2-$; and each of $R_W$ is independently selected from hydrogen, deuterium, halogen, $-NH_2$, $-CN$, $-OH$, $-NO_2$, carboxyl, $-CO-C_{1-6}$alkyl, $-CO-OC_{1-6}$alkyl, $-C_{1-6}$alkyl-O-$C_{1-6}$alkoxy, substituted or unsubstituted $-C_{1-6}$alkoxy, or substituted or unsubstituted $-C_{1-6}$alkyl;

ring C is absent, a 5-12 membered aromatic ring, a 5-12 membered heteroaromatic ring or a 5-12 membered heterocyclic ring, and each of the ring systems is independently optionally substituted or unsubstituted;

when ring C is absent, $Y_5$ is $CR_{5a}R_{5b}$, $NR_{5a}$ or O, and $Y_6$ is $CR_{6a}R_{6b}$, $NR_{6a}$ or O;

when ring C is 5-12 membered aromatic ring, 5-12 membered heteroaromatic ring or 5-12 membered heterocyclic ring;

i) $Y_5$ is $CR_{5a}$ or N, and $Y_6$ is $CR_{6a}$ or N, when the "------" in the term "$Y_5$------ $Y_6$" represents a single bond; or ii) $Y_5$ is C, and $Y_6$ is C, when the "------" in the term "$Y_5$------ $Y_6$" represents a double bond;

each of $R_{5a}$ and $R_{5b}$ is independently selected from hydrogen, deuterium, halogen, $-NH_2$, $-CN$, $-OH$, $-NO_2$, carboxyl, substituted or unsubstituted $-C_{1-6}$alkoxy, or substituted or unsubstituted $-C_{1-6}$alkyl;

each of $R_{6a}$ and $R_{6b}$ is independently selected from hydrogen, deuterium, halogen, $-NH_2$, $-CN$, $-OH$, $-NO_2$, carboxyl, substituted or unsubstituted $-C_{1-6}$alkoxy, or substituted or unsubstituted $-C_{1-6}$alkyl;

each of Ra is independently hydrogen, deuterium, halogen, $-NR_{a1}R_{a2}$, $-CN$, $-OH$, $-NO_2$, oxo, =O, carboxyl, $-C_{1-6}$alkoxy, $-C_{1-6}$alkyl, $-C_{3-8}$cycloalkyl, $-C_{1-6}$alkylene-$NR_{a1}R_{a2}$, $-C_{1-6}$alkylene-O-$C_{1-6}$alkyl, $-C_{1-6}$alkylene-CO-$OR_{a1}$, $-C_{1-6}$alkylene-(3-10 membered heterocyclic), $-C_{1-6}$alkylene-(5-10 membered heteroaryl), $-C_{1-6}$alkylene-CO-$NR_{a1}R_{a2}$, $-C_{1-6}$alkylene-$NR_{a1}$-CO-$NR_{a1}R_{a2}$, $-C_{1-6}$alkylene-$NR_1$-CO-$C_{1-6}$alkyl, $-CO-NR_{a1}R_{a2}$, $-COO-C_{1-6}$alkyl, $-CO-CO-NR_{a1}R_{a2}$, $-C_{3-10}$carbocyclic, -5-10 membered heteroaryl, -3-10 membered heterocyclic, $-CO-C_{1-6}$alkyl, $-CO-C_{1-6}$ alkylene-$NR_{a1}R_{a2}$, $-CO-NR_{a1}$-(3-10 membered heterocyclic), $-CO-NR_{a1}$-(3-10 membered heterocyclic), $-CO$-(3-10 membered heterocyclic), $-O-C_{1-6}$alkylene-CO-$OR_{a1}$, $-O-C_{1-6}$alkylene-CO-$NR_{a1}R_{a2}$, $-O-C_{1-6}$alkylene-$NR_{a1}R_{a2}$, —O—$C_{3-10}$carbocyclic, —O-(3-10 membered heterocyclic), —$NR_1$—CO—$C_{1-6}$alkyl, —$NR_{a1}$—CO—$NR_{a1}R_{a2}$, —$NR_{a1}$—CO-(5-10 membered heteroaryl), —$NR_1$—CO—$C_{3-8}$cycloalkyl, —$NR_1$—$C_{1-6}$alkylene-$NR_{a1}R_{a2}$, —$NR_{a1}$—$C_{1-6}$alkylene-(3-10 membered heterocyclic), —$NR_{a1}$—$C_{1-6}$alkylene-(5-10 membered heteroaryl), —$NR_{a1}$—$SO_2C_{1-6}$alkyl, —S—$C_{1-6}$alkyl, —$SONR_{a1}R_{a2}$, —$SO_2NR_{a1}R_{a2}$, —SO—$C_{1-6}$alkyl, —$SO_2C_{1-6}$alkyl, —$PO(C_{1-6}$alkyl$)_2$, —$PO(C_{1-6}$alkoxy$)_2$, -3-10 membered heterocyclic or -5-10 membered heteroaryl; each of which is independently optionally substituted; and n is 0, 1, 2, 3, 4, 5 or 6; or two adjacent Ra can be joined together to form a 6-membered aromatic ring, 5-membered heteroaromatic ring, 6-membered heteroaromatic ring, -3-6 membered heterocyclic ring or -3-6 membered carbocyclic ring, wherein each of the ring systems is independently optionally substituted; or Ra and $R_W$ with the atom to which they are both attached form a 3-10 membered aromatic ring, 3-10 membered heteroaromatic ring or 3-10 membered heterocyclic ring; and each of the ring systems is independently optionally substituted;

each of $R_1$ and $R_2$ is independently selected from hydrogen, deuterium, halogen, —$NH_2$, —CN, —OH, —$NO_2$, carboxyl, substituted or unsubstituted —$C_{1-6}$alkoxy, or substituted or unsubstituted —$C_{1-6}$alkyl.

In some embodiments of Formula III, $X_1$ is N, S, $NR_{X1}$, $C(R_{X1})_2$, or $CR_{X1}$; each of $R_{X1}$ is independently selected from hydrogen, deuterium, F, Cl, Br, —$NH_2$, —$CONH_2$, —CN, —$C_{1-6}$alkyl or —$C_{1-6}$alkoxy, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-6}$alkyl or —$C_{1-6}$alkoxy.

In some embodiments of Formula III, $X_1$ is N, S, $NR_{X1}$, $C(R_{X1})_2$, or $CR_{X1}$; each of $R_{X1}$ is independently selected from hydrogen, deuterium, F, Cl, Br, —$NH_2$, —$CONH_2$, —CN, —$C_{1-6}$alkyl or —$C_{1-6}$alkoxy, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula III, $X_1$ is N, S, $NR_{X1}$, $C(R_{X1})_2$, or $CR_{X1}$; each of $R_{X1}$ is independently selected from hydrogen, deuterium, F, Cl, Br, —$NH_2$, —$CONH_2$, —CN, —$C_{1-3}$alkyl or —$C_{1-3}$alkoxy, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula III, $X_1$ is N, S, $NR_{X1}$, $C(R_{X1})_2$, or $CR_{X1}$; each of $R_{X1}$ is independently selected from hydrogen, deuterium, F, Cl, Br, —$NH_2$, —$CONH_2$, —CN, methyl, ethyl, propyl, isopropyl, methoxy, ethoxy, propoxy or isopropoxy, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, methyl, ethyl, propyl, isopropyl, methoxy, ethoxy, propoxy or isopropoxy.

In some embodiments of Formula III, $X_1$ is N, S, $NR_{X1}$, $C(R_{X1})_2$, or $CR_{X1}$; each of $R_{X1}$ is independently selected from hydrogen, deuterium, F, Cl, Br, —$NH_2$, —$CONH_2$, —CN, methyl, ethyl, propyl, isopropyl, methoxy, ethoxy, propoxy or isopropoxy, and each of which is independently optionally substituted with 1, 2 or 3 substituents, and the said each substituents is independently selected from deuterium, F, Cl, Br, I, —$NH_2$, —CN, —OH, —$NO_2$, carboxyl, methyl, ethyl, propyl, isopropyl, methoxy, ethoxy, propoxy or isopropoxy.

In some embodiments of Formula III, $X_2$ is N, S, $NR_{X2}$, $C(R_{X2})_2$, $CR_{X2}$ or CO; each of $R_{X2}$ is independently selected from hydrogen, deuterium, F, Cl, Br, —$NH_2$, —CN, —$C_{1-6}$alkyl, —$C_{1-6}$alkoxy, —CO—$C_{1-6}$alkyl, —NH—$C_{1-6}$alkyl, —N—($C_{1-6}$alkyl$)_2$, —$SF_5$, —NHCO—$C_{3-8}$cycloalkyl, —NH—$C_{3-8}$cycloalkyl, —$C_{1-6}$alkylene-(3-8 membered heterocyclyl), —NHCO-(5-12 membered heterocyclyl), —NH—$C_{1-6}$alkylene-$C_{3-8}$cycloalkyl or 3-8 membered heterocyclic, and each of which is independently optionally substituted with 1, 2, 3, 4, 5, or 6 substituents, and the said each substituents is independently selected from deuterium, F, Cl, Br, I, —$NH_2$, —CN, —OH, -oxo, =O, —$NO_2$, carboxyl, —$C_{1-6}$alkyl or —$C_{1-6}$alkoxy.

In some embodiments of Formula III, $X_2$ is N, S, $NR_{X2}$, $C(R_{X2})_2$, $CR_{X2}$ or CO; each of $R_{X2}$ is independently selected from hydrogen, deuterium, F, Cl, Br, —$NH_2$, —CN, —$C_{1-6}$alkyl, —$C_{1-6}$alkoxy, —CO—$C_{1-6}$alkyl, —NH—$C_{1-6}$alkyl, —N—($C_{1-6}$alkyl$)_2$, —$SF_5$, —NHCO—$C_{3-8}$cycloalkyl, —NH—$C_{3-8}$cycloalkyl, —$C_{1-6}$alkylene-(3-8 membered heterocyclyl), —NHCO-(5-12 membered heterocyclyl), —NH—$C_{1-6}$alkylene-$C_{3-8}$cycloalkyl or 3-8 membered heterocyclic, and each of which is independently optionally substituted with 1, 2, 3, 4, 5, or 6 substituents, and the said each substituents is independently selected from deuterium, F, Cl, Br, I, —$NH_2$, —CN, —OH, -oxo, =O, —$NO_2$, carboxyl, —$C_{1-3}$alkyl or —$C_{1-3}$alkoxy.

In some embodiments of Formula III, $X_2$ is N, S, $NR_{X2}$, $C(R_{X2})_2$, $CR_{X2}$ or CO; each of $R_{X2}$ is independently selected from hydrogen, deuterium, F, Cl, Br, —$NH_2$, —CN, —$C_{1-6}$alkyl, —$C_{1-3}$alkoxy, —CO—$C_{1-3}$alkyl, —NH—$C_{1-3}$alkyl, —N—($C_{1-3}$alkyl$)_2$, —$SF_5$, —NHCO—$C_{3-6}$cycloalkyl, —NH—$C_{3-6}$cycloalkyl, —$C_{1-3}$alkylene-(3-6 membered heterocyclyl), —NHCO-(5-10 membered heterocyclyl), —NH—$C_{1-3}$alkylene-$C_{3-6}$cycloalkyl or 3-6 membered heterocyclic, and each of which is independently optionally substituted with 1, 2, 3, 4, 5, or 6 substituents, and the said each substituents is independently selected from deuterium, F, Cl, Br, I, —$NH_2$, —CN, —OH, -oxo, =O, —$NO_2$, carboxyl, —$C_{1-3}$alkyl or —$C_{1-3}$alkoxy.

In some embodiments of Formula III, $X_2$ is N, S, $NR_{X2}$, $C(R_{X2})_2$, $CR_{X2}$ or CO; each of $R_{X2}$ is independently selected from hydrogen, deuterium, F, Cl, Br, —$NH_2$, —CN, methyl, ethyl, propyl, isopropyl, butyl, isobutyl, methoxy, ethoxy, propoxy, isopropoxy, —CO—$C_{1-3}$alkyl, —NH—$C_{1-3}$alkyl, —N—($C_{1-3}$alkyl$)_2$, —$SF_5$, —NHCO—$C_{3-6}$cycloalkyl, —NH—$C_{3-6}$cycloalkyl, —$C_{1-3}$alkylene-(3-6 membered heterocyclyl), —NHCO-(5-10 membered heterocyclyl), —NH—$C_{1-3}$alkylene-$C_{3-6}$cycloalkyl, 3 membered heterocyclic, 4 membered heterocyclic, 5 membered heterocyclic or 6 membered heterocyclic, and each of which is independently optionally substituted with 1, 2, 3, 4, 5, or 6 substituents, and the said each substituents is independently selected from deuterium, F, Cl, Br, I, —$NH_2$, —CN, —OH, -oxo, =O, —$NO_2$, carboxyl, methyl, ethyl, propyl, isopropyl, methoxy, ethoxy, propoxy or isopropoxy.

In some embodiments of Formula III, $X_2$ is N, S, $NR_{X2}$, $C(R_{X2})_2$, $CR_{X2}$ or CO; each of $R_{X2}$ is independently selected from hydrogen, deuterium, F, Cl, Br, —$NH_2$, —CN, methyl, ethyl, propyl, isopropyl, butyl, isobutyl, methoxy, ethoxy, propoxy, isopropoxy, —CO—$C_{1-3}$alkyl, —NH—$C_{1-3}$alkyl, —N—($C_{1-3}$alkyl$)_2$, —$SF_5$, —NHCO—$C_{3-6}$cycloalkyl, —NH—$C_{3-6}$cycloalkyl, —$C_{1-3}$alkylene-(3-6 membered heterocyclyl), —NHCO-(5-10 membered heterocyclyl), —NH—$C_{1-3}$alkylene-$C_{3-6}$cycloalkyl, 3 membered heterocyclic, 4 membered heterocyclic, 5 membered heterocyclic or 6 membered heterocyclic, and each of which is independently optionally substituted with 1, 2 or 3 substituents, and the said each substituents is independently selected from deuterium, F, Cl, Br, I, —$NH_2$, —CN, —OH, -oxo, =O, —$NO_2$, carboxyl, methyl, ethyl, propyl, isopropyl, methoxy, ethoxy, propoxy or isopropoxy.

In some embodiments of Formula III, $R_{X1}$ and $R_{X2}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula III, $R_{X1}$ and $R_{X2}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula III, $R_{X1}$ and $R_{X2}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring or a 10 membered heterocyclic ring, and each of the heteroaromatic ring contains 1, 2 or 3 heteroatoms selected from N, O or S, and each of the heterocyclic ring contains 1, 2 or 3 heteroatoms selected from N or O, and each of the ring systems is independently optionally substituted or unsubstituted.

In some embodiments of Formula III, $X_3$ is N, S, O, $NR_{X3}$, $C(R_{X3})_2$ or $CR_{X3}$; each of $R_{X3}$ is independently selected from hydrogen, deuterium, F, Cl, Br, carboxyl, —$NO_2$, —$NH_2$, —CN, —$CONH_2$, —$C_{1-6}$alkyl, —$C_{1-6}$alkoxy, $C_{3-8}$cycloalkyl, $C_{5-8}$aryl, —S—$C_{1-6}$alkyl, 3-12 membered heterocyclyl, —O—$C_{3-8}$cycloalkyl or —O—$C_{1-6}$alkylene-$C_{1-6}$alkyl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-6}$alkyl or —$C_{1-6}$alkoxy.

In some embodiments of Formula III, $X_3$ is N, S, O, $NR_{X3}$, $C(R_{X3})_2$ or $CR_{X3}$; each of $R_{X3}$ is independently selected from hydrogen, deuterium, F, Cl, Br, carboxyl, —$NO_2$, —$NH_2$, —CN, —$CONH_2$, —$C_{1-6}$alkyl, —$C_{1-6}$alkoxy, $C_{3-8}$cycloalkyl, $C_{5-8}$aryl, —S—$C_{1-6}$alkyl, 3-12 membered heterocyclyl, —O—$C_{3-8}$cycloalkyl or —O—$C_{1-6}$alkylene-$C_{1-6}$alkyl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula III, $X_3$ is N, S, O, $NR_{X3}$, $C(R_{X3})_2$ or $CR_{X3}$; each of $R_{X3}$ is independently selected from hydrogen, deuterium, F, Cl, Br, carboxyl, —$NO_2$, —$NH_2$, —CN, —$CONH_2$, —$C_{1-3}$alkyl, —$C_{1-3}$alkoxy, $C_{3-6}$cycloalkyl, $C_{5-8}$aryl, —S—$C_{1-3}$alkyl, 3-10 membered heterocyclyl, —O—$C_{3-6}$cycloalkyl or —O—$C_{1-3}$alkylene-$C_{1-3}$alkyl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, —$C_{1-3}$alkyl or —$C_{1-3}$alkoxy.

In some embodiments of Formula III, $X_3$ is N, S, O, $NR_{X3}$, $C(R_{X3})_2$ or $CR_{X3}$; each of $R_{X3}$ is independently selected from hydrogen, deuterium, F, Cl, Br, carboxyl, —$NO_2$, —$NH_2$, —CN, —$CONH_2$, methyl, ethyl, propyl, isopropyl, methoxy, ethoxy, propoxy, isopropoxy, $C_{3-6}$cycloalkyl, $C_{5-8}$aryl, —S—$C_{1-3}$alkyl, 3-10 membered heterocyclyl, —O—$C_{3-6}$cycloalkyl or —O—$C_{1-3}$alkylene-$C_{1-3}$alkyl, and each of which is independently optionally substituted with 1, 2, 3, 4, 5, or 6 substituents, and the said each substituents is independently selected from deuterium, F, Cl, Br, I, —$NH_2$, —CN, —OH, —$NO_2$, carboxyl, methyl, ethyl, propyl, isopropyl, methoxy, ethoxy, propoxy or isopropoxy.

In some embodiments of Formula III, $X_3$ is N, S, O, $NR_{X3}$, $C(R_{X3})_2$ or $CR_{X3}$; each of $R_{X3}$ is independently selected from hydrogen, deuterium, F, Cl, Br, carboxyl, —$NO_2$, —$NH_2$, —CN, —$CONH_2$, methyl, ethyl, propyl, isopropyl, methoxy, ethoxy, propoxy, isopropoxy, $C_{3-6}$cycloalkyl, $C_{5-8}$aryl, —S—$C_{1-3}$alkyl, 3-10 membered heterocyclyl, —O—$C_{3-6}$cycloalkyl or —O—$C_{1-3}$alkylene-$C_{1-3}$alkyl, and each of which is independently optionally substituted with 1, 2 or 3 substituents, and the said each substituents is independently selected from deuterium, F, Cl, Br, I, —$NH_2$, —CN, —OH, —$NO_2$, carboxyl, methyl, ethyl, propyl, isopropyl, methoxy, ethoxy, propoxy or isopropoxy.

In some embodiments of Formula III, $R_{X2}$ and $R_{X3}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula III, $R_{X2}$ and $R_{X3}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula III, $R_{X2}$ and $R_{X3}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring, or a 10 membered heterocyclic ring, and each of the heteroaromatic ring contains 1, 2 or 3 heteroatoms selected from N, O or S, and each of the heterocyclic ring contains 1, 2 or 3 heteroatoms In some embodiments of Formula III, $X_4$ is N, S, $NR_{X4}$, $C(R_{X4})_2$ or $CR_{X4}$; each of $R_{X4}$ is independently selected from hydrogen, deuterium, F, Cl, Br, $-NH_2$, $-CN$, $-C_{1-6}$alkyl, $-C_{1-6}$alkoxy, $-NHCO$-(5-12 membered heterocyclyl) or 5-12 membered heteroaryl, and each of which is independently optionally substituted with 1, 2, 3, 4, 5, or 6 substituents, and the said each substituents is independently selected from deuterium, F, Cl, Br, I, $-NH_2$, $-CN$, $-OH$, oxo, $=O$, $-NO_2$, carboxyl, $-C_{1-6}$alkyl or $-C_{1-6}$alkoxy.

In some embodiments of Formula III, $X_4$ is N, S, $NR_{X4}$, $C(R_{X4})_2$ or $CR_{X4}$; each of $R_{X4}$ is independently selected from hydrogen, deuterium, F, Cl, Br, $-NH_2$, $-CN$, $-C_{1-6}$alkyl, $-C_{1-6}$alkoxy, $-NHCO$-(5-12 membered heterocyclyl) or 5-12 membered heteroaryl, and each of which is independently optionally substituted with 1, 2, 3, 4, 5, or 6 substituents, and the said each substituents is independently selected from deuterium, F, Cl, Br, I, $-NH_2$, $-CN$, $-OH$, oxo, $=O$, $-NO_2$, carboxyl, $-C_{1-3}$alkyl or $-C_{1-3}$alkoxy.

In some embodiments of Formula III, $X_4$ is N, S, $NR_{X4}$, $C(R_{X4})_2$ or $CR_{X4}$; each of $R_{X4}$ is independently selected from hydrogen, deuterium, F, Cl, Br, $-NH_2$, $-CN$, $-C_{1-3}$alkyl, $-C_{1-3}$alkoxy, $-NHCO$-(5-10 membered heterocyclyl) or 5-10 membered heteroaryl, and each of which is independently optionally substituted with 1, 2, 3, 4, 5, or 6 substituents, and the said each substituents is independently selected from deuterium, F, Cl, Br, I, $-NH_2$, $-CN$, $-OH$, oxo, $=O$, $-NO_2$, carboxyl, $-C_{1-3}$alkyl or $-C_{1-3}$alkoxy.

In some embodiments of Formula III, $X_4$ is N, S, $NR_{X4}$, $C(R_{X4})_2$ or $CR_{X4}$; each of $R_{X4}$ is independently selected from hydrogen, deuterium, F, Cl, Br, $-NH_2$, $-CN$, methyl, ethyl, propyl, isopropyl, methoxy, ethoxy, propoxy, isopropoxy, $-NHCO$-(5-10 membered heterocyclyl), 5 membered heteroaryl, 6 membered heteroaryl, 7 membered heteroaryl, 8 membered heteroaryl, 9 membered heteroaryl or 10 membered heteroaryl, and each of which is independently optionally substituted with 1, 2, 3, 4, 5, or 6 substituents, and the said each substituents is independently selected from deuterium, F, Cl, Br, I, $-NH_2$, $-CN$, $-OH$, oxo, $=O$, $-NO_2$, carboxyl, methyl, ethyl, propyl, isopropyl, methoxy, ethoxy, propoxy or isopropoxy.

In some embodiments of Formula III, $X_4$ is N, S, $NR_{X4}$, $C(R_{X4})_2$ or $CR_{X4}$; each of $R_{X4}$ is independently selected from hydrogen, deuterium, F, Cl, Br, $-NH_2$, $-CN$, methyl, ethyl, propyl, isopropyl, methoxy, ethoxy, propoxy, isopropoxy, $-NHCO$-(5-10 membered heterocyclyl), 5 membered heteroaryl, 6 membered heteroaryl, 7 membered heteroaryl, 8 membered heteroaryl, 9 membered heteroaryl or 10 membered heteroaryl, and each of which is independently optionally substituted with 1, 2 or 3 substituents, and the said each substituents is independently selected from deuterium, F, Cl, Br, I, $-NH_2$, $-CN$, $-OH$, oxo, $=O$, $-NO_2$, carboxyl, methyl, ethyl, propyl, isopropyl, methoxy, ethoxy, propoxy or isopropoxy.

In some embodiments of Formula III, $R_{X3}$ and $R_{X4}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula III, $R_{X3}$ and $R_{X4}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula III, $R_{X3}$ and $R_{X4}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring or a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula III, $X_5$ is N, S, $NR_{X5}$ $C(R_{X5})_2$ or $CR_{X5}$; each of $R_{X5}$ is independently selected from hydrogen, deuterium, F, Cl, Br, $-NH_2$, $-CN$, $-C_{1-6}$alkyl or $-C_{1-6}$alkoxy, and each of which is independently optionally substituted with 1, 2, 3, 4, 5, or 6 substituents, and the said each substituents is independently selected from deuterium, F, Cl, Br, I, $-NH_2$, $-CN$, $-OH$, $-NO_2$, carboxyl, $-C_{1-6}$alkyl or $-C_{1-6}$alkoxy.

In some embodiments of Formula III, $X_5$ is N, S, $NR_{X5}$ $C(R_{X5})_2$ or $CR_{X5}$; each of $R_{X5}$ is independently selected from hydrogen, deuterium, F, Cl, Br, $-NH_2$, $-CN$, $-C_{1-6}$alkyl or $-C_{1-6}$alkoxy, and each of which is independently optionally substituted with 1, 2, 3, 4, 5, or 6 substituents, and the said each substituents is independently selected from deuterium, F, Cl, Br, I, $-NH_2$, $-CN$, $-OH$, $-NO_2$, carboxyl, $-C_{1-3}$alkyl or $-C_{1-3}$alkoxy.

In some embodiments of Formula III, $X_5$ is N, S, $NR_{X5}$ $C(R_{X5})_2$ or $CR_{X5}$; each of $R_{X5}$ is independently selected from hydrogen, deuterium, F, Cl, Br, $-NH_2$, $-CN$, $-C_{1-3}$alkyl or $-C_{1-3}$alkoxy, and each of which is independently optionally substituted with 1, 2, 3, 4, 5, or 6 substituents, and the said each substituents is independently selected from deuterium, F, Cl, Br, I, $-NH_2$, $-CN$, $-OH$, $-NO_2$, carboxyl, $-C_{1-3}$alkyl or $-C_{1-3}$alkoxy.

In some embodiments of Formula III, $X_5$ is N, S, $NR_{X5}$ $C(R_{X5})_2$ or $CR_{X5}$; each of $R_{X5}$ is independently selected from hydrogen, deuterium, F, Cl, Br, $-NH_2$, $-CN$, methyl, ethyl, propyl, isopropyl, methoxy, ethoxy, propoxy or isopropoxy, and each of which is independently optionally substituted with 1, 2, 3, 4, 5, or 6 substituents, and the said each substituents is independently selected from deuterium, F, Cl, Br, I, $-NH_2$, $-CN$, $-OH$, $-NO_2$, carboxyl, methyl, ethyl, propyl, isopropyl, methoxy, ethoxy, propoxy or isopropoxy.

In some embodiments of Formula III, $X_5$ is N, S, $NR_{X5}$ $C(R_{X5})_2$ or $CR_{X5}$; each of $R_{X5}$ is independently selected from hydrogen, deuterium, F, Cl, Br, $-NH_2$, $-CN$, methyl, ethyl, propyl, isopropyl, methoxy, ethoxy, propoxy or isopropoxy, and each of which is independently optionally substituted with 1, 2 or 3 substituents, and the said each substituents is independently selected from deuterium, F, Cl, Br, I, $-NH_2$, $-CN$, $-OH$, $-NO_2$, carboxyl, methyl, ethyl, propyl, isopropyl, methoxy, ethoxy, propoxy or isopropoxy.

In some embodiments of Formula III, $R_{X4}$ and $R_{X5}$ together with the ring to which they are attached form a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula III, $R_{X4}$ and $R_{X5}$ together with the ring to which they are attached form a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula III, $R_{X4}$ and $R_{X5}$ together with the ring to which they are attached form a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring or a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula III, ring A is selected from

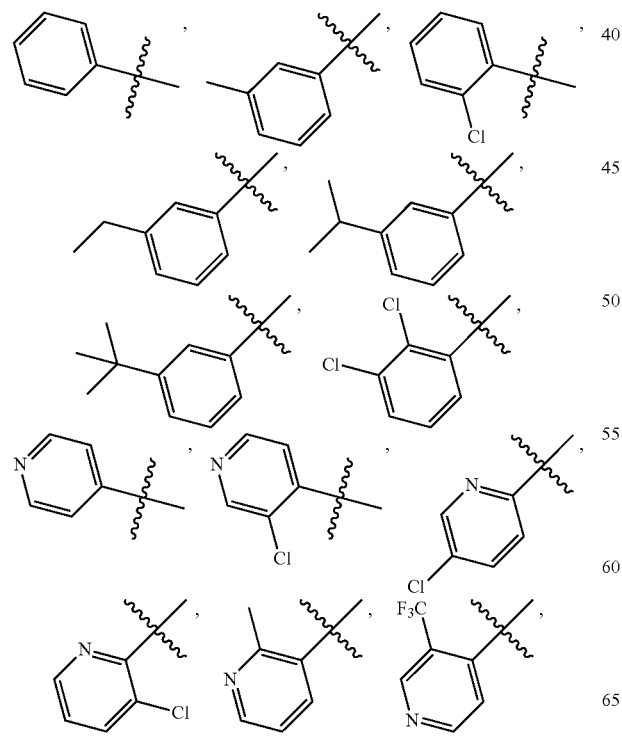

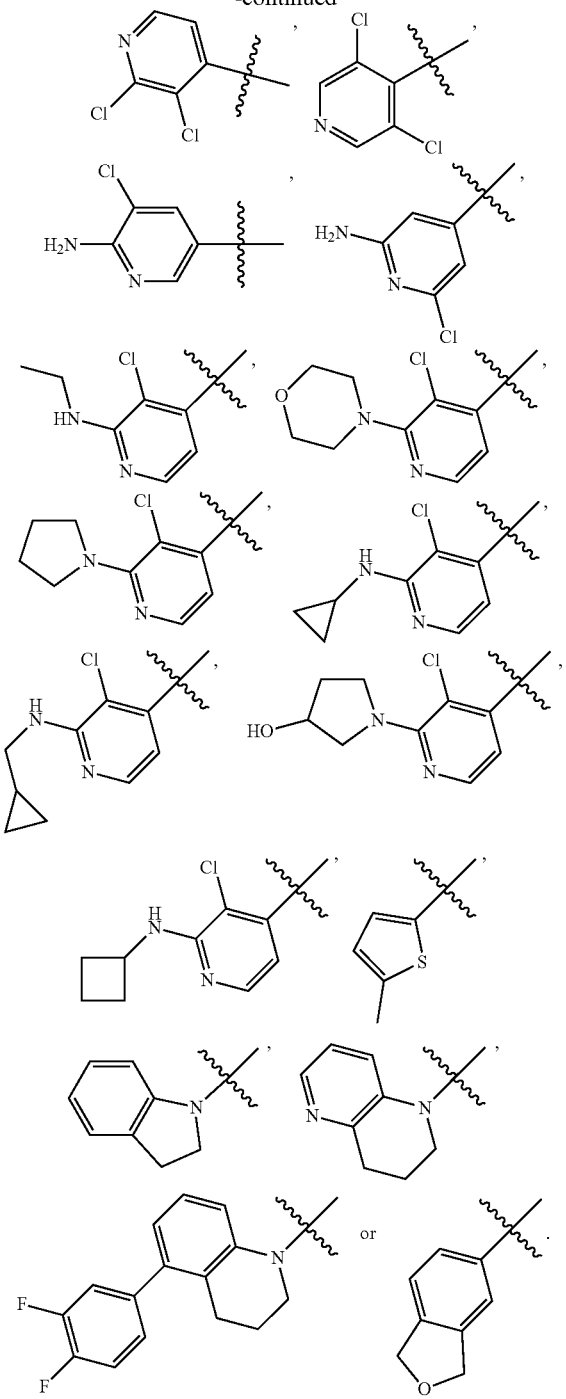

In some embodiments of Formula III, G is selected from absent, S, —SO—, —SO$_2$—, O, —CO—, —NR$_G$—,

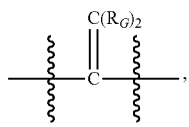

—C(R$_G$)$_2$— or —SO$_2$—NR$_G$—; each of R$_G$ is independent selected from hydrogen, deuterium, F, Cl, Br, —NH$_2$, —CN, —OH, —$C_{1-6}$alkyl or —$C_{1-6}$alkoxy, and each of which is independently optionally substituted or unsubstituted.

In some embodiments of Formula III, G is selected from absent, S, —SO—, —SO$_2$—, O, —CO—, —NR$_G$—,

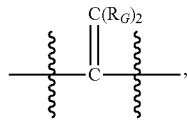

—C(R$_G$)$_2$— or —SO$_2$—NR$_G$—; each of R$_G$ is independent selected from hydrogen, deuterium, F, Cl, Br, —NH$_2$, —CN, —OH, —$C_{1-3}$alkyl or —$C_{1-3}$alkoxy, and each of which is independently optionally substituted or unsubstituted.

In some embodiments of Formula III, G is selected from absent, S, —SO—, —SO$_2$—, O, —CO—, —NR$_G$—,

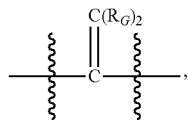

—C(R$_G$)$_2$— or —SO$_2$—NR$_G$—; each of R$_G$ is independent selected from hydrogen, deuterium, F, Cl, Br, —NH$_2$, —CN, —OH, methyl, ethyl, propyl, isopropyl, methoxy, ethoxy, propoxy or isopropoxy, and each of which is independently optionally substituted or unsubstituted.

In some embodiments of Formula III, Y$_1$ is N or CR$_{Y1}$; R$_{Y1}$ is selected from hydrogen, deuterium, F, Cl, Br, —NH$_2$, —CN, —$C_{1-6}$alkyl, —$C_{1-6}$alkoxy, —NH—$C_{1-6}$alkyl, —N—(C$_{1-6}$alkyl)$_2$, —$C_{1-6}$alkenyl, —$C_{3-8}$cycloalkyl or —$C_{5-10}$aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —$C_{1-6}$alkyl or —$C_{1-6}$alkoxy.

In some embodiments of Formula III, Y$_1$ is N or CR$_{Y1}$; R$_{Y1}$ is selected from hydrogen, deuterium, F, Cl, Br, —NH$_2$, —CN, —$C_{1-6}$alkyl, —$C_{1-6}$alkoxy, —NH—$C_{1-6}$alkyl, —N—(C$_{1-6}$alkyl)$_2$, —$C_{1-6}$alkenyl, —$C_{3-8}$cycloalkyl or —Cm-aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —$C_{1-3}$alkyl or —$C_{1-3}$alkoxy.

In some embodiments of Formula III, Y$_1$ is N or CR$_{Y1}$; R$_{Y1}$ is selected from hydrogen, deuterium, F, Cl, Br, —NH$_2$, —CN, —$C_{1-3}$alkyl, —$C_{1-3}$alkoxy, —NH—$C_{1-3}$alkyl, —N—(C$_{1-3}$alkyl)$_2$, —$C_{1-3}$alkenyl, —$C_{3-6}$cycloalkyl or —Cm-aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —$C_{1-3}$alkyl or —$C_{1-3}$alkoxy.

In some embodiments of Formula III, Y$_1$ is N or CR$_{Y1}$; R$_{Y1}$ is selected from hydrogen, deuterium, F, Cl, Br, —NH$_2$, —CN, methyl, ethyl, propyl, isopropyl, methoxy, ethoxy, propoxy, isopropoxy, —NH—$C_{1-3}$alkyl, —N—(C$_{1-3}$alkyl)$_2$, —$C_{1-3}$alkenyl, —$C_{3-6}$cycloalkyl or —$C_{5-8}$aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, methyl, ethyl, propyl, isopropyl, methoxy, ethoxy, propoxy or isopropoxy.

In some embodiments of Formula III, Y$_2$ is N or CR$_{Y2}$; R$_{Y2}$ is selected from hydrogen, deuterium, F, Cl, Br, —NH$_2$, —CN, —$C_{1-6}$alkyl, —$C_{1-6}$alkoxy, —NH—$C_{1-6}$alkyl, —N—(C$_{1-6}$alkyl)$_2$, —$C_{1-6}$ alkenyl, —$C_{3-8}$cycloalkyl or —$C_{5-10}$aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —$C_{1-6}$alkyl or —$C_{1-6}$alkoxy.

In some embodiments of Formula III, Y$_2$ is N or CR$_{Y2}$; R$_{Y2}$ is selected from hydrogen, deuterium, F, Cl, Br, —NH$_2$, —CN, —$C_{1-6}$alkyl, —$C_{1-6}$alkoxy, —NH—$C_{1-6}$alkyl, —N—(C$_{1-6}$alkyl)$_2$, —$C_{1-6}$ alkenyl, —$C_{3-8}$cycloalkyl or —$C_{5-10}$aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —$C_{1-3}$alkyl or —$C_{1-3}$alkoxy.

In some embodiments of Formula III, Y$_2$ is N or CR$_{Y2}$; R$_{Y2}$ is selected from hydrogen, deuterium, F, Cl, Br, —NH$_2$, —CN, —$C_{1-3}$alkyl, —$C_{1-3}$alkoxy, —NH—$C_{1-3}$alkyl, —N—(C$_{1-3}$alkyl)$_2$, —$C_{1-3}$alkenyl, —$C_{3-6}$cycloalkyl or —$C_{5-8}$aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —$C_{1-3}$alkyl or —$C_{1-3}$alkoxy.

In some embodiments of Formula III, Y$_2$ is N or CR$_{Y2}$; R$_{Y2}$ is selected from hydrogen, deuterium, F, Cl, Br, —NH$_2$, —CN, methyl, ethyl, propyl, isopropyl, methoxy, ethoxy, propoxy, isopropoxy, —NH—$C_{1-3}$alkyl, —N—(C$_{1-3}$alkyl)$_2$, —$C_{1-3}$alkenyl, —$C_{3-6}$cycloalkyl or —$C_{5-8}$aryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, methyl, ethyl, propyl, isopropyl, methoxy, ethoxy, propoxy or isopropoxy.

In some embodiments of Formula III, R$_{Y3}$ and R$_{Y4}$ are independently selected from hydrogen, deuterium, F, Cl, Br, —NH$_2$, —OH, —CN, —$C_{1-6}$alkyl, carboxyl, —COO—$C_{1-6}$alkyl, —NH—$C_{1-6}$alkylene-OH, —$C_{1-6}$alkylene-OH, —CONH$_2$ or -5-8 membered heteroaryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —$C_{1-6}$alkyl or —$C_{1-6}$alkoxy.

In some embodiments of Formula III, R$_{Y3}$ and R$_{Y4}$ are independently selected from hydrogen, deuterium, F, Cl, Br, —NH$_2$, —OH, —CN, —$C_{1-6}$alkyl, carboxyl, —COO—$C_{1-6}$alkyl, —NH—$C_{1-6}$alkylene-OH, —$C_{1-6}$alkylene-OH, —CONH$_2$ or -5-8 membered heteroaryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —$C_{1-3}$alkyl or —$C_{1-3}$alkoxy.

In some embodiments of Formula III, R$_{Y3}$ and R$_{Y4}$ are independently selected from hydrogen, deuterium, F, Cl, Br, —NH$_2$, —OH, —CN, —$C_{1-3}$alkyl, carboxyl, —COO—$C_{1-3}$alkyl, —NH—$C_{1-3}$alkylene-OH, —$C_{1-3}$alkylene-OH, —CONH$_2$ or -5-8 membered heteroaryl, and each of which is independently optionally substituted with 1, 2, 3, 4, 5, or 6 substituents, and the said each substituents is independently selected from deuterium, F, Cl, Br, I, —NH$_2$, —CN, —OH, —NO$_2$, carboxyl, —$C_{1-3}$alkyl or —$C_{1-3}$alkoxy.

In some embodiments of Formula III, $R_{y3}$ and $R_{y4}$ are independently selected from hydrogen, deuterium, F, Cl, Br, —NH₂, —OH, —CN, methyl, ethyl, propyl, isopropyl, carboxyl, —COO—$C_{1-3}$alkyl, —NH—$C_{1-3}$alkylene-OH, —$C_{1-3}$alkylene-OH, —CONH₂ or -5-8 membered heteroaryl, and each of which is independently optionally substituted with 1, 2, 3, 4, 5, or 6 substituents, and the said each substituents is independently selected from deuterium, F, Cl, Br, I, —NH₂, —CN, —OH, —NO₂, carboxyl, methyl, ethyl, propyl, isopropyl, methoxy, ethoxy, propoxy or isopropoxy.

In some embodiments of Formula III, ring B is selected from

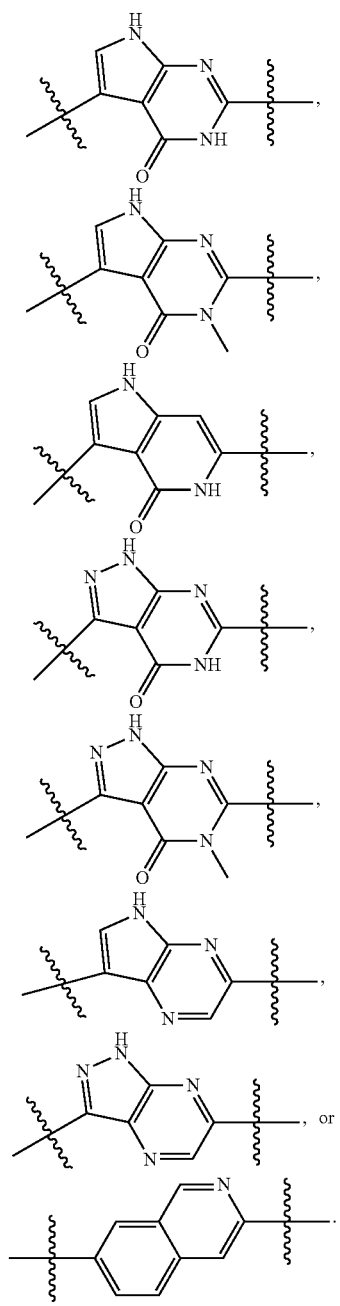

In some embodiments of Formula III, each of $R_1$ and $R_2$ is independently selected from hydrogen, deuterium, F, Cl, Br, —NH₂, —CN, —OH, —NO₂, carboxyl, —NH—$C_{1-3}$alkyl, —N($C_{1-3}$alkyl)₂, substituted or unsubstituted —$C_{1-3}$alkoxy, or substituted or unsubstituted —$C_{1-3}$alkyl.

In some embodiments of Formula III, each of $R_1$ and $R_2$ is independently selected from hydrogen, deuterium, F, Cl, Br, —NH₂, —CN, —OH, —NO₂, carboxyl, —NH—$C_{1-3}$alkyl, —N($C_{1-3}$alkyl)₂, substituted or unsubstituted —$C_{1-3}$alkoxy, or substituted or unsubstituted —$C_{1-3}$alkyl.

In some embodiments of Formula III, each of $R_1$ and $R_2$ is independently selected from hydrogen; deuterium; F; Cl; Br; —NH₂; —CN; —OH; —NO₂; carboxyl; —NH—$C_{1-3}$alkyl; —N($C_{1-3}$alkyl)₂; methoxy; ethoxy; propoxy; isopropoxy; —$C_{1-3}$alkoxy substituted with halogen, NH₂, CN, OH, NO₂, carboxyl, $C_{1-3}$alkyl or $C_{1-3}$alkoxy; methyl; ethyl; propyl; isopropyl; —$C_{1-3}$alkyl substituted with halogen, NH₂, CN, O, NO₂, carboxyl, $C_{1-3}$alkyl or $C_{1-3}$alkoxy.

In some embodiments of Formula III, each of R and $R_2$ is independently selected from hydrogen; deuterium; F; Cl; Br; —NH₂; —CN; —OH; —NO₂; carboxyl; —NH—$C_{1-3}$alkyl; —N($C_{1-3}$alkyl)₂; methoxy; ethoxy; propoxy; isopropoxy; —$C_{1-3}$alkoxy substituted with F, Cl, Br, NH₂, CN, OH, NO₂, carboxyl, methyl, ethyl, propyl, isopropyl, methoxy, ethoxy, propoxy or isopropoxy; methyl; ethyl; propyl; isopropyl; —$C_{1-3}$alkyl substituted with F, Cl, Br, NH₂, CN, OH, NO₂, carboxyl, methyl, ethyl, propyl, isopropyl, methoxy, ethoxy, propoxy or isopropoxy.

In some embodiments of Formula III, $R_1$ and $R_2$ together with the carbon atom to which they are both attached form CO or C=NR₅.

In some embodiments of Formula III, $R_1$ and $R_2$ together with the carbon atom to which they are both attached form CO.

In some embodiments of Formula III, $R_1$ and $R_2$ together with the carbon atom to which they are both attached form C=NR₅.

In some embodiments of Formula III, each of $R_3$ and $R_4$ is independently selected from hydrogen, deuterium, F, Cl, Br, —NH₂, —CN, —OH, —NO₂, carboxyl, —NH—$C_{1-6}$alkyl, —N($C_{1-6}$alkyl)₂, substituted or unsubstituted —$C_{1-6}$alkoxy, or substituted or unsubstituted —$C_{1-6}$alkyl.

In some embodiments of Formula III, each of $R_3$ and $R_4$ is independently selected from hydrogen, deuterium, F, Cl, Br, —NH₂, —CN, —OH, —NO₂, carboxyl, —NH—$C_{1-3}$alkyl, —N($C_{1-3}$alkyl)₂, substituted or unsubstituted —$C_{1-3}$alkoxy, or substituted or unsubstituted —$C_{1-3}$alkyl.

In some embodiments of Formula III, each of $R_3$ and $R_4$ is independently selected from hydrogen; deuterium; F; Cl; Br; —NH₂; —CN; —OH; —NO₂; carboxyl; —NH—$C_{1-3}$alkyl; —N($C_{1-3}$alkyl)₂; methoxy; ethoxy; propoxy; isopropoxy; —$C_{1-3}$alkoxy substituted with halogen, NH₂, CN, OH, NO₂, carboxyl, $C_{1-3}$alkyl or $C_{1-3}$alkoxy; methyl; ethyl; propyl; isopropyl; —$C_{1-3}$alkyl substituted with halogen, NH₂, CN, OH, NO₂, carboxyl, $C_{1-3}$alkyl or $C_{1-3}$alkoxy.

In some embodiments of Formula III, each of $R_3$ and $R_4$ is independently selected from hydrogen; deuterium; F; Cl; Br; —NH₂; —CN; —OH; —NO₂; carboxyl; —NH—$C_{1-3}$alkyl; —N($C_{1-3}$alkyl)₂; methoxy; ethoxy; propoxy; isopropoxy; —$C_{1-3}$alkoxy substituted with F, Cl, Br, NH₂, CN, OH, NO₂, carboxyl, methyl, ethyl, propyl, isopropyl, methoxy, ethoxy, propoxy or isopropoxy; methyl; ethyl; propyl; isopropyl; —$C_{1-3}$alkyl substituted with F, Cl, Br, NH$_2$, CN, OH, NO$_2$, carboxyl, methyl, ethyl, propyl, isopropyl, methoxy, ethoxy, propoxy or isopropoxy.

In some embodiments of Formula III, R$_3$ and R$_4$ together with the carbon atom to which they are both attached form 3-12 membered heterocyclic ring or 5-12 membered heteroaromatic ring or C=NR$_5$, and each of the heterocyclic ring contains 1, 2 or 3 heteroatoms selected from N, O or S, and each of the heteroaromatic ring contains 1, 2 or 3 heteroatoms selected from N, O or S, and each of the ring systems is independently optionally substituted or unsubstituted.

In some embodiments of Formula III, R$_3$ and R$_4$ together with the carbon atom to which they are both attached form 3-10 membered heterocyclic ring or 5-10 membered heteroaromatic ring or C=NR$_5$, and each of the heterocyclic ring contains 1, 2 or 3 heteroatoms selected from N, O or S, and each of the heteroaromatic ring contains 1, 2 or 3 heteroatoms selected from N, O or S, and each of the ring systems is independently optionally substituted or unsubstituted.

In some embodiments of Formula III, R$_3$ and R$_4$ together with the carbon atom to which they are both attached form 3 membered heterocyclic ring, 4 membered heterocyclic ring, 5 membered heterocyclic ring, 6 membered heterocyclic ring, 7 membered heterocyclic ring, 8 membered heterocyclic ring, 9 membered heterocyclic ring, 10 membered heterocyclic ring, 5 membered heteroaromatic ring, 6 membered heteroaromatic ring, 7 membered heteroaromatic ring, 8 membered heteroaromatic ring, 9 membered heteroaromatic ring, 10 membered heteroaromatic ring or C=NR$_5$, and each of the heterocyclic ring contains 1, 2 or 3 heteroatoms selected from N, O or S, and each of the heteroaromatic ring contains 1, 2 or 3 heteroatoms selected from N, O or S, and each of the ring systems is independently optionally substituted or unsubstituted.

In some embodiments of Formula III, each of R$_5$ is independently selected from hydrogen, deuterium, F, Cl, Br, —NH$_2$, —CN, —OH, —C$_{1-6}$alkyl or —C$_{1-6}$alkoxy.

In some embodiments of Formula III, each of R$_5$ is independently selected from hydrogen, deuterium, F, Cl, Br, —NH$_2$, —CN, —OH, —C$_{1-3}$alkyl or —C$_{1-3}$alkoxy.

In some embodiments of Formula III, each of R$_5$ is independently selected from hydrogen, deuterium, F, Cl, Br, —NH$_2$, —CN, —OH, methyl, ethyl, propyl, isopropyl, methoxy, ethoxy, propoxy or isopropoxy.

In some embodiments of Formula III, W is absent, —O, —S or —C(R$_W$)$_2$—; and each of R$_W$ is independently selected from hydrogen, deuterium, F, Cl, Br, —NH$_2$, —CN, —OH, —NO$_2$, carboxyl, —CO—C$_{1-6}$alkyl, —CO—OC$_{1-6}$alkyl, —C$_{1-6}$alkyl-O— C$_{1-6}$alkoxy, substituted or unsubstituted —C$_{1-6}$alkoxy, or substituted or unsubstituted —C$_{1-6}$alkyl.

In some embodiments of Formula III, W is absent, —O, —S or —C(R$_W$)$_2$—; and each of R$_W$ is independently selected from hydrogen, deuterium, F, Cl, Br, —NH$_2$, —CN, —OH, —NO$_2$, carboxyl, —CO—C$_{1-3}$alkyl, —CO—OC$_{1-3}$alkyl, —C$_{1-3}$alkyl-O—C$_{1-3}$alkoxy, substituted or unsubstituted —C$_{1-3}$alkoxy, or substituted or unsubstituted —C$_{1-3}$alkyl.

In some embodiments of Formula III, W is absent, —O, —S or —C(R$_W$)$_2$—; and each of R$_W$ is independently selected from hydrogen; deuterium; F; Cl; Br; —NH$_2$; —CN; —OH; —NO$_2$; carboxyl; —CO—C$_{1-3}$alkyl; —CO—OC$_{1-3}$alkyl; —C$_{1-3}$alkyl-O—C$_{1-3}$alkoxy; methoxy; ethoxy; propoxy; isopropoxy; —C$_{1-3}$alkoxy substituted with halogen, NH$_2$, CN, OH, NO$_2$, carboxyl, C$_{1-3}$alkyl or C$_{1-3}$alkoxy; methyl; ethyl; propyl; isopropyl; —C$_{1-3}$alkyl substituted with halogen, NH$_2$, CN, OH, NO$_2$, carboxyl, C$_{1-3}$alkyl or C$_{1-3}$alkoxy.

In some embodiments of Formula III, W is absent, —O, —S or —C(R$_W$)$_2$—; and each of R$_W$ is independently selected from hydrogen; deuterium; F; Cl; Br; —NH$_2$; —CN; —OH; —NO$_2$; carboxyl; —CO—C$_{1-3}$alkyl; —CO—OC$_{1-3}$alkyl; —C$_{1-3}$alkyl-O—C$_{1-3}$alkoxy; methoxy; ethoxy; propoxy; isopropoxy; —C$_{1-3}$alkoxy substituted with halogen, NH$_2$, CN, OH, NO$_2$, carboxyl, C$_{1-3}$alkyl or C$_{1-3}$alkoxy; methyl; ethyl; propyl; isopropyl; —C$_{1-3}$alkyl substituted with halogen, NH$_2$, CN, OH, NO$_2$, carboxyl, C$_{1-3}$alkyl or C$_{1-3}$alkoxy.

In some embodiments of Formula III, W is absent, —O, —S or —C(R$_W$)$_2$—; and each of R$_W$ is independently selected from hydrogen; deuterium; F; Cl; Br; —NH$_2$; —CN; —OH; —NO$_2$; carboxyl; —CO—C$_{1-3}$alkyl; —CO—OC$_{1-3}$alkyl; —C$_{1-3}$alkyl-O—C$_{1-3}$alkoxy; methoxy; ethoxy; propoxy; isopropoxy; —C$_{1-3}$alkoxy substituted with F, Cl, Br, NH$_2$, CN, OH, NO$_2$, carboxyl, methyl, ethyl, propyl, isopropyl, methoxy, ethoxy, propoxy or isopropoxy; methyl; ethyl; propyl; isopropyl; —C$_{1-3}$alkyl substituted with F, Cl, Br, NH$_2$, CN, OH, NO$_2$, carboxyl, methyl, ethyl, propyl, isopropyl, methoxy, ethoxy, propoxy or isopropoxy.

In some embodiments of Formula III, ring C is absent, a 5-12 membered aromatic ring, a 5-12 membered heteroaromatic ring or a 5-12 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula III, ring C is absent, a 5-10 membered aromatic ring, a 5-10 membered heteroaromatic ring or a 5-10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula III, ring C is absent, a 5 membered aromatic ring, a 6 membered aromatic ring, a 7 membered aromatic ring, an 8 membered aromatic ring, a 9 membered aromatic ring, a 10 membered aromatic ring, a 5 membered heteroaromatic ring, a 6 membered heteroaromatic ring, a 7 membered heteroaromatic ring, an 8 membered heteroaromatic ring, a 9 membered heteroaromatic ring, a 10 membered heteroaromatic ring, a 5 membered heterocyclic ring, a 6 membered heterocyclic ring, a 7 membered heterocyclic ring, an 8 membered heterocyclic ring, a 9 membered heterocyclic ring, a 10 membered heterocyclic ring, and each of the heteroaromatic ring contains 1, 2 or 3 heteroatoms selected from N, O or S, and each of the heterocyclic ring contains 1, 2 or 3 heteroatoms selected from N, O or S, and each of the ring systems is independently optionally substituted or unsubstituted.

In some embodiments of Formula III, ring C is selected from

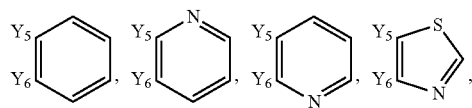

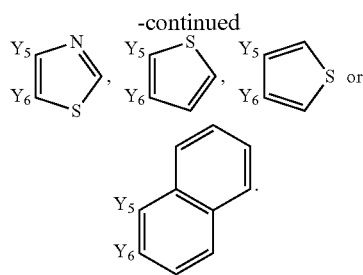

In some embodiments of Formula III, each of $R_{5a}$ and $R_{5b}$ is independently selected from hydrogen, deuterium, F, Cl, Br, —$NH_2$, —CN, —OH, —$NO_2$, carboxyl, substituted or unsubstituted —$C_{1-6}$alkoxy, or substituted or unsubstituted —$C_{1-6}$alkyl.

In some embodiments of Formula III, each of $R_{5a}$ and $R_{5b}$ is independently selected from hydrogen, deuterium, F, Cl, Br, —$NH_2$, —CN, —OH, —$NO_2$, carboxyl, substituted or unsubstituted —$C_{1-6}$alkoxy, or substituted or unsubstituted —$C_{1-6}$alkyl.

In some embodiments of Formula III, each of $R_{5a}$ and $R_{5b}$ is independently selected from hydrogen; deuterium; F; Cl; Br; —$NH_2$; —CN; —OH; —$NO_2$; carboxyl; methoxy; ethoxy; propoxy; isopropoxy; —$C_{1-3}$alkoxy substituted with halogen, $NH_2$, CN, OH, $NO_2$, carboxyl, $C_{1-3}$alkyl or $C_{1-3}$alkoxy; methyl; ethyl; propyl; isopropyl; —$C_{1-3}$alkyl substituted with halogen, $NH_2$, CN, OH, $NO_2$, carboxyl, $C_{1-3}$alkyl or $C_{1-3}$alkoxy.

In some embodiments of Formula III, each of $R_{5a}$ and $R_{5b}$ is independently selected from hydrogen; deuterium; F; Cl; Br; —$NH_2$; —CN; —OH; —$NO_2$; carboxyl; methoxy; ethoxy; propoxy; isopropoxy; —$C_{1-3}$alkoxy substituted with F, Cl, Br, $NH_2$, CN, OH, $NO_2$, carboxyl, methyl, ethyl, propyl, isopropyl, methoxy, ethoxy, propoxy or isopropoxy; —$C_{1-3}$alkyl substituted with F, Cl, Br, $NH_2$, CN, OH, $NO_2$, carboxyl, methyl, ethyl, propyl, isopropyl, methoxy, ethoxy, propoxy or isopropoxy.

In some embodiments of Formula III, each of $R_{6a}$ and $R_{6b}$ is independently selected from hydrogen, deuterium, F, Cl, Br, —$NH_2$, —CN, —OH, —$NO_2$, carboxyl, substituted or unsubstituted —$C_{1-6}$alkoxy, or substituted or unsubstituted —$C_{1-6}$alkyl.

In some embodiments of Formula III, each of $R_{6a}$ and $R_{6b}$ is independently selected from hydrogen, deuterium, F, Cl, Br, —$NH_2$, —CN, —OH, —$NO_2$, carboxyl, substituted or unsubstituted —$C_{1-3}$alkoxy, or substituted or unsubstituted —$C_{1-3}$alkyl.

In some embodiments of Formula III, each of $R_{6a}$ and $R_{6b}$ is independently selected from hydrogen; deuterium; F; Cl; Br; —$NH_2$; —CN; —OH; —$NO_2$; carboxyl; methoxy; ethoxy; propoxy; isopropoxy; —$C_{1-3}$alkoxy substituted with halogen, $NH_2$, CN, OH, $NO_2$, carboxyl, $C_{1-3}$alkyl or $C_{1-3}$alkoxy; methyl; ethyl; propyl; isopropyl; —$C_{1-3}$alkyl substituted with halogen, $NH_2$, CN, OH, $NO_2$, carboxyl, $C_{1-3}$alkyl or $C_{1-3}$alkoxy.

In some embodiments of Formula III, each of $R_{6a}$ and $R_{6b}$ is independently selected from hydrogen; deuterium; F; Cl; Br; —$NH_2$; —CN; —OH; —$NO_2$; carboxyl; methoxy; ethoxy; propoxy; isopropoxy; —$C_{1-3}$alkoxy substituted with F, Cl, Br, $NH_2$, CN, OH, $NO_2$, carboxyl, methyl, ethyl, propyl, isopropyl, methoxy, ethoxy, propoxy or isopropoxy; methyl; ethyl; propyl; isopropyl; —$C_{1-3}$alkyl substituted with F, Cl, Br, $NH_2$, CN, OH, $NO_2$, carboxyl, methyl, ethyl, propyl, isopropyl, methoxy, ethoxy, propoxy or isopropoxy.

In some embodiments of Formula III, each of Ra is independently selected from hydrogen, deuterium, F, Cl, Br, —$NR_{a1}R_{a2}$, —CN, —OH, —$NO_2$, oxo, =O, carboxyl, —$C_{1-3}$alkoxy, —$C_{1-6}$alkyl, —$C_{3-6}$cycloalkyl, —$C_{1-3}$alkylene-$NR_{a1}R_{a2}$, —$C_{1-3}$alkylene-O—$C_{1-6}$alkyl, —$C_{1-3}$alkylene-CO—$OR_{a1}$, —$C_{1-3}$alkylene-(3-8 membered heterocyclic), —$C_{1-3}$alkylene-(5-8 membered heteroaryl), —$C_{1-3}$alkylene-CO—$NR_{a1}R_{a2}$, —$C_{1-3}$alkylene-$NR_{a1}$—CO—$NR_{a1}R_{a2}$, —$C_{1-3}$alkylene-$NR_{a1}$—CO—$C_{1-3}$alkyl, —CO—$NR_{a1}R_{a2}$, —CO—CO—$NR_{a1}R_{a2}$, —$C_{3-8}$carbocyclic, -3-8 membered heterocyclic, —CO—$C_{1-3}$alkyl, —COO—$C_{1-3}$alkyl, —CO—$C_{1-3}$alkylene-$NR_{a1}R_{a2}$, —CO—$NR_{a1}$-(3-8 membered heterocyclic), —CO—$NR_1$-(3-8 membered heterocyclic), —CO-(3-8 membered heterocyclic), —O—$C_{1-3}$alkylene-CO—$OR_{a1}$, —O—$C_{1-3}$alkylene-CO—$NR_{a1}R_2$, —O—$C_{1-3}$alkylene-$NR_{a1}R_{a2}$, —O—$C_{3-8}$carbocyclic, —O-(3-8 membered heterocyclic), —$NR_{a1}$—CO—$C_{1-3}$alkyl, —$NR_{a1}$—CO—$NR_{a1}R_{a2}$, —$NR_1$—CO-(5-8 membered heteroaryl), —$NR_{a1}$—CO—$C_{3-6}$cycloalkyl, —$NR_{a1}$—$C_{1-3}$alkylene-$NR_{a1}R_{a2}$, —$NR_{a1}$—$C_{1-3}$alkylene-(3-8 membered heterocyclic), —$NR_{a1}$—$C_{1-3}$alkylene-(5-8 membered heteroaryl), —$NR_{a1}$—$SO_2C_{1-3}$alkyl, —S—$C_{1-3}$alkyl, —$SONR_{a1}R_{a2}$, —$SO_2NR_{a1}R_{a2}$, —SO—$C_{1-3}$alkyl, —$SO_2C_{1-3}$alkyl, —PO($C_{1-3}$alkyl)$_2$, —PO($C_{1-3}$alkoxy)$_2$, -3-8 membered heterocyclic or -5-8 membered heteroaryl; each of which is independently optionally substituted; and n is 0, 1, 2, 3, 4, 5 or 6.

In some embodiments of Formula III, each of Ra is independently selected from hydrogen, deuterium, F, Cl, Br, —$NR_{a1}R_{a2}$, —CN, —OH, —$NO_2$, oxo, =O, carboxyl, methoxy, ethoxy, propoxy, isopropoxy methyl, ethyl, propyl, isopropyl, butyl, isobutyl, —$C_{3-6}$cycloalkyl, —$C_{1-3}$alkylene-$NR_{a1}R_{a2}$, —$C_{1-3}$alkylene-O—$C_{1-6}$alkyl, —$C_{1-3}$alkylene-CO—$OR_{a1}$, —$C_{1-3}$alkylene-(3-8 membered heterocyclic), —$C_{1-3}$alkylene-(5-8 membered heteroaryl), —$C_{1-3}$alkylene-CO—$NR_{a1}R_{a2}$, —$C_{1-3}$alkylene-$NR_{a1}$—CO—$NR_{a1}R_{a2}$, —$C_{1-3}$alkylene-$NR_{a1}$—CO—$C_{1-3}$alkyl, —CO—$NR_{a1}R_{a2}$, —CO—CO—$NR_{a1}R_{a2}$, —$C_{3-8}$carbocyclic, -3-8 membered heterocyclic, —CO—$C_{1-3}$alkyl, —COO—$C_{1-3}$alkyl, —CO—$C_{1-3}$alkylene-$NR_{a1}R_{a2}$, —CO—$NR_1$-(3-8 membered heterocyclic), —CO—$NR_1$-(3-8 membered heterocyclic), —CO-(3-8 membered heterocyclic), —O—$C_{1-3}$alkylene-CO—$OR_{a1}$, —O—$C_{1-3}$alkylene-CO—$NR_{a1}R_{a2}$, —O—$C_{1-3}$alkylene-$NR_{a1}R_{a2}$, —O—$C_{3-8}$carbocyclic, —O-(3-8 membered heterocyclic), —$NR_{a1}$—CO—$C_{1-3}$alkyl, —$NR_{a1}$—CO—$NR_{a1}R_{a2}$, —$NR_1$—CO-(5-8 membered heteroaryl), —$NR_1$—CO—$C_{3-6}$cycloalkyl, —$NR_{a1}$—$C_{1-3}$alkylene-$NR_{a1}R_{a2}$, —$NR_{a1}$—$C_{1-3}$alkylene-(3-8 membered heterocyclic), —$NR_{a1}$—$C_{1-3}$alkylene-(5-8 membered heteroaryl), —$NR_{a1}$—$SO_2C_{1-3}$alkyl, —S—$C_{1-3}$alkyl, —$SONR_{a1}R_{a2}$, —$SO_2NR_{a1}R_{a2}$, —SO—$C_{1-3}$alkyl, —$SO_2C_{1-3}$alkyl, —PO($C_{1-3}$alkyl)$_2$, —PO($C_{1-3}$alkoxy)$_2$, -3-8 membered heterocyclic or -5-8 membered heteroaryl; each of which is independently optionally substituted; and n is 0, 1, 2, 3, 4, 5 or 6.

In some embodiments of Formula III, two adjacent Ra can be joined together to form a 6-membered aromatic ring, a 5-membered heteroaromatic ring, a 6-membered heteroaromatic ring, a 3-6 membered heterocyclic ring or a 3-6 membered carbocyclic ring, wherein each of the ring systems is independently optionally substituted with deuterium, halogen, —$NH_2$, —CN, —OH, —$NO_2$, carboxyl, —$C_{1-6}$alkyl or —$C_{1-6}$alkoxy.

In some embodiments of Formula III, two adjacent Ra can be joined together to form a 6-membered aromatic ring, a 5-membered heteroaromatic ring, a 6-membered heteroaromatic ring, a 3-6 membered heterocyclic ring or a 3-6 membered carbocyclic ring, wherein each of the ring systems is independently optionally substituted with deuterium, F, Cl, Br, —NH$_2$, —CN, —OH, —NO$_2$, carboxyl, —C$_{1-3}$alkyl or —C$_{1-3}$alkoxy.

In some embodiments of Formula III, two adjacent Ra can be joined together to form a 6-membered aromatic ring, a 5-membered heteroaromatic ring, a 6-membered heteroaromatic ring, a 3 membered heterocyclic ring, a 4 membered heterocyclic ring, a 5 membered heterocyclic ring, a 6 membered heterocyclic ring, a 3 membered carbocyclic ring, a 4 membered carbocyclic ring, a 5 membered carbocyclic ring, a 6 membered carbocyclic ring, wherein each of the heteroaryl contains 1, 2 or 3 heteroatoms selected from N, O or S, and each of the heterocyclic ring contains 1, 2 or 3 heteroatoms selected from N, O or S, each of the ring systems is independently optionally substituted with deuterium, F, Cl, Br, —NH$_2$, —CN, —OH, —NO$_2$, carboxyl, —C$_{1-3}$alkyl or —C$_{1-3}$alkoxy.

In some embodiments of Formula III, Ra and R$_W$ with the atom to which they are both attached form a 3-10 membered aromatic ring, a 3-10 membered heteroaromatic ring or 3-10 membered heterocyclic ring; and each of the ring systems is independently optionally substituted with deuterium, halogen, —NH$_2$, —CN, —OH, —NO$_2$, carboxyl, —C$_{1-6}$alkyl or —C$_{1-6}$alkoxy.

In some embodiments of Formula III, Ra and R$_W$ with the atom to which they are both attached form a 3-10 membered aromatic ring, 3-10 membered heteroaromatic ring or 3-10 membered heterocyclic ring; and each of the ring systems is independently optionally substituted with deuterium, F, Cl, Br, —NH$_2$, —CN, —OH, —NO$_2$, carboxyl, —C$_{1-3}$alkyl or —C$_{1-3}$alkoxy.

In some embodiments of Formula III, Ra and R$_W$ with the atom to which they are both attached form a 3-10 membered aromatic ring, a 3-10 membered heteroaromatic ring or a 3-10 membered heterocyclic ring; each of the heteroaromatic ring contains 1, 2 or 3 heteroatoms selected from N, O or S; each of the heterocyclic ring contains 1, 2 or 3 heteroatoms selected from N, O or S; and each of the ring systems is independently optionally substituted with deuterium, F, Cl, Br, —NH$_2$, —CN, —OH, —NO$_2$, carboxyl, —C$_{1-3}$alkyl or —C$_{1-3}$alkoxy.

In some embodiments of Formula III, Ra and R$_W$ with the atom to which they are both attached form a 5 membered aromatic ring, a 6 membered aromatic ring, a 5 membered heteroaryl ring, a 6 membered heteroaryl ring, a 5 membered heterocyclic ring or a 6 membered heterocyclic ring; each of the heteroaromatic ring contains 1, 2 or 3 heteroatoms selected from N, O or S; each of the heterocyclic ring contains 1, 2 or 3 heteroatoms selected from N, O or S; and each of the ring systems is independently optionally substituted with deuterium, F, Cl, Br, —NH$_2$, —CN, —OH, —NO$_2$, carboxyl, —C$_{1-3}$alkyl or —C$_{1-3}$alkoxy.

In some embodiments of Formula III, each of R$_{a1}$ and R$_{a2}$ is independently selected from hydrogen, deuterium, F, Cl, Br, —NH$_2$, —CN, —OH, —NO$_2$, carboxyl, substituted or unsubstituted —C$_{1-6}$alkoxy, or substituted or unsubstituted —C$_{1-6}$alkyl.

In some embodiments of Formula III, each of R$_{a1}$ and R$_{a2}$ is independently selected from hydrogen, deuterium, F, Cl, Br, —NH$_2$, —CN, —OH, —NO$_2$, carboxyl, substituted or unsubstituted —C$_{1-3}$alkoxy, or substituted or unsubstituted —C$_{1-3}$alkyl.

In some embodiments of Formula III, each of R$_{a1}$ and R$_{a2}$ is independently selected from hydrogen; deuterium; F; Cl; Br; —NH$_2$; —CN; —OH; —NO$_2$; carboxyl; methoxy; ethoxy; propoxy; isopropoxy; —C$_{1-3}$alkoxy substituted with halogen, NH$_2$, CN, OH, NO$_2$, carboxyl, C$_{1-3}$alkyl or C$_{1-3}$alkoxy; methyl; ethyl; propyl; isopropyl; —C$_{1-3}$alkyl substituted with halogen, NH$_2$, CN, OH, NO$_2$, carboxyl, C$_{1-3}$alkyl or C$_{1-3}$alkoxy.

In some embodiments of Formula III, each of R$_{a1}$ and R$_{a2}$ is independently selected from hydrogen; deuterium; F; Cl; Br; —NH$_2$; —CN; —OH; —NO$_2$; carboxyl; methoxy; ethoxy; propoxy; isopropoxy; —C$_{1-3}$alkoxy substituted with F, Cl, Br, NH$_2$, CN, OH, NO$_2$, carboxyl, methyl, ethyl, propyl, isopropyl, methoxy, ethoxy, propoxy or isopropoxy; methyl; ethyl; propyl; isopropyl; —C$_{1-3}$alkyl substituted with F, Cl, Br, NH$_2$, CN, OH, NO$_2$, carboxyl, methyl, ethyl, propyl, isopropyl, methoxy, ethoxy, propoxy or isopropoxy.

In some embodiments of Formula III, the compound is of Formula III-a:

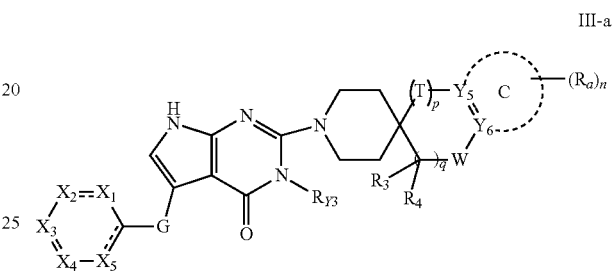

III-a

Wherein X$_1$, X$_2$, X$_3$, X$_4$, X$_5$, G, R$_{Y3}$, T, R$_3$, R$_4$, W, Y$_5$, Y$_6$, R$_a$, p, q and n are as defined herein.

In some embodiments of Formula II, the compound is of Formula III-b:

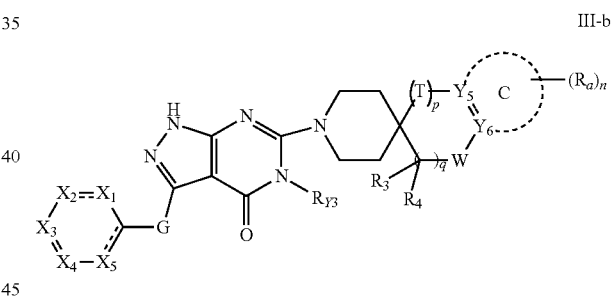

III-b

Wherein X$_1$, X$_2$, X$_3$, X$_4$, X$_5$, G, R$_{Y3}$, T, R$_3$, R$_4$, W, Y$_5$, Y$_6$, R$_a$, p, q and n are as defined herein.

In some embodiments of Formula III, the compound is of Formula III-c:

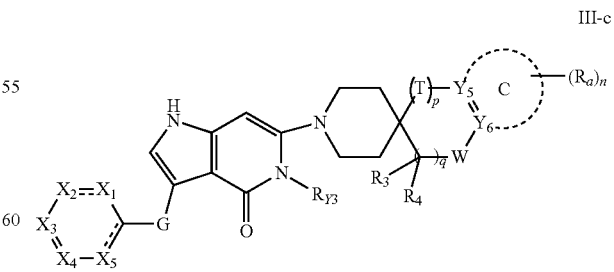

III-c

Wherein X$_1$, X$_2$, X$_3$, X$_4$, X$_5$, G, R$_{Y3}$, T, R$_3$, R$_4$, W, Y$_5$, Y$_6$, R$_a$, p, q and n are as defined herein.

In some embodiments of Formula III, the compound is of Formula III-d:

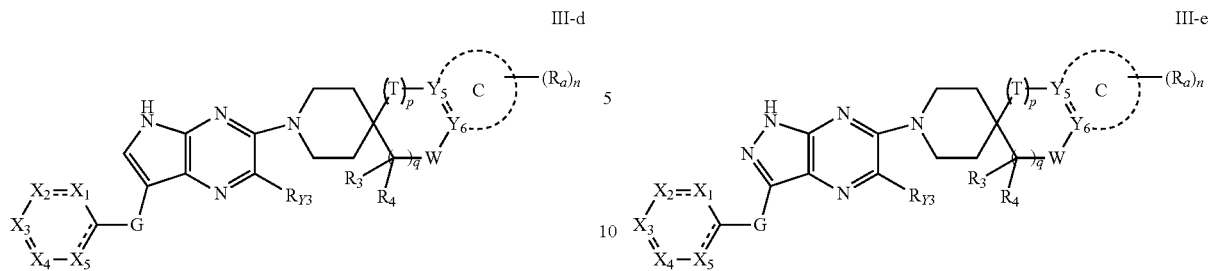

Wherein X₁, X₂, X₃, X₄, X₅, G, R_{Y3}, T, R₃, R₄, W, Y₅, Y₆, R_a, p, q and n are as defined herein.

In some embodiments of Formula III, the compound is of Formula III-e:

Wherein X₁, X₂, X₃, X₄, X₅, G, R_{Y3}, T, R₃, R₄, W, Y₅, Y₆, R_a, p, q and n are as defined herein.

In some embodiments, the present invention provides a compound selected from the group consisting of:

1. ethyl (S)-3-(1-amino-1,3-dihydrospiro[indene-2,4'-piperidin]-1'-yl)-6-(2,3-dichlorophenyl)-5-methylpyrazine-2-carboxylate
2. (S)-1'-(5-(2,3-dichlorophenyl)-6-methylpyrazin-2-yl)-5,7-dihydrospiro[cyclopenta[b]pyridine-6,4'-piperidin]-5-amine
3. (S)-3-(1-amino-1,3-dihydrospiro[indene-2,4'-piperidin]-1'-yl)-6-(2,3-dichlorophenyl)-5-methylpyrazine-2-carboxylic acid
4. (S)-3-(1-amino-1,3-dihydrospiro[indene-2,4'-piperidin]-1'-yl)-6-(2,3-dichlorophenyl)-5-methylpyrazine-2-carboxamide
5. ethyl (S)-3-(1-amino-1,3-dihydrospiro[indene-2,4'-piperidin]-1'-yl)-6-((2-amino-3-chloropyridin-4-yl)thio)-5-methylpyrazine-2-carboxylate
6. (S)-1'-(5-((2-amino-3-chloropyridin-4-yl)thio)-6-methylpyrazin-2-yl)-1,3-dihydrospiro[indene-2,4'-piperidin]-1-amine
7. (S)-1'-(6-amino-5-((2,3-dichlorophenyl)thio)pyrazin-2-yl)-5,7-dihydrospiro[cyclopenta[b]pyridine-6,4'-piperidin]-5-amine
8. (S)-1'-(4-amino-5-((2-amino-3-chloropyridin-4-yl)thio)pyrimidin-2-yl)-5,7-dihydrospiro[cyclopenta[b]pyridine-6,4'-piperidin]-5-amine
9. (S)-1'-(5-((2-amino-3-chloropyridin-4-yl)thio)pyridin-2-yl)-5,7-dihydrospiro[cyclopenta[b]pyridine-6,4'-piperidin]-5-amine
10. (S)-1'-(5-((2-amino-3-chloropyridin-4-yl)thio)-6-(methylamino)pyrazin-2-yl)-5,7-dihydrospiro[cyclopenta[b]pyridine-6,4'-piperidin]-5-amine
11. (S)-1'-(5-((2-amino-3-chloropyridin-4-yl)thio)-6-(dimethylamino)pyrazin-2-yl)-5,7-dihydrospiro[cyclopenta[b]pyridine-6,4'-piperidin]-5-amine
12. (S)-1'-(6-amino-5-(thiazol-4-ylthio)pyrazin-2-yl)-5,7-dihydrospiro[cyclopenta[b]pyridine-6,4'-piperidin]-5-amine
13. (S)-1'-(6-amino-5-(thiazol-2-ylthio)pyrazin-2-yl)-5,7-dihydrospiro[cyclopenta[b]pyridine-6,4'-piperidin]-5-amine
14. (S)-1'-(6-amino-5-(quinolin-3-ylthio)pyrazin-2-yl)-5,7-dihydrospiro[cyclopenta[b]pyridine-6,4'-piperidin]-5-amine
15. (S)-(3-(1-amino-1,3-dihydrospiro[indene-2,4'-piperidin]-1'-yl)-6-(2,3-dichlorophenyl)-5-methylpyrazin-2-yl)methanol
16. (S)-(3-(1-amino-1,3-dihydrospiro[indene-2,4'-piperidin]-1'-yl)-6-((2-amino-3-chloropyridin-4-yl)thio)-5-methylpyrazin-2-yl)methanol
17. (S)-1'-(3-bromo-5-(2,3-dichlorophenyl)-6-methylpyrazin-2-yl)-5,7-dihydrospiro[cyclopenta[b]pyridine-6,4'-piperidin]-5-amine
18. (S)-3-(5-amino-5,7-dihydrospiro[cyclopenta[b]pyridine-6,4'-piperidin]-1'-yl)-6-(2,3-dichlorophenyl)-5-methylpyrazine-2-carbonitrile
19. (S)-3-(5-amino-5,7-dihydrospiro[cyclopenta[b]pyridine-6,4'-piperidin]-1'-yl)-6-(2,3-dichlorophenyl)-5-methylpyrazine-2-carboxamide
20. (S)-3-(5-amino-5,7-dihydrospiro[cyclopenta[b]pyridine-6,4'-piperidin]-1'-yl)-6-(2,3-dichlorophenyl)-5-methylpyrazin-2-ol
21. (S)-1'-(6-amino-3-bromo-5-((2,3-dichlorophenyl)thio)pyrazin-2-yl)-5,7-dihydrospiro[cyclopenta[b]pyridine-6,4'-piperidin]-5-amine
22. (S)-5-amino-3-(5-amino-5,7-dihydrospiro[cyclopenta[b]pyridine-6,4'-piperidin]-1'-yl)-6-((2,3-dichlorophenyl)thio)pyrazine-2-carbonitrile
23. (S)-5-amino-3-(5-amino-5,7-dihydrospiro[cyclopenta[b]pyridine-6,4'-piperidin]-1'-yl)-6-((2,3-dichlorophenyl)thio)pyrazine-2-carboxamide
24. (S)-1'-(6-amino-5-((2-amino-3-chloropyridin-4-yl)thio)pyridin-2-yl)-5,7-dihydrospiro[cyclopenta[b]pyridine-6,4'-piperidin]-5-amine
25. (S)-1'-(6-((2-amino-3-chloropyridin-4-yl)thio)pyridin-3-yl)-5,7-dihydrospiro[cyclopenta[b]pyridine-6,4'-piperidin]-5-amine
26. (S)-1'-(4-((2-amino-3-chloropyridin-4-yl)thio)phenyl)-5,7-dihydrospiro[cyclopenta[b]pyridine-6,4'-piperidin]-5-amine
27. (S)-6-(5-amino-5,7-dihydrospiro[cyclopenta[b]pyridine-6,4'-piperidin]-1'-yl)-3-(2,3-dichlorophenyl)-5-methyl-1,5-dihydro-4H-pyrazolo[3,4-d]pyrimidin-4-one
28. (S)-6-(1-amino-6-fluoro-1,3-dihydrospiro[indene-2,4'-piperidin]-1'-yl)-3-(2,3-dichlorophenyl)-5-methyl-1,5-dihydro-4H-pyrazolo[3,4-d]pyrimidin-4-one
29. (S)-2-(5-amino-5,7-dihydrospiro[cyclopenta[b]pyridine-6,4'-piperidin]-1'-yl)-5-(2,3-dichlorophenyl)-3,7-dihydro-4H-pyrrolo[2,3-d]pyrimidin-4-one 30 (S)-6-amino-2-(1-amino-1,3-dihydrospiro[indene-2,4'-piperidin]-1'-yl)-5-((2-amino-3-chloropyridin-4-yl)thio)-3-methylpyrimidin-4(3H)-one
31 (S)-1'-(6-amino-5-((4-chlorothiazol-2-yl)thio)pyrazin-2-yl)-4,6-dihydrospiro[cyclopenta[d]thiazole-5,4'-piperidin]-4-amine
32 (S)-1'-(6-amino-5-(2-chloro-3-methylphenyl)pyrazin-2-yl)-6-bromo-1,3-dihydrospiro[indene-2,4'-piperidin]-1-amine
33 (R)-1'-(5-(2,3-dichloro-5-methoxyphenyl)pyridin-2-yl)-2,3-dihydrospiro[indene-1,4'-piperidin]-2-amine
34 (S)-1'-(5-(3-amino-2-(trifluoromethyl)phenyl)pyrimidin-2-yl)-1,3-dihydrospiro[indene-2,4'-piperidine]-1,6-diamine
35 (S)-1'-(6-(5-chlorothiophen-2-yl)pyridazin-3-yl)-5-methyl-1,3-dihydrospiro[indene-2,4'-piperidin]-1-amine
36 (S)-1-amino-1'-(6-((3-amino-2-chlorophenyl)thio)-1,2,4-triazin-3-yl)-1,3-dihydrospiro[indene-2,4'-piperidine]-6-carbonitrile
37 (S)-1-amino-1'-(2-((2-cyanopyridin-3-yl)thio)pyrimidin-5-yl)-1,3-dihydrospiro[indene-2,4'-piperidine]-4-carbonitrile
38 1-(5-((5-((1S)-1-amino-6-(methylsulfinyl)-1,3-dihydrospiro[indene-2,4'-piperidin]-1'-yl)pyrazin-2-yl)thio)-2-chlorophenyl)ethan-1-one
39 (S)-1'-(5-(pyrimidin-2-ylthio)pyrazin-2-yl)-6-(trifluoromethyl)-1,3-dihydrospiro[indene-2,4'-piperidin]-1-amine
40 (S)-1'-(5-((3-chloro-2-methoxypyridin-4-yl)thio)pyrazin-2-yl)-6-(methylthio)-1,3-dihydrospiro[indene-2,4'-piperidin]-1-amine
41 (S)-6-bromo-5-fluoro-1'-(5-(quinolin-4-ylthio)pyrazin-2-yl)-1,3-dihydrospiro[indene-2,4'-piperidin]-1-amine
42 (S)-6-(1-amino-5,6,7-trifluoro-1,3-dihydrospiro[indene-2,4'-piperidin]-1'-yl)-5-methyl-3-(5-methylthiophen-2-yl)-1,5-dihydro-4H-pyrazolo[3,4-d]pyrimidin-4-one
43 (S)-6-(4-amino-4,6-dihydrospiro[cyclopenta[b]thiophene-5,4'-piperidin]-1'-yl)-3-(3-(trifluoromethyl)pyridin-4-yl)-1,5-dihydro-4H-pyrazolo[3,4-d]pyrimidin-4-one
44 (S)-2-(1-amino-6-chloro-5-methoxy-1,3-dihydrospiro[indene-2,4'-piperidin]-1'-yl)-5-(3,5-dichloropyridin-4-yl)-3-methyl-3,7-dihydro-4H-pyrrolo[2,3-d]pyrimidin-4-one
45 (S)-1'-(7-(5-chloropyridin-2-yl)-5H-pyrrolo[2,3-b]pyrazin-3-yl)-1,3-dihydrospiro[cyclopenta[a]naphthalene-2,4'-piperidin]-3-amine
46 (S)-1'-(7-(3-chloropyridin-2-yl)-5H-pyrrolo[2,3-b]pyrazin-3-yl)-1H,3H-spiro[phenalene-2,4'-piperidin]-1-amine
47 (R)-1'-(3-(2-methylpyridin-3-yl)-1H-pyrazolo[3,4-b]pyrazin-6-yl)-3,4-dihydro-1H-spiro[naphthalene-2,4'-piperidin]-3-amine
48 (S)-6-amino-2-(1-amino-7-bromo-1,3-dihydrospiro[indene-2,4'-piperidin]-1'-yl)-3-methyl-5-phenylpyrimidin-4(3H)-one
49 (S)-1-amino-1'-(4-amino-6-oxo-5-(pyridazin-3-ylthio)-1,6-dihydropyrimidin-2-yl)-1,3-dihydrospiro[indene-2,4'-piperidine]-7-carbonitrile
50 (S)-1-amino-1'-(1-methyl-6-oxo-5-(pyrazin-2-yl)-1,6-dihydropyrimidin-2-yl)-1,3-dihydrospiro[indene-2,4'-piperidine]-7-carbonitrile
51 (S)-2-(1-amino-6-chloro-5-methoxy-1,3-dihydrospiro[indene-2,4'-piperidin]-1'-yl)-5-((4-isopropylphenyl)thio)pyrimidin-4(3H)-one
52 (S)-4-amino-6-(1-amino-6-bromo-5-fluoro-1,3-dihydrospiro[indene-2,4'-piperidin]-1'-yl)-3-(2-chloro-3-methylphenyl)-1-methylpyridin-2(1H)-one
53 (S)-6-(4-acetyl-1-amino-1,3-dihydrospiro[indene-2,4'-piperidin]-1'-yl)-4-amino-3-(4-(trifluoromethyl)phenyl)pyridin-2(1H)-one
54 (S)-6'-(1-amino-4-methoxy-1,3-dihydrospiro[indene-2,4'-piperidin]-1'-yl)-1'-methyl-2'-oxo-1',2'-dihydro-[3,3'-bipyridine]-2-carboxamide
55 (S)-6'-(1-amino-4-hydroxy-1,3-dihydrospiro[indene-2,4'-piperidin]-1'-yl)-2'-oxo-1',2'-dihydro-[3,3'-bipyridine]-2-carbonitrile
56 (S)-1'-(3-bromo-5-(1H-indol-6-yl)-6-methylpyrazin-2-yl)-4,6-dihydrospiro[cyclopenta[d]thiazole-5,4'-piperidin]-4-amine
57 (S)-3-(4-amino-4,6-dihydrospiro[cyclopenta[d]thiazole-5,4'-piperidin]-1'-yl)-5-methyl-6-(2-oxoindolin-7-yl)pyrazine-2-carbonitrile
58 (S)-1'-(5-amino-6-((2-amino-3-chloropyridin-4-yl)thio)-1,2,4-triazin-3-yl)-5,7-dihydrospiro[cyclopenta[b]pyridine-6,4'-piperidin]-5-amine
59 (S)-1'-(5-amino-6-((2-amino-3-chloropyridin-4-yl)thio)pyridin-3-yl)-6-chloro-1,3-dihydrospiro[indene-2,4'-piperidin]-1-amine
60 (S)-1'-(4-amino-5-((2-amino-3-chloropyridin-4-yl)thio)pyridin-2-yl)-5,7-dihydrospiro[cyclopenta[b]pyridine-6,4'-piperidin]-5-amine
61 (S)-1'-(5-((2,3-dichlorophenyl)thio)thiazol-2-yl)-5,7-dihydrospiro[cyclopenta[b]pyridine-6,4'-piperidin]-7-amine
62 (R)-1'-(4-((3-chloropyridin-4-yl)thio)thiazol-2-yl)spiro[indoline-2,4'-piperidin]-3-amine
63 (R)-1'-(2-(7-chloro-1H-indol-1-yl)thiazol-4-yl)-2,3-dihydrospiro[indene-1,4'-piperidin]-2-amine
64 (R)-1'-(2-((2-(trifluoromethyl)phenyl)thio)thiazol-5-yl)-3H-spiro[benzofuran-2,4'-piperidin]-3-amine
65 (S)-(5-(1-amino-1,3-dihydrospiro[indene-2,4'-piperidin]-1'-yl)pyrazin-2-yl)(2,3-dichlorophenyl)methanone
66 (S)-2-(1-amino-6-fluoro-1,3-dihydrospiro[indene-2,4'-piperidin]-1'-yl)-5-(indolin-1-yl)-3-methyl-3,7-dihydro-4H-pyrrolo[2,3-d]pyrimidin-4-one
67 (S)-1'-(5-((1,2,3,4-tetrahydroquinolin-8-yl)thio)pyrazin-2-yl)-1,3-dihydrospiro[cyclopenta[b]naphthalene-2,4'-piperidin]-1-amine
68 (S)-1'-(5-((2-amino-3-chloropyridin-4-yl)thio)pyrazin-2-yl)-1,3-dihydrospiro[cyclopenta[a]naphthalene-2,4'-piperidin]-1-amine
69 1'-(5-((3-amino-2-chlorophenyl)thio)-6-methylpyrazin-2-yl)-1-methyl-1,3-dihydrospiro[indene-2,4'-piperidin]-1-amine -continued 70 (S)-1'-(5-((2-amino-3-chloropyridin-4-yl)thio)pyrazin-2-yl)-N-methyl-1,3-dihydrospiro[indene-2,4'-piperidin]-1-amine
71 (R)-1'-(7-((2-amino-3-chloropyridin-4-yl)thio)-1H-indol-4-yl)-3H-spiro[benzofuran-2,4'-piperidin]-3-amine
72 (S)-1'-(7-((2-amino-3-chloropyridin-4-yl)thio)isoquinolin-3-yl)-5,6-dibromo-1,3-dihydrospiro[indene-2,4'-piperidin]-1-amine
73 (S)-1'-(4-((2-amino-3-chloropyridin-4-yl)thio)isoquinolin-1-yl)-1,3-dihydrospiro[indene-2,4'-piperidin]-1-amine
74 (S)-4-((5-(5-acetyl-1-amino-1,3-dihydrospiro[indene-2,4'-piperidin]-1'-yl)-3-aminopyrazin-2-yl)thio)-3-chloro-1-methylpyridin-2(1H)-one
75 (S)-5-(1-amino-6-bromo-1,3-dihydrospiro[indene-2,4'-piperidin]-1'-yl)-2-((2,3-dichlorophenyl)thio)-6-(hydroxymethyl)pyridin-3-ol
76 (S)-6-bromo-1'-(5-(2,3-dichlorophenyl)-6-methylimidazo[1,5-a]pyrazin-8-yl)-1,3-dihydrospiro[indene-2,4'-piperidin]-1-amine
77 (S)-1'-(7-((2-amino-3-chloropyridin-4-yl)thio)-[1,2,5]thiadiazolo[3,4-c]pyridin-4-yl)-6-bromo-1,3-dihydrospiro[indene-2,4'-piperidin]-1-amine
78 (S)-1'-(8-((2-amino-3-chloropyridin-4-yl)thio)pyrido[4,3-d]pyrimidin-5-yl)-6-bromo-1,3-dihydrospiro[indene-2,4'-piperidin]-1-amine
79 (S)-3-(5-(1-amino-6-methoxy-1,3-dihydrospiro[indene-2,4'-piperidin]-1'-yl)pyridin-2-yl)-4,5-dichlorophenol
80 (S)-1-amino-1'-(5-(5-methylthiophen-2-yl)pyrazin-2-yl)-1,3-dihydrospiro[indene-2,4'-piperidin]-6-ol
81 (S)-1'-(5-(1H-indol-7-yl)pyrazin-2-yl)-5-ethyl-1,3-dihydrospiro[indene-2,4'-piperidin]-1-amine
82 (S)-1'-(5-(cyclohex-1-en-1-yl)pyrazin-2-yl)-5-isopropyl-1,3-dihydrospiro[indene-2,4'-piperidin]-1-amine
83 (S)-N-(1-amino-1'-(5-(2-(trifluoromethyl)phenyl)pyrimidin-2-yl)-1,3-dihydrospiro[indene-2,4'-piperidin]-6-yl)methanesulfonamide
84 (S)-1'-(5-((4-(trifluoromethyl)pyrimidin-5-yl)thio)pyrazin-2-yl)-5,7-dihydrospiro[cyclopenta[c]pyridine-6,4'-piperidin]-7-amine
85 (S)-1'-(5-((2-chloropyridin-3-yl)thio)pyrazin-2-yl)-5,7-dihydrospiro[cyclopenta[c]pyridine-6,4'-piperidin]-5-amine
86 (S)-4-((5-(5-amino-5,7-dihydrospiro[cyclopenta[d]pyrimidine-6,4'-piperidin]-1'-yl)pyrazin-2-yl)thio)-3-chlorobenzoic acid
87 (S)-1'-(5-((3-(trifluoromethyl)pyrazin-2-yl)thio)pyrazin-2-yl)-5,7-dihydrospiro[cyclopenta[b]pyridine-6,4'-piperidin]-7-amine
88 (S)-1'-(5-((3-chloropyridazin-4-yl)thio)pyrazin-2-yl)-5,7-dihydrospiro[cyclopenta[d]pyrimidine-6,4'-piperidin]-7-amine
89 (S)-4-((5-(5-amino-5,7-dihydrospiro[cyclopenta[b]pyrazine-6,4'-piperidin]-1'-yl)pyrazin-2-yl)thio)-3-chlorobenzamide
90 (S)-(1-amino-1'-(5-((3-chloro-2-(methylamino)pyridin-4-yl)thio)pyrazin-2-yl)-1,3-dihydrospiro[indene-2,4'-piperidin]-6-yl)dimethylphosphine oxide
91 (S)-1-amino-1'-(6-amino-5-((3-chloro-2-(dimethylamino)pyridin-4-yl)thio)pyrazin-2-yl)-1,3-dihydrospiro[indene-2,4'-piperidine]-5-carboxylic acid
92 ethyl (S)-1-amino-1'-(5-((3-chloro-2-(methylamino)pyridin-4-yl)thio)pyrazin-2-yl)-1,3-dihydrospiro[indene-2,4'-piperidine]-5-carboxylate
93 (S)-1'-(5-((3-(morpholinomethyl)phenyl)thio)pyrazin-2-yl)-6-(trifluoromethyl)-1,3-dihydrospiro[indene-2,4'-piperidin]-1-amine
94 (S)-6-bromo-5-fluoro-1'-(5-((3-(pentafluoro-16-sulfanyl)phenyl)thio)pyrazin-2-yl)-1,3-dihydrospiro[indene-2,4'-piperidin]-1-amine
95 (S)-N-(3-((5-(1-amino-6-(methylthio)-1,3-dihydrospiro[indene-2,4'-piperidin]-1'-yl)pyrazin-2-yl)thio)phenyl)cyclopropanecarboxamide
96 (S)-1'-(5-((3-chloro-2-(isopropylamino)pyridin-4-yl)thio)pyrazin-2-yl)-6-(methylsulfonyl)-1,3-dihydrospiro[indene-2,4'-piperidin]-1-amine
97 (S)-6-(6-amino-1-bromo-4H,6H-spiro[cyclopenta[c]thiophene-5,4'-piperidin]-1'-yl)-3-(m-tolyl)-1,5-dihydro-4H-pyrazolo[3,4-d]pyrimidin-4-one
98 (S)-2-(1-amino-5,6,7-trifluoro-1,3-dihydrospiro[indene-2,4'-piperidin]-1'-yl)-5-(3-ethylphenyl)-3-methyl-3,7-dihydro-4H-pyrrolo[2,3-d]pyrimidin-4-one
99 (R)-1'-(3-(3-(tert-butyl)phenyl)-1H-pyrazolo[3,4-b]pyrazin-6-yl)-3,4-dihydro-1H-spiro[naphthalene-2,4'-piperidin]-3-amine
100 (S)-2-(3-amino-1,3-dihydrospiro[cyclopenta[a]naphthalene-2,4'-piperidin]-1'-yl)-5-(3-isopropylphenyl)-3,7-dihydro-4H-pyrrolo[2,3-d]pyrimidin-4-one
101 (S)-1-amino-1'-(3-(3-chloro-2-morpholinopyridin-4-yl)-4-oxo-4,5-dihydro-1H-pyrrolo[3,2-c]pyridin-6-yl)-5-fluoro-1,3-dihydrospiro[indene-2,4'-piperidine]-6-carbonitrile
102 (S)-1'-(7-(3-chloro-2-(cyclobutylamino)pyridin-4-yl)-5H-pyrrolo[2,3-b]pyrazin-3-yl)-1,3-dihydrospiro[cyclopenta[a]naphthalene-2,4'-piperidin]-3-amine
103 (S)-1'-(3-(3-chloro-2-(cyclopropylamino)pyridin-4-yl)-1H-pyrazolo[3,4-b]pyrazin-6-yl)-N6-methyl-1,3-dihydrospiro[indene-2,4'-piperidine]-1,6-diamine
104 (S)-5-amino-1'-(3-(3-chloro-2-(pyrrolidin-1-yl)pyridin-4-yl)-1H-pyrazolo[3,4-b]pyrazin-6-yl)-2-fluoro-5,7-dihydrospiro[cyclopenta[b]pyridine-6,4'-piperidine]-3-carboxamide
105 1-(4-(6-((S)-4-amino-2-chloro-4,6-dihydrospiro[cyclopenta[d]thiazole-5,4'-piperidin]-1'-yl)-1H-pyrazolo[3,4-b]pyrazin-3-yl)-3-chloropyridin-2-yl)pyrrolidin-3-ol
106 (S)-1'-(3-(3-chloro-2-((cyclopropylmethyl)amino)pyridin-4-yl)-1H-pyrazolo[3,4-b]pyrazin-6-yl)-N6,N6-dimethyl-1,3-dihydrospiro[indene-2,4'-piperidine]-1,6-diamine
107 (S)-1'-(3-(2-amino-6-chloropyridin-4-yl)-1H-pyrazolo[3,4-b]pyrazin-6-yl)-2-(tert-butyl)-4,6-dihydrospiro[cyclopenta[b]thiophene-5,4'-piperidin]-4-amine
108 (S)-2-chloro-1'-(3-(1,3-dihydroisobenzofuran-5-yl)-1H-pyrazolo[3,4-b]pyrazin-6-yl)-4,6-dihydrospiro[cyclopenta[d] thiazole-5,4'-piperidin]-6-amine 109 (S)-3-chloro-1'-(3-((2-chlorophenyl)thio)-1H-pyrazolo[3,4-b]pyrazin-6-yl)-5,7-dihydrospiro[cyclopenta[b]pyridine-6,4'-piperidin]-5-amine
110 (S)-1'-(3-(3-chloro-2-(ethylamino)pyridin-4-yl)-1H-pyrazolo[3,4-b]pyrazin-6-yl)-4,6-dihydrospiro[cyclopenta[b]thiophene-5,4'-piperidin]-4-amine
111 (R)-1'-(7-(methyl(pyridin-4-yl)amino)-5H-pyrrolo[2,3-b]pyrazin-3-yl)-3H-spiro[furo[2,3-b]pyridine-2,4'-piperidin]-3-amine
112 (R)-1'-(3-((3-chloropyridin-4-yl)amino)-1H-pyrazolo[3,4-b]pyrazin-6-yl)-6,7-dihydrospiro[cyclopenta[b]pyridine-5,4'-piperidin]-6-amine
113 (S)-2-methoxy-1'-(3-(1-phenylvinyl)-1H-pyrazolo[3,4-b]pyrazin-6-yl)-4,6-dihydrospiro[cyclopenta[d]thiazole-5,4'-piperidin]-4-amine
114 (R)-1-(3-benzyl-1H-pyrazolo[3,4-b]pyrazin-6-yl)-1',3'-dihydrospiro[piperidine-4,2'-pyrrolo[2,3-b]pyridin]-3'-amine
115 (S)-(6-(6-amino-4,6-dihydrospiro[cyclopenta[d]thiazole-5,4'-piperidin]-1'-yl)-1H-pyrazolo[3,4-b]pyrazin-3-yl)(phenyl)methanone
116 (4S)-1'-(3-(1-phenylethyl)-1H-pyrazolo[3,4-b]pyrazin-6-yl)-4,6-dihydrospiro[cyclopenta[d]thiazole-5,4'-piperidin]-4-amine
117 1-(6-((S)-5-amino-2-methoxy-5,7-dihydrospiro[cyclopenta[b]pyridine-6,4'-piperidin]-1'-yl)-1H-pyrazolo[3,4-b]pyrazin-3-yl)-1-phenylethan-1-ol
118 (S)-1'-(3-((2,3-dichloropyridin-4-yl)oxy)-1H-pyrazolo[3,4-b]pyrazin-6-yl)-5,7-dihydrospiro[cyclopenta[b]pyridine-6,4'-piperidin]-5-amine
119 (S)-1'-(3-(3,4-dihydro-1,5-naphthyridin-1(2H)-yl)-1H-pyrazolo[3,4-b]pyrazin-6-yl)-1,3-dihydrospiro[indene-2,4'-piperidin]-1-amine
120 (S)-6-bromo-1'-(3-(5-(3,4-difluorophenyl)-3,4-dihydroquinolin-1(2H)-yl)-1H-pyrazolo[3,4-b]pyrazin-6-yl)-1,3-dihydrospiro[indene-2,4'-piperidin]-1-amine
121 (S)-6-amino-2-(1-amino-6-bromo-1,3-dihydrospiro[indene-2,4'-piperidin]-1'-yl)-5-(4-cyclopropoxyphenyl)-3-methylpyrimidin-4(3H)-one
122 (S)-N-(1-amino-1'-(4-amino-5-((4-(methylthio)phenyl)thio)-6-oxo-1,6-dihydropyrimidin-2-yl)-1,3-dihydrospiro[indene-2,4'-piperidin]-6-yl)acetamide
123 (S)-2-(1-amino-6-(methylamino)-1,3-dihydrospiro[indene-2,4'-piperidin]-1'-yl)-5-(4-(benzyloxy)phenyl)-3-methylpyrimidin-4(3H)-one
124 (S)-2-(7-acetyl-1-amino-1,3-dihydrospiro[indene-2,4'-piperidin]-1'-yl)-5-(benzo[d][1,3]dioxol-4-ylthio)pyrimidin-4(3H)-one
125 4-amino-6-((1S)-1-amino-7-(1-hydroxyethyl)-1,3-dihydrospiro[indene-2,4'-piperidin]-1'-yl)-3-(4-(difluoromethoxy)phenyl)-1-methylpyridin-2(1H)-one
126 (S)-1-amino-1'-(4-amino-6-oxo-5-(4-phenoxyphenyl)-1,6-dihydropyridin-2-yl)-1,3-dihydrospiro[indene-2,4'-piperidine]-4-carbonitrile
127 (S)-6-(1-amino-4-hydroxy-1,3-dihydrospiro[indene-2,4'-piperidin]-1'-yl)-3-(4-cyclohexylphenyl)-1-methylpyridin-2(1H)-one
128 (S)-3-([1,1'-biphenyl]-4-yl)-6-(1-amino-4-methoxy-1,3-dihydrospiro[indene-2,4'-piperidin]-1'-yl)pyridin-2(1H)-one
129 (S)-6-amino-2-(1-amino-6-(2-oxopiperidin-1-yl)-1,3-dihydrospiro[indene-2,4'-piperidin]-1'-yl)-3-methyl-5-(4-(trifluoromethoxy)phenyl)pyrimidin-4(3H)-one
130 (S)-1-(1-amino-1'-(4-amino-5-((4-cyanophenyl)thio)-1-methyl-6-oxo-1,6-dihydropyrimidin-2-yl)-1,3-dihydrospiro[indene-2,4'-piperidin]-6-yl)urea
131 (S)-4-amino-6-(1-amino-6-chloro-5-fluoro-1,3-dihydrospiro[indene-2,4'-piperidin]-1'-yl)-1-methyl-3-(4-(tetrahydro-2H-pyran-4-yl)phenyl)pyridin-2(1H)-one
132 (S)-6-(1-amino-6-(trifluoromethyl)-1,3-dihydrospiro[indene-2,4'-piperidin]-1'-yl)-3-(4-(2-methoxyethoxy)phenyl)-1-methylpyridin-2(1H)-one
133 (S)-6-amino-2-(1-amino-6-(piperidine-1-carbonyl)-1,3-dihydrospiro[indene-2,4'-piperidin]-1'-yl)-3-methyl-5-(quinolin-8-ylthio)pyrimidin-4(3H)-one
134 (S)-6-amino-2-(1-amino-6-morpholino-1,3-dihydrospiro[indene-2,4'-piperidin]-1'-yl)-3-methyl-5-((4-nitrophenyl)thio)pyrimidin-4(3H)-one
135 (S)-6-amino-2-(5-amino-3-nitro-5,7-dihydrospiro[cyclopenta[b]pyridine-6,4'-piperidin]-1'-yl)-3-methyl-5-(quinolin-8-ylthio)pyrimidin-4(3H)-one
136 (S)-6-(5-amino-3-(4-methylpiperazin-1-yl)-5,7-dihydrospiro[cyclopenta[b]pyridine-6,4'-piperidin]-1'-yl)-1-methyl-3-(naphthalen-1-ylthio)pyridin-2(1H)-one
137 (S)-2-(1-amino-6-(1H-pyrrol-1-yl)-1,3-dihydrospiro[indene-2,4'-piperidin]-1'-yl)-5-((2,2-difluorobenzo[d][1,3]dioxol-4-yl)thio)pyrimidin-4(3H)-one
138 (S)-7-(5-(1-amino-6-(1H-imidazol-1-yl)-1,3-dihydrospiro[indene-2,4'-piperidin]-1'-yl)-6-(hydroxymethyl)-3-methylpyrazin-2-yl)isoindolin-1-one
139 (S)-3-(1-amino-6-(ethylamino)-1,3-dihydrospiro[indene-2,4'-piperidin]-1'-yl)-6-(1H-indol-5-yl)-5-methylpyrazine-2-carboxamide
140 (S)-N-(1-amino-1'-(3-bromo-5-(1H-indol-6-yl)-6-methylpyrazin-2-yl)-1,3-dihydrospiro[indene-2,4'-piperidin]-6-yl)cyclopropanecarboxamide
141 (S)-4-(6-amino-5-(1-amino-4-methoxy-1,3-dihydrospiro[indene-2,4'-piperidin]-1'-yl)-3-methylpyrazin-2-yl)-1,3-dihydro-2H-benzo[d]imidazol-2-one
142 (S)-3-(1-amino-5-methoxy-1,3-dihydrospiro[indene-2,4'-piperidin]-1'-yl)-5-methyl-6-(2-oxoindolin-7-yl)pyrazine-2-carbonitrile
143 (S)-N-(5-(1-amino-7-methoxy-1,3-dihydrospiro[indene-2,4'-piperidin]-1'-yl)-6-((2-hydroxyethyl)amino)-3-methylpyrazin-2-yl)benzenesulfonamide
144 (S)-1'-(6-methyl-3-(1H-pyrazol-5-yl)-5-(1H-pyrrolo[2,3-b]pyridin-4-yl)pyrazin-2-yl)-5,7-dihydrospiro[cyclopenta[b]pyridine-6,4'-piperidin]-5-amine
145 (S)-2-(3-(5-amino-5,7-dihydrospiro[cyclopenta[b]pyridine-6,4'-piperidin]-1'-yl)-6-(8-chlorochroman-7-yl)-5-methylpyrazin-2-yl)propan-2-ol
146 (S)-6-chloro-1'-(5-(7-chloro-2,3-dihydrobenzofuran-6-yl)pyrazin-2-yl)-1,3-dihydrospiro[indene-2,4'-piperidin]-1-amine
147 (S)-4-bromo-1'-(5-(3-(1-methyl-1H-pyrazol-5-yl)phenyl)pyrazin-2-yl)-1,3-dihydrospiro[indene-2,4'-piperidin]-1-amine -continued 148 (S)-1-amino-1'-(6-cyano-5-(1H-indazol-7-yl)pyrazin-2-yl)-5-fluoro-1,3-dihydrospiro[indene-2,4'-piperidine]-6-carboxamide
149 (S)-1'-(5-(1H-indol-3-yl)-6-iodopyrazin-2-yl)-5,7-dihydrospiro[cyclopenta[b]pyridine-6,4'-piperidin]-5-amine
150 (R)-6-(5-(7'-amino-7',8'-dihydro-5'H-spiro[piperidine-4,6'-quinolin]-1-yl)-3-vinylpyrazin-2-yl)isoindolin-1-one
151 (R)-1-(4-(5-(6-amino-6,7-dihydrospiro[cyclopenta[b]pyridine-5,4'-piperidin]-1'-yl)-3-ethylpyrazin-2-yl)-3,3-difluoroindolin-1-yl)ethan-1-one
152 (S)-1'-(5-(3-methyl-1H-indazol-6-yl)-6-phenylpyrazin-2-yl)-5,7-dihydrospiro[cyclopenta[b]pyridine-6,4'-piperidin]-5-amine
153 (S)-1'-(5-(1H-benzo[d][1,2,3]triazol-6-yl)-6-cyclopropylpyrazin-2-yl)-6-((tetrahydro-2H-pyran-4-yl)oxy)-1,3-dihydrospiro[indene-2,4'-piperidin]-1-amine
154 (S)-1-amino-1'-(4-(6-bromonaphthalen-2-yl)thiazol-2-yl)-1,3-dihydrospiro[indene-2,4'-piperidine]-6-carbonitrile The present invention further provides a pharmaceutical composition comprising at least one compound or a pharmaceutically acceptable salt thereof as defined herein and at least one pharmaceutically acceptable excipient.

In some embodiments, the compound in a weight ratio to the said excipient within the range from about 0.0001 to about 10.

The present invention additionally provides a combination pharmaceutical product comprising the compound or a pharmaceutically acceptable salt thereof mentioned above, together with one or more other therapeutically active agents.

The present invention further provides use of the above-mentioned compound or a pharmaceutically acceptable salt thereof, the above-mentioned pharmaceutical composition, or the above-mentioned combination pharmaceutical product for the preparation of a medicament.

In some embodiments, the medicament is used for the treatment or prevention of cancer, cancer metastasis, cardiovascular disease, an immunological disorder or an ocular disorder.

The present invention additionally provides use, in the manufacture of a medicament for use as an inhibitor of SHP2, of at least one above-mentioned compound or a pharmaceutically acceptable salt thereof, the above-mentioned pharmaceutical composition, or the above-mentioned combination pharmaceutical product.

The present invention further provides use of the above-mentioned compound or a pharmaceutically acceptable salt thereof, the above-mentioned pharmaceutical composition, or the above-mentioned combination pharmaceutical product for the preparation of a medicament in the treatment of diseases or conditions mediated by the activity of SHP2.

In some embodiments, wherein the diseases or conditions mediated by the activity of SHP2 is cancer.

In some embodiments, the diseases or conditions mediated by the activity of SHP2 is selected from Noonan syndrome, leopard syndrome, juvenile myelomonocytic leukemias, liver cancer, neuroblastoma, melanoma, squamous-cell carcinoma of the head and neck, acute myeloid leukemia, breast cancer, esophageal cancer, lung cancer, colon cancer, head cancer, gastric carcinoma, neuroblastoma, anaplastic large-cell lymphoma and glioblastoma.

The present invention additionally provides a method for preventing or treating a disease, lessening a disease symptoms, delaying the progression or onset of a disease, comprising administering to the patient in need thereof a therapeutically effective amount of the above-mentioned compound or the pharmaceutically acceptable salt thereof, the above-mentioned pharmaceutical composition, or the above-mentioned combination pharmaceutical product, and the disease is cancer, cancer metastasis, cardiovascular disease, an immunological disorder or an ocular disorder.

The present invention further provides a method for inhibiting the activity of SHP2 level, comprising administering to the patient in need thereof a therapeutically effective amount of the above-mentioned compound or the pharmaceutically acceptable salt thereof, or the above-mentioned pharmaceutical composition, or the above-mentioned combination pharmaceutical product.

The present invention additionally provides a method for preventing or treating a disease, lessening a disease symptoms, delaying the progression or onset of a disease, comprising administering to the patient in need thereof a therapeutically effective amount of the above-mentioned compound or the pharmaceutically acceptable salt thereof, the above-mentioned pharmaceutical composition, or the above-mentioned combination pharmaceutical product, and the disease is mediated by the activity of SHP2.

In some embodiments, the disease mediated by the activity of SHP2 is cancer.

In some embodiments, the disease mediated by the activity of SHP2 is selected from Noonan syndrome, leopard syndrome, juvenile myelomonocytic leukemias, liver cancer, neuroblastoma, melanoma, squamous-cell carcinoma of the head and neck, acute myeloid leukemia, breast cancer, esophageal cancer, lung cancer, colon cancer, head cancer, gastric carcinoma, neuroblastoma, anaplastic large-cell lymphoma and glioblastoma.

The present invention further provides the above-mentioned compound or the pharmaceutically acceptable salt thereof, the above-mentioned pharmaceutical composition, or the above-mentioned combination pharmaceutical product for use in preventing or treating a disease, lessening a disease symptom, delaying the progression or onset of a disease, wherein the disease is cancer, cancer metastasis, cardiovascular disease, an immunological disorder or an ocular disorder.

The present invention additionally provides the above-mentioned compound or the pharmaceutically acceptable slat thereof, the above-mentioned pharmaceutical composition, or the above-mentioned combination pharmaceutical product, for use in inhibiting the activity of SHP2.

The present invention further provides the above-mentioned compound or the pharmaceutically acceptable salt thereof, the above-mentioned pharmaceutical composition, or the above-mentioned combination pharmaceutical product for use in preventing or treating a disease, lessening a disease symptom, delaying the progression or onset of a disease, and the disease is mediated by the activity of SHP2.

In some embodiments, the disease mediated by the activity of SHP2 is cancer.

In some embodiments, the disease mediated by the activity of SHP2 is selected from Noonan syndrome, leopard syndrome, juvenile myelomonocytic leukemias, liver cancer, neuroblastoma, melanoma, squamous-cell carcinoma of the head and neck, acute myeloid leukemia, breast cancer, esophageal cancer, lung cancer, colon cancer, head cancer, gastric carcinoma, neuroblastoma, anaplastic large-cell lymphoma and glioblastoma.

Definition

As used herein, the singular form "a", "an", and "the" include plural references unless indicated otherwise. For example, "a" substituent includes one or more substituents.

As used herein, the term "alkyl" is defined to include saturated aliphatic hydrocarbons including straight chains and branched chains. In some embodiments, the alkyl group has 1 to 20 carbon atoms, 1 to 10 carbon atoms, 1 to 6 carbon atoms, or 1 to 4 carbon atoms. For example, the term "$C_{1-6}$ alkyl," as well as the alkyl moieties of other groups referred to herein (e.g., $C_{1-6}$ alkoxy) refers to linear or branched radicals of 1 to 6 carbon atoms (e.g., methyl, ethyl, n-propyl, isopropyl, n-butyl, isobutyl, sec-butyl, tert-butyl, n-pentyl, or n-hexyl). For yet another example, the term "$C_{1-6}$ alkyl" refers to linear or branched aliphatic hydrocarbon chains of 1 to 4 carbon atoms; the term "$C_{1-3}$ alkyl" refers to linear or branched aliphatic hydrocarbon chains of 1 to 3 carbon atoms; the term "$C_{1-2}$ alkyl" refers to methyl and/or ethyl; and the term "$C_1$ alkyl" refers to methyl. An alkyl group optionally can be substituted by one or more (e.g., 1 to 5) suitable substituents.

As used herein, the term "alkoxy" or "alkyloxy" refers to an —O-alkyl group. For example, the term "$C_{1-6}$ alkoxy" or "$C_{1-6}$ alkyloxy" refers to an —O—($C_{1-6}$ alkyl) group; and the term "$C_{1-6}$ alkoxy" or "$C_{1-6}$ alkyloxy" refers to an —O—($C_{1-6}$ alkyl) group; For another example, the term "$C_{1-2}$ alkoxy" or "$C_{1-2}$ alkyloxy" refers to an —O—($C_{1-2}$ alkyl) group. Examples of alkoxy include methoxy, ethoxy, propoxy (e.g., n-propoxy and isopropoxy), tert-butoxy, and the like. The alkoxy or alkyloxy group optionally can be substituted by 1 or more (e.g., 1 to 5) suitable substituents.

As used herein, the term "Alkylene" refers to a divalent hydrocarbyl group having the specified number of carbon atoms which can link two other groups together. Sometimes it refers to a group —$(CH_2)_t$— where t is 1-8, and preferably t is 1-4. Where specified, an alkylene can also be substituted by other groups and may include one or more degrees of unsaturation (i.e., an alkenylene or alkynlene moiety) or rings. The open valences of an alkylene need not be at opposite ends of the chain. Thus branched alkylene groups such as —CH(Me)-, —CH$_2$CH(Me)- and —C(Me)$_2$- are also included within the scope of the term "alkylenes" as are cyclic groups such as cyclopropan-1,1-diyl and unsaturated groups such as ethylene (—CH=CH—) or propylene (—CH$_2$—CH=CH—). Where an alkylene group is described as optionally substituted, the substituents include those typically present on alkyl groups as described herein.

As used herein, the term "halo" or "halogen" refers to fluoro (which may be depicted as —F), chloro (which may be depicted as —Cl), bromo (which may be depicted as —Br), or iodo (which may be depicted as —I). The preferred halogen groups include F, Cl and Br. The terms "halo$C_{1-6}$alkyl", "halo$C_{2-6}$alkenyl", "halo$C_{2-6}$alkynyl" and "halo$C_{1-6}$alkoxy" mean a $C_{1-6}$alkyl, $C_{2-6}$alkenyl, $C_{2-6}$alkynyl or $C_{1-6}$alkoxy in which one or more (in particular, 1 to 3) hydrogen atoms have been replaced by halogen atoms, especially fluorine or chlorine atoms. In some embodiment, preferred are fluoro$C_{1-6}$alkyl, fluoro$C_{2-6}$alkenyl, fluoro$C_{2-6}$alkynyl and fluoro$C_{1-6}$alkoxy groups, in particular fluoro$C_{1-3}$alkyl, for example, $CF_3$, $CHF_2$, $CH_2F$, $CH_2CH_2F$, $CH_2CHF_2$, $CH_2CF_3$ and fluoro$C_{1-3}$alkoxy groups, for example, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

As used herein, the term "n-membered", where n is an integer, typically describes the number of ring-forming atoms in a moiety where the number of ring-forming atoms is n. For example, pyridine is an example of a 6-membered heteroaryl ring and thiophene is an example of a 5-membered heteroaryl group.

At various places in the present specification, substituents of compounds of the invention are disclosed in groups or in ranges. It is specifically intended that the invention include each and every individual sub-combination of the members of such groups and ranges. For example, the term "$C_{1-6}$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl. For another example, the term "a 5- to 12-membered heteroaryl group" is specifically intended to include any 5-, 6-, 7-, 8-, 9-, 10-, 11- or 12-membered heteroaryl group.

As used herein, the term "oxo" refers to =O. When an oxo is substituted on a carbon atom, they together form a carbonyl moiety [—C(=O)—]. When an oxo is substituted on a sulfur atom, they together form a sulfinyl moiety [—S(=O)—]; when two oxo groups are substituted on a sulfur atom, they together form a sulfonyl moiety [—S(=O)$_2$—].

As used herein, the term "aryl" or "aromatic" refers to an optionally substituted monocyclic or fused bicyclic or polycyclic ring system having the well-known characteristics of aromaticity, wherein at least one ring contains a completely conjugated pi-electron system. Typically, aryl groups contain 6 to 20 carbon atoms ("$C_6$-$C_{20}$ aryl") as ring members, preferably 6 to 14 carbon atoms ("$C_6$-$C_{14}$ aryl") or more preferably, 6 to 12 carbon atoms ("$C_6$-$C_{12}$ aryl"). Fused aryl groups may include an aryl ring (e.g., a phenyl ring) fused to another aryl or heteroaryl ring, or fused to a saturated or partially unsaturated carbocyclic or heterocyclic ring, provided the point of attachment to the base molecule on such fused ring systems is an atom of the aromatic portion of the ring system. Examples, without limitation, of aryl groups include phenyl, biphenyl, naphthyl, anthracenyl, phenanthrenyl, indanyl, indenyl, and tetrahydronaphthyl. The aryl group is unsubstituted or substituted as further described herein.

As used herein, the term "heteroaryl" or "heteroaromatic" refers to monocyclic or fused bicyclic or polycyclic ring systems having the well-known characteristics of aromaticity that contain the specified number of ring atoms and include at least one heteroatom selected from N, O and S as a ring member in an aromatic ring. The inclusion of a heteroatom permits aromaticity in 5-membered rings as well as 6-membered rings. Typically, heteroaryl groups contain 5 to 20 ring atoms ("5-20 membered heteroaryl"), preferably 5 to 14 ring atoms ("5-14 membered heteroaryl"), and more preferably 5 to 12 ring atoms ("5-12 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. Heteroaryl groups may also be fused to another aryl or heteroaryl ring, or fused to a saturated or partially unsaturated carbocyclic or heterocyclic ring, provided the point of attachment to the base molecule on such fused ring systems is an atom of the heteroaromatic portion of the ring system.

Examples of unsubstituted heteroaryl groups often include, but are not limited to, pyrrole, furan, thiophene, pyrazole, imidazole, isoxazole, oxazole, isothiazole, thiazole, triazole, oxadiazole, thiadiazole, tetrazole, pyridine, pyridazine, pyrimidine, pyrazine, benzofuran, benzothiophene, indole, benzimidazole, indazole, quinoline, isoquinoline, purine, triazine, naphthryidine and carbazole. In frequent preferred embodiments, 5- or 6-membered heteroaryl groups are selected from the group consisting of pyrrolyl, furanyl, thiophenyl, pyrazolyl, imidazolyl, isoxazolyl, oxazolyl, isothiazolyl, thiazolyl, triazolyl, pyridinyl and pyrimidinyl, pyrazinyl or pyridazinyl rings. The heteroaryl group is unsubstituted or substituted as further described herein.

As used herein, the term "heterocyclyl", "heterocyclic" or "heteroalicyclic" used interchangeably herein refers to a non-aromatic, saturated or partially unsaturated ring system containing the specified number of ring atoms, including at least one heteroatom selected from N, O and S as a ring member, where ring S atoms are optionally substituted by one or two oxo groups (i.e., $S(O)_x$, where x is 0, 1 or 2) and where the heterocyclic ring is connected to the base molecule via a ring atom, which may be C or N. Heterocyclic rings include rings which are spirocyclic, bridged, or fused to one or more other heterocyclic or carbocyclic rings, where such spirocyclic, bridged, or fused rings may themselves be saturated, partially unsaturated or aromatic to the extent unsaturation or aromaticity makes chemical sense, provided the point of attachment to the base molecule is an atom of the heterocyclic portion of the ring system. Preferably, heterocyclic rings contain 1 to 4 heteroatoms selected from N, O, and $S(O)_q$ as ring members, and more preferably 1 to 2 ring heteroatoms, provided that such heterocyclic rings do not contain two contiguous oxygen atoms. Heterocyclyl groups are unsubstituted or substituted by suitable substituent groups, for example the same groups that are described herein as suitable for alkyl, aryl or heteroaryl. Such substituents may be present on the heterocyclic ring attached to the base molecule, or on a spirocyclic, bridged or fused ring attached thereto. In addition, ring N atoms are optionally substituted by groups suitable for an amine, e.g., alkyl, acyl, carbamoyl, sulfonyl substituents, and the like.

As used herein, the term "cycloalkyl" refers to a non-aromatic, saturated or partially unsaturated carbocyclic ring system containing the specified number of carbon atoms, which may be a monocyclic, spirocyclic, bridged or fused bicyclic or polycyclic ring system that is connected to the base molecule through a carbon atom of the cycloalkyl ring. Typically, the cycloalkyl groups of the invention contain 3 to 12 carbon atoms ("$C_3$-$C_{12}$ cycloalkyl"), preferably 3 to 8 carbon atoms ("C3-C8 cycloalkyl"). Representative examples include, e.g., cyclopropane, cyclobutane, cyclopentane, cyclopentene, cyclohexane, cyclohexene, cyclohexadiene, cycloheptane, cycloheptatriene, adamantane, and the like. Cycloalkyl groups are unsubstituted or substituted by the same groups that are described herein as suitable for alkyl.

Compounds described herein can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention. In some embodiments, one or more hydrogen atoms of any of the compounds described herein can be substituted with deuterium to provide the corresponding deuterium-labeled or -enriched compounds.

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

"SHP2" means "Src Homolgy-2 phosphatase" and is also known as SH-PTP2, SH-PTP3, Syp, PTP1D, PTP2C, SAP-2 or PTPN11.

Cancers harboring "PTPN11 mutations" include but are not limited to: N58Y, D61Y, V; E69K; A72V, T, D; E76G, Q, K (ALL); G60A: D61Y; E69V; F71K; A72V; T731; E76G, K; R289G; G503V (AML); G60R, D61Y, V, N; $Y_{62}$D; E69K; A72T, V; T731; E76K, V, G, A, Q; E139D; G503A, R; Q506P (JMML); G60V; D61V; E69K; F71L; A72V; E76A (MDS), $Y_{63}$C (CMML); $Y_{62}$C; E69K; T507K (neuroblastoma); V46L; N58S; E76V (Lung cancer), R138Q (melanoma); E76G (colon cancer).

The term "subject" (alternatively referred to herein as "patient") as used herein refers to an animal, preferably a mammal, most preferably a human, who has been the object of treatment, observation or experiment.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. When the compound of the present invention is basic, its corresponding salt can be conveniently prepared from pharmaceutically acceptable non-toxic acids, including inorganic and organic acids. Since the compounds of Formula I, II, III or IV are intended for pharmaceutical use they are preferably provided in substantially pure form, for example at least 60% pure, more suitably at least 75% pure, especially at least 98% pure (% are on a weight for weight basis).

The compounds of the present invention may also be present in the form of pharmaceutically acceptable salts. For use in medicine, the salts of the compounds of this invention refer to non-toxic "pharmaceutically acceptable salts". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic. Pharmaceutically acceptable basic/cationic salts include, and are not limited to aluminum, calcium, chloroprocaine, choline, diethanolamine, ethylenediamine, lithium, magnesium, potassium, sodium and zinc.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of Formula (I) exists, the present invention includes any possible tautomers and pharmaceutically acceptable salts thereof, and mixtures thereof, except where specifically stated otherwise.

When the compound of Formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. When the compound of the present invention is basic, its corresponding salt can be conveniently prepared from pharmaceutically acceptable non-toxic acids, including inorganic and organic acids. Since the compounds of Formula (I) are intended for pharmaceutical use they are preferably provided in substantially pure form, for example at least 60% pure, more suitably at least 75% pure, especially at least 98% pure (% are on a weight for weight basis).

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or a prodrug, or a metabolite, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas.

Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like.

Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

These and other aspects will become apparent from the following written description of the invention.

EXAMPLES

The following Examples are provided to better illustrate the present invention. All parts and percentages are by weight and all temperatures are degrees Celsius, unless explicitly stated otherwise. The following abbreviations have been used in the examples:

| | |
|---|---|
| DMF | N,N-Dimethylformamide |
| EA | Ethyl acetate |
| Hex | Hexane |
| MeOH | Methanol |
| DCM | Dichloromethane |
| DCE | 1,2-Dichloroethane |
| EtOH | Ethanol |
| t-BuOH | tert-Butanol |
| iPrOH | Propan-2-ol |
| $CD_3I$ | Iodomethane-d3 |
| LiHMDS | Lithium bis(trimethylsilyl)amide |
| THF | Tetrahydrofuran |
| $Ti(OEt)_4$ | Titanium ethoxide |
| NMP | 1-Methyl-2-pyrrolidinone |
| DIPEA | N,N-Diisopropylethylamine |
| $(Boc)_2O$ | Di-tert-butyl dicarbonate |
| LDA | Lithium diisopropylamide |
| LiHMDS | Lithium bis(trimethylsilyl)amide |
| PPA | Polyphosphoric acids |
| TEA | Triethylamine |
| $PPh_3$ | Triphenylphosphane |
| $Pd(PPh_3)_4$ | Tetrakis(triphenylphosphine)palladium |
| DBU | 1,8-Diazabicyclo[5.4.0]undec-7-ene |
| XantPhos | 4,5-Bis(diphenylphosphino)-9,9-dimethylxanthene |
| BINAP | 2,2'-Bis(diphenylphosphanyl)-1,1'-binaphthalene |
| DavePhos | 2'-(dicyclohexylphosphanyl)-N,N-dimethyl-[1,1'-biphenyl]-2-amine |
| $Pd(OAc)_2$ | Palladium diacetate |

-continued

| | |
|---|---|
| Pd₂(dba)₃ | Tris(dibenzylideneacetone)dipalladium(0) |
| Pd(dppf)Cl₂ | [1,1'-Bis(diphenylphosphino)ferrocene]dichloropalladium(II) |
| Pd(dppf)Cl₂• CH₂Cl₂ | [1,1'-Bis(diphenylphosphino)ferrocene]dichloropalladium(II) dichloromethane complex |
| BOP | Benzotriazol-1-yloxytris(dimethylamino)-phosphonium hexafluorophosphate |
| PyBOP | Benzotriazole-1-yl-oxytripyrrolidinophosphonium hexafluorophosphate |
| K₄Fe(CN)₆•3H₂O | Potassium ferrocyanide trihyrate |
| Cy₃PH•BF₄ | Tricyclohexylphosphonium tetrafluoroborate |
| t-BuOK | Potassium tert-butoxide |
| NaOEt | Sodium ethoxide |
| NCS | N-Chlorosuccinimide |
| NBS | N-Bromosuccinimide |
| NIS | N-Iodosuccinimide |
| TFA | 2,2,2-Trifluoroacetic acid |
| RT | Room temperature |
| min | minute(s) |
| h | hour(s) |
| aq | aqueous |
| sat | saturated |
| TLC | Thin layer chromatography |
| Prep - TLC | Preparative thin layer chromatography |

Intermediate A1

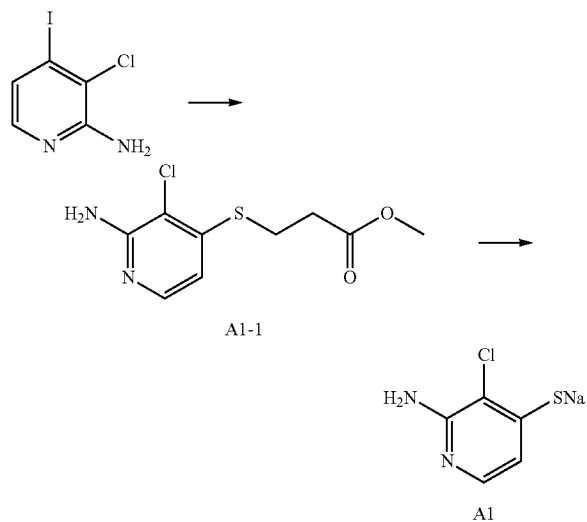

A mixture of 3-chloro-4-iodopyridin-2-amine (25.55 g, 100.41 mmol), methyl 3-mercaptopropanoate (12.72 g, 105.85 mmol), Pd₂(dba)₃ (0.96 g, 1.05 mmol), XantPhos (1.21 g, 2.09 mmol) and DIPEA (26.01 g, 201.25 mmol) in 1,4-dioxane (80 mL) was stirred for 18 h at 100° C. under nitrogen atmosphere. After cooling to RT, the reaction mixture was diluted with EA (80 mL), filtered and concentrated under reduced pressure. The residue was diluted with EA (50 mL) and Hex (250 mL), the resulting suspension was stirred for 10 min and filtered. The filter cake was collected. The filtration was concentrated under reduced pressure and the residue was purified by silica gel chromatography (eluting with EA:Hex=1:1, v/v). The product was combined with the filter cake to give compound A1-1 (21.62 g). MS: 247 [M+1]⁺.

Sodium (2.48 g, 107.83 mmol) was dissolved in EtOH (200 mL) and added to a suspension of compound A-1 (21.62 g, 87.63 mmol) in EtOH (100 mL) dropwise at 0° C. The resulting mixture was allowed to warm to RT and stirred for 2 h. The mixture was diluted with EtOH (20 mL) and DCM (200 mL), stirred for another 20 min, filtered and washed with DCM (30 mL). The filter cake was collected and dried in an high vacuum oven to afford intermediate A1 (12.72 g). MS: 161 [M+H]⁺.

The following compounds were synthesized using the above procedure with the corresponding starting materials.

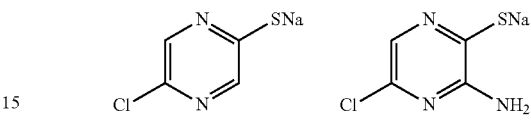

Intermediate B1

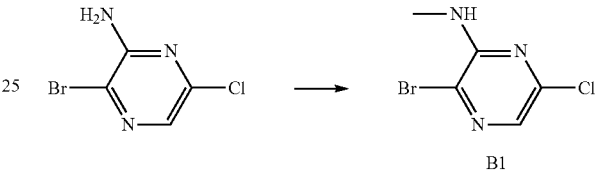

To a 0° C. mixture of 3-bromo-6-chloropyrazin-2-amine (511 mg, 2.45 mmol) in DMF (5 mL) under nitrogen atmosphere was added NaH (60%, 153 mg, 3.83 mmol). The resulting mixture was allowed to warm to RT and stirred for 30 min. Then CH₃I (453 mg, 3.19 mmol) was added and the resulting mixture was stirred for 1 h at RT. The reaction mixture was quenched with brine (50 mL) and extracted with EA (80 mL). The organic layer was washed with brine (3×50 mL), dried over anhydrous Na₂SO₄, filtered and concentrated under reduced pressure to give intermediate B1 (503 mg) as a brown solid which was used in next step without further purification. MS: 222 [M+1]⁺.

The following compound was synthesized using the above procedure.

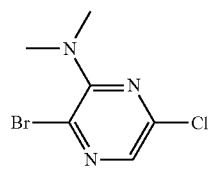

Intermediate C1

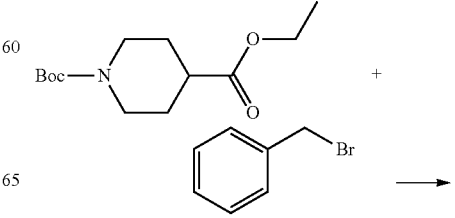

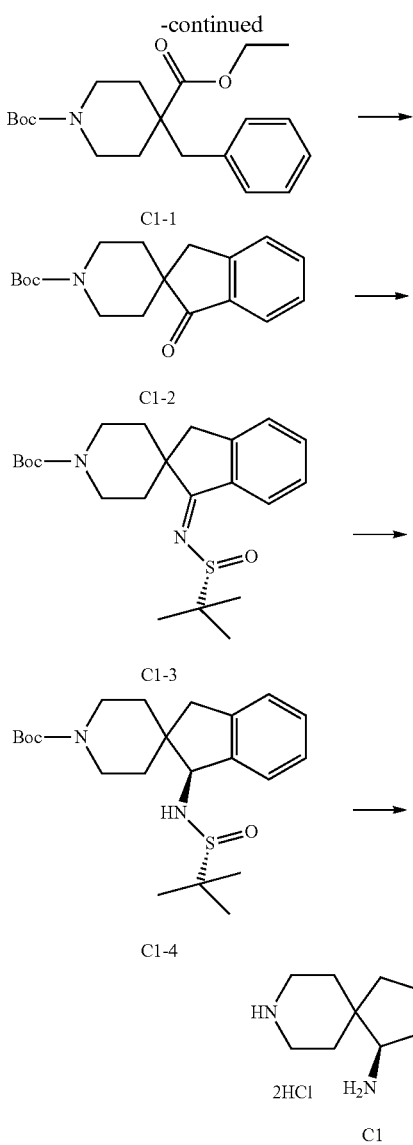

C1-1

C1-2

C1-3

C1-4

C1

To a −70° C. solution of 1-(tert-butyl) 4-ethyl piperidine-1,4-dicarboxylate (26.02 g, 101.18 mmol) in THF (100 mL) under nitrogen atmosphere was added LDA (2 M, 65.00 mL, 130.00 mmol) dropwise. The resulting mixture was stirred for 1 h at −70° C. Then (bromomethyl)benzene (17.98 g, 105.12 mmol) was added and the resulting mixture was stirred for 30 min. The reaction mixture was quenched by the addition of brine (100 mL) dropwise. The layers were separated and the organic layer was washed with brine (1×80 mL), dried over anhydrous Na$_2$SO$_4$, filtered and concentrated under reduced pressure to give compound C1-1 (38.05 g, crude) as a yellow oil. MS: 348 [M+1]$^+$.

A mixture of compound C1-1 (38.05 g, 0.11 mol) and PPA (50.00 g) was stirred for 1.5 h at 130° C. After cooling to RT, the reaction mixture was poured into ice/water and the pH value of the resulting mixture was adjusted to 9 with NaOH. (Boc)$_2$O (40.12 g, 0.18 mol) was added and the resulting mixture was stirred for 16 h at RT. The reaction mixture was extracted with EA (3×150 mL), the organic layers combined, dried over anhydrous Na$_2$SO$_4$, filtered and concentrated under reduced pressure. The residue was purified by silica gel chromatography (eluting with EA:Hex=1:10, v/v) to give compound C1-2 (10.00 g). MS: 302 [M+1]$^+$.

A mixture of compound C1-2 (10.00 g, 0.033 mol) and (R)-(+)-2-methyl-2-propanesulfinamide (8.33 g, 0.069 mol) in Ti(OEt)$_4$ (50 mL) was stirred for 2 h at 120° C. The reaction mixture was poured into water (100 mL) and diluted with EA (300 mL). The resulting mixture was filtered through a pad of Celite, the filtrate was separated and the organic layer was dried over anhydrous Na$_2$SO$_4$, filtered and concentrated under reduced pressure to give compound C1-3 (18.49 g, crude) as a yellow oil. MS: 405 [M+1]$^+$.

To a −50° C. solution of compound C1-3 (18.49 g, 0.046 mol) in THF (100 mL) was added BH$_3$/THF (1 M, 125.00 mL, 0.13 mol) dropwise. The resulting mixture was allowed to warm to RT and stirred for 16 h. The reaction mixture was quenched by the addition of brine dropwise. The layers were separated and the organic layer was washed with brine (1×100 mL), dried over anhydrous Na$_2$SO$_4$, filtered and concentrated under reduced pressure. The residue was purified by silica gel chromatography (eluting with EA:Hex=1:2, v/v) to give compound C1-4 (8.06 g) as a yellow oil. MS: 407 [M+1]$^+$.

A mixture of compound C1-4 (8.06 g, 0.020 mol) and HCl/EA (4 M, 20.00 mL, 80.00 mmol) in DCM (120 mL) was stirred for 1 h at RT. Another portion of HCl/EA (4 M, 10.00 mL, 40.00 mmol) was added and stirred for 1.5 h at RT. The reaction mixture was filtered followed by EA (50 mL) wash. The filter cake was collected, dried under high vacuum to give intermediate C1 (4.57 g) as a white solid. MS: 203 [M+1]$^+$.

The following compound was synthesized using the above procedure or modified procedure with the corresponding starting materials.

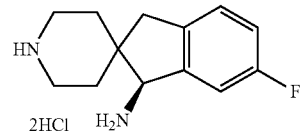

Intermediate C2

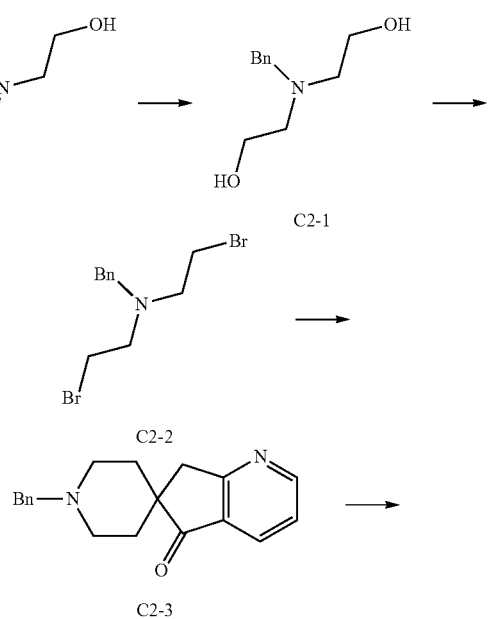

C2-1

C2-2

C2-3

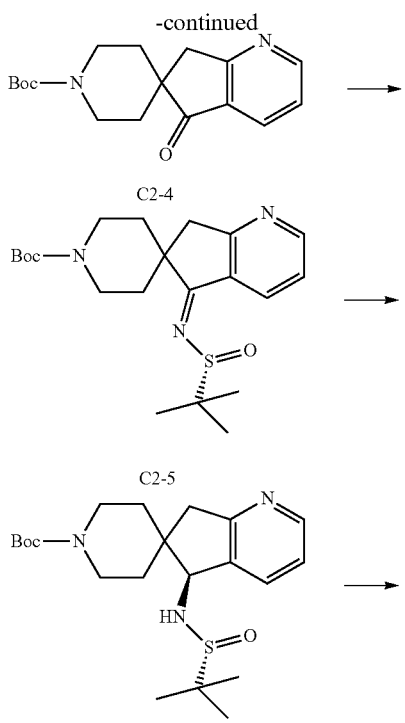

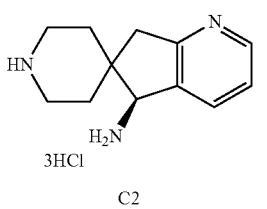

A solution of 2,2'-azanediylbis(ethan-1-ol) (198.15 g, 1.88 mol), K₂CO₃ (520.95 g, 3.77 mol) and (bromomethyl) benzene (386.79 g, 2.26 mol) in acetonitrile (2000 mL) was stirred at 90° C. for 2.5 h. After cooling to RT, the reaction mixture was filtered followed by EA (2×100 mL) wash. The filtrate was concentrated under reduced pressure. The residue was purified by silica gel chromatography (eluting with MeOH:DCM=1:10, v/v) to give C2-1 (89.44 g) as a colorless oil. MS: 196 [M+H]⁺.

To a 0° C. solution of C2-1 (30.66 g, 0.16 mol) in toluene (300 mL) was added tribromophosphane (69.13 g, 0.26 mol) dropwise. The resulting mixture was stirred at 105° C. for 16 h. After cooling to RT, the volatiles were removed under reduce pressure.

The residue was diluted with water (300 mL), and the pH value was adjusted to 9 with NaOH. The resulting mixture was extracted with EA (3×150 mL), the organic layers combined, dried over anhydrous Na₂SO₄ and filtered. The filtrate was concentrated under reduced pressure to give C2-2 (41.58 g) which was used in next step without any further purification. MS: 320 [M+H]⁺.

To a 0° C. solution of C2-2 (1.70 g, 12.77 mmol) in DMF (20 mL) under nitrogen atmosphere was added NaH (60% dispersion in mineral oil, 982 mg, 24.55 mmol) in three portions, and the mixture was heated to 60° C., stirred for 1 h at this temperature. Then N-benzyl-2-bromo-N-(2-bromoethyl)ethan-1-amine (4.54 g, 14.14 mmol) was added and stirred at 60° C. for another 1 h. After cooling to RT, the reaction mixture was quenched with water (80 mL), extracted with EA (3×80 mL). The combined organic layers were washed with water (3×80 mL), dried over anhydrous Na₂SO₄, filtered and concentrated under reduced pressure. The residue was purified by silica gel chromatography (eluting with EA) to give C2-3 (1.14 g). MS: 293 [M+H]⁺.

To a 0° C. solution of C2-3 (1.05 g, 3.59 mmol) in DCE (10 mL) was added 1-chloroethyl carbonochloridate (903 mg, 6.32 mmol) dropwise. The resulting mixture was stirred at RT for 1.5 h. The volatiles were removed under reduced pressure and the residue was dissolved in MeOH (20 mL), stirred at 80° C. for 4 h. The volatiles were removed under reduced pressure and dissolved in DCM (20 mL). DIPEA (1.33 g, 10.32 mmol) and (Boc)₂O (1.38 g, 6.32 mmol) were added. The resulting solution was stirred for 16 h at RT. The reaction mixture was concentrated under reduced pressure. The residue was purified by silica gel chromatography (eluting with EA:Hex=1:1, v/v) to give C2-4 (438 mg). MS: 303 [M+H]⁺.

Intermediate C2 was synthesized in the manner similar to intermediate C1, except compound C1-2 was replaced with compound C2-4.

Intermediate C3

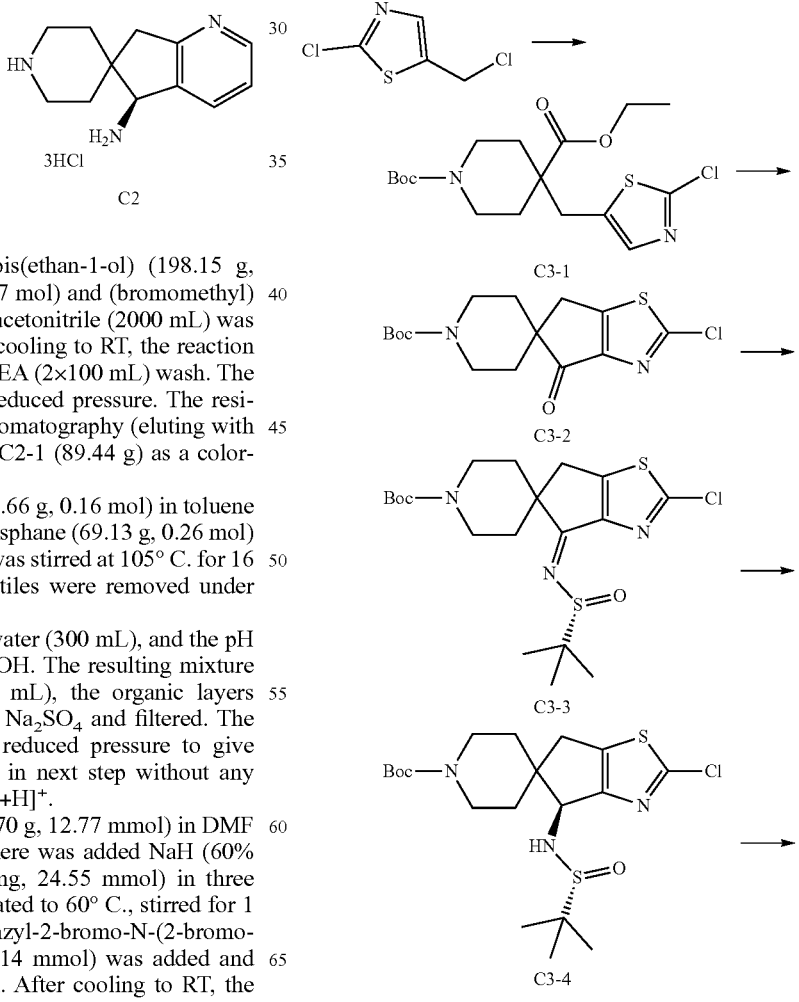

-continued

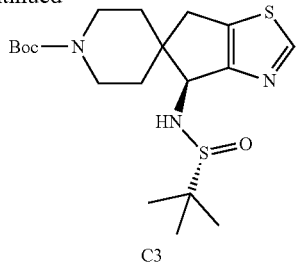

C3

To a −78° C. solution of 1-(tert-butyl) 4-ethyl piperidine-1,4-dicarboxylate (2.83 g, 11.00 mmol) in THF (50 mL) was added LDA (2 M, 6.00 mL, 12.00 mmol) dropwise under nitrogen atmosphere. The resulting mixture was stirred for 1 h at this temperature. Then 2-chloro-5-(chloromethyl)thiazole (in 3 mL THF, 1.69 g, 10.06 mmol) was added dropwise and stirred for 1 h. The reaction mixture was quenched with brine (50 mL), extracted with EA (2×30 mL). The combined organic layers were dried over anhydrous $Na_2SO_4$, filtered and concentrated under reduced pressure. The residue was purified by silica gel chromatography (eluting with EA:Hex=1:20, v/v) to give compound C3-1 (1.15 g). MS: 389 [M+H]$^+$.

To a −78° C. solution of compound C3-1 (900 mg, 2.31 mmol) in THF (50 mL) was added LDA (2 M, 3.00 mL, 6.00 mmol) dropwise under nitrogen atmosphere. The resulting mixture was stirred for 30 min at this temperature, and quenched with brine (30 mL). The resulting mixture was extracted with EA (2×30 mL), the organic layers combined, dried over anhydrous $Na_2SO_4$, filtered and concentrated under reduced pressure to give compound C3-2 (832 mg). MS: 343 [M+1]$^+$.

Compound C3-4 was synthesized in the manner similar to intermediate C1-4, except compound C1-2 was replaced with compound C3-2.

A suspension of compound C3-4 (2.50 g, 5.58 mmol), TEA (2 mL) and Pd/C (10%, 690 mg) in MeOH (50 mL) was stirred for 24 h at 40° C. under hydrogen atmosphere. The resulting mixture was filtered, and an additional portion of Pd/C (10%, 1.32 g) was added to the filtration. The resulting mixture was stirred for another 16 h at 50° C. under hydrogen atmosphere. The resulting mixture was filtered, the filtration was concentrated under reduced pressure. The residue was purified by silica gel chromatography (eluting with EA:Hex=1:1, v/v) to give compound C3 (1.28 g). MS: 414 [M+H]$^+$.

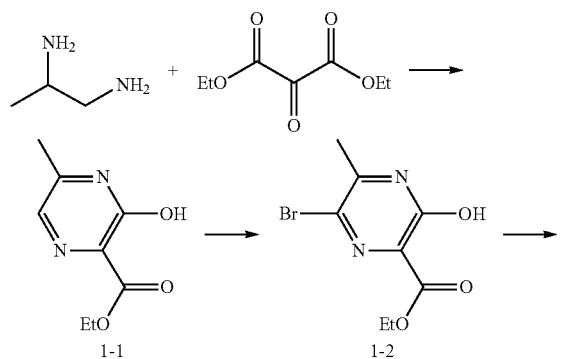

-continued

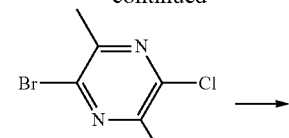
1-3

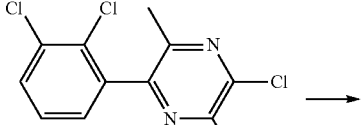
1-4

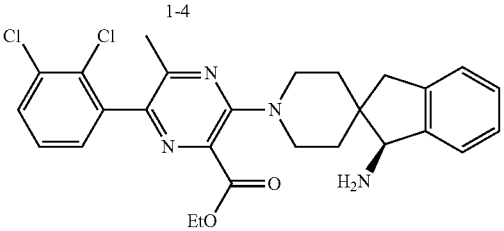
1

A solution of propane-1,2-diamine (11.00 mL, 129.11 mmol) in EtOH (220 mL) was cooled to 0° C. Diethyl 2-oxomalonate (20.00 mL, 131.15 mmol) was added to the solution dropwise. Then the cooling bath was removed. The solution was allowed to warmed to RT and stirred for 1 h. The clear solution had become a thick mixture. The mixture was warmed to reflux temperature and stirred for 24 h. After cooling to RT, the reaction mixture was concentrated under reduced pressure to give compound 1-1 (27.12 g, crude) as a solid. MS: 183 [M+1]$^+$.

To a 0° C. solution of compound 1-1 (27.12 g, crude) in DMF (100 mL) under nitrogen atmosphere was added NBS (21.30 g, 0.12 mol). The resulting mixture was allowed to warm to RT and stirred for 2 h. The reaction mixture was diluted with brine (100 mL) and EA (400 mL). The organic layer was separated, washed with water (2×100 mL) and brine (3×100 mL), dried over anhydrous $Na_2SO_4$, filtered and concentrated under reduced pressure. The residue was purified by silica gel chromatography (eluting with MeOH:DCM=1:100, v/v) to give compound 1-2 (7.75 g) as a yellow solid. MS: 261 [M+1]$^+$. $^1$HNMR (400 MHz, DMSO-$d_6$) δ 12.72 (brs, 1H), 4.29 (q, J=7.1 Hz, 2H), 2.44 (s, 3H), 1.28 (t, J=7.1 Hz, 1H).

To a solution of PPh$_3$ (31.03 g, 80.18 mmol) in 1,4-dioxane (280 mL) was added NCS (10.77 g, 80.66 mmol). The resulting mixture was stirred for 30 min at RT. Compound 1-2 (6.96 g, 26.66 mmol) was added, the resulting mixture was warmed to 100° C. and stirred for 1 h. After cooling to RT, the reaction mixture was concentrated under reduced pressure. The residue was purified by silica gel chromatography (eluting with EA:Hex=1:5, v/v) to give compound 1-3 (6.66 g) as a yellow oil. MS: 279 [M+1]$^+$.

A mixture of compound 1-3 (1.19 g, 4.26 mmol), (2,3-dichlorophenyl)boronic acid (1.21 g, 6.34 mmol), $K_2CO_3$ (2.42 g, 17.51 mmol), Pd(dppf)Cl$_2$—CH$_2$Cl$_2$ (0.44 g, 0.54 mmol) in CH$_3$CN/H$_2$O (15 mL/1 mL) was stirred for 2.5 h at 100° C. under nitrogen atmosphere. After cooling to RT, the reaction mixture was diluted with EA (50 mL) and washed with brine (2×50 mL). The organic layer was dried over anhydrous Na$_2$SO$_4$, filtered and concentrated under reduced pressure. The residue was purified by silica gel chromatography (eluting with EA:Hex=1:30, v/v) to give compound 1-4 (0.67 g). MS: 345 [M+1]$^+$.

A mixture of compound 1-4 (0.67 g, 1.94 mmol), intermediate C1 (0.64 g, 2.33 mmol) and K$_2$CO$_3$ (2.70 g, 19.54 mmol) in CH$_3$CN (15 mL) was stirred for 24 h at 100° C. After cooling to RT, the reaction mixture was diluted with EA (60 mL) and water (100 mL). The organic layer was separated, the aqueous layer was extracted with EA (1×50 mL). The organic layers were combined, dried over anhydrous Na$_2$SO$_4$, filtered and concentrated under reduced pressure. The residue was purified by silica gel chromatography (eluting with MeOH:DCM=1:50, v/v) to give example 1 (468 mg) as a yellow solid. MS: 511 [M+1]$^+$. $^1$HNMR (400 MHz, methanol-d$_4$) δ 7.65 (dd, J=7.9, 1.6 Hz, 1H), 7.47-7.34 (m, 3H), 7.29-7.14 (m, 3H), 4.40 (q, J=7.1 Hz, 2H), 4.02-3.91 (m, 3H), 3.41-3.37 (m, 1H), 3.32-3.30 (m, 1H), 3.19-3.15 (m, 1H), 2.85-2.81 (m, 1H), 2.27 (s, 3H), 1.94-1.82 (m, 2H), 1.62-1.55 (m, 1H), 1.46 (m, 1H), 1.39 (t, J=7.1 Hz, 3H).

The following compound was synthesized using the above procedure or modified procedure with the corresponding starting materials.

A mixture of example 1 (302 mg, 0.59 mmol) and LiOH (81 mg, 3.38 mmol) in MeOH/H$_2$O (20 mL/3 mL) was stirred for 4 h at 60° C. After cooling to RT, MeOH was removed under reduced pressure. The residue was dissolved in brine (50 mL), extracted with EA (3×40 mL), the organic layers combined, dried over anhydrous Na$_2$SO$_4$, filtered and concentrated under reduced pressure to give example 3 (258 mg) as a light yellow solid. MS: 483 [M+1]$^+$.

Example 4

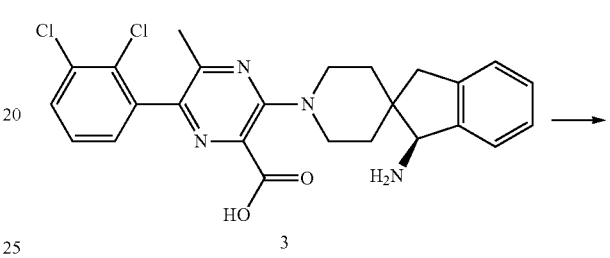

3

| Ex No. | Chemical Name | Structure | MS & $^1$HNMR |
|---|---|---|---|
| 2 | (S)-1'-(5-(2,3-dichlorophenyl)-6-methylpyrazin-2-yl)-5,7-dihydrospiro[cyclopenta[b]pyridine-6,4'-piperidin]-5-amine | 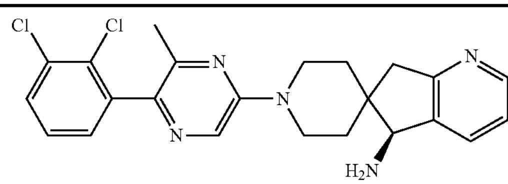 | MS: 440 [M + 1]$^+$. $^1$HNMR (400 MHz, methanol-d$_4$) δ 8.34 (d, J = 4.6 Hz, 1H), 8.05 (s, 1H), 7.83 (d, J = 7.6 Hz, 1H), 7.61 (dd, J = 8.0, 1.5 Hz, 1H), 7.40 (t, J = 7.8 Hz, 1H), 7.32-7.25 (m, 2H), 4.38-4.33 (m, 2H), 4.03 (s, 1H), 3.29-3.22 (m, 3H), 2.96-2.90 (m, 1H), 2.19 (s, 3H), 1.96-1.80 (m, 2H), 1.68-1.62 (m, 1H), 1.46-1.39 (m, 1H). |

Example 3

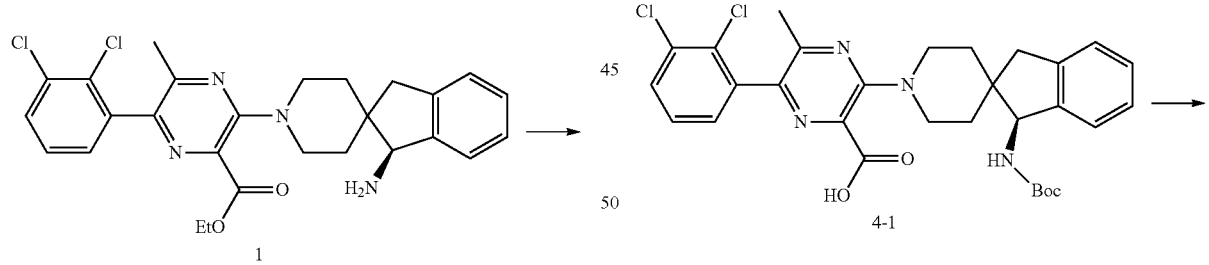

-continued

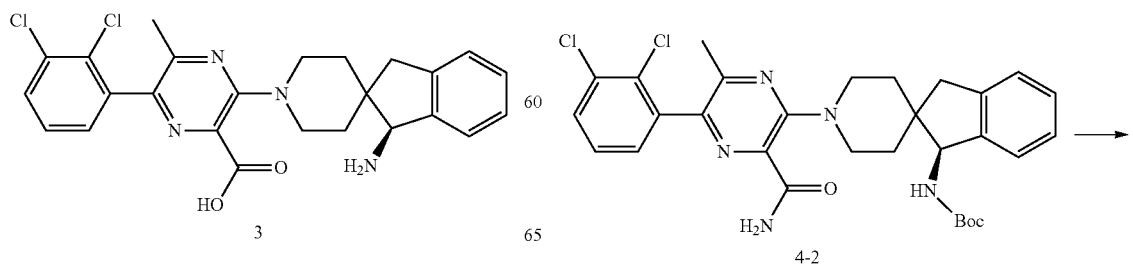

-continued

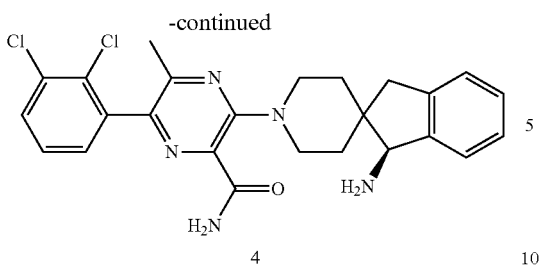

4

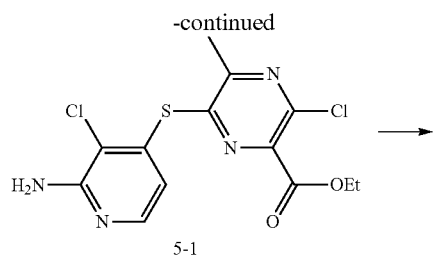

5-1

A solution of example 3 (60 mg, 0.12 mmol), (Boc)$_2$O (0.50 mL, 2.18 mmol) and DIPEA (1.00 mL, 6.05 mmol) in DCM was stirred for 1 h at 40° C. The reaction solution was concentrated under reduced pressure to give compound 4-1 (0.39 g, crude), which was used in next step without further purification. MS: 583 [M+1]$^+$.

A solution of compound 4-1 (0.39 g, crude), NH$_4$C$_1$ (466 mg, 8.71 mmol), PyBOP (194 mg, 0.37 mmol) and DIPEA (0.50 mL, 3.03 mmol) in NMP (8 mL) was stirred for 2 h at 80° C. The reaction solution was diluted with EA (40 mL) and washed with brine (3×30 mL). The organic layer was dried over anhydrous Na$_2$SO$_4$, filtered and concentrated under reduced pressure to give compound 4-2 (0.37 g, crude) as a yellow oil, which was used in next step without further purification. MS: 582 [M+1]$^+$.

A mixture of compound 4-2 (0.37 g, crude) and HCl/EA (4 M, 3.00 mL, 12.00 mmol) in DCM (20 mL) was stirred for 2.5 h at RT. The reaction mixture was diluted with brine (50 mL) and the pH value was taken to 9 with NH$_3$H$_2$O (25%). The resulting mixture was extracted with DCM (1×50 mL). The organic layer was dried over anhydrous Na$_2$SO$_4$, filtered and concentrated under reduced pressure. The residue was purified by Prep-TLC (MeOH:DCM=1:10, v/v) to give example 4 (9 mg) as a light yellow solid. MS: 482 [M+1]$^+$. $^1$HNMR (400 MHz, methanol-d$_4$) δ 7.66 (d, J=9.4 Hz, 1H), 7.52 (d, J=7.3 Hz, 1H), 7.48-7.29 (m, 5H), 4.39 (s, 1H), 4.13-4.00 (m, 2H), 3.39-3.35 (m, 1H), 3.31-3.28 (m, 1H), 3.24-3.12 (m, 2H), 2.29 (s, 3H), 2.03-1.88 (m, 2H), 1.73-1.62 (m, 2H).

Example 5

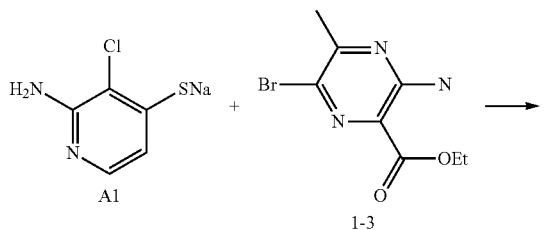

A mixture of compound A1 (504 mg, 2.76 mmol), compound 1-3 (769 mg, 2.75 mmol), Pd$_2$(dba)$_3$ (127 mg, 0.14 mmol), XantPhos (144 mg, 0.25 mmol) and DIPEA (1.10 g, 8.51 mmol) in 1,4-dioxane (20 mL) was stirred for 3 h at 110° C. under nitrogen atmosphere. After cooling to RT, the reaction mixture was quenched with brine (100 mL), extracted with EA (1×60 mL), the organic layer dried over anhydrous Na$_2$SO$_4$, filtered and concentrated under reduced pressure. The residue was purified by silica gel chromatography (eluting with EA:Hex=1:2, v/v) to give compound 5-1 (489 mg) as a yellow solid. MS: 359 [M+1]$^+$.

Example 5 was synthesized in the manner similar to example 1, except compound 1-4 was replaced with compound 5-1. MS: 525 [M+1]$^+$. $^1$HNMR (400 MHz, methanol-d$_4$) δ 7.63 (d, J=5.5 Hz, 1H), 7.47-7.34 (m, 1H), 7.26-7.19 (m, 3H), 5.91 (d, J=5.5 Hz, 1H), 4.40 (q, J=7.1 Hz, 2H), 4.06-3.98 (m, 2H), 3.97 (s, 1H), 3.43-3.35 (m, 2H), 3.18-3.14 (m, 1H), 2.85-2.81 (m, 1H), 2.49 (s, 3H), 1.96-1.76 (m, 2H), 1.64-1.57 (m, 1H), 1.48-1.42 (m, 1H), 1.39 (t, J=8.0 Hz, 3H).

The following compounds were synthesized using the above procedure or modified procedure with the corresponding starting materials.

| EX No | Chemical Name | Structure | MS & $^1$HNMR |
|---|---|---|---|
| 6 | (S)-1'-(5-((2-amino-3-chloropyridin-4-yl)thio)-6-methyl-pyrazin-2-yl)-1,3-dihydrospiro[indene-2,4'-piperidin]-1-amine | 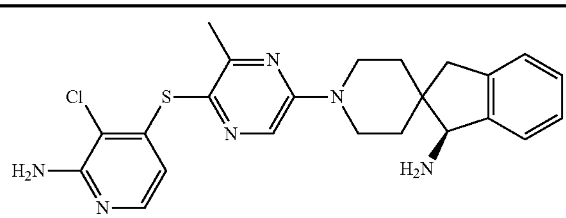 | MS: 453 [M + 1]$^+$. $^1$HNMR (400 MHz, methanol-d$_4$) δ 8.16 (s, 1H), 7.60-7.32 (m, 5H), 5.80 (s, 1H), 4.46-4.25 (m, 3H), 3.46-3.35 (m, 2H), 3.23-3.08 (m, 2H), 2.45 (s, 3H), 1.89-1.57 (m, 4H). |

-continued

| EX No | Chemical Name | Structure | MS & ¹HNMR |
|---|---|---|---|
| 7 | (S)-1'-(6-amino-5-((2,3-dichlorophenyl)thio)pyrazin-2-yl)-5,7-dihydrospiro[cyclopenta[b]pyridine-6,4'-piperidin]-5-amine | 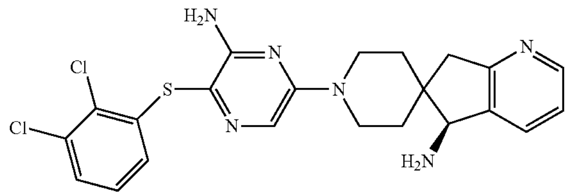 [SMILES: Nc1nc(N2CCC3(CC2)Cc2ncccc2[C@H]3N)cnc1Sc1cccc(Cl)c1Cl] | MS: 473 [M + 1]⁺. ¹HNMR (400 MHz, methanol-$d_4$) δ 8.36 (d, J = 4.7 Hz, 1H), 7.84 (d, J = 7.4 Hz, 1H), 7.62 (s, 1H), 7.37-7.22 (m, 2H), 7.13 (t, J = 8.0 Hz, 1H), 6.66 (d, J = 8.0 Hz, 1H), 4.33 (d, J = 13.4 Hz, 2H), 4.05 (s, 1H), 3.29-3.17 (m, 3H), 2.94 (d, J = 16.5 Hz, 1H), 1.98-1.75 (m, 2H), 1.70-1.57 (m, 1H), 1.48-1.37 (m, 1H). |
| 8 | (S)-1'-(4-amino-5-((2-amino-3-chloro-pyridin-4-yl)thio)pyrimidin-2-yl)-5,7-dihydrospiro[cyclopenta[b]pyridine-6,4'-piperidin]-5-amine | 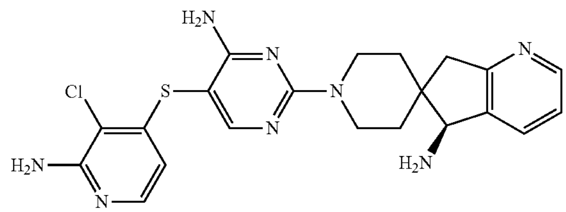 [SMILES: Nc1nc(N2CCC3(CC2)Cc2ncccc2[C@H]3N)ncc1Sc1ccnc(N)c1Cl] | MS: 455 [M + 1]⁺. ¹HNMR (400 MHz, methanol-$d_4$) δ 8.41 (d, J = 4.4 Hz, 1H), 7.96 (s, 1H), 7.88 (d, J = 7.6 Hz, 1H), 7.63 (d, J = 5.5 Hz, 1H), 7.31 (dd, J = 7.6, 5.2 Hz, 1H), 6.03 (d, J = 5.5 Hz, 1H), 4.62 (t, J = 13.3 Hz, 2H), 4.19 (s, 1H), 3.24 (m, 3H), 3.09-2.95 (m, 1H), 1.92-1.63 (m, 2H), 1.63-1.42 (m, 2H). |
| 9 | (S)-1'-(5-((2-amino-3-chloropyridin-4-yl)thio)pyridin-2-yl)-5,7-dihydrospiro[cyclopenta[b]pyridine-6,4'-piperidin]-5-amine | 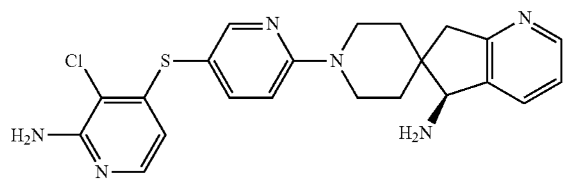 [SMILES: Nc1nccc(Sc2ccc(N3CCC4(CC3)Cc3ncccc3[C@H]4N)nc2)c1Cl] | MS: 439 [M + 1]⁺. ¹HNMR (400 MHz, methanol-$d_4$) δ 8.38 (d, J = 4.5 Hz, 1H), 8.21 (s, 1H), 7.87 (d, J = 7.5 Hz, 1H), 7.72-7.55 (m, 2H), 7.38-7.26 (m, 1H), 6.97 (d, J = 9.0 Hz, 1H), 5.92 (d, J = 5.5 Hz, 1H), 4.43-4.26 (m, 2H), 4.10 (s, 1H), 3.32-3.19 (m, 3H), 3.03-2.91 (m, 1H), 1.98-1.79 (m, 2H), 1.70-1.60 (m, 1H), 1.54-1.44 (m, 1H). |
| 10 | (S)-1'-(5-((2-amino-3-chloropyridin-4-yl)thio)-6-(methylamino)pyrazin-2-yl)-5,7-dihydrospiro[cyclopenta[b]pyridine-6,4'-piperidin]-5-amine | 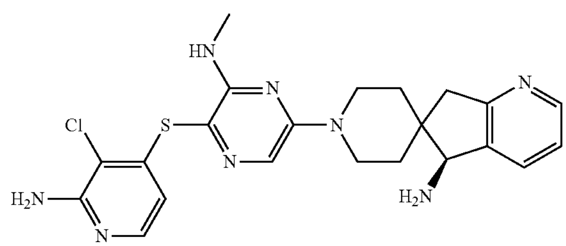 [SMILES: CNc1nc(N2CCC3(CC2)Cc2ncccc2[C@H]3N)cnc1Sc1ccnc(N)c1Cl] | MS: 469 [M + 1]⁺. ¹HNMR (400 MHz, methanol-$d_4$) δ 8.36 (d, J = 4.3 Hz, 1H), 7.83 (d, J = 10.6 Hz, 1H), 7.73-7.71, 7.51-7.49 (m, 1H), 7.59 (dd, J = 9.9, 4.4 Hz, 1H), 7.29 (dd, J = 7.4, 5.2 Hz, 1H), 5.89-5.84 (m, 1H), 4.45-4.13 (m, 2H), 4.06 (s, 1H), 3.31-3.13 (m, 3H), 3.07 (s, 1H), 2.88 (s, 3H), 2.00-1.77 (m, 2H), 1.67-1.63 (m, 1H), 1.47-1.43 (m, 1H). |
| 11 | (S)-1'-(5-((2-amino-3-chloropyridin-4-yl)thio)-6-(dimethylamino)pyrazin-2-yl)-5,7-dihydrospiro[cyclopenta[b]pyridine-6,4'-piperidin]-5-amine | 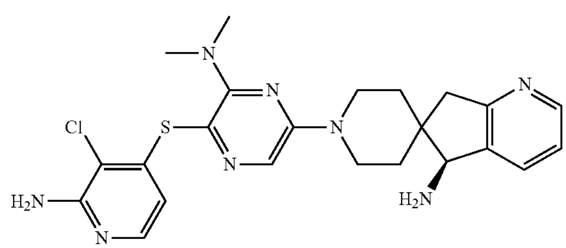 [SMILES: CN(C)c1nc(N2CCC3(CC2)Cc2ncccc2[C@H]3N)cnc1Sc1ccnc(N)c1Cl] | MS: 483 [M + 1]⁺. ¹HNMR (400 MHz, methanol-$d_4$) δ 8.36 (d, J = 4.5 Hz, 1H), 7.85 (d, J = 7.5 Hz, 1H), 7.72-7.50 (m, 1H), 7.64-7.57 (m, 1H), 7.29 (dd, J = 7.5, 5.2 Hz, 1H), 5.89-5.84 (m, 1H), 4.36 (t, J = 15.0 Hz, 2H), 4.07 (s, 1H), 3.31-3.16 (m, 3H), 3.10 (s, 3H), 3.06 (s, 1H), 2.88 (s, 3H), 1.98-1.77 (m, 2H), 1.71-1.57 (m, 1H), 1.71-1.44 (m, 1H). |
| 12 | (S)-1'-(6-amino-5-(thiazol-4-ylthio)pyrazin-2-yl)-5,7-dihydrospiro[cyclopenta[b]pyridine-6,4'-piperidin]-5-amine | 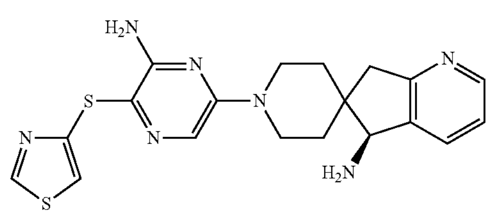 [SMILES: Nc1nc(N2CCC3(CC2)Cc2ncccc2[C@H]3N)cnc1Sc1cscn1] | MS: 412 [M + 1]⁺. ¹HNMR (400 MHz, methanol-$d_4$) δ 9.00 (d, J = 2.0 Hz, 1H), 8.49 (d, J = 4.3 Hz, 1H), 7.94 (d, J = 7.5 Hz, 1H), 7.53 (s, 1H), 7.40-7.34 (m, 1H), 7.20 (d, J = 2.0 Hz, 1H), 4.40-4.23 (m, 3H), 3.28-3.06 (m, 4H), 1.90-1.79 (m, 2H), 1.68-1.56 (m, 2H). |
| 13 | (S)-1'-(6-amino-5-(thiazol-2-ylthio)pyrazin-2-yl)-5,7-dihydrospiro[cyclopenta[b]pyridine-6,4'-piperidin]-5-amine | 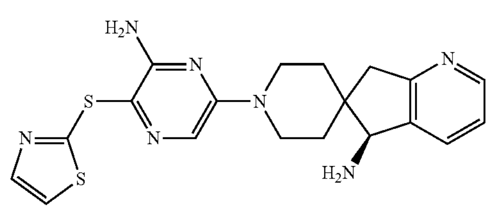 [SMILES: Nc1nc(N2CCC3(CC2)Cc2ncccc2[C@H]3N)cnc1Sc1nccs1] | MS: 412 [M + 1]⁺. ¹HNMR (400 MHz, methanol-$d_4$) δ 8.41 (d, J = 4.7 Hz, 1H), 7.89 (d, J = 7.6 Hz, 1H), 7.67 (d, J = 3.4 Hz, 1H), 7.60 (s, 1H), 7.45 (d, J = 3.4 Hz, 1H), 7.32 (dd, J = 7.5, 5.2 Hz, 1H), 4.45-4.29 (m, 2H), 4.17 (s, 1H), 3.31-3.20 (m, 3H), 3.08-2.96 (m, 1H), 1.97-1.78 (m, 2H), 1.70-1.59 (m, 1H), 1.55-1.44 (m, 1H). |

-continued

| EX No | Chemical Name | Structure | MS & ¹HNMR |
|---|---|---|---|
| 14 | (S)-1'-(6-amino-5-(quinolin-3-ylthio)pyrazin-2-yl)-5,7-dihydrospiro[cyclopenta[b]pyridine-6,4'-piperidin]-5-amine | 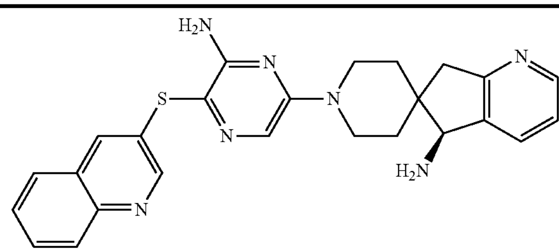 | MS: 456 [M + 1]⁺. ¹HNMR (400 MHz, methanol-d₄) δ 8.69 (d, J = 2.1 Hz, 1H), 8.42 (d, J = 4.6 Hz, 1H), 8.09 (d, J = 1.6 Hz, 1H), 8.00 (d, J = 8.5 Hz, 1H), 7.90 (d, J = 7.5 Hz, 1H), 7.84 (d, J = 8.1 Hz, 1H), 7.74 (t, J = 7.2 Hz, 1H), 7.62 (t, J = 7.1 Hz, 2H), 7.33 (dd, J = 7.4, 5.2 Hz, 1H), 4.34 (t, J = 11.8 Hz, 2H), 4.17 (s, 1H), 3.30-3.19 (m, 3H), 3.08-2.95 (m, 1H), 1.92-1.82 (m, 2H) , 1.64 (d, J = 12.5 Hz, 1H), 1.51 (d, J = 12.2 Hz, 1H). |

Example 15

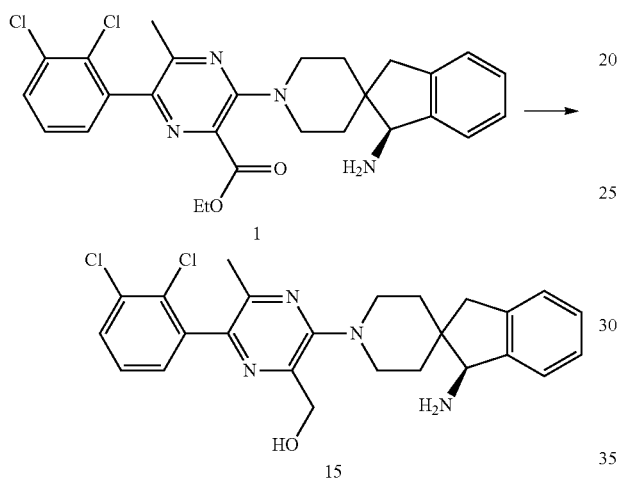

Example 17

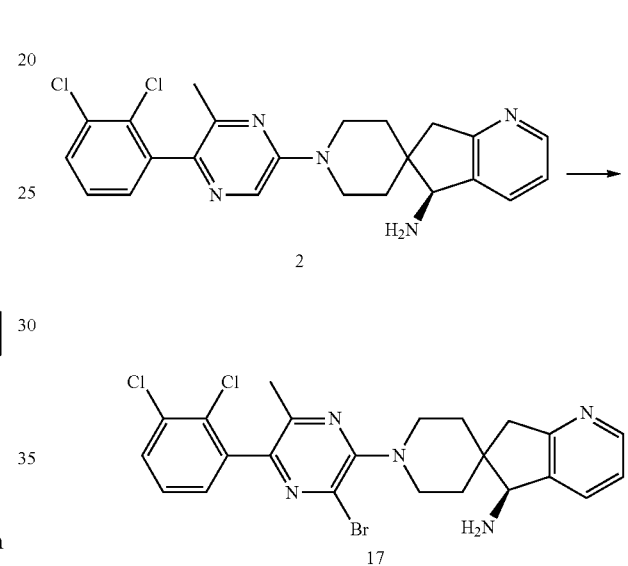

To a 0° C. solution of example 1 (132 mg, 0.26 mmol) in THF (8 mL) under nitrogen atmosphere was added LiBH₄ (2M/THF, 0.30 mL, 0.60 mmol). The resulting mixture was stirred for 16 h at 70° C. After cooling to RT, the reaction mixture was quenched with brine (50 mL), extracted with EA (3×40 mL), the organic layers combined, dried over anhydrous Na₂SO₄, filtered and concentrated under reduced pressure. The residue was purified by Prep-TLC (MeOH:DCM=1:16, v/v) to give example 15 (11 mg). MS: 469 [M+1]⁺. ¹HNMR (400 MHz, methanol-d₄) δ 7.63 (dd, J=7.9, 1.3 Hz, 1H), 7.50-7.39 (m, 2H), 7.37-7.24 (m, 4H), 4.69 (s, 2H), 4.29 (s, 1H), 3.80-3.58 (m, 2H), 3.26-2.96 (m, 4H), 2.26 (s, 3H), 3.01-1.89 (m, 2H), 1.74-1.59 (m, 2H).

The following compound was synthesized using the above procedure or modified procedure with the corresponding starting materials.

To a 0° C. solution of example 2 (0.57 g, 1.29 mmol) in DCM (20 mL) was added NBS (0.35 g, 1.97 mmol). The resulting mixture was stirred for 4 h at RT. The reaction mixture was concentrated under reduced pressure. The residue was purified by silica gel chromatography (eluting with MeOH:DCM=1:30, v/v) to give example 17 (451 mg). MS: 518 [M+1]⁺. ¹HNMR (400 MHz, methanol-d₄) δ 8.34 (d, J=4.5 Hz, 1H), 7.84 (d, J=7.6 Hz, 1H), 7.65 (dd, J=8.0, 1.5 Hz, 1H), 7.42 (t, J=7.8 Hz, 1H), 7.36-7.32 (m, 1H), 7.29-7.25 (m, 1H), 4.09-4.07 (m, 1H), 3.97-3.92 (m, 2H), 3.25-3.16 (m, 3H), 2.95-2.89 (m, 1H), 2.68 (s, 3H), 2.03-1.99 (m, 2H), 1.70-1.65 (m, 1H), 1.51-1.47 (m, 1H).

| EX No | Chemical Name | Structure | MS & ¹HNMR |
|---|---|---|---|
| 24 | (S)-(3-(1-amino-1,3-dihydrospiro[indene-2,4'-piperidin]-1'-yl)-6-((2-amino-3-chloropyridin-4-yl)thio)-5-methylpyrazin-2-yl)methanol | 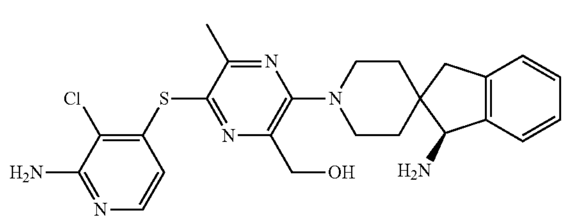 [SMILES: Cc1nc(N2CCC3(CC2)Cc2ccccc2[C@H]3N)c(CO)nc1Sc1ccnc(N)c1Cl] | MS: 483 [M + 1]⁺. ¹HNMR (400 MHz, methanol - d₄) δ 7.62 (d, J = 5.5 Hz, 1H), 7.54-7.50 (m, 1H), 7.39-7.36 (m, 3H), 5.93 (d, J = 5.5 Hz, 1H), 4.68 (s, 2H), 4.38 (s, 1H), 4.14-3.85 (m, 4H), 3.21-3.14 (m, 2H), 2.51 (s, 3H), 1.76-1.72 (m, 2H), 1.64-1.57 (m, 2H). |

Example 18 & Example 19

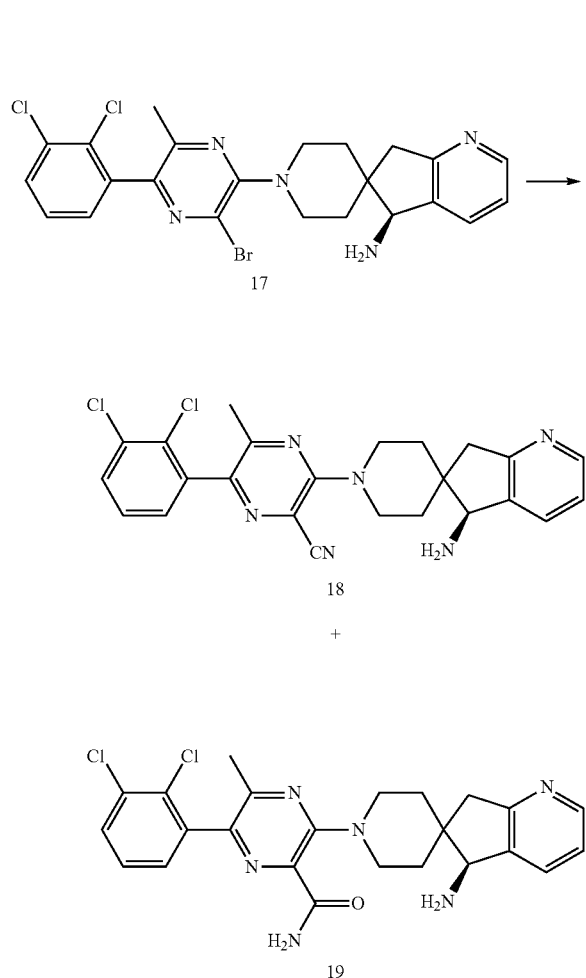

Example 20

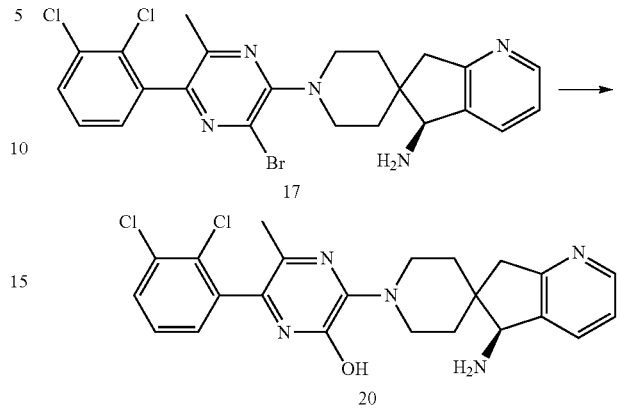

A mixture of example 17 (64 mg, 0.12 mmol) and HCl/EA (4 M, 4 mL) was stirred for 1 h at RT. The reaction mixture was filtered followed by EA wash. The solid was dissolved in EA (20 mL) and washed with NH$_3$H$_2$O (10%, 20 mL). The organic layer was dried over anhydrous Na$_2$SO$_4$, filtered and concentrated under reduced pressure and dried under high vacuum for 2 h to give example 20 (17 mg) as a yellow solid. MS: 456 [M+1]$^+$. $^1$HNMR (400 MHz, methanol-d$_4$) δ 8.37 (d, J=4.7 Hz, 1H), 7.87 (d, J=7.5 Hz, 1H), 7.67 (dd, J=8.0, 1.4 Hz, 1H), 7.44 (t, J=7.8 Hz, 1H), 7.38-7.34 (m, 1H), 7.32-7.28 (m, 1H), 4.11 (s, 1H), 4.04-3.99 (m, 2H), 3.28-3.21 (m, 3H), 2.98-2.93 (m, 1H), 2.27 (s, 3H), 2.10-1.98 (m, 2H), 1.73-1.67 (d, J=11.9 Hz, 2H).

A mixture of example 17 (155 mg, 0.30 mmol), K$_4$Fe(CN)$_6$·3H$_2$O (156 mg, 0.37 mmol), DBU (242 mg, 1.59 mmol) and Pd(PPh$_3$)$_4$ (39 mg, 0.034 mmol) in t-BuOH/H$_2$O (6 mL/6 mL) was stirred for 3.5 h at 100° C. under nitrogen atmosphere. After cooling to RT, the resulting mixture was quenched with brine (50 mL) and extracted with EA (2×30 mL). The organic layers were combined, dried over anhydrous Na$_2$SO$_4$, filtered and concentrated under reduced pressure. The residue was purified by Prep-TLC (MeOH:DCM=1:8, v/v) to give example 18 (19 mg) and example 19 (25 mg).

Example 18: MS: 465 [M+1]$^+$. $^1$HNMR (400 MHz, methanol-d$_4$) δ 8.39 (d, J=4.7 Hz, 1H), 7.87 (d, J=7.6 Hz, 1H), 7.66 (dd, J=8.0, 1.4 Hz, 1H), 7.43 (t, J=7.8 Hz, 1H), 7.35 (dd, J=7.6, 1.4 Hz, 1H), 7.32-7.28 (m, 1H), 4.55-4.49 (m, 2H), 4.18 (s, 1H), 3.52-3.43 (m, 2H), 3.26-3.24 (m, 1H), 3.04-2.99 (m, 1H), 2.29 (s, 3H), 2.03-1.91 (m, 2H), 1.76-1.66 (m, 1H), 1.60-1.54 (m, 1H).

Example 19: MS: 483 [M+1]$^+$. $^1$HNMR (400 MHz, methanol-d$_4$) δ 8.42 (d, J=4.5 Hz, 1H), 7.89 (d, J=7.6 Hz, 1H), 7.62 (dd, J=7.3, 2.3 Hz, 1H), 7.47-7.37 (m, 1H), 7.32 (dd, J=7.5, 5.2 Hz, 1H), 4.24 (s, 1H), 4.13-3.97 (m, 2H), 3.39-3.33 (m, 1H), 3.29-3.20 (m, 2H), 3.09-2.99 (m, 1H), 2.26 (s, 3H), 2.02-1.87 (m, 2H), 1.66-1.50 (m, 2H).

Example 21 & Example 22 & Example 23

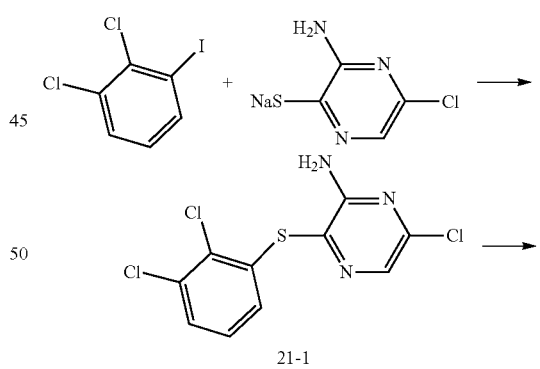

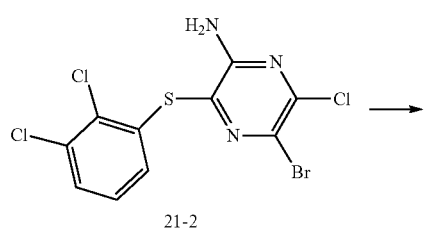

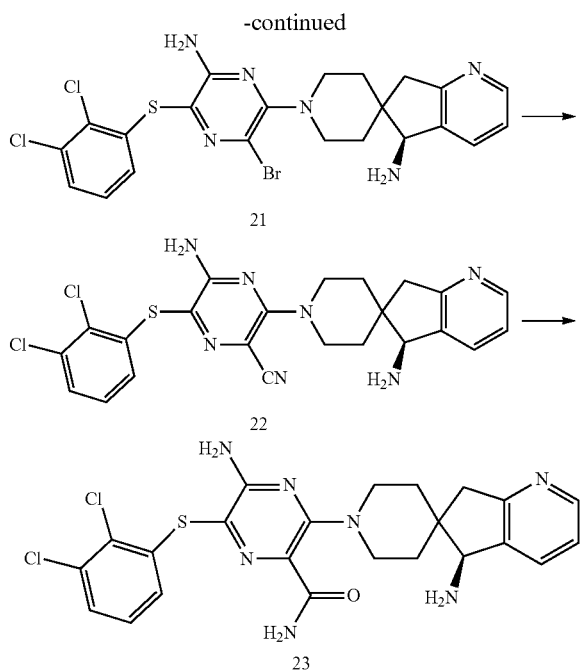

raphy (eluting with MeOH:DCM=1:12, v/v) to give example 22 (117 mg) as a yellow solid. MS: 498 [M+1]+. 1HNMR (400 MHz, methanol-d4) δ 8.37 (d, J=4.9 Hz, 1H), 7.85 (d, J=7.5 Hz, 1H), 7.42-7.38 (m, 1H), 7.34-7.27 (m, 1H), 7.23-7.11 (m, 1H), 6.89-6.86, 6.68-6.65 (m, 1H), 4.55-4.43 (m, 1H), 4.38-4.26 (m, 1H), 4.15-3.99 (m, 1H), 3.65 (t, J=6.9 Hz, 1H), 3.25-3.12 (m, 2H), 3.02-2.91 (m, 1H), 2.13-1.81 (m, 2H), 1.65-1.59 (m, 1H), 1.50-1.42 (m, 1H).

A mixture of example 22 (105 mg, 0.21 mmol) in sulfuric acid (98%, 5 mL) was stirred for 16 h at 80° C. After cooling to RT, the reaction mixture was poured into water and the pH value was taken to 10 with NH3—H2O (25%). The resulting mixture was extracted with EA (2×50 mL), the organic layers combined, dried over anhydrous Na2SO4, filtered and concentrated under reduced pressure. The residue was purified by Prep-TLC (MeOH:DCM=1:8, v/v) to give example 23 (30 mg). MS: 516 [M+1]+. 1HNMR (400 MHz, methanol-d4) δ 8.36 (d, J=4.6 Hz, 1H), 7.85 (d, J=7.5 Hz, 1H), 7.36 (dd, J=8.0, 1.1 Hz, 1H), 7.29 (dd, J=7.5, 5.2 Hz, 1H), 7.17 (t, J=8.0 Hz, 1H), 6.81 (dd, J=8.0, 1.1 Hz, 1H), 4.07 (s, 1H), 3.99 (d, J=13.7 Hz, 2H), 3.30-3.17 (m, 3H), 2.93 (d, J=16.5 Hz, 1H), 2.03-1.86 (m, 2H), 1.64-1.55 (m, 1H), 1.46-1.40 (m, 1H).

Example 24

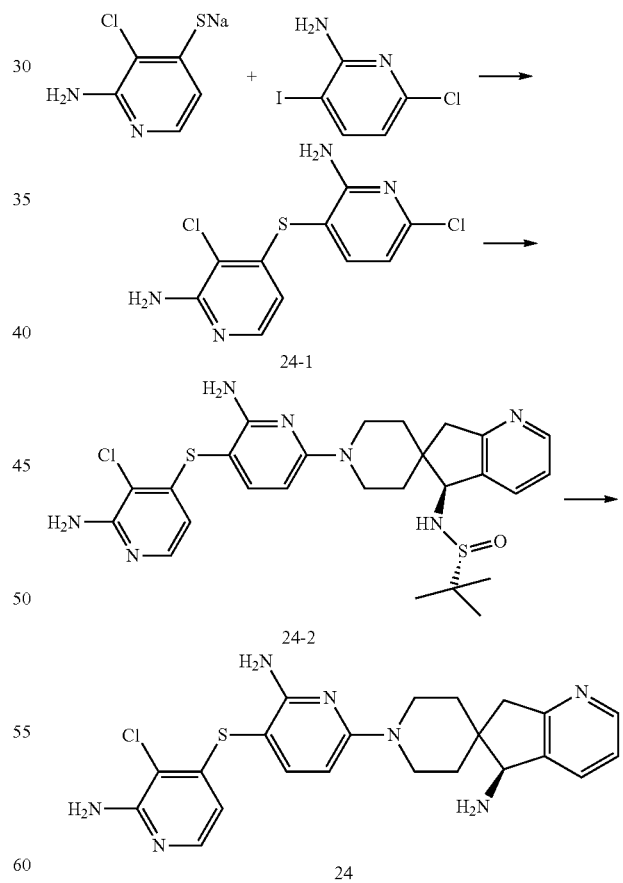

A mixture of 1,2-dichloro-3-iodobenzene (575 mg, 3.13 mmol), sodium 3-amino-5-chloropyrazine-2-thiolate (813 mg, 2.98 mmol), Pd2(dba)3 (134 mg, 0.15 mmol), XantPhos (176 mg, 0.30 mmol) and DIPEA (1.41 g, 10.92 mmol) in 1,4-dioxane (20 mL) was stirred for 3 h at 110° C. under nitrogen atmosphere. After cooling to RT, the reaction mixture was concentrated under reduced pressure. The residue was purified by silica gel chromatography (eluting with EA:Hex=1:10, v/v) to give compound 21-1 (0.41 g). MS: 306 [M+1]+.

To a 0° C. solution of compound 21-1 (0.40 g, 1.31 mmol) in DCM (20 mL) was added NBS (0.32 g, 1.80 mmol). The resulting mixture was stirred for 17 h at RT. The reaction mixture was diluted with EA (50 mL) and brine (100 mL). The aqueous layer was separated, extracted with EA (1×50 mL), the organic layers combined, dried over anhydrous Na2SO4, filtered and concentrated under reduced pressure to give compound 21-2 (0.43 g) as a brown solid.

A mixture of compound 21-2 (0.43 g, 1.11 mmol), intermediate C2 (0.43 g, 1.38 mmol) and K2CO3 (1.60 g, 11.58 mmol) in CH3CN (20 mL) was stirred for 5 h at 100° C. After cooling to RT, the resulting mixture was concentrated under reduced pressure. The residue was purified by silica gel chromatography (eluting with MeOH:DCM=1:20, v/v) to give example 21 (191 mg) an a brown solid. MS: 551 [M+1]+. 1HNMR (400 MHz, methanol-d4) δ 8.35 (d, J=4.6 Hz, 1H), 7.85 (d, J=7.5 Hz, 1H), 7.35 (dd, J=8.0, 1.2 Hz, 1H), 7.28 (dd, J=7.5, 5.2 Hz, 1H), 7.17 (t, J=8.0 Hz, 1H), 6.77 (dd, J=8.0, 1.2 Hz, 1H), 4.14-3.95 (m, 3H), 3.28-3.12 ((m, 3H), 2.91 (d, J=16.5 Hz, 1H), 2.08-1.93 (m, 2H), 1.70-1.59 (m, 1H), 1.50-1.42 (m, 1H).

A mixture of example 21 (173 mg, 0.31 mmol), K4Fe(CN)6 3H2O (168 mg, 0.40 mmol), DBU (240 mg, 1.58 mmol) and Pd(PPh3)4 (35 mg, 0.030 mmol) in t-BuOH/H2O (1/1, 16 mL) was stirred for 16 h at 100° C. under nitrogen atmosphere. After cooling to RT, the reaction mixture was diluted with water (50 mL) and extracted with EA (2×50 mL). The organic layers were combined, dried over anhydrous Na2SO4, filtered and concentrated under reduced pressure. The residue was purified by silica gel chromatog- Compound 24-1 was synthesized in the manner of compound 5-1, except compound 1-3 was replaced with 6-chloro-3-iodopyridin-2-amine.

A mixture of compound C2-6 (351 mg, 0.86 mmol) and TFA (1 mL) in DCM (20 mL) was stirred for 30 min at RT.

The resulting mixture was concentrated under reduced pressure. Compound 24-1 (200 mg, 0.70 mmol), Pd(OAc)$_2$ (33 mg, 0.15 mmol), DavePhos (65 mg, 0.17 mmol), t-BuOK (1.21 g, 10.78 mmol) and toluene (30 mL) was added. The resulting mixture was stirred for 18 h at 100° C. under nitrogen atmosphere.

After cooling to RT, the reaction mixture was diluted with water (100 mL) and extracted with EA (2×50 mL). The organic layers were combined, dried over anhydrous Na$_2$SO$_4$, filtered and concentrated under reduced pressure to give compound 24-2 (0.37 g) as a brown solid. MS: 558 [M+1]$^+$.

A mixture of compound 24-2 (0.37 g, 0.66 mmol) and HCl/EA (4 M, 3.00 mL, 12.00 mmol) in DCM (20 mL) was stirred for 30 min at RT. The resulting mixture was diluted with water (50 mL) and the pH value was adjusted to 9 with NH$_3$H$_2$O (25%).

The resulting mixture was extracted with DCM (1×50 mL), the organic layer dried over anhydrous Na$_2$SO$_4$, filtered and concentrated under reduced pressure. The residue was purified by Prep-TLC (MeOH:DCM=1:8, v/v) to give example 24 (10 mg). MS: 454 [M+1]$^+$. $^1$HNMR (400 MHz, methanol-d$_4$) δ 8.43 (dd, J=13.1, 4.3 Hz, 1H), 7.96-7.88 (m, 1H), 7.60 (d, J=5.2 Hz, 1H), 7.43-7.29 (m, 2H), 6.24 (d, J=8.5 Hz, 1H), 6.01 (d, J=5.2 Hz, 1H), 4.42-4.15 (m, 3H), 3.26-3.08 (m, 4H), 1.86-1.77 (m, 2H), 1.59-1.43 (m, 2H).

Example 25

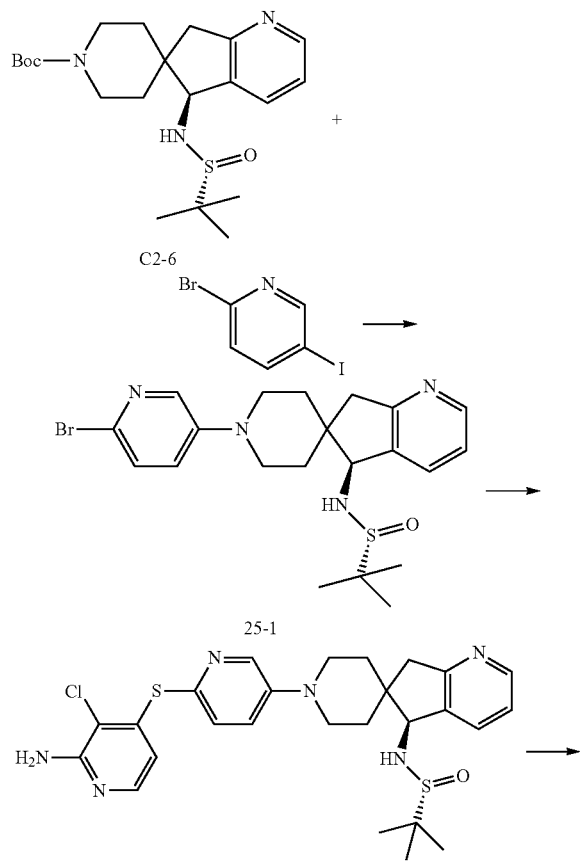

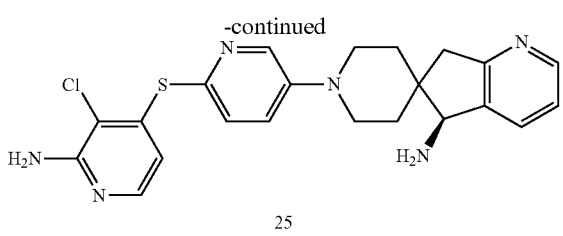

A mixture of compound C2-6 (552 mg, 1.35 mmol) and TFA (2.50 mL) in DCM (30 mL) was stirred for 1 h at RT. The resulting mixture was concentrated under reduced pressure. 2-Bromo-5-iodopyridine (354 mg, 1.25 mmol), Pd$_2$(dba)$_3$ (66 mg, 0.072 mmol), BINAP (86 mg, 0.14 mmol), t-BuOK (3204 mg, 28.55 mmol) and toluene (20 mL) was added. The resulting mixture was stirred for 21 h at 100° C. under nitrogen atmosphere. After cooling to RT, the reaction mixture was diluted with EA (50 mL) and filtered through Kieselguhr. The filtrate was concentrated under reduced pressure. The residue was purified by silica gel chromatography (eluting with MeOH:DCM=1:20, v/v) to give compound 25-1 (392 mg) as a yellow solid. MS: 463 [M+1]$^+$.

A mixture of compound 25-1 (184 mg, 0.40 mmol), intermediate A1 (80 mg, 0.44 mmol), Pd$_2$(dba)$_3$ (41 mg, 0.045 mmol), XantPhos (55 mg, 0.095 mmol) and DIPEA (193 mg, 1.49 mmol) in 1,4-dioxane (20 mL) was stirred for 16 h at 110° C. under nitrogen atmosphere. After cooling to RT, the reaction mixture was concentrated under reduced pressure. The residue was purified by silica gel chromatography (eluting with MeOH:DCM=1:12, v/v) to give compound 25-2 (127 mg). MS: 543 [M+1]$^+$.

A mixture of compound 25-2 (127 mg, 0.23 mmol) and HCl/EA (4 M, 3.00 mL, 12.00 mmol) in DCM (20 mL) was stirred for 1.5 h at RT. The reaction mixture was diluted with water (50 mL) and the pH value was adjusted to 9 with NH$_3$·H$_2$O (25%). The resulting mixture was extracted with DCM (2×50 mL), the organic layers combined, dried over anhydrous Na$_2$SO$_4$, filtered and concentrated under reduced pressure. The residue was purified by Prep-TLC (MeOH:DCM=1:8, v/v) to give example 25 (28 mg). MS: 439 [M+1]$^+$. $^1$HNMR (400 MHz, methanol-d$_4$) δ 8.45-8.34 (m, 2H), 7.87 (d, J=7.5 Hz, 1H), 7.67-7.54 (m, 2H), 7.53-7.44 (m, 1H), 7.37-7.25 (m, 1H), 5.95 (d, J=5.5 Hz, 1H), 4.11 (s, 1H), 3.93-3.75 (m, 2H), 3.28-3.10 (m, 3H), 3.01-2.83 (m, 1H), 2.07-1.84 (m, 2H), 1.76-1.66 (m, 1H), 1.57-1.45 (m, 1H).

Example 26

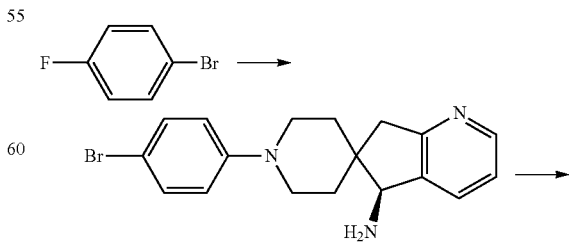

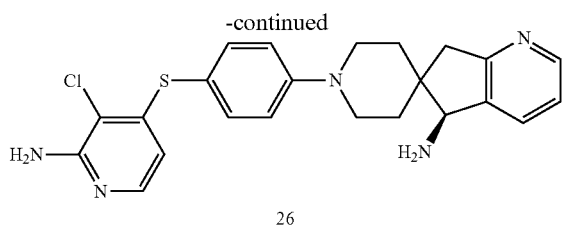

26

1-Bromo-4-fluorobenzene (3.69 g, 21.09 mmol), intermediate C2 (0.95 g, 3.04 mmol), K$_2$CO$_3$ (5.21 g, 37.70 mmol) and NMP (6 mL) was added to a 15 mL sealed tube. The resulting mixture was stirred for 6.5 h at 140° C. An additional batch of 1-bromo-4-fluorobenzene (1.22 g, 6.97 mmol) was added and the resulting mixture was stirred for 18 h at 160° C. After cooling to RT, the reaction mixture was poured into water (50 mL) and extracted with EA (2×50 mL). The organic layers were combined, dried over anhydrous Na$_2$SO$_4$, filtered and concentrated under reduced pressure. The residue was purified by silica gel chromatography (eluting with MeOH:DCM=1:15, v/v) to give compound 26-1 (249 mg) as a brown oil. MS: 358 [M+1]$^+$.

A mixture of compound 26-1 (120 mg, 0.33 mmol), intermediate A1 (65 mg, 0.36 mmol), Pd$_2$(dba)$_3$ (61 mg, 0.067 mmol), XantPhos (83 mg, 0.14 mmol) and DIPEA (303 mg, 2.34 mmol) in 1,4-dioxane (10 mL) was stirred for 18 h at 110° C. under nitrogen atmosphere. After cooling to RT, the reaction mixture was concentrated under reduced pressure. The residue was purified by silica gel chromatography (eluting with MeOH:DCM=1:20, v/v) to give example 26 (47 mg). MS: 438 [M+1]$^+$. $^1$HNMR (400 MHz, methanol-d$_4$) δ 8.47 (d, J=4.6 Hz, 1H), 7.93 (d, J=7.5 Hz, 1H), 7.56 (d, J=5.5 Hz, 1H), 7.43 (d, J=8.7 Hz, 2H), 7.39-7.33 (m, 1H), 7.13 (d, J=8.7 Hz, 2H), 5.88 (d, J=5.5 Hz, 1H), 4.31 (s, 1H), 3.87-3.74 (m, 2H), 3.27-3.02 (m, 4H), 2.02-1.91 (m, 2H), 1.73-1.60 (m, 2H).

Example 27

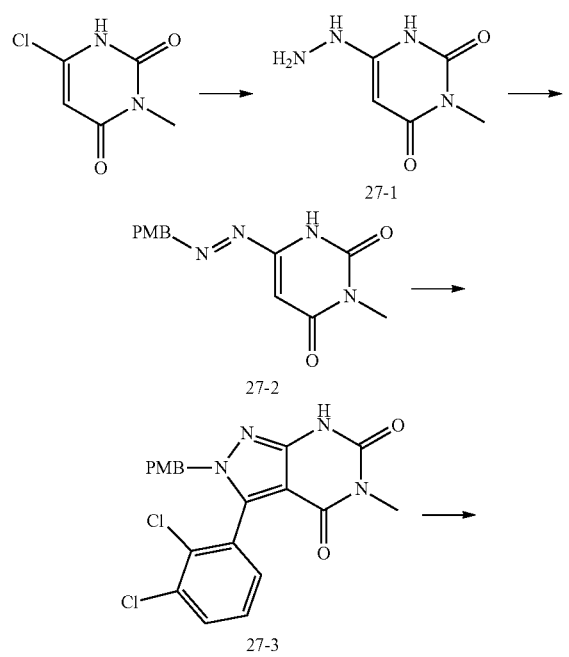

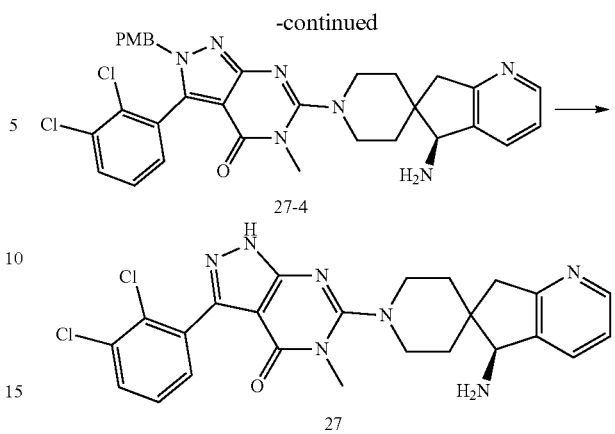

To a solution of 6-chloro-3-methylpyrimidine-2,4(1H, 3H)-dione (10.00 g, 62.28 mmol) in EtOH (200 mL) was added hydrazine hydrate (80%, 52.00 mL) at RT. The resulting mixture was stirred for 4 h at 80° C. After cooling to RT, the reaction mixture was concentrated to about 100 mL under reduced pressure and filtered. The filtered cake was washed with EtOH (2×50 mL). The filtered cake was collected and dried in a high vacuum oven to give compound 27-1 (5.56 g) as a light yellow solid. MS: 157 [M+1]$^+$.

A mixture of compound 27-1 (5.56 g, 35.61 mmol) and 4-methoxybenzaldehyde (7.02 g, 51.56 mmol) in MeOH was stirred for 6 h at 70° C. After cooling to RT, the reaction mixture was filtered and the filtered cake was washed with MeOH. The filtered cake was collected and dried under high vacuum to give compound 27-2 (5.78 g) as a yellow solid. MS: 275 [M+1]$^+$.

A mixture of compound 27-2 (2.03 g, 7.40 mmol), 2,3-dichlorobenzaldehyde (1.36 g, 7.77 mmol) and piperidine (0.77 g, 9.04 mmol) in DMF/iPrOH (20 mL/10 mL) was stirred for 18 h at 85° C. After cooling to RT, the reaction mixture was diluted with EA (200 mL) and washed with brine (2×50 mL). The organic layer was dried over anhydrous Na$_2$SO$_4$, filtered and concentrated under reduced pressure. The residue was purified by silica gel chromatography (eluting with EA:Hex=1:2, v/v) to give compound 27-3 (2.40 g) as a light yellow solid. MS: 431 [M+1]$^+$.

A mixture of compound 27-3 (197 mg, 0.46 mmol) and BOP (649 mg, 1.47 mmol) in DMF (17 mL) was stirred for 10 min at RT. Then DBU (748 mg, 4.91 mmol) and C$_2$ (229 mg, 0.73 mmol) was added and stirred for 20 h at RT. The reaction mixture was diluted with EA (100 mL) wad washed with brine (3×100 mL). The organic layer was dried over anhydrous Na$_2$SO$_4$, filtered and concentrated under reduced pressure. The residue was purified by silica gel chromatography (eluting with MeOH:DCM=1:8, v/v) to give compound 27-4 (210 mg). MS: 615 [M+1]$^+$.

A mixture of compound 27-4 (210 mg, 0.34 mmol) and TFA (15 mL) was stirred for 1.5 h at 100° C. The reaction mixture was diluted with water (100 mL) and the pH value was taken to 10 with NH$_3$H$_2$O (25%). The resulting mixture was extracted with DCM (2×50 mL), the organic layers combined, dried over anhydrous Na$_2$SO$_4$, filtered and concentrated under reduced pressure. The residue was purified by Prep-TLC (MeOH:DCM=1:8, v/v) to give example 27 (21 mg). MS: 496 [M+1]$^+$. $^1$HNMR (400 MHz, methanol-d$_4$) δ 8.38 (d, J=4.7 Hz, 1H), 7.87 (d, J=7.5 Hz, 1H), 7.65 (dd, J=7.9, 1.5 Hz, 1H), 7.46 (dd, J=7.6, 1.5 Hz, 1H), 7.39 (t, J=7.8 Hz, 1H), 7.31 (dd, J=7.4, 5.2 Hz, 1H), 4.14 (s, 1H), 3.68-3.58 (m, 2H), 3.55 (s, 3H), 3.29-3.12 ((m, 3H), 3.01-2.90 (m, 1H), 2.15-1.96 (m, 2H), 1.74-1.65 (m, 1H), 1.57-1.45 (m, 1H).

The following compound was synthesized using the above procedure or modified procedure with the corresponding starting materials.

| EX No | Chemical Name | Structure | MS & ¹HNMR |
|---|---|---|---|
| 28 | (S)-6-(1-amino-6-fluoro-1,3-dihydrospiro[indene-2,4'-piperidin]-1'-yl)-3-(2,3-dichlorophenyl)-5-methyl-1,5-dihydro-4H-pyrazolo[3,4-d]pyrimidin-4-one | 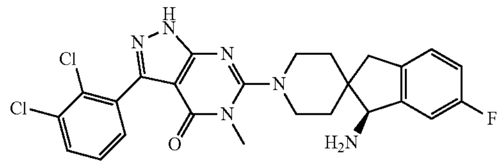 [SMILES: Cn1c(N2CCC3(CC2)Cc2ccc(F)cc2[C@H]3N)nc2[nH]nc(-c3cccc(Cl)c3Cl)c2c1=O] | MS: 513 [M + 1]⁺. ¹HNMR (400 MHz, methanol - $d_4$) δ 7.65 (dd, J = 7.9, 1.7 Hz, 1H), 7.45 (dd, J = 7.6, 1.7 Hz, 1H), 7.39 (t, J = 7.8 Hz, 1H), 7.26 (dd, J = 8.2, 5.1 Hz, 1H), 7.16 (dd, J = 8.8, 2.0 Hz, 1H), 7.03-6.93 (m, 1H), 4.10 (s, 1H), 3.63-3.55 (m, 2H), 3.54 (s, 3H), 3.25-3.09 (m, 3H), 2.88-2.79 (m, 1H), 2.10-1.95 (m, 2H), 1.72-1.65 (m, 1H), 1.57-1.49 (m, 1H). |

Example 29

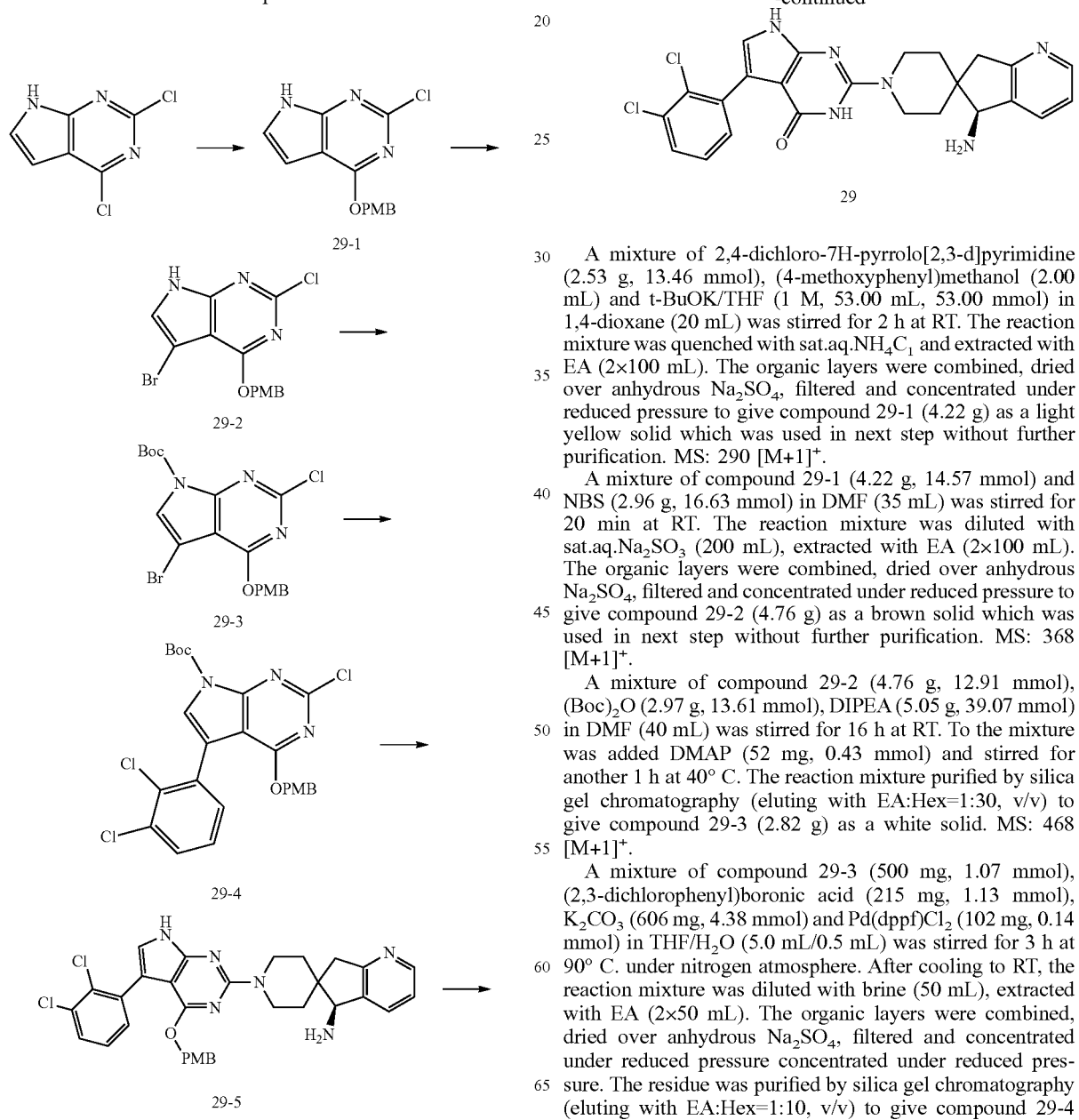

A mixture of 2,4-dichloro-7H-pyrrolo[2,3-d]pyrimidine (2.53 g, 13.46 mmol), (4-methoxyphenyl)methanol (2.00 mL) and t-BuOK/THF (1 M, 53.00 mL, 53.00 mmol) in 1,4-dioxane (20 mL) was stirred for 2 h at RT. The reaction mixture was quenched with sat.aq.$NH_4C_1$ and extracted with EA (2×100 mL). The organic layers were combined, dried over anhydrous $Na_2SO_4$, filtered and concentrated under reduced pressure to give compound 29-1 (4.22 g) as a light yellow solid which was used in next step without further purification. MS: 290 [M+1]⁺.

A mixture of compound 29-1 (4.22 g, 14.57 mmol) and NBS (2.96 g, 16.63 mmol) in DMF (35 mL) was stirred for 20 min at RT. The reaction mixture was diluted with sat.aq.$Na_2SO_3$ (200 mL), extracted with EA (2×100 mL). The organic layers were combined, dried over anhydrous $Na_2SO_4$, filtered and concentrated under reduced pressure to give compound 29-2 (4.76 g) as a brown solid which was used in next step without further purification. MS: 368 [M+1]⁺.

A mixture of compound 29-2 (4.76 g, 12.91 mmol), (Boc)₂O (2.97 g, 13.61 mmol), DIPEA (5.05 g, 39.07 mmol) in DMF (40 mL) was stirred for 16 h at RT. To the mixture was added DMAP (52 mg, 0.43 mmol) and stirred for another 1 h at 40° C. The reaction mixture purified by silica gel chromatography (eluting with EA:Hex=1:30, v/v) to give compound 29-3 (2.82 g) as a white solid. MS: 468 [M+1]⁺.

A mixture of compound 29-3 (500 mg, 1.07 mmol), (2,3-dichlorophenyl)boronic acid (215 mg, 1.13 mmol), $K_2CO_3$ (606 mg, 4.38 mmol) and Pd(dppf)Cl₂ (102 mg, 0.14 mmol) in THF/H₂O (5.0 mL/0.5 mL) was stirred for 3 h at 90° C. under nitrogen atmosphere. After cooling to RT, the reaction mixture was diluted with brine (50 mL), extracted with EA (2×50 mL). The organic layers were combined, dried over anhydrous $Na_2SO_4$, filtered and concentrated under reduced pressure concentrated under reduced pressure. The residue was purified by silica gel chromatography (eluting with EA:Hex=1:10, v/v) to give compound 29-4 (380 mg). MS: 534 [M+1]⁺.

A mixture of compound 29-4 (241 mg, 0.56 mmol), C$_2$ (210 mg, 0.67 mmol) and K$_2$CO$_3$ (1903 mg, 13.77 mmol) in NMP (15 mL) was stirred for 23 h at 140° C. After cooling to RT, the reaction mixture was diluted with EA (100 mL) and washed with brine (3×50 mL). The organic layer was dried over anhydrous Na$_2$SO$_4$, filtered and concentrated under reduced pressure. The residue was purified by Prep-TLC (MeOH:DCM=1:10, v/v) to give compound 29-5 (39 mg) as a brown solid. MS: 601 [M+1]$^+$.

A mixture of compound 29-5 (38 mg, 0.063 mmol) and TFA (2 mL) in DCM (10 mL) was stirred for 1 h at RT. The reaction mixture was diluted with brine (50 mL) and the pH value was taken to 10 with NH$_3$—H$_2$O (25%). The resulting mixture was extracted with DCM (2×30 mL), the organic layers combined, dried over anhydrous Na$_2$SO$_4$, filtered and concentrated under reduced pressure. The residue was purified by Prep-TLC (MeOH:DCM=1:6, v/v) to give example 29 (12 mg). MS: 481 [M+1]$^+$. $^1$HNMR (400 MHz, methanol-d$_4$) δ 8.43 (d, J=4.7 Hz, 1H), 7.90 (d, J=7.5 Hz, 1H), 7.42 (dd, J=7.8, 1.5 Hz, 2H), 7.33 (dd, J=7.5, 5.2 Hz, 1H), 7.28-7.21 (m, 1H), 6.87 (s, 1H), 4.28-4.18 (m, 2H), 4.16 (s, 1H), 3.31-3.20 (m, 3H), 3.05-2.94 (m, 1H), 1.98-1.82 (m, 2H), 1.65-1.58 (m, 1H), 1.51-1.45 (m, 1H).

Example 30

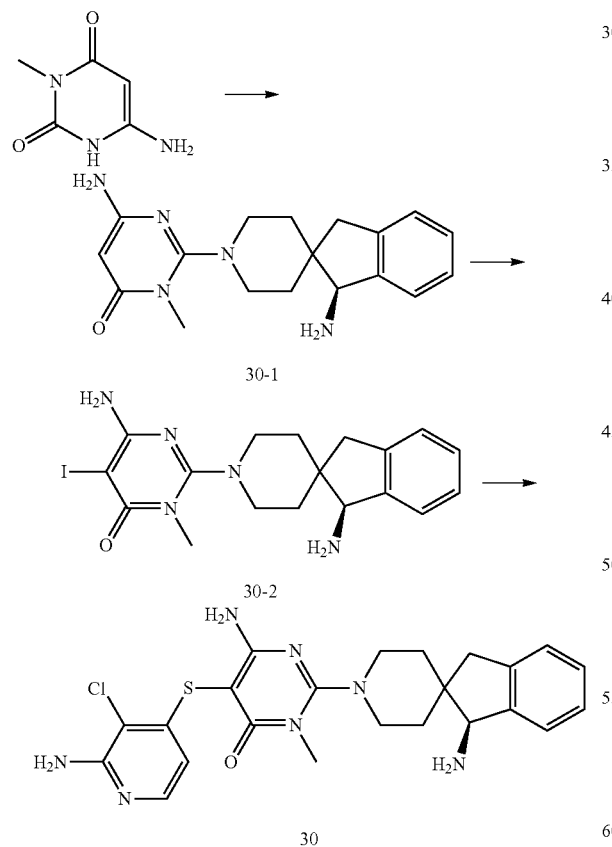

A mixture of 6-amino-3-methylpyrimidine-2,4(1H,3H)-dione (0.50 g, 3.54 mmol) and PyBOP (5.62 g, 10.80 mmol) in DMF (15 mL) was stirred for 10 min at RT. Then DBU (5.62 g, 36.92 mmol) and C$_1$ (1.39 g, 5.05 mmol) was added and stirred for 3 h at RT. The reaction mixture was diluted with EA (100 mL) wad washed with brine (3×100 mL). The organic layer was dried over anhydrous Na$_2$SO$_4$, filtered and concentrated under reduced pressure. The residue was purified by silica gel chromatography (eluting with MeOH:DCM=1:5, v/v) to give compound 30-1 (1135 mg) as a yellow oil. MS: 326 [M+1]$^+$.

A mixture of compound 30-1 (1.13 g, 3.47 mmol) and NIS (859 mg, 3.82 mmol) in DMF (10 mL) was stirred for 17 h at RT. The reaction mixture was diluted with EA (200 mL) and washed sat.aq.Na$_2$SO$_3$ with EA (2×80 mL) and sat.aq.NH$_4$C$_1$ (1×80 mL). The organic layer was dried over anhydrous Na$_2$SO$_4$, filtered and concentrated under reduced pressure. The residue was purified by silica gel chromatography (eluting with MeOH:DCM=1:8, v/v) to give compound 30-2 (828 mg). MS: 452 [M+1]$^+$.

A mixture of compound 30-2 (103 mg, 0.23 mmol), intermediate A1 (48 mg, 0.26 mmol), Pd$_2$(dba)$_3$ (21 mg, 0.023 mmol), XantPhos (25 mg, 0.043 mmol) and DIPEA (103 mg, 0.80 mmol) in 1,4-dioxane (10 mL) was stirred for 15 h at 110° C. under nitrogen atmosphere. After cooling to RT, the reaction mixture was filtered through Kieselguhr and the filtrate was concentrated under reduced pressure. The residue was purified by Prep-TLC (eluting with MeOH:DCM=1:10, v/v) to give example 30 (12 mg). MS: 484 [M+1]$^+$. $^1$HNMR (400 MHz, methanol-d$_4$) δ 7.62 (d, J=5.5 Hz, 1H), 7.53 (d, J=7.3 Hz, 1H), 7.45-7.32 (m, 3H), 6.19 (d, J=5.5 Hz, 1H), 4.42 (s, 1H), 3.80-3.63 (m, 2H), 3.47 (s, 3H), 3.30-3.09 (m, 4H), 2.11-1.89 (m, 2H), 1.75 (d, J=12.9 Hz, 1H), 1.66 (d, J=13.2 Hz, 1H).

Example 31

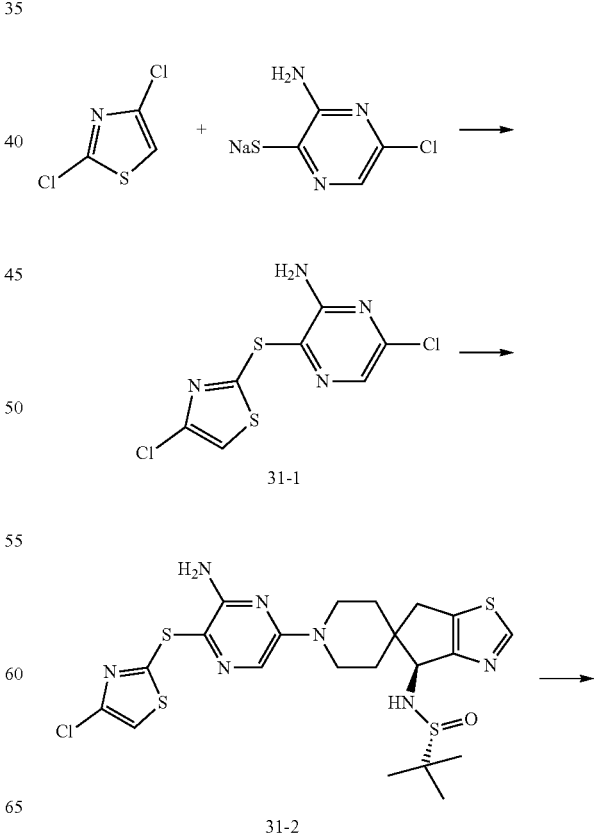

-continued

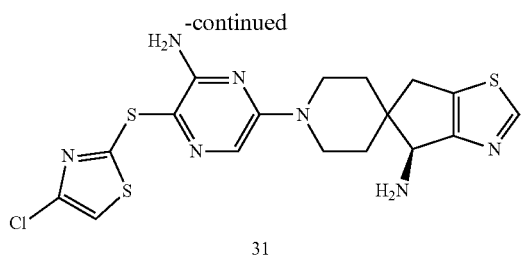

31

A mixture of 2,4-dichlorothiazole (1.54 g, 10.00 mmol), sodium 3-amino-5-chloropyrazine-2-thiolate- (2.77 g, 15.10 mmol) and K$_2$CO$_3$ (2.92 g, 21.10 mmol) in DMF (15 mL) was stirred for 3 h at 75° C. After cooling to RT, the reaction mixture was diluted with EA (50 mL) and water (50 mL). The organic layer was separated, dried over anhydrous Na$_2$SO$_4$, filtered and concentrated under reduced pressure. The residue was purified by silica gel chromatography (eluting with EA:Hex=1:5, v/v) to give compound 31-1 (281 mg) as a yellow solid. MS: 279 [M+1]$^+$.

To solution of intermediate C3 (288 mg, 0.70 mmol) in DCM (17 mL) was added TFA (2 mL), and stirred for 1.5 h at RT. The resulting mixture was concentrated under reduced pressure. The residue was dissolved in NMP (5 mL), 31-1 (232 mg, 1.19 mmol) and K$_2$CO$_3$ (1.18 g, 8.52 mmol) was added. The resulting mixture was stirred for 16 h at 95° C. After cooling to RT, the reaction mixture was diluted with water (30 mL) and EA (30 mL). The aqueous layer was separated and extracted with EA (2×20 mL). The combined organic layers were washed with brine (50 mL), dried over anhydrous Na$_2$SO$_4$, filtered and concentrated under reduced pressure to give 31-2 (272 mg) as a red oil. MS: 556 [M+H]$^+$.

A mixture of 31-2 (254 mg, 0.43 mmol) and HCl/1,4-dioxane (4M, 1 mL) in DCM was stirred for 30 min at RT. The reaction mixture was concentrated under reduced pressure. The residue was purified by Prep-TLC (MeOH:DCM=1:8, v/v) to give 31 (34 mg) as a yellow solid. MS: 452 [M+H]$^+$. $^1$HNMR (400 MHz, methanol-d$_4$) δ 9.01 (s, 1H), 7.63 (s, 1H), 7.26 (s, 1H), 4.50-4.28 (m, 3H), 3.46-3.35 (m, 1H), 3.31-3.21 (m, 2H), 3.19-3.09 (m, 1H), 2.00-1.76 (m, 4H).

The following compounds were synthesized using the above procedure or modified procedure with the corresponding starting materials.

| EX No | Chemical Name | Structure | MS:[M + 1]⁺ |
|---|---|---|---|
| 32 | (S)-1'-(6-amino-5-(2-chloro-3-methylphenyl)pyrazin-2-yl)-6-bromo-1,3-dihydrospiro[indene-2,4'-piperidin]-1-amine | 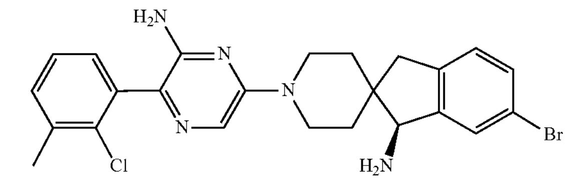 [SMILES: Cc1cccc(-c2ncc(N3CCC4(CC3)Cc3ccc(Br)cc3[C@H]4N)nc2N)c1Cl] | 498 |
| 33 | (R)-1'-(5-(2,3-dichloro-5-methoxyphenyl)pyridin-2-yl)-2,3-dihydrospiro[indene-1,4'-piperidin]-2-amine | 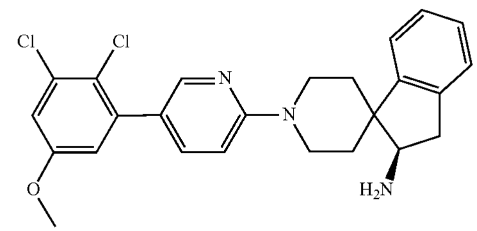 [SMILES: COc1cc(Cl)c(Cl)c(-c2ccc(N3CCC4(CC3)c3ccccc3C[C@H]4N)nc2)c1] | 454 |
| 34 | (S)-1'-(5-(3-amino-2-(trifluoromethyl)phenyl)pyrimidin-2-yl)-1,3-dihydrospiro[indene-2,4'-piperidine]-1,6-diamine | 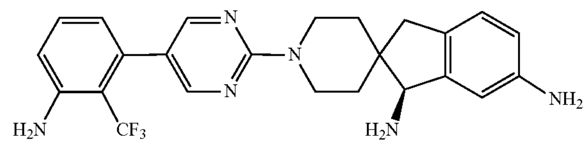 | 455 |
| 35 | (S)-1'-(6-(5-chlorothiophen-2-yl)pyridazin-3-yl)-5-methyl-1,3-dihydrospiro[indene-2,4'-piperidin]-1-amine | 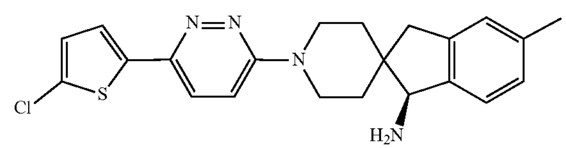 | 411 |
| 36 | (S)-1-amino-1'-(6-((3-amino-2-chlorophenyl)thio)-1,2,4-triazin-3-yl)-1,3-dihydrospiro[indene-2,4'-piperidine]-6-carbonitrile | 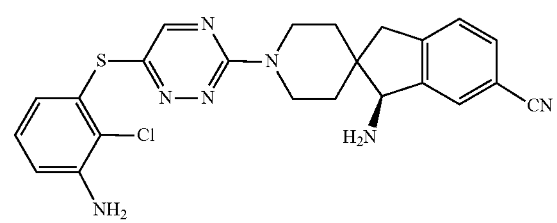 [SMILES: N#Cc1ccc2c(c1)[C@@H](N)C1(CCN(c3ncc(Sc4cccc(N)c4Cl)nn3)CC1)C2] | 464 |

-continued

| EX No | Chemical Name | Structure | MS:[M + 1]+ |
|---|---|---|---|
| 37 | (S)-1-amino-1'-(2-((2-cyanopyridin-3-yl)thio)pyrimidin-5-yl)-1,3-dihydrospiro[indene-2,4'-piperidine]-4-carbonitrile | 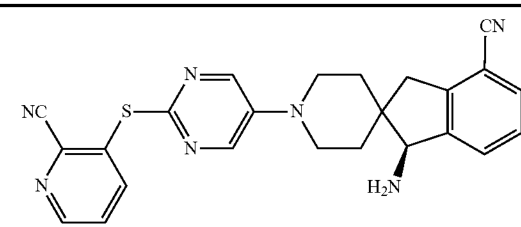 | 440 |
| 38 | 1-(5-((1S)-1-amino-6-(methylsulfinyl)-1,3-dihydrospiro[indene-2,4'-piperidin]-1'-yl)pyrazin-2-yl)thio)-2-chlorophenyl)ethan-1-one | 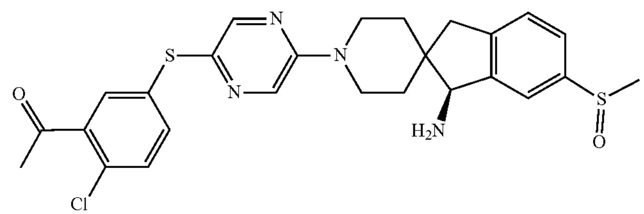 [SMILES: CC(=O)c1cc(Sc2cnc(N3CCC4(CC3)Cc3ccc(S(C)=O)cc3[C@H]4N)cn2)ccc1Cl] | 527 |
| 39 | (S)-1'-(5-(pyrimidin-2-ylthio)pyrazin-2-yl)-6-(trifluoromethyl)-1,3-dihydrospiro[indene-2,4'-piperidin]-1-amine | 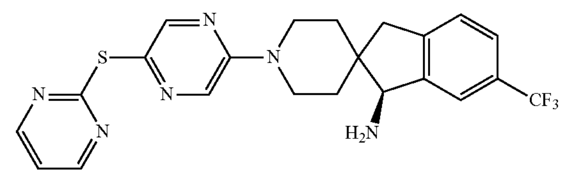 [SMILES: N[C@@H]1c2cc(C(F)(F)F)ccc2CC12CCN(c1cnc(Sc3ncccn3)cn1)CC2] | 459 |
| 40 | (S)-1'-(5-((3-chloro-2-methoxypyridin-4-yl)thio)pyrazin-2-yl)-6-(methylthio)-1,3-dihydrospiro[indene-2,4'-piperidin]-1-amine | 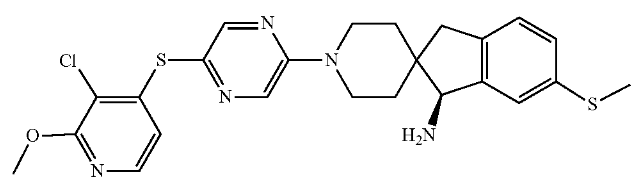 | 500 |
| 41 | (S)-6-bromo-5-fluoro-1'-(5-(quinolin-4-ylthio)pyrazin-2-yl)-1,3-dihydrospiro[indene-2,4'-piperidin]-1-amine | 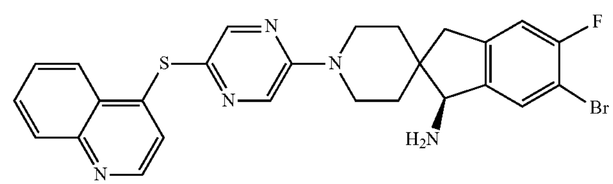 [SMILES: N[C@@H]1c2cc(Br)c(F)cc2CC12CCN(c1cnc(Sc3ccnc4ccccc34)cn1)CC2] | 536 |

-continued

| EX No | Chemical Name | Structure | MS:[M + 1]+ |
|---|---|---|---|
| 42 | (S)-6-(1-amino-5,6,7-trifluoro-1,3-dihydrospiro[indene-2,4'-piperidin]-1'-yl)-5-methyl-3-(5-methylthiophen-2-yl)-1,5-dihydro-4H-pyrazolo[3,4-d]pyrimidin-4-one | 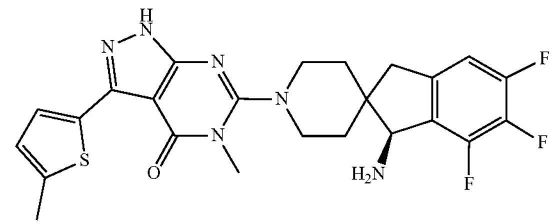 [SMILES: Cc1ccc(-c2n[nH]c3nc(N4CCC5(CC4)Cc4cc(F)c(F)c(F)c4[C@H]5N)n(C)c(=O)c23)s1] | 501 |
| 43 | (S)-6-(4-amino-4,6-Dihydrospiro[cyclopenta[b]thiophene-5,4'-piperidin]-1'-yl)-3-(3-(trifluoromethyl)pyridin-4-yl)-1,5-dihydro-4H-pyrazolo[3,4-d]pyrimidin-4-one | 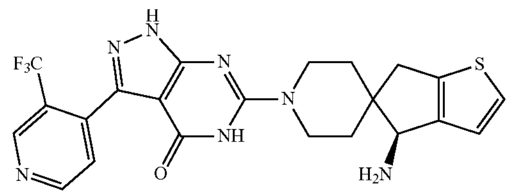 [SMILES: N[C@@H]1c2ccsc2CC12CCN(c1nc3[nH]nc(-c4ccncc4C(F)(F)F)c3c(=O)[nH]1)CC2] | 488 |
| 44 | (S)-2-(1-amino-6-chloro-5-methoxy-1,3-dihydrospiro[indene-2,4'-piperidin]-1'-yl)-5-(3,5-dichloropyridin-4-yl)-3-methyl-3,7-dihydro-4H-pyrrolo[2,3-d]pyrimidin-4-one | 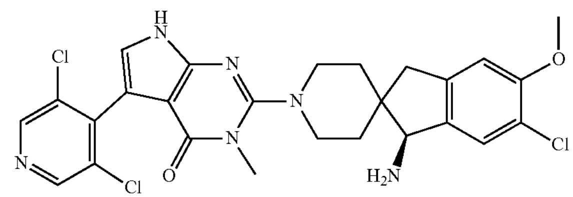 [SMILES: COc1cc2c(cc1Cl)[C@@H](N)C1(CCN(c3nc4[nH]cc(-c5c(Cl)cncc5Cl)c4c(=O)n3C)CC1)C2] | 559 |
| 45 | (S)-1'-(7-(5-chloropyridin-2-yl)-5H-pyrrolo[2,3-b]pyrazin-3-yl)-1,3-dihydrospiro[cyclopenta[a]naphthalene-2,4'-piperidin]-3-amine | 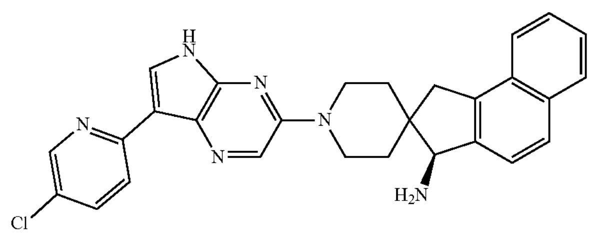 [SMILES: N[C@@H]1c2ccc3ccccc3c2CC12CCN(c1cnc3c(-c4ccc(Cl)cn4)c[nH]c3n1)CC2] | 481 |
| 46 | (S)-1'-(7-(3-chloropyridin-2-yl)-5H-pyrrolo[2,3-b]pyrazin-3-yl)-1H,3H-spiro[phenalene-2,4'-piperidin]-1-AMINE | 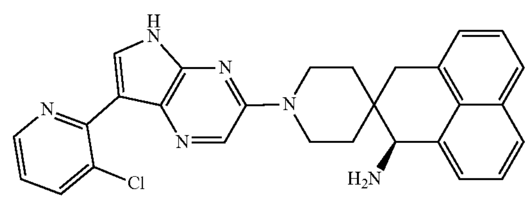 [SMILES: N[C@@H]1c2cccc3cccc(c23)CC12CCN(c1cnc3c(-c4ncccc4Cl)c[nH]c3n1)CC2] | 481 |

-continued

| EX No | Chemical Name | Structure | MS:[M + 1]⁺ |
|---|---|---|---|
| 47 | (R)-1'-(3-(2-methylpyridin-3-yl)-1H-pyrazolo[3,4-b]pyrazin-6-yl)-3,4-dihydro-1H-spiro[naphthalene-2,4'-piperidin]-3-amine | 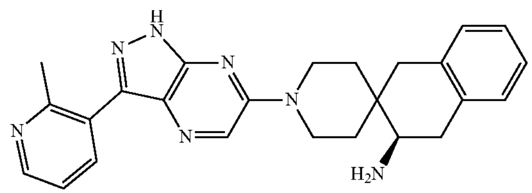 [SMILES: Cc1ncccc1-c1n[nH]c2nc(N3CCC4(CC3)Cc3ccccc3C[C@H]4N)cnc12] | 426 |
| 48 | (S)-6-amino-2-(1-amino-7-bromo-1,3-dihydrospiro[indene-2,4'-piperidin]-1'-yl)-3-methyl-5-phenylpyrimidin-4(3H)-one | 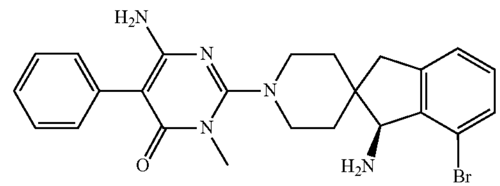 [SMILES: Cn1c(N2CCC3(CC2)Cc2cccc(Br)c2[C@H]3N)nc(N)c(-c2ccccc2)c1=O] | 480 |
| 49 | (S)-1-amino-1'-(4-amino-6-oxo-5-(pyridazin-3-ylthio)-1,6-dihydropyrimidin-2-yl)-1,3-dihydrospiro[indene-2,4'-piperidine]-7-carbonitrile | 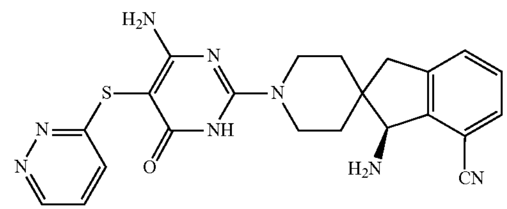 [SMILES: N#Cc1cccc2c1[C@@H](N)C1(CCN(c3nc(N)c(Sc4cccnn4)c(=O)[nH]3)CC1)C2] | 447 |
| 50 | (S)-1-amino-1'-(1-methyl-6-oxo-5-(pyrazin-2-yl)-1,6-dihydropyrimidin-2-yl)-1,3-dihydrospiro[indene-2,4'-piperidine]-7-carbonitrile | 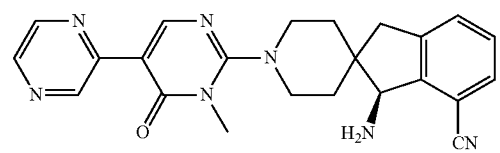 [SMILES: Cn1c(N2CCC3(CC2)Cc2cccc(C#N)c2[C@H]3N)ncc(-c2cnccn2)c1=O] | 414 |
| 51 | (S)-2-(1-amino-6-chloro-5-methoxy-1,3-dihydrospiro[indene-2,4'-piperidin]-1'-yl)-5-((4-isopropylphenyl)thio)pyrimidin-4(3H)-one | 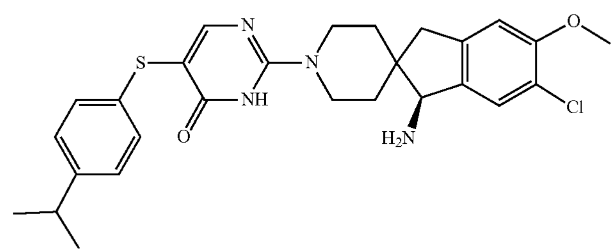 [SMILES: COc1cc2c(cc1Cl)[C@@H](N)C1(CCN(c3ncc(Sc4ccc(C(C)C)cc4)c(=O)[nH]3)CC1)C2] | 511 |

-continued

| EX No | Chemical Name | Structure | MS:[M + 1]+ |
|---|---|---|---|
| 52 | (S)-4-amino-6-(1-amino-6-bromo-5-fluoro-1,3-dihydrospiro[indene-2,4'-piperidin]-1'-yl)-3-(2-chloro-3-methylphenyl)-1-methylpyridin-2(1H)-one | 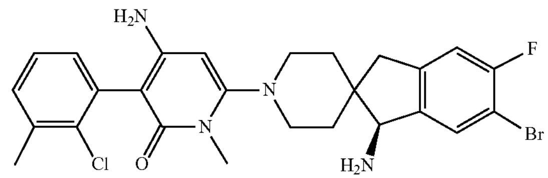 | 545 |
| 53 | (S)-6-(4-acetyl-1-amino-1,3-dihydrospiro[indene-2,4'-piperidin]-1'-yl)-4-amino-3-(4-(trifluoromethyl)phenyl)pyridin-2(1H)-one | 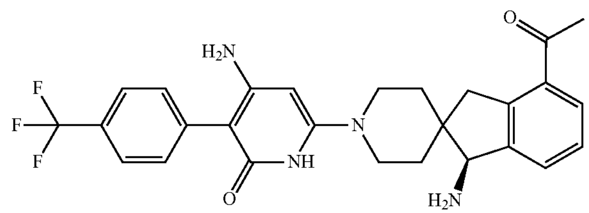 | 497 |
| 54 | (S)-6-(1-amino-4-methoxy-1,3-dihydrospiro[indene-2,4'-piperidin]-1'-yl)-1'-methyl-2'-oxo-1',2'-dihydro-[3,3'-bipyridine]-2-carboxamide | 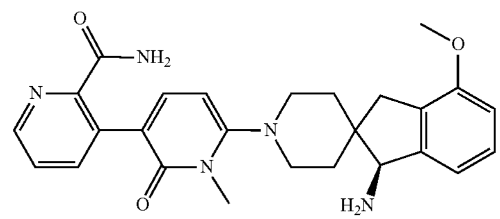 | 460 |
| 55 | (S)-6'-(1-amino-4-hydroxy-1,3-dihydrospiro[indene-2,4'-piperidin]-1'-yl)-2'-oxo-1',2'-dihydro-[3,3'-bipyridine]-2-carbonitrile | 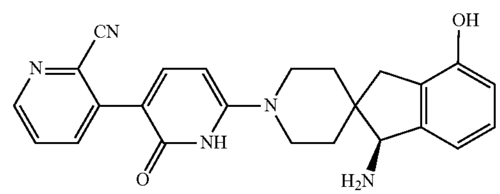 | 414 |
| 56 | (S)-1'-(3-bromo-5-(1H-indol-6-yl)-6-methylpyrazin-2-yl)-4,6-dihydrospiro[cyclopenta[d]thiazole-5,4'-piperidin]-4-amine | 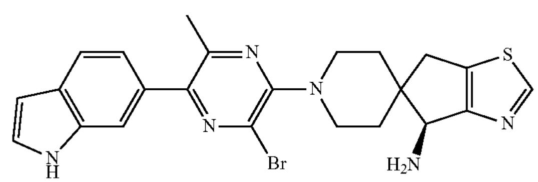 [SMILES: Cc1nc(N2CCC3(CC2)Cc2scnc2[C@H]3N)c(Br)nc1-c1ccc2cc[nH]c2c1] | 495 |

-continued

| EX No | Chemical Name | Structure | MS:[M + 1]+ |
|---|---|---|---|
| 57 | (S)-3-(4-amino-4,6-dihydrospiro[cyclopenta[d]thiazole-5,4'-piperidin]-1'-yl)-5-methyl-6-(2-oxoindolin-7-yl)pyrazine-2-carbonitrile | 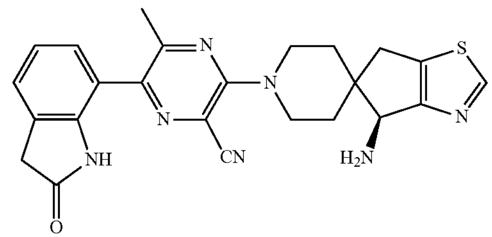 [SMILES: Cc1nc(N2CCC3(CC2)Cc2scnc2[C@H]3N)c(C#N)nc1-c1cccc2c1NC(=O)C2] | 458 |
| 58 | (S)-1'-(5-amino-6-((2-amino-3-chloropyridin-4-yl)thio)-1,2,4-triazin-3-yl)-5,7-dihydrospiro[cyclopenta[b]pyridine-6,4'-piperidin]-5-amine | 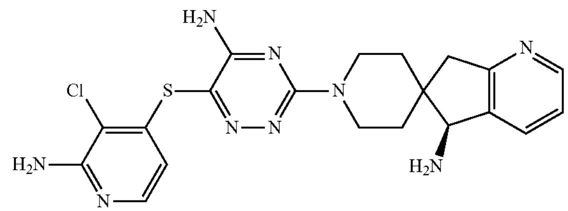 [SMILES: Nc1nc(N2CCC3(CC2)Cc2ncccc2[C@H]3N)nnc1Sc1ccnc(N)c1Cl] | 456 |
| 59 | (S)-1'-(5-amino-6-((2-amino-3-chloropyridin-4-yl)thiopyridin-3-yl)-6-chloro-1,3-dihydrospiro[indene-2,4'-piperidin]-1-amine | 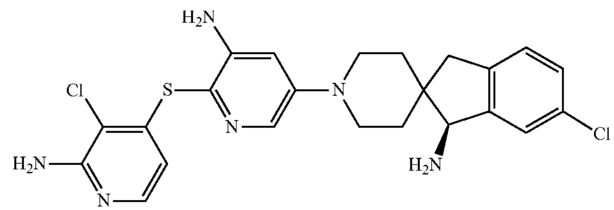 [SMILES: Nc1cc(N2CCC3(CC2)Cc2ccc(Cl)cc2[C@H]3N)cnc1Sc1ccnc(N)c1Cl] | 487 |
| 60 | (S)-1'-(4-amino-5-((2-amino-3-chloropyridin-4-yl)thiopyridin-2-yl)-5,7-dihydrospiro[cyclopenta[b]pyridine-6,4'-piperidin]-5-amine | 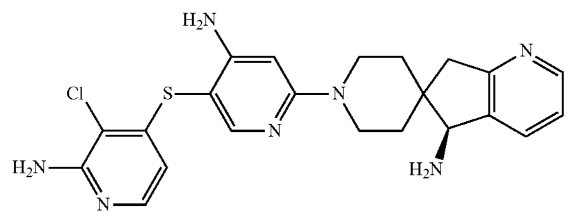 [SMILES: Nc1cc(N2CCC3(CC2)Cc2ncccc2[C@H]3N)ncc1Sc1ccnc(N)c1Cl] | 454 |
| 61 | (S)-1'-(5-((2,3-dichlorophenyl)thio)thiazol-2-yl)-5,7-dihydrospiro[cyclopenta[b]pyridine-6,4'-piperidin]-7-amine | 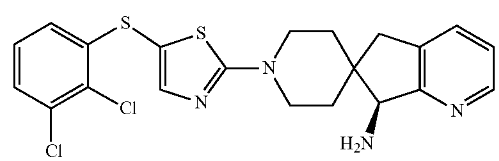 [SMILES: N[C@@H]1c2ncccc2CC12CCN(c1ncc(Sc3cccc(Cl)c3Cl)s1)CC2] | 463 |

| EX No | Chemical Name | Structure | MS:[M + 1]+ |
|---|---|---|---|
| 62 | (R)-1'-(4-((3-chloropyridin-4-yl)thio)thiazol-2-yl)spiro[indoline-2,4'-piperidin]-3-amine | 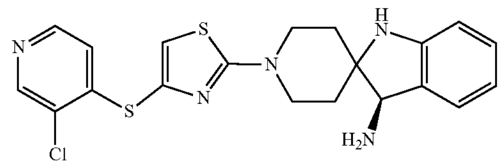 [SMILES: N[C@@H]1c2ccccc2NC12CCN(c1nc(Sc3ccncc3Cl)cs1)CC2] | 430 |
| 63 | (R)-1'-(2-(7-chloro-1H-indol-1-yl)thiazol-4-yl)-2,3-dihydrospiro[indene-1,4'-piperidin]-2-amine | 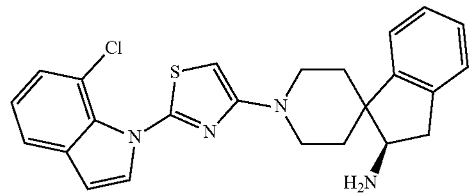 [SMILES: N[C@@H]1Cc2ccccc2C12CCN(c1csc(-n3ccc4cccc(Cl)c43)n1)CC2] | 435 |
| 64 | (R)-1'-(2-((2-(trifluoromethyl)phenyl)thio)thiazol-5-yl)-3H-spiro[benzofuran-2,4'-piperidin]-3-amine | 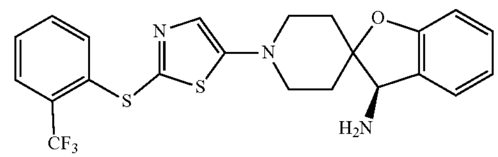 [SMILES: N[C@@H]1c2ccccc2OC12CCN(c1cnc(Sc3ccccc3C(F)(F)F)s1)CC2] | 464 |
| 65 | (S)-(5-(1-amino-1,3-dihydrospiro[indene-2,4'-piperidin]-1'-yl)pyrazin-2-yl)(2,3-dichlorophenyl)methanone | 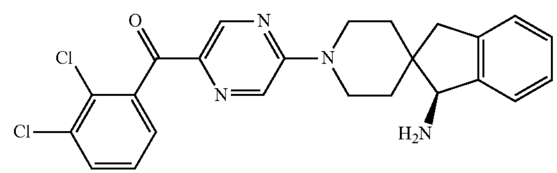 [SMILES: N[C@@H]1c2ccccc2CC12CCN(c1cnc(C(=O)c3cccc(Cl)c3Cl)cn1)CC2] | 453 |
| 66 | (S)-2-(1-amino-6-fluoro-1,3-dihydrospiro[indene-2,4'-piperidin]-1'-yl)-5-(indolin-1-yl)-3-methyl-3,7-dihydro-4H-pyrrolo[2,3-d]pyrimidin-4-one | 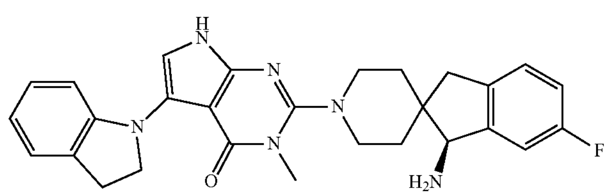 [SMILES: Cn1c(N2CCC3(CC2)Cc2ccc(F)cc2[C@H]3N)nc2[nH]cc(N3CCc4ccccc43)c2c1=O] | 485 |

-continued

| EX No | Chemical Name | Structure | MS:[M + 1]+ |
|---|---|---|---|
| 67 | (S)-1'-(5-((1,2,3,4-tetrahydroquinolin-8-yl)thio)pyrazin-2-yl)-1,3-dihydrospiro[cyclopenta[b]naphthalene-2,4'-piperidin]-1-amine | 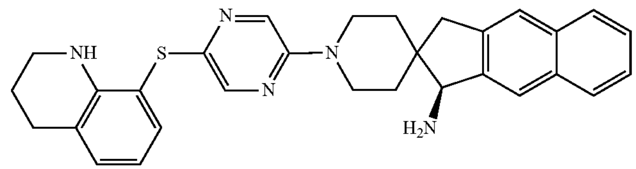 [SMILES: N[C@@H]1c2cc3ccccc3cc2CC12CCN(c1cnc(Sc3cccc4c3NCCC4)cn1)CC2] | 494 |
| 68 | (S)-1'-(5-((2-amino-3-chloropyridin-4-yl)thio)pyrazin-2-yl)-1,3-dihydrospiro[cyclopenta[a]naphthalene-2,4'-piperidin]-1-amine | 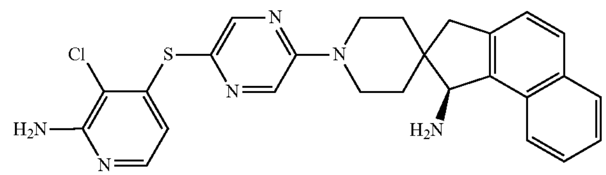 [SMILES: Nc1nccc(Sc2cnc(N3CCC4(CC3)Cc3ccc5ccccc5c3[C@H]4N)cn2)c1Cl] | 489 |
| 69 | 1'-(5-((3-amino-2-chlorophenyl)thio)-6-methylpyrazin-2-yl)-1-methyl-1,3-dihydrospiro[indene-2,4'-piperidin]-1-amine | 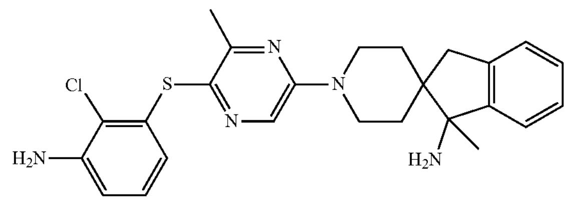 [SMILES: Cc1nc(N2CCC3(CC2)Cc2ccccc2C3(C)N)cnc1Sc1cccc(N)c1Cl] | 466 |
| 70 | (S)-1'-(5-((2-amino-3-chloropyridin-4-yl)thio)pyrazin-2-yl)-N-methyl-1,3-dihydrospiro[indene-2,4'-piperidin]-1-amine | 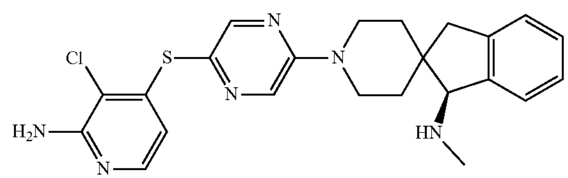 [SMILES: CN[C@@H]1c2ccccc2CC12CCN(c1cnc(Sc3ccnc(N)c3Cl)cn1)CC2] | 453 |
| 71 | (R)-1'-(7-((2-amino-3-chloropyridin-4-yl)thio)-1H-indol-4-yl)-3H-spiro[benzofuran-2,4'-piperidin]-3-amine | 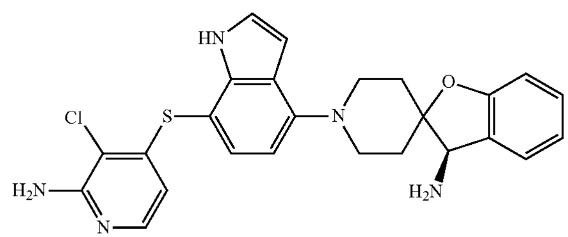 [SMILES: Nc1nccc(Sc2ccc(N3CCC4(CC3)Oc3ccccc3[C@H]4N)c3cc[nH]c23)c1Cl] | 478 |

-continued

| EX No | Chemical Name | Structure | MS:[M + 1]+ |
|---|---|---|---|
| 72 | (S)-1'-(7-((2-amino-3-chloropyridin-4-yl)thio)isoquinolin-3-yl)-5,6-dibromo-1,3-dihydrospiro[indene-2,4'-piperidin]-1-amine | 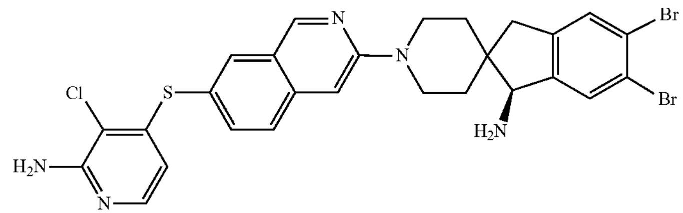 [SMILES: Nc1nccc(Sc2ccc3cc(N4CCC5(CC4)Cc4cc(Br)c(Br)cc4[C@H]5N)ncc3c2)c1Cl] | 644 |
| 73 | (S)-1'-(4-((2-amino-3-chloropyridin-4-yl)thio)isoquinolin-1-yl)-1,3-dihydrospiro[indene-2,4'-piperidin]-1-amine | 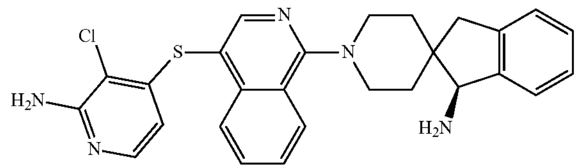 [SMILES: Nc1nccc(Sc2cnc(N3CCC4(CC3)Cc3ccccc3[C@H]4N)c3ccccc23)c1Cl] | 488 |
| 74 | (S)-4-((5-(5-acetyl-1-amino-1,3-dihydrospiro[indene-2,4'-piperidin]-1'-yl)-3-aminopyrazin-2-yl)thio)-3-chloro-1-methylpyridin-2(1H)-one | 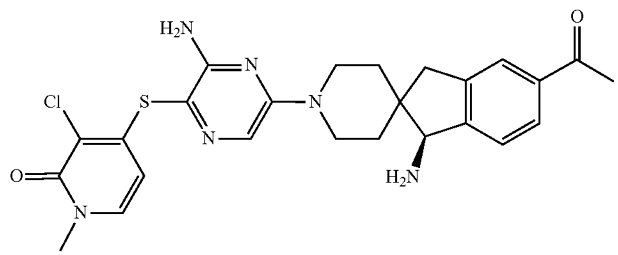 [SMILES: CC(=O)c1ccc2c(c1)CC1(CCN(c3cnc(Sc4ccn(C)c(=O)c4Cl)c(N)n3)CC1)[C@@H]2N] | 511 |
| 75 | (S)-5-(1-amino-6-bromo-1,3-dihydrospiro[indene-2,4'-piperidin]-1'-yl)-2-((2,3-dichlorophenyl)thio)-6-(hydroxymethyl)pyridin-3-ol | 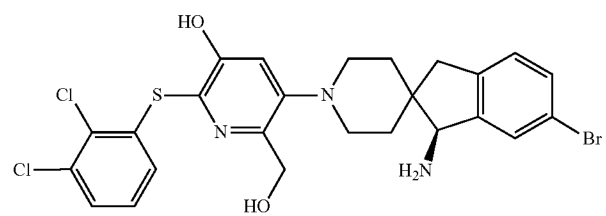 [SMILES: N[C@@H]1c2cc(Br)ccc2CC12CCN(c1cc(O)c(Sc3cccc(Cl)c3Cl)nc1CO)CC2] | 480 |

-continued

| EX No | Chemical Name | Structure | MS:[M + 1]+ |
|---|---|---|---|
| 76 | (S)-6-bromo-1'-(5-(2,3-dichlorophenyl)-6-methylimidazo[1,5-a]pyrazin-8-yl)-1,3-dihydrospiro[indene-2,4'-piperidin]-1-amine | 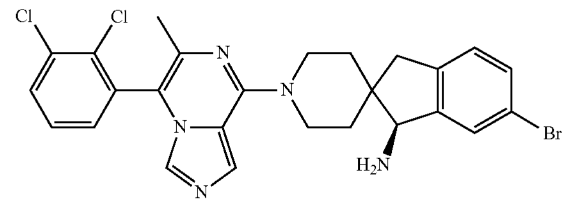 [SMILES: Cc1nc(N2CCC3(CC2)Cc2ccc(Br)cc2[C@H]3N)c2cncn2c1-c1cccc(Cl)c1Cl] | 556 |
| 77 | (S)-1'-(7-((2-amino-3-chloropyridin-4-yl)thio)benzo[1,2,5]thiadiazolo[3,4-c]pyridin-4-yl)-6-bromo-1,3-dihydrospiro[indene-2,4'-piperidin]-1-amine | 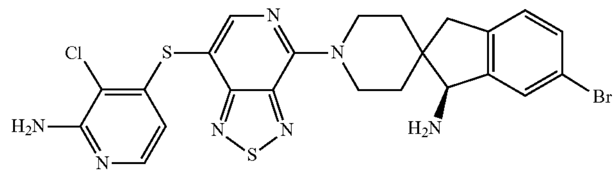 [SMILES: Nc1nccc(Sc2cnc(N3CCC4(CC3)Cc3ccc(Br)cc3[C@H]4N)c3nsnc23)c1Cl] | 574 |
| 78 | (S)-1'-(8-((2-amino-3-chloropyridin-4-yl)thio)pyrido[4,3-d]pyrimidin-5-yl)-6-bromo-1,3-dihydrospiro[indene-2,4'-piperidin]-1-amine | 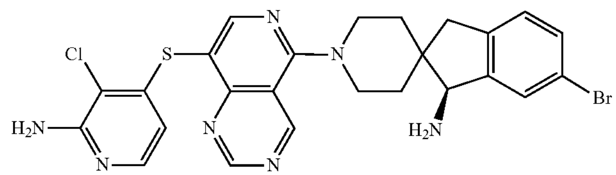 [SMILES: Nc1nccc(Sc2cnc(N3CCC4(CC3)Cc3ccc(Br)cc3[C@H]4N)c3cncnc23)c1Cl] | 568 |
| 79 | (S)-3-(5-(1-amino-6-methoxy-1,3-dihydrospiro[indene-2,4'-piperidin]-1'-yl)pyridin-2-yl)-4,5-dichlorophenol | 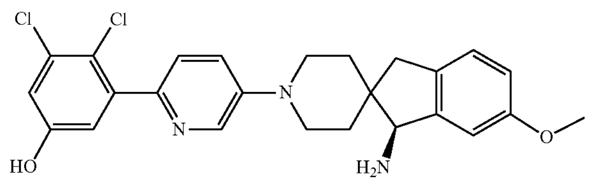 [SMILES: COc1ccc2c(c1)[C@@H](N)C1(CCN(c3ccc(-c4cc(O)cc(Cl)c4Cl)nc3)CC1)C2] | 470 |
| 80 | (S)-1-amino-1'-(5-(5-methylthiophen-2-yl)pyrazin-2-yl)-1,3-dihydrospiro[indene-2,4'-piperidin]-6-ol | 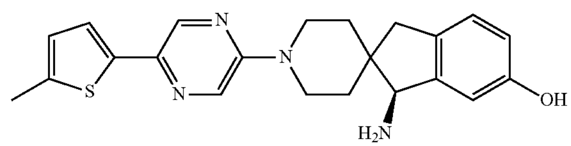 | 393 |

-continued

| EX No | Chemical Name | Structure | MS:[M + 1]+ |
|---|---|---|---|
| 81 | (S)-1'-(5-(1H-indol-7-yl)pyrazin-2-yl)-5-ethyl-1,3-dihydrospiro[indene-2,4'-piperidin]-1-amine | 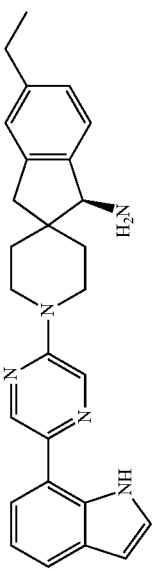 | 424 |
| 82 | (S)-1'-(5-(cyclohex-1-en-1-yl)pyrazin-2-yl)-5-isopropyl-1,3-dihydrospiro[indene-2,4'-piperidin]-1-amine | 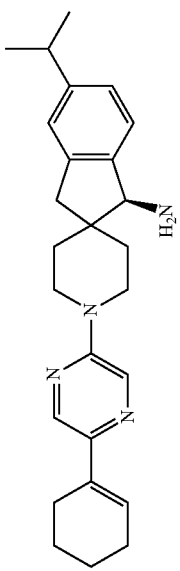 | 403 |
| 83 | (S)-N-(1-amino-1'-(5-(2-(trifluoromethyl)phenyl)pyrimidin-2-yl)-1,3-dihydrospiro[indene-2,4'-piperidin]-6-yl)methanesulfonamide | 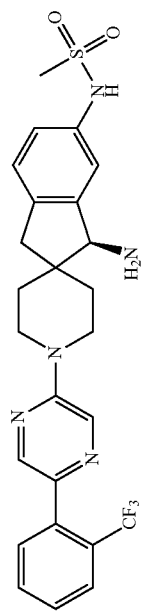 | 518 |
| 84 | (S)-1'-(5-((4-(trifluoromethyl)pyrimidin-5-yl)thio)pyrazin-2-yl)-5,7-dihydrospiro[cyclopenta[c]pyridine-6,4'-piperidin]-7-amine | 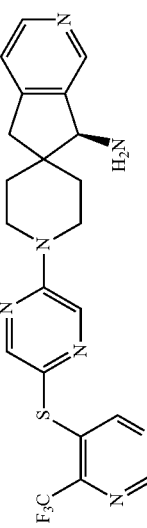 | 460 |
| 85 | (S)-1'-(5-((2-chloropyridin-3-yl)thio)pyrazin-2-yl)-5,7-dihydrospiro[cyclopenta[c]pyridine-6,4'-piperidin]-5-amine | 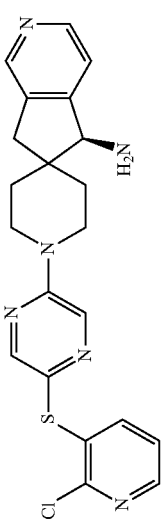 | 425 |

-continued

| EX No | Chemical Name | Structure | MS:[M + 1]+ |
|---|---|---|---|
| 86 | (S)-4-((5-(5-amino-5,7-dihydrospiro[cyclopenta[d]pyrimidine-6,4'-piperidin]-1'-yl)pyrazin-2-yl)thio)-3-chlorobenzoic acid | 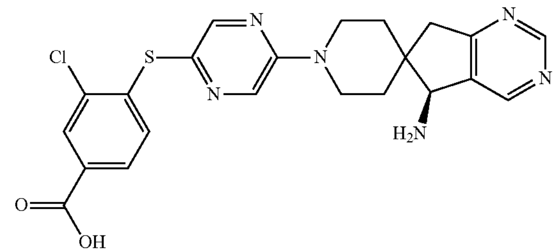 [SMILES: N[C@@H]1c2cncnc2CC12CCN(c1cnc(Sc3ccc(C(=O)O)cc3Cl)cn1)CC2] | 469 |
| 87 | (S)-1'-(5-((3-(trifluoromethyl)pyrazin-2-yl)thio)pyrazin-2-yl)-5,7-dihydrospiro[cyclopenta[b]pyridine-6,4'-piperidin]-7-amine | 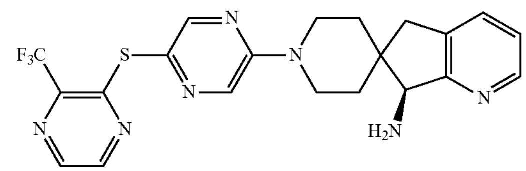 [SMILES: N[C@@H]1c2ncccc2CC12CCN(c1cnc(Sc3nccnc3C(F)(F)F)cn1)CC2] | 460 |
| 88 | (S)-1'-(5-((3-chloropyridazin-4-yl)thio)pyrazin-2-yl)-5,7-dihydrospiro[cyclopenta[d]pyrimidine-6,4'-piperidin]-7-amine | 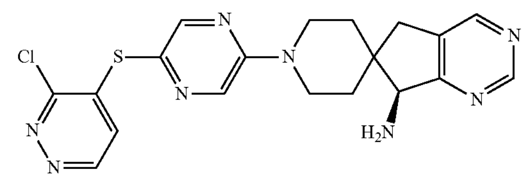 [SMILES: N[C@@H]1c2ncncc2CC12CCN(c1cnc(Sc3ccnnc3Cl)cn1)CC2] | 427 |
| 89 | (S)-4-((5-(5-amino-5,7-dihydrospiro[cyclopenta[b]pyrazine-6,4'-piperidin]-1'-yl)pyrazin-2-yl)thio)-3-chlorobenzamide | 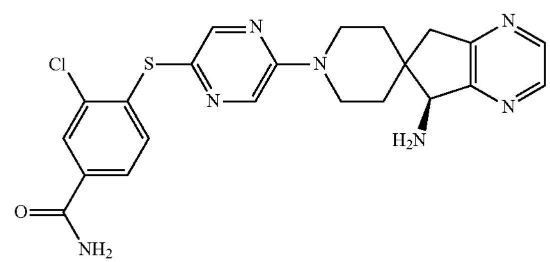 [SMILES: NC(=O)c1ccc(Sc2cnc(N3CCC4(CC3)Cc3nccnc3[C@H]4N)cn2)c(Cl)c1] | 468 |
| 90 | (S)-(1-amino-1'-(5-((3-chloro-2-(methylamino)pyridin-4-yl)thio)pyrazin-2-yl)-1,3-dihydrospiro[indene-2,4'-piperidin]-6-yl)dimethylphosphine oxide | 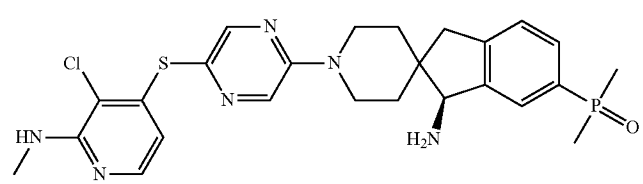 [SMILES: CNc1nccc(Sc2cnc(N3CCC4(CC3)Cc3ccc(P(C)(C)=O)cc3[C@H]4N)cn2)c1Cl] | 529 |

-continued

| EX No | Chemical Name | Structure | MS:[M + 1]+ |
|---|---|---|---|
| 91 | (S)-1-amino-1'-(6-amino-5-((3-chloro-2-(dimethylamino)pyridin-4-yl)thio)pyrazin-2-yl)-1,3-dihydrospiro[indene-2,4'-piperidine]-5-carboxylic acid | 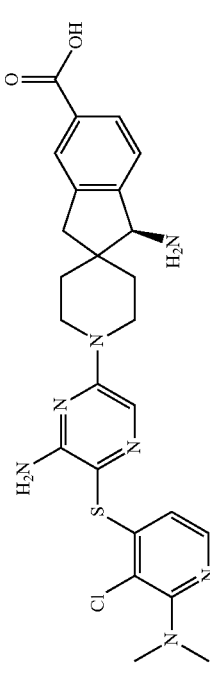 | 526 |
| 92 | ethyl (S)-1-amino-1'-(5-((3-chloro-2-(methylamino)pyridin-4-yl)thio)pyrazin-2-yl)-1,3-dihydrospiro[indene-2,4'-piperidine]-5-carboxylate | 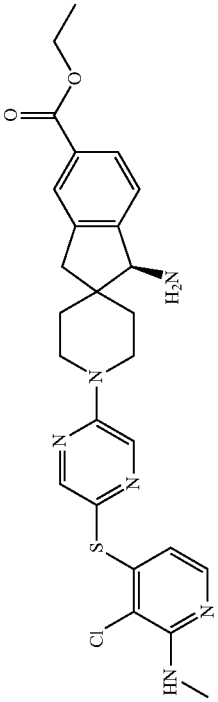 | 525 |
| 93 | (S)-1'-(5-((3-(morpholinomethyl)phenyl)thio)pyrazin-2-yl)-6-(trifluoromethyl)-1,3-dihydrospiro[indene-2,4'-piperidin]-1-amine | 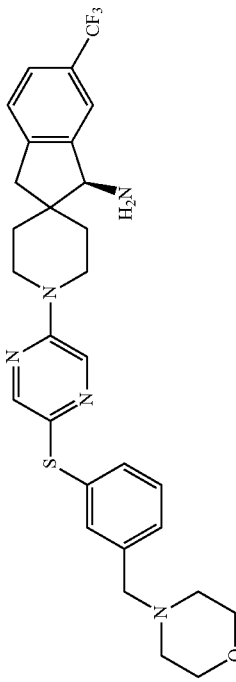 | 556 |
| 94 | (S)-6-bromo-5-fluoro-1'-(5-((3-(pentafluoro-16-sulfanyl)phenyl)thio)pyrazin-2-yl)-1,3-dihydrospiro[indene-2,4'-piperidin]-1-amine | 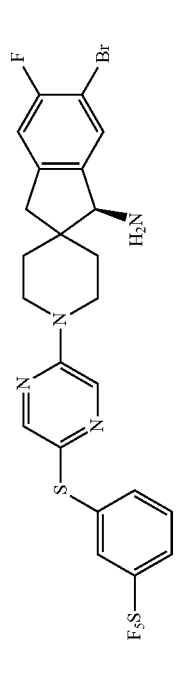 | 611 |

-continued

| EX No | Chemical Name | Structure | MS:[M + 1]+ |
|---|---|---|---|
| 95 | (S)-N-(3-((5-(1-amino-6-(methylthio)-1,3-dihydrospiro[indene-2,4'-piperidin]-1'-yl)pyrazin-2-yl)thio)phenyl)cyclopropanecarboxamide | 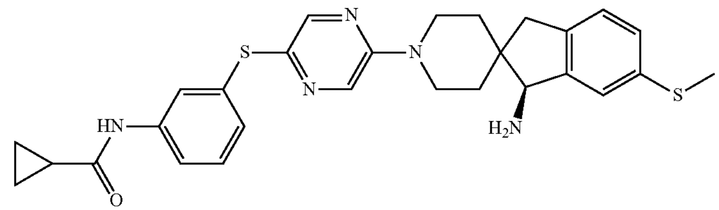 [SMILES: CSc1ccc2c(c1)[C@@H](N)C1(CCN(c3cnc(Sc4cccc(NC(=O)C5CC5)c4)cn3)CC1)C2] | 518 |
| 96 | (S)-1'-(5-((3-chloro-2-(isopropylamino)pyridin-4-yl)thio)pyrazin-2-yl)-6-(methylsulfonyl)-1,3-dihydrospiro[indene-2,4'-piperidin]-1-amine | 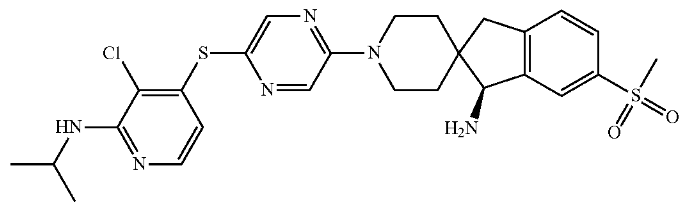 [SMILES: CC(C)Nc1nccc(Sc2cnc(N3CCC4(CC3)Cc3ccc(S(C)(=O)=O)cc3[C@H]4N)cn2)c1Cl] | 559 |
| 97 | (S)-6-(6-amino-1-bromo-4H,6H-spiro[cyclopenta[c]thiophene-5,4'-piperidin]-1'-yl)-3-(m-tolyl)-1,5-dihydro-4H-pyrazolo[3,4-d]pyrimidin-4-one | 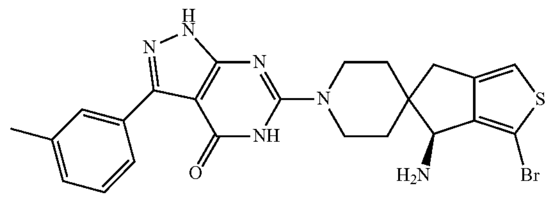 [SMILES: Cc1cccc(-c2n[nH]c3nc(N4CCC5(CC4)Cc4csc(Br)c4[C@H]5N)[nH]c(=O)c23)c1] | 511 |
| 98 | (S)-2-(1-amino-5,6,7-trifluoro-1,3-dihydrospiro[indene-2,4'-piperidin]-1'-yl)-5-(3-ethylphenyl)-3-methyl-3,7-dihydro-4H-pyrrolo[2,3-d]pyrimidin-4-one | 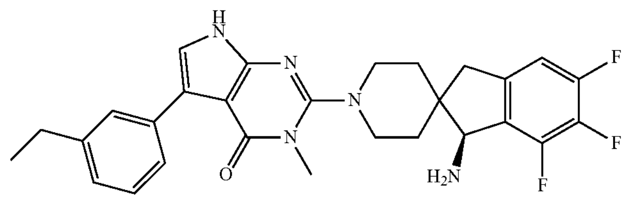 [SMILES: CCc1cccc(-c2c[nH]c3nc(N4CCC5(CC4)Cc4cc(F)c(F)c(F)c4[C@H]5N)n(C)c(=O)c23)c1] | 508 |
| 99 | (R)-1'-(3-(3-(tert-butyl)phenyl)-1H-pyrazolo[3,4-b]pyrazin-6-yl)-3,4-dihydro-1H-spiro[naphthalene-2,4'-piperidin]-3-amine | 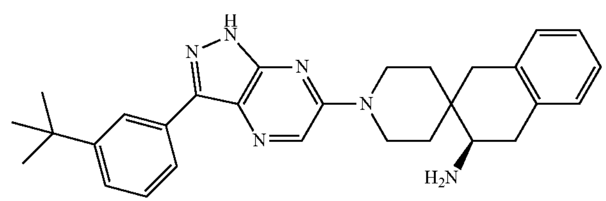 [SMILES: CC(C)(C)c1cccc(-c2n[nH]c3nc(N4CCC5(CC4)Cc4ccccc4C[C@H]5N)cnc23)c1] | 467 |

-continued

| EX No | Chemical Name | Structure | MS:[M + 1]+ |
|---|---|---|---|
| 100 | (S)-2-(3-amino-1,3-dihydrospiro[cyclopenta[a]naphthalene-2,4'-piperidin]-1'-yl)-5-(3-isopropylphenyl)-3,7-dihydro-4H-pyrrolo[2,3-d]pyrimidin-4-one | 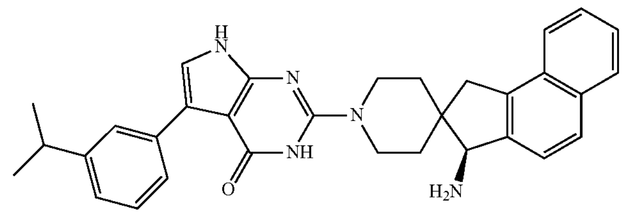 [SMILES: CC(C)c1cccc(-c2c[nH]c3nc(N4CCC5(CC4)Cc4c(ccc6ccccc46)[C@H]5N)[nH]c(=O)c23)c1] | 504 |
| 101 | (S)-1-amino-1'-(3-(3-chloro-2-morpholinopyridin-4-yl)-4-oxo-4,5-dihydro-1H-pyrrolo[3,2-c]pyridin-6-yl)-5-fluoro-1,3-dihydrospiro[indene-2,4'-piperidine]-6-carbonitrile | 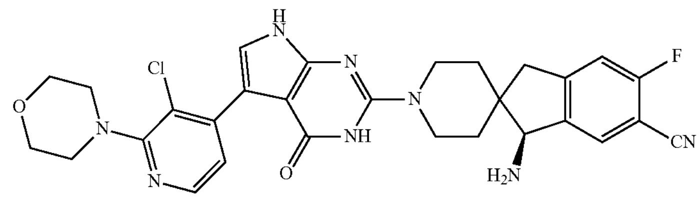 [SMILES: N#Cc1cc2c(cc1F)CC1(CCN(c3nc4[nH]cc(-c5ccnc(N6CCOCC6)c5Cl)c4c(=O)[nH]3)CC1)[C@@H]2N] | 574 |
| 102 | (S)-1'-(7-(3-chloro-2-(cyclobutylamino)pyridin-4-yl)-5H-pyrrolo[2,3-b]pyrazin-3-yl)-1,3-dihydrospiro[cyclopenta[a]naphthalene-2,4'-piperidin]-3-amine | 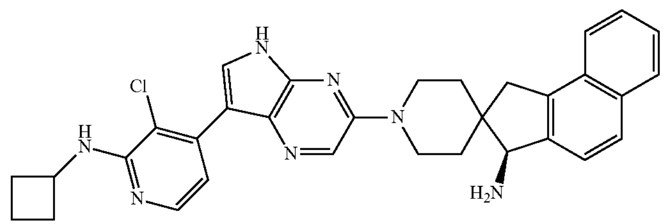 [SMILES: N[C@@H]1c2ccc3ccccc3c2CC12CCN(c1cnc3c(-c4ccnc(NC5CCC5)c4Cl)c[nH]c3n1)CC2] | 550 |
| 103 | (S)-1'-(3-(3-chloro-2-(cyclopropylamino)pyridin-4-yl)-1H-pyrazolo[3,4-b]pyrazin-6-yl)-N6-methyl-1,3-dihydrospiro[indene-2,4'-piperidine]-1,6-diamine | 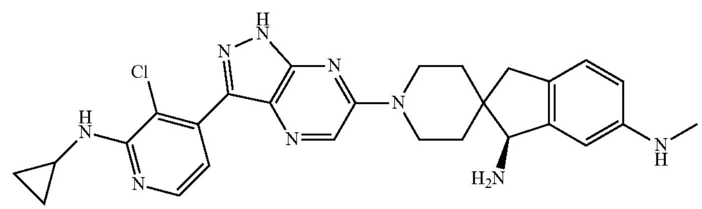 [SMILES: CNc1ccc2c(c1)[C@@H](N)C1(CCN(c3cnc4c(-c5ccnc(NC6CC6)c5Cl)n[nH]c4n3)CC1)C2] | 516 |
| 104 | (S)-5-amino-1'-(3-(3-chloro-2-(pyrrolidin-1-yl)pyridin-4-yl)-1H-pyrazolo[3,4-b]pyrazin-6-yl)-2-fluoro-5,7-dihydrospiro[cyclopenta[b]pyridine-6,4'-piperidine]-3-carboxamide | 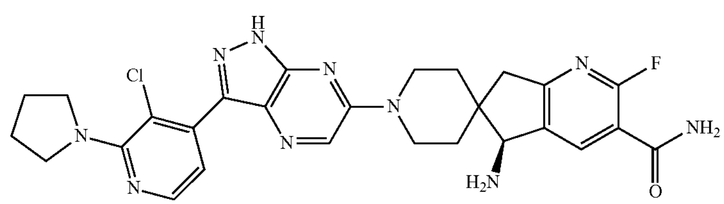 [SMILES: NC(=O)c1cc2c(nc1F)CC1(CCN(c3cnc4c(-c5ccnc(N6CCCC6)c5Cl)n[nH]c4n3)CC1)[C@@H]2N] | 563 |

-continued

| EX No | Chemical Name | Structure | MS:[M + 1]+ |
|---|---|---|---|
| 105 | 1-(4-(6-((S)-4-amino-2-chloro-4,6-dihydrospiro[cyclopenta[d]thiazole-5,4'-piperidin]-1'-yl)-1H-pyrazolo[3,4-b]pyrazin-3-yl)-3-chloropyridin-2-yl)pyrrolidin-3-ol | 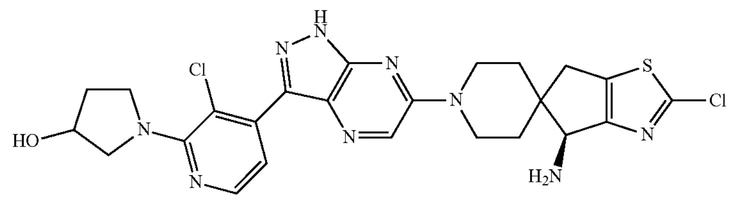 [SMILES: N[C@@H]1c2nc(Cl)sc2CC12CCN(c1cnc3c(-c4ccnc(N5CCC(O)C5)c4Cl)n[nH]c3n1)CC2] | 503 |
| 106 | (S)-1'-(3-(3-chloro-2-((cyclopropylmethyl)amino)pyridin-4-yl)-1H-pyrazolo[3,4-b]pyrazin-6-yl)-N6,N6-dimethyl-1,3-dihydrospiro[indene-2,4'-piperidine]-1,6-diamine | 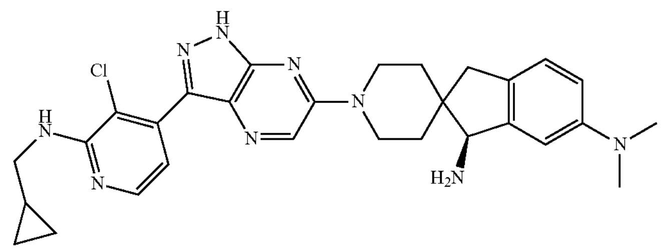 [SMILES: CN(C)c1ccc2c(c1)[C@@H](N)C1(CCN(c3cnc4c(-c5ccnc(NCC6CC6)c5Cl)n[nH]c4n3)CC1)C2] | 544 |
| 107 | (S)-1'-(3-(2-amino-6-chloropyridin-4-yl)-1H-pyrazolo[3,4-b]pyrazin-6-yl)-2-(tert-butyl)-4,6-dihydrospiro[cyclopenta[b]thiophene-5,4'-piperidin]-4-amine | 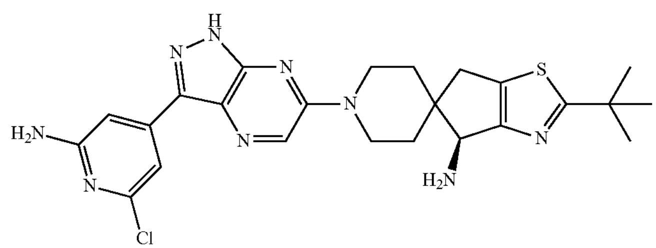 [SMILES: CC(C)(C)c1nc2c(s1)CC1(CCN(c3cnc4c(-c5cc(N)nc(Cl)c5)n[nH]c4n3)CC1)[C@@H]2N] | 509 |
| 108 | (S)-2-chloro-1'-(3-(1,3-dihydroisobenzofuran-5-yl)-1H-pyrazolo[3,4-b]pyrazin-6-yl)-4,6-dihydrospiro[cyclopenta[d]thiazole-5,4'-piperidin]-6-amine | 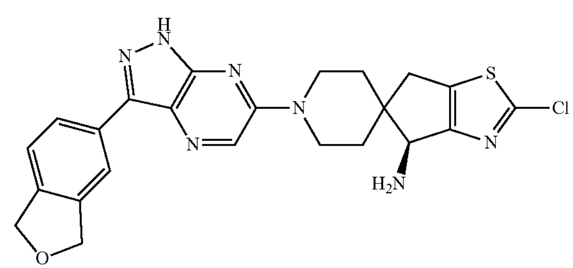 [SMILES: N[C@@H]1c2nc(Cl)sc2CC12CCN(c1cnc3c(-c4ccc5c(c4)COC5)n[nH]c3n1)CC2] | 480 |

-continued

| EX No | Chemical Name | Structure | MS:[M + 1]⁺ |
|---|---|---|---|
| 109 | (S)-3-chloro-1'-(3-((2-chlorophenyl)thio)-1H-pyrazolo[3,4-b]pyrazin-6-yl)-5,7-dihydrospiro[cyclopenta[b]pyridine-6,4'-piperidin]-5-amine | 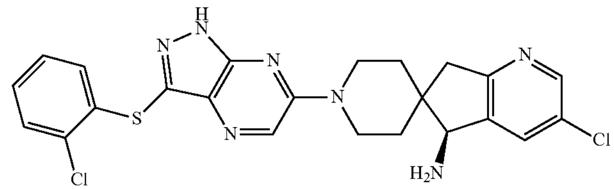 [SMILES: N[C@@H]1c2cc(Cl)cnc2CC12CCN(c1cnc3c(Sc4ccccc4Cl)n[nH]c3n1)CC2] | 498 |
| 110 | (S)-1'-(3-(3-chloro-2-(ethylamino)pyridin-4-yl)-1H-pyrazolo[3,4-b]pyrazin-6-yl)-4,6-dihydrospiro[cyclopenta[b]thiophene-5,4'-piperidin]-4-amine | 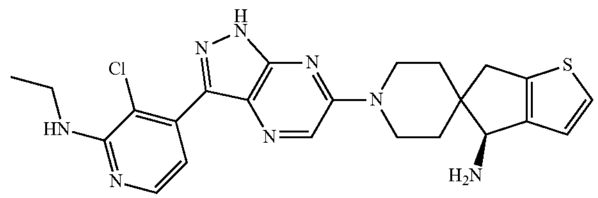 [SMILES: CCNc1nccc(-c2n[nH]c3nc(N4CCC5(CC4)Cc4sccc4[C@H]5N)cnc23)c1Cl] | 481 |
| 111 | (R)-1'-(7-(methyl(pyridin-4-yl)amino)-5H-pyrrolo[2,3-b]pyrazin-3-yl)-3H-spiro[furo[2,3-b]pyridine-2,4'-piperidin]-3-amine | 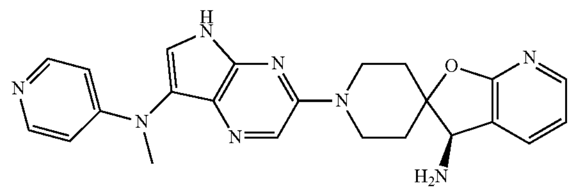 | 429 |
| 112 | (R)-1'-(3-((3-chloropyridin-4-yl)amino)-1H-pyrazolo[3,4-b]pyrazin-6-yl)-6,7-dihydrospiro[cyclopenta[b]pyridine-5,4'-piperidin]-6-amine | 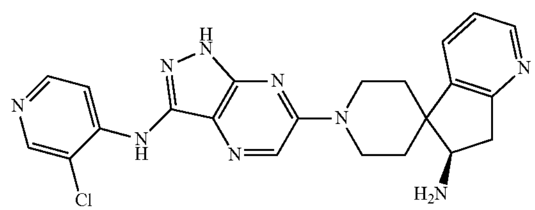 [SMILES: N[C@@H]1Cc2ncccc2C12CCN(c1cnc3c(Nc4ccncc4Cl)n[nH]c3n1)CC2] | 448 |
| 113 | (S)-2-methoxy-1'-(3-(1-phenylvinyl)-1H-pyrazolo[3,4-b]pyrazin-6-yl)-4,6-dihydrospiro[cyclopenta[d]thiazole-5,4'-piperidin]-4-amine | 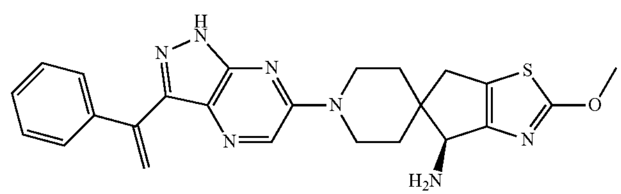 [SMILES: C=C(c1ccccc1)c1n[nH]c2nc(N3CCC4(CC3)Cc3sc(OC)nc3[C@H]4N)cnc12] | 460 |

-continued

| EX No | Chemical Name | Structure | MS:[M + 1]+ |
|---|---|---|---|
| 114 | (R)-1-(3-benzyl-1H-pyrazolo[3,4-b]pyrazin-6-yl)-1',3'-dihydrospiro[piperidine-4,2'-pyrrolo[2,3-b]pyridin]-3'-amine | 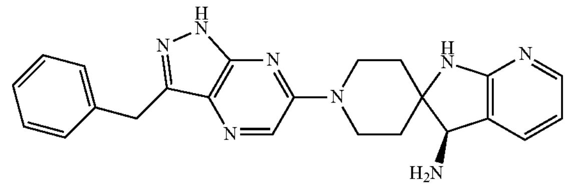 | 413 |
| 115 | (S)-(6-(6-amino-4,6-dihydrospiro[cyclopenta[d]thiazole-5,4'-piperidin]-1'-yl)-1H-pyrazolo[3,4-b]pyrazin-3-yl)(phenyl)methanone | 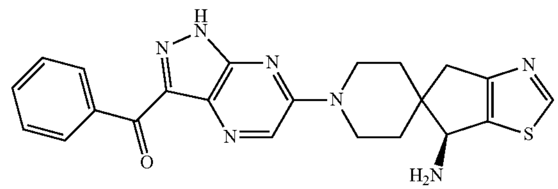 | 432 |
| 116 | (4S)-1'-(3-(1-phenylethyl)-1H-pyrazolo[3,4-b]pyrazin-6-yl)-4,6-dihydrospiro[cyclopenta[d]thiazole-5,4'-piperidin]-4-amine | 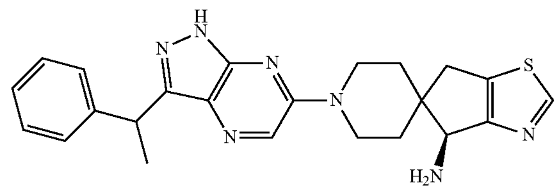 | 432 |
| 117 | 1-(6-((S)-5-amino-2-methoxy-5,7-dihydrospiro[cyclopenta[b]pyridine-6,4'-piperidin]-1'-yl)-1H-pyrazolo[3,4-b]pyrazin-3-yl)-1-phenylethan-1-ol | 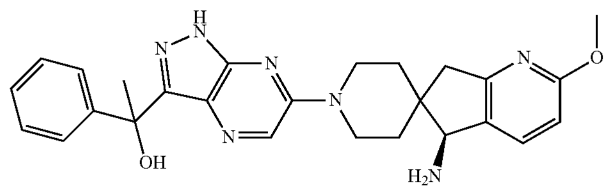 | 472 |
| 118 | (S)-1'-(3-((2,3-dichloropyridin-4-yl)oxy)-1H-pyrazolo[3,4-b]pyrazin-6-yl)-5,7-dihydrospiro[cyclopenta[b]pyridine-6,4'-piperidin]-5-amine | 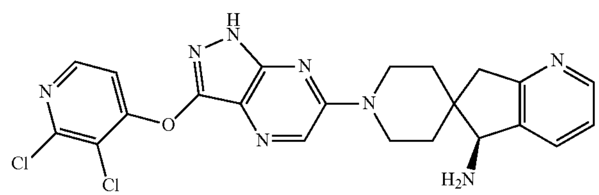 [SMILES: N[C@@H]1c2cccnc2CC12CCN(c1cnc3c(Oc4ccnc(Cl)c4Cl)n[nH]c3n1)CC2] | 483 |

| EX No | Chemical Name | Structure | MS:[M + 1]+ |
|---|---|---|---|
| 119 | (S)-1'-(3-(3,4-dihydro-1,5-naphthyridin-1(2H)-yl)-1H-pyrazolo[3,4-b]pyrazin-6-yl)-1,3-dihydrospiro[indene-2,4'-piperidin]-1-amine | 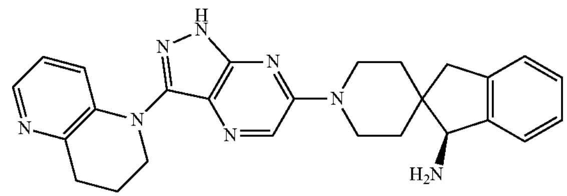 [SMILES: N[C@@H]1c2ccccc2CC12CCN(c1cnc3c(N4CCCc5ncccc54)n[nH]c3n1)CC2] | 453 |
| 120 | (S)-6-bromo-1'-(3-(5-(3,4-difluorophenyl))-3,4-dihydroquinolin-1(2H)-yl)-1H-pyrazolo[3,4-b]pyrazin-6-yl)-1,3-dihydrospiro[indene-2,4'-piperidin]-1-amine | 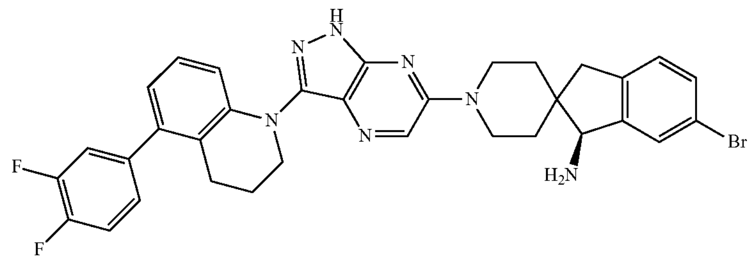 [SMILES: N[C@@H]1c2cc(Br)ccc2CC12CCN(c1cnc3c(N4CCCc5c(-c6ccc(F)c(F)c6)cccc54)n[nH]c3n1)CC2] | 642 |
| 121 | (S)-6-amino-2-(1-amino-6-bromo-1,3-dihydrospiro[indene-2,4'-piperidin]-1'-yl)-5-(4-cyclopropoxyphenyl)-3-methylpyrimidin-4(3H)-one | 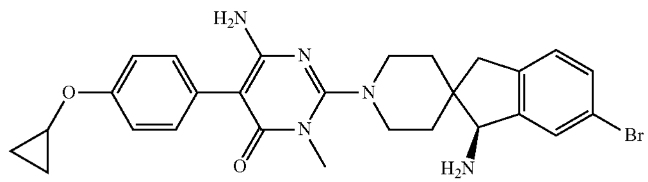 | 536 |
| 122 | (S)-N-(1-amino-1'-(4-amino-5-((4-(methylthio)phenyl)thio)-6-oxo-1,6-dihydropyrimidin-2-yl)-1,3-dihydrospiro[indene-2,4'-piperidin]-6-yl)acetamide | 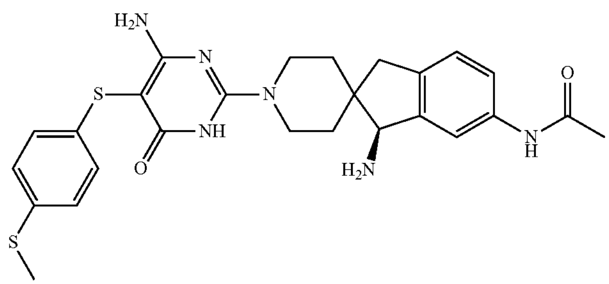 [SMILES: CSc1ccc(Sc2c(N)nc(N3CCC4(CC3)Cc3ccc(NC(C)=O)cc3[C@H]4N)[nH]c2=O)cc1] | 523 |

| EX No | Chemical Name | Structure | MS:[M + 1]+ |
|---|---|---|---|
| 123 | (S)-2-(1-amino-6-(methylamino)-1,3-dihydrospiro[indene-2,4'-piperidin]-1'-yl)-5-(4-(benzyloxy)phenyl)-3-methylpyrimidin-4(3H)-one | 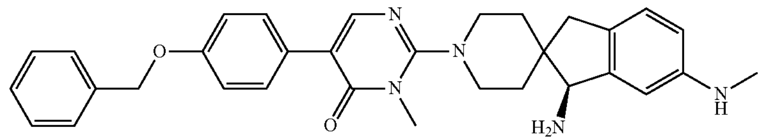 | 522 |
| 124 | (S)-2-(7-acetyl-1-amino-1,3-dihydrospiro[indene-2,4'-piperidin]-1'-yl)-5-(benzo[d][1,3]dioxol-4-ylthio)pyrimidin-4(3H)-one | 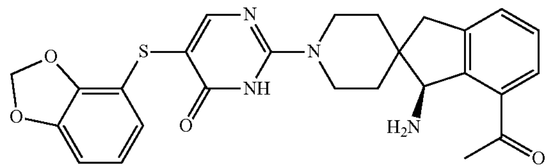 [SMILES: CC(=O)c1cccc2c1[C@@H](N)C1(CCN(c3ncc(Sc4cccc5c4OCO5)c(=O)[nH]3)CC1)C2] | 491 |
| 125 | 4-amino-6-((1S)-1-amino-7-(1-hydroxyethyl)-1,3-dihydrospiro[indene-2,4'-piperidin]-1'-yl)-3-(4-(difluoromethoxy)phenyl)-1-methylpyridin-2(1H)-one | 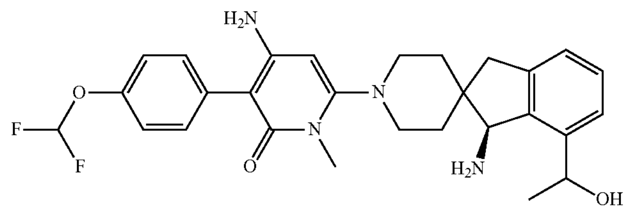 [SMILES: CC(O)c1cccc2c1[C@@H](N)C1(CCN(c3cc(N)c(-c4ccc(OC(F)F)cc4)c(=O)n3C)CC1)C2] | 511 |
| 126 | (S)-1-amino-1'-(4-amino-6-oxo-5-(4-phenoxyphenyl)-1,6-dihydropyridin-2-yl)-1,3-dihydrospiro[indene-2,4'-piperidine]-4-carbonitrile | 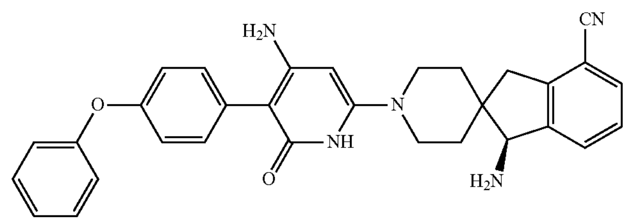 [SMILES: N#Cc1cccc2c1CC1(CCN(c3cc(N)c(-c4ccc(Oc5ccccc5)cc4)c(=O)[nH]3)CC1)[C@@H]2N] | 504 |
| 127 | (S)-6-(1-amino-4-hydroxy-1,3-dihydrospiro[indene-2,4'-piperidin]-1'-yl)-3-(4-cyclohexylphenyl)-1-methylpyridin-2(1H)-one | 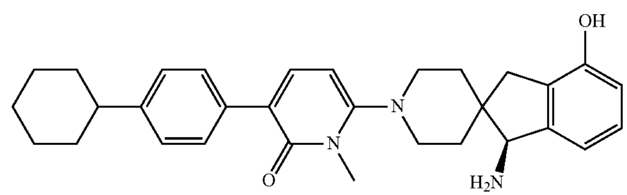 [SMILES: Cn1c(N2CCC3(CC2)Cc2c(O)cccc2[C@H]3N)ccc(-c2ccc(C3CCCCC3)cc2)c1=O] | 484 |

-continued

| EX No | Chemical Name | Structure | MS:[M + 1]⁺ |
|---|---|---|---|
| 128 | (S)-3-([1,1'-biphenyl]-4-yl)-6-(1-amino-4-methoxy-1,3-dihydrospiro[indene-2,4'-piperidin]-1'-yl)pyridin-2(1H)-one | 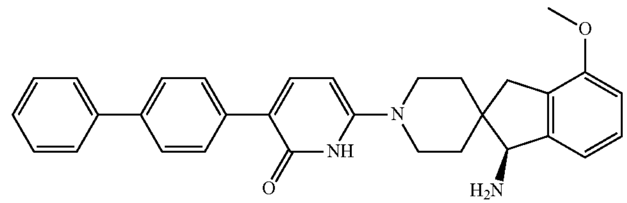 [SMILES: COc1cccc2c1CC1(CCN(c3ccc(-c4ccc(-c5ccccc5)cc4)c(=O)[nH]3)CC1)[C@@H]2N] | 478 |
| 129 | (S)-6-amino-2-(1-amino-6-(2-oxopiperidin-1-yl)-1,3-dihydrospiro[indene-2,4'-piperidin]-1'-yl)-3-methyl-5-(4-(trifluoromethoxy)phenyl)pyrimidin-4(3H)-one | 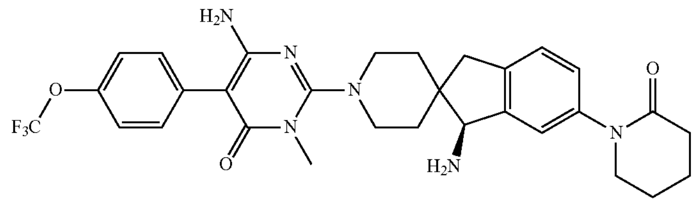 [SMILES: Cn1c(N2CCC3(CC2)Cc2ccc(N4CCCCC4=O)cc2[C@H]3N)nc(N)c(-c2ccc(OC(F)(F)F)cc2)c1=O] | 583 |
| 130 | (S)-1-(1-amino-1'-(4-amino-5-((4-cyanophenyl)thio)-1-methyl-6-oxo-1,6-dihydropyrimidin-2-yl)-1,3-dihydrospiro[indene-2,4'-piperidin]-6-yl)urea | 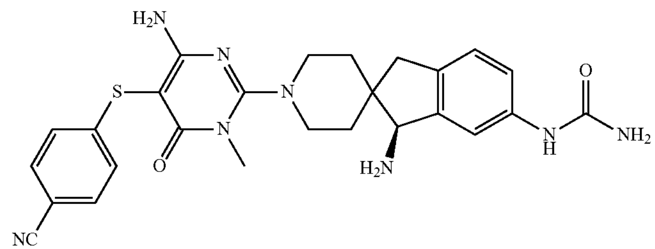 [SMILES: Cn1c(N2CCC3(CC2)Cc2ccc(NC(N)=O)cc2[C@H]3N)nc(N)c(Sc2ccc(C#N)cc2)c1=O] | 517 |
| 131 | (S)-4-amino-6-(1-amino-6-chloro-5-fluoro-1,3-dihydrospiro[indene-2,4'-piperidin]-1'-yl)-1-methyl-3-(4-(tetrahydro-2H-pyran-4-yl)phenyl)pyridin-2(1H)-one | 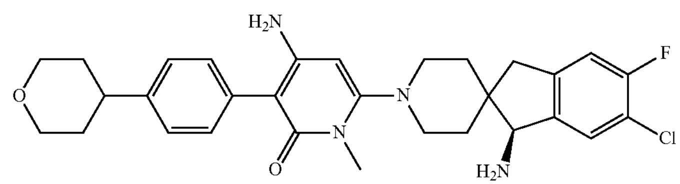 | 537 |
| 132 | (S)-6-(1-amino-6-(trifluoromethyl)-1,3-dihydrospiro[indene-2,4'-piperidin]-1'-yl)-3-(4-(2-methoxyethoxy)phenyl)-1-methylpyridin-2(1H)-one | 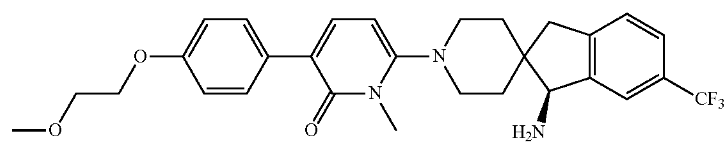 | 528 |

| EX No | Chemical Name | Structure | MS:[M + 1]+ |
|---|---|---|---|
| 133 | (S)-6-amino-2-(1-amino-6-(piperidine-1-carbonyl)-1,3-dihydrospiro[indene-2,4'-piperidin]-1'-yl)-3-methyl-5-(quinolin-8-ylthio)pyrimidin-4(3H)-one | 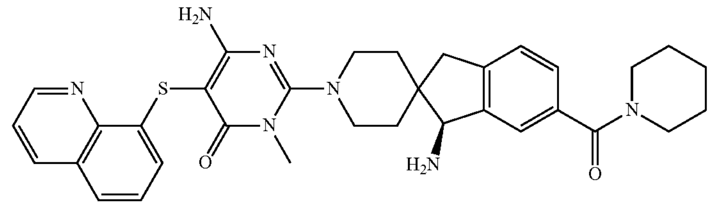 [SMILES: Cn1c(N2CCC3(CC2)Cc2ccc(C(=O)N4CCCCC4)cc2[C@H]3N)nc(N)c(Sc2cccc3cccnc23)c1=O] | 596 |
| 134 | (S)-6-amino-2-(1-amino-6-morpholino-1,3-dihydrospiro[indene-2,4'-piperidin]-1'-yl)-3-methyl-5-((4-nitrophenyl)thio)pyrimidin-4(3H)-one | 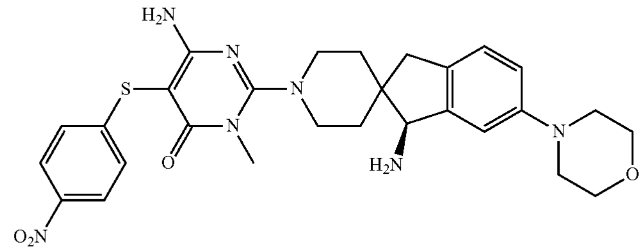 [SMILES: Cn1c(N2CCC3(CC2)Cc2ccc(N4CCOCC4)cc2[C@H]3N)nc(N)c(Sc2ccc([N+](=O)[O-])cc2)c1=O] | 564 |
| 135 | (S)-6-amino-2-(5-amino-3-nitro-5,7-dihydrospiro[cyclopenta[b]pyridine-6,4'-piperidin]-1'-yl)-3-methyl-5-((quinolin-8-ylthio)pyrimidin-4(3H)-one | 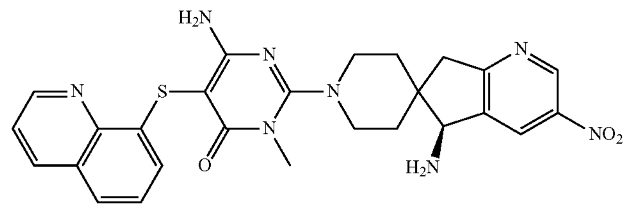 [SMILES: Cn1c(N2CCC3(CC2)Cc2ncc([N+](=O)[O-])cc2[C@H]3N)nc(N)c(Sc2cccc3cccnc23)c1=O] | 531 |
| 136 | (S)-6-(5-amino-3-(4-methylpiperazin-1-yl)-5,7-dihydrospiro[cyclopenta[b]pyridine-6,4'-piperidin]-1'-yl)-1-methyl-3-(naphthalen-1-ylthio)pyridin-2(1H)-one | 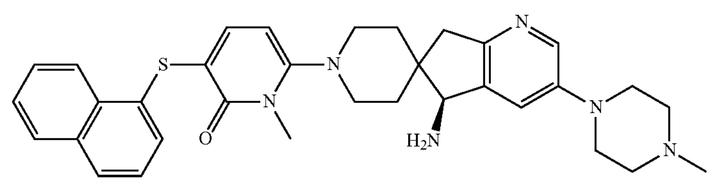 [SMILES: CN1CCN(c2cnc3c(c2)[C@@H](N)C2(CCN(c4ccc(Sc5cccc6ccccc56)c(=O)n4C)CC2)C3)CC1] | 567 |
| 137 | (S)-2-(1-amino-6-(1H-pyrrol-1-yl)-1,3-dihydrospiro[indene-2,4'-piperidin]-1'-yl)-5-((2,2-difluorobenzo[d][1,3]dioxol-4-yl)thio)pyrimidin-4(3H)-one | 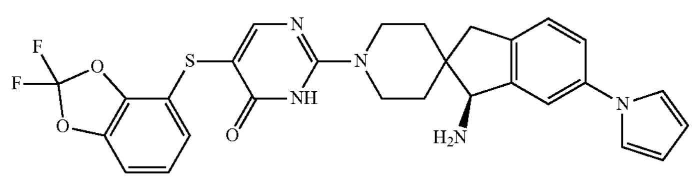 [SMILES: N[C@@H]1c2cc(-n3cccc3)ccc2CC12CCN(c1ncc(Sc3cccc4c3OC(F)(F)O4)c(=O)[nH]1)CC2] | 550 |

-continued

| EX No | Chemical Name | Structure | MS:[M + 1]+ |
|---|---|---|---|
| 138 | (S)-7-(5-(1-amino-6-(1H-imidazol-1-yl)-1,3-dihydrospiro[indene-2,4′-piperidin]-1′-yl)-6-(hydroxymethyl)-3-methylpyrazin-2-yl)isoindolin-1-one | 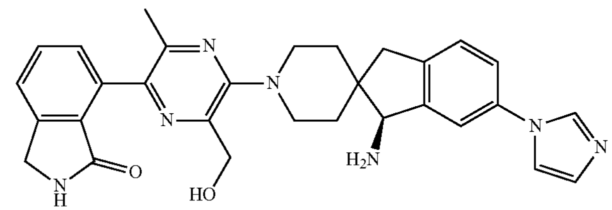 [SMILES: Cc1nc(N2CCC3(CC2)Cc2ccc(-n4ccnc4)cc2[C@H]3N)c(CO)nc1-c1cccc2c1C(=O)NC2] | 522 |
| 139 | (S)-3-(1-amino-6-(ethylamino)-1,3-dihydrospiro[indene-2,4′-piperidin]-1′-yl)-6-(1H-indol-5-yl)-5-methylpyrazine-2-carboxamide | 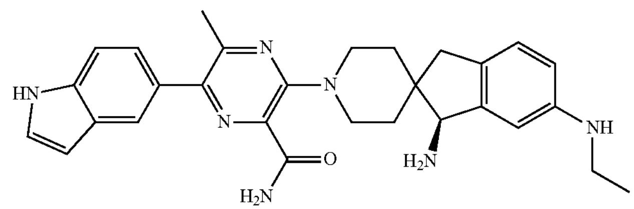 [SMILES: CCNc1ccc2c(c1)[C@@H](N)C1(CCN(c3nc(C)c(-c4ccc5[nH]ccc5c4)nc3C(N)=O)CC1)C2] | 496 |
| 140 | (S)-N-(1-amino-1′-(3-bromo-5-(1H-indol-6-yl)-6-methylpyrazin-2-yl)-1,3-dihydrospiro[indene-2,4′-piperidin]-6-yl)cyclopropanecarboxamide | 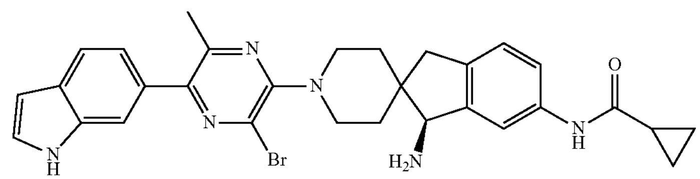 [SMILES: Cc1nc(N2CCC3(CC2)Cc2ccc(NC(=O)C4CC4)cc2[C@H]3N)c(Br)nc1-c1ccc2cc[nH]c2c1] | 571 |
| 141 | (S)-4-(6-amino-5-(1-amino-4-methoxy-1,3-dihydrospiro[indene-2,4′-piperidin]-1′-yl)-3-methylpyrazin-2-yl)-1,3-dihydro-2H-benzo[d]imidazol-2-one | 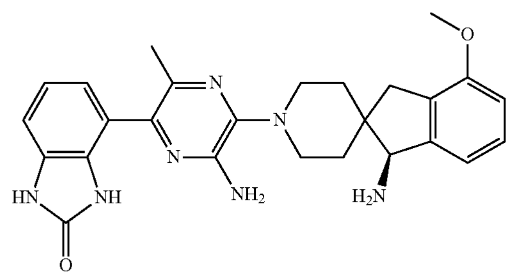 [SMILES: COc1cccc2c1CC1(CCN(c3nc(C)c(-c4cccc5[nH]c(=O)[nH]c45)nc3N)CC1)[C@@H]2N] | 472 |

-continued

| EX No | Chemical Name | Structure | MS:[M + 1]+ |
|---|---|---|---|
| 142 | (S)-3-(1-amino-5-methoxy-1,3-dihydrospiro[indene-2,4'-piperidin]-1'-yl)-5-methyl-6-(2-oxoindolin-7-yl)pyrazine-2-carbonitrile | 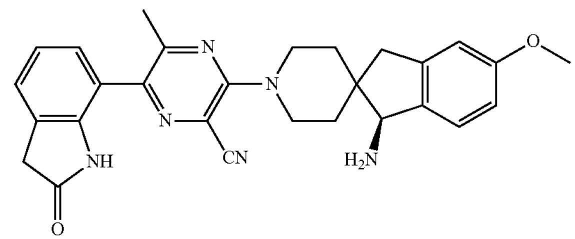 [SMILES: COc1ccc2c(c1)CC1(CCN(c3nc(C)c(-c4cccc5c4NC(=O)C5)nc3C#N)CC1)[C@@H]2N] | 481 |
| 143 | (S)-N-(5-(1-amino-7-methoxy-1,3-dihydrospiro[indene-2,4'-piperidin]-1'-yl)-6-((2-hydroxyethyl)amino)-3-methylpyrazin-2-yl)benzenesulfonamide | 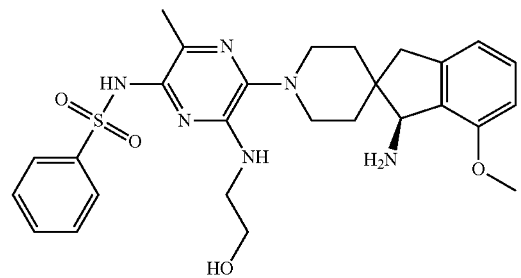 [SMILES: COc1cccc2c1[C@@H](N)C1(CCN(c3nc(C)c(NS(=O)(=O)c4ccccc4)nc3NCCO)CC1)C2] | 539 |
| 144 | (S)-1'-(6-methyl-3-(1H-pyrazol-5-yl)-5-(1H-pyrrolo[2,3-b]pyridin-4-yl)pyrazin-2-yl)-5,7-dihydrospiro[cyclopenta[b]pyridine-6,4'-piperidin]-5-amine | 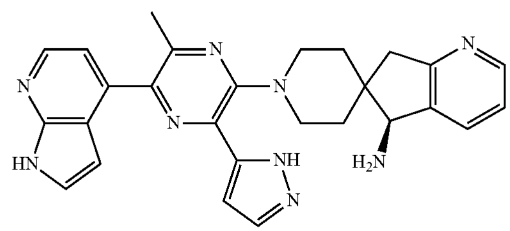 [SMILES: Cc1nc(N2CCC3(CC2)Cc2ncccc2[C@H]3N)c(-c2ccn[nH]2)nc1-c1ccnc2[nH]ccc12] | 478 |
| 145 | (S)-2-(3-(5-amino-5,7-dihydrospiro[cyclopenta[b]pyridine-6,4'-piperidin]-1'-yl)-6-(8-chlorochroman-7-yl)-5-methylpyrazin-2-yl)propan-2-ol | 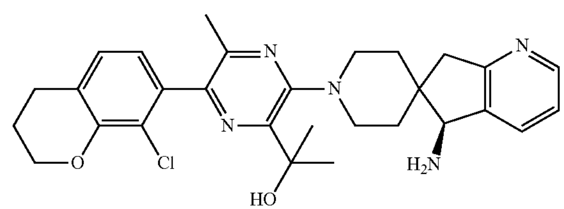 [SMILES: Cc1nc(N2CCC3(CC2)Cc2ncccc2[C@H]3N)c(C(C)(C)O)nc1-c1ccc2c(c1Cl)OCCC2] | 520 |

-continued

| EX No | Chemical Name | Structure | MS:[M + 1]+ |
|---|---|---|---|
| 146 | (S)-6-chloro-1'-(5-(7-chloro-2,3-dihydrobenzofuran-6-yl)pyrazin-2-yl)-1,3-dihydrospiro[indene-2,4'-piperidin]-1-amine | 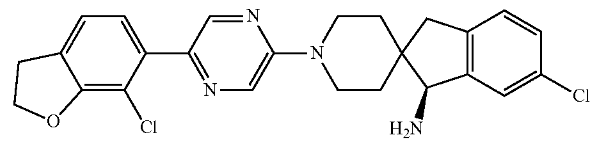 | 467 |
| 147 | (S)-4-bromo-1'-(5-(3-(1-methyl-1H-pyrazol-5-yl)phenyl)pyrazin-2-yl)-1,3-dihydrospiro[indene-2,4'-piperidin]-1-amine | 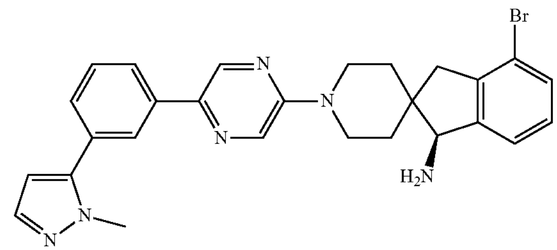 [SMILES: Cn1nccc1-c1cccc(-c2cnc(N3CCC4(CC3)Cc3c(Br)cccc3[C@H]4N)cn2)c1] | 515 |
| 148 | (S)-1-amino-1'-(6-cyano-5-(1H-indazol-7-yl)pyrazin-2-yl)-5-fluoro-1,3-dihydrospiro[indene-2,4'-piperidine]-6-carboxamide | 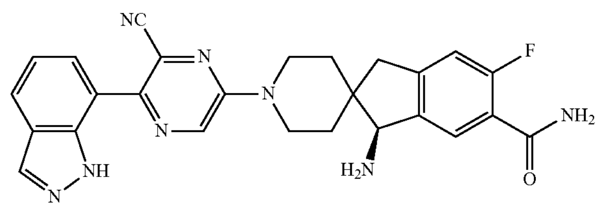 [SMILES: N#Cc1nc(N2CCC3(CC2)Cc2cc(F)c(C(N)=O)cc2[C@H]3N)cnc1-c1cccc2cn[nH]c12] | 483 |
| 149 | (S)-1'-(5-(1H-indol-3-yl)-6-iodopyrazin-2-yl)-5,7-dihydrospiro[cyclopenta[b]pyridine-6,4'-piperidin]-5-amine | 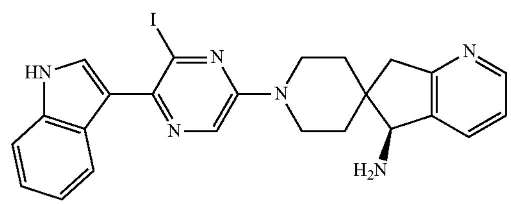 [SMILES: N[C@@H]1c2cccnc2CC12CCN(c1cnc(-c3c[nH]c4ccccc34)c(I)n1)CC2] | 523 |
| 150 | (R)-6-(5-(7'-amino-7,8-dihydro-5H-spiro[piperidine-4,6'-quinolin]-1-yl)-3-vinylpyrazin-2-yl)isoindolin-1-one | 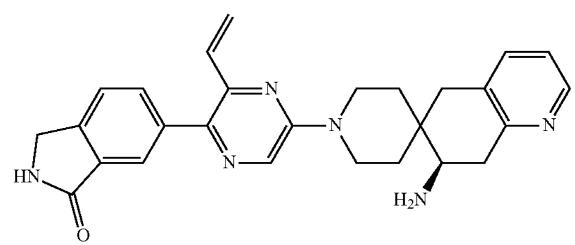 [SMILES: C=Cc1nc(N2CCC3(CC2)Cc2cccnc2C[C@H]3N)cnc1-c1ccc2c(c1)C(=O)NC2] | 453 |

-continued

| EX No | Chemical Name | Structure | MS:[M + 1]+ |
|---|---|---|---|
| 151 | (R)-1-(4-(5-(6-amino-6,7-dihydrospiro[cyclopenta[b]pyridine-5,4'-piperidin]-1'-yl)-3-ethylpyrazin-2-yl)-3,3-difluoroindolin-1-yl)ethan-1-one | 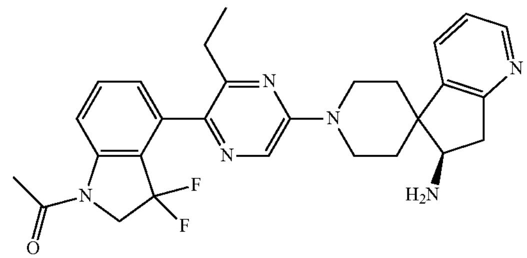 [SMILES: CCc1nc(N2CCC3(CC2)c2cccnc2C[C@H]3N)cnc1-c1cccc2c1C(F)(F)CN2C(C)=O] | 505 |
| 152 | (S)-1'-(5-(3-methyl-1H-indazol-6-yl)-6-phenylpyrazin-2-yl)-5,7-dihydrospiro[cyclopenta[b]pyridine-6,4'-piperidin]-5-amine | 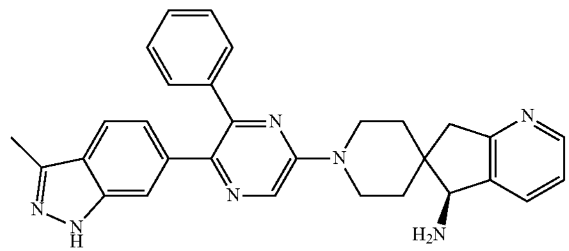 [SMILES: Cc1n[nH]c2cc(-c3ncc(N4CCC5(CC4)Cc4ncccc4[C@H]5N)nc3-c3ccccc3)ccc12] | 488 |
| 153 | (S)-1'-(5-(1H-benzo[d][1,2,3]triazol-6-yl)-6-cyclopropylpyrazin-2-yl)-6-((tetrahydro-2H-pyran-4-yl)oxy)-1,3-dihydrospiro[indene-2,4'-piperidin]-1-amine | 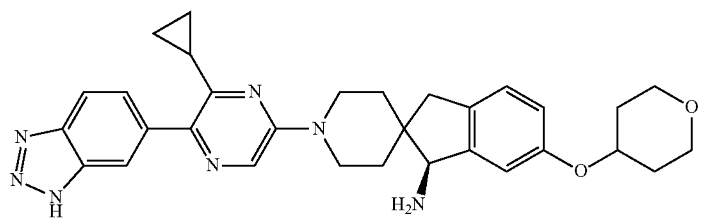 [SMILES: N[C@@H]1c2cc(OC3CCOCC3)ccc2CC12CCN(c1cnc(-c3ccc4nn[nH]c4c3)c(C3CC3)n1)CC2] | 538 |
| 154 | (S)-1-amino-1'-(4-(6-bromonaphthalen-2-yl)thiazol-2-yl)-1,3-dihydrospiro[indene-2,4'-piperidine]-6-carbonitrile | 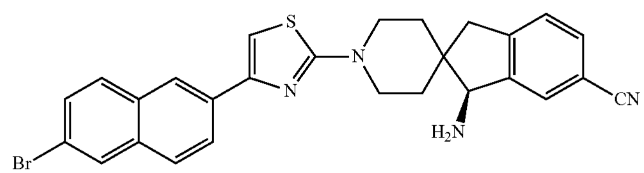 [SMILES: N#Cc1ccc2c(c1)[C@@H](N)C1(CCN(c3nc(-c4ccc5cc(Br)ccc5c4)cs3)CC1)C2] | 515 |

What is claimed is:

1. A compound of Formula II:

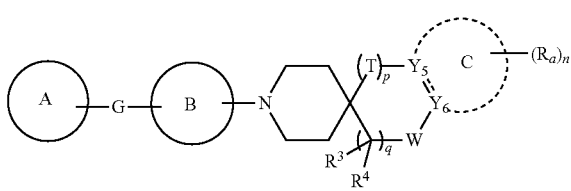

II;
or a pharmaceutically acceptable salt thereof;
wherein:
----- represents a single bond or a double bond;
ring A is

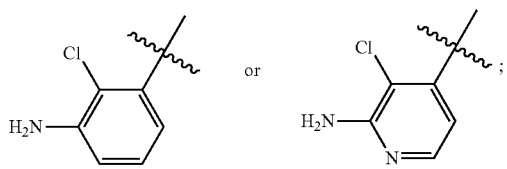 [SMILES: *c1cccc(N)c1Cl ; *c1ccnc(N)c1Cl]

ring B is

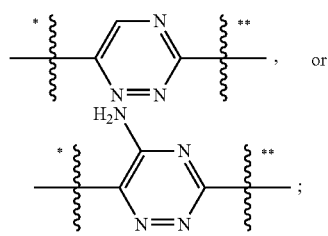

wherein * represents the connection point to G and ** represents the connection point to N;
G is S;
T is CR₁R₂;
each of $R_1$ and $R_2$ is independently selected from hydrogen, deuterium, or —NH₂;
p is 1;
each of $R_3$ and $R_4$ is independently hydrogen or deuterium;
q is 1;
W is absent;
$Y_5$ is C;
$Y_6$ is C;
ring C is

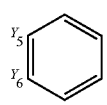 or 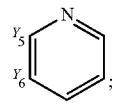 ;

$R_a$ is H; and
n is 0.

2. The compound of claim 1, or a pharmaceutically acceptable salt thereof, wherein Ring A is

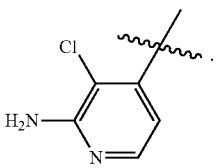 [SMILES: *c1ccnc(N)c1Cl]

3. The compound of claim 1, or a pharmaceutically acceptable salt thereof, wherein Ring B is

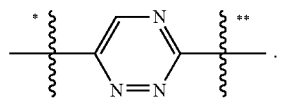 [SMILES: *c1cnc(*)nn1]

4. The compound of claim 1, or a pharmaceutically acceptable salt thereof, wherein $R^1$ is H, and $R^2$ is NH₂.

5. The compound of claim 1, or a pharmaceutically acceptable salt thereof, wherein ring C is

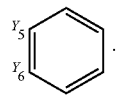

6. The compound of claim 2, or a pharmaceutically acceptable salt thereof, wherein Ring B is

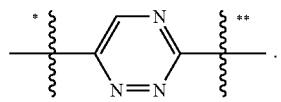 [SMILES: *c1cnc(*)nn1]

7. The compound of claim 6, or a pharmaceutically acceptable salt thereof, wherein $R^1$ is H, and $R^2$ is NH₂.

8. The compound of claim 7, or a pharmaceutically acceptable salt thereof, wherein ring C is

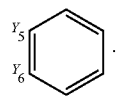

9. A compound which is:
(S)-1-amino-1'-(6-((3-amino-2-chlorophenyl)thio)-1,2,4-triazin-3-yl)-1,3-dihydrospiro [indene-2,4'-piperidine]-6-carbonitrile; or
(S)-1'-(5-amino-6-((2-amino-3-chloropyridin-4-yl)thio)-1,2,4-triazin-3-yl)-5,7-dihydrospiro [cyclopenta[b]pyridine-6,4'-piperidin]-5-amine;
or a pharmaceutically acceptable salt thereof.

10. A pharmaceutical composition comprising the compound of claim 1, or pharmaceutically acceptable salt thereof, and at least one pharmaceutically acceptable excipient.

11. A pharmaceutical composition comprising the compound of claim 9, or pharmaceutically acceptable salt thereof, and at least one pharmaceutically acceptable excipient.

* * * * *